US011564942B2

(12) United States Patent
Mansour et al.

(10) Patent No.: US 11,564,942 B2
(45) Date of Patent: Jan. 31, 2023

(54) METHODS FOR GENERATING UNIVERSAL AND CUSTOM MHC/HLA-COMPATIBLE HEMATOPOIETIC PROGENITOR CELLS

(71) Applicants: THE GENERAL HOSPITAL CORPORATION, Boston, MA (US); PRESIDENT AND FELLOWS OF HARVARD COLLEGE, Cambridge, MA (US)

(72) Inventors: Michael K. Mansour, Boston, MA (US); David B. Sykes, Cambridge, MA (US); David T. Scadden, Boston, MA (US)

(73) Assignees: The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 554 days.

(21) Appl. No.: 15/999,463

(22) PCT Filed: Feb. 17, 2017

(86) PCT No.: PCT/US2017/018401

§ 371 (c)(1),
(2) Date: Aug. 17, 2018

(87) PCT Pub. No.: WO2017/143210

PCT Pub. Date: Aug. 24, 2017

(65) Prior Publication Data

US 2019/0201440 A1 Jul. 4, 2019

Related U.S. Application Data

(60) Provisional application No. 62/440,823, filed on Dec. 30, 2016, provisional application No. 62/297,303, filed on Feb. 19, 2016.

(51) Int. Cl.

| | |
|---|---|
| ***A61K 35/15*** | (2015.01) |
| ***C07K 14/47*** | (2006.01) |
| ***C07K 14/72*** | (2006.01) |
| ***C07K 14/82*** | (2006.01) |
| ***C12N 5/0787*** | (2010.01) |

(52) U.S. Cl.

CPC .......... *A61K 35/15* (2013.01); *C07K 14/4702* (2013.01); *C07K 14/721* (2013.01); *C07K 14/82* (2013.01); *C12N 5/0642* (2013.01); *C07K 2319/10* (2013.01); *C12N 2501/125* (2013.01); *C12N 2501/145* (2013.01); *C12N 2501/2303* (2013.01); *C12N 2501/2306* (2013.01); *C12N 2501/26* (2013.01); *C12N 2501/998* (2013.01)

(58) Field of Classification Search

CPC ..................................................... A61K 35/15
USPC ........................................................ 424/93.7
See application file for complete search history.

(56) References Cited

U.S. PATENT DOCUMENTS

| | | | | |
|---|---|---|---|---|
| 8,450,458 | B2 | 5/2013 | Wu et al. | |
| 8,795,650 | B2 | 8/2014 | Kamps et al. | |
| 2004/0082003 | A1 | 4/2004 | Sauvageau et al. | |
| 2009/0068157 | A1 * | 3/2009 | Kamps et al. | A61K 35/12 424/93.21 |
| 2009/0227496 | A1 | 9/2009 | Wu et al. | |
| 2009/0298772 | A1 | 12/2009 | Thirman | |

FOREIGN PATENT DOCUMENTS

WO 2014/197821 A1 12/2014

OTHER PUBLICATIONS

Krosl et al. "In vitro expansion of hematopoietic stem cells by recombinant TAT-HOXB4 protein." Nature medicine 9.11 (2003): 1428-1432 (Year: 2003).*
Hacke et al., "Suppression of HLA expression by lentivirus-mediated gene transfer of siRNA cassettes and in vivo chemoselection to enhance hematopoietic stem cell transplantation." Immunologic Research 44(1):112-126 (2009).
Jude et al., "Unique and independent roles for MLL in adult hematopoietic stem cells and progenitors." Cell Stem Cell 1(3):324-337 (2007).

* cited by examiner

*Primary Examiner* — Janet L Epps-Smith
*Assistant Examiner* — Alexander W Nicol
(74) *Attorney, Agent, or Firm* — Nixon Peabody LLP; David S. Resnick; Jeanne Jodoin

(57) ABSTRACT

Disclosed herein are methods for generating universal MHC/HLA-compatible hematopoietic progenitor cells and methods for generating custom patient-specific MHC/HLA-compatible hematopoietic progenitor cells. Compositions comprising the universal and custom hematopoietic progenitor cells and therapeutic applications thereof are also disclosed.

3 Claims, 16 Drawing Sheets

Specification includes a Sequence Listing.

**YGRKKRRQRRR*GGGGS*** MAHSCRWRFPARPGTTGGGGGGGRRGLGGAPRQRVPALLLPPGP
PVGGGGPGAPPSPPAVAAAAAAAGSSGAGVPGGAAAASAASSSSASSSSSSSSSASSG
PALLRVGPGFDAALQVSAAIGTNLRRFRAVFGESGGGGGSGEDEQFLGFGSDEEVRVR
SPTRSPSVKTSPRKPRGRPRSGSDRNSAILSDPSVFSPLNKSETKSGDKIKKKDSKSI
EKKRGRPPTFPGVKIKITHGKDISELPKGNKEDSLKKIKRTPSATFQQATKIKKLRAG
KLSPLKSKFKTGKLQIGRKGVQIVRRRGRPPSTERIKTPSGLLINSELEKPQKVRKDK
EGTPPLTKEDKTVVRQSPRRIKPVRIIPSSKRTDATIAKQLLQRAKKGAQKKIEKEAA
QLQGRKVKTQVKNIRQFIMPVVSAISSRIIKTPRRFIEDEDYDPPIKIARLESTPNSR
FSAPSCGSSEKSSAASQHSSQMSSDSSRSSSPSVDTSTDSQASEEIQVLPEERSDTPE
VHPPLPISQSPENESNDRRSRRYSVSERSFGSRTTKKLSTLQSAPQQQTSSSPPPPLL
TPPPPLQPASSISDHTPWLMPPTIPLASPFLPASTAPMQGKRKSILREPTFRWTSLKH
SRSEPQYFSSAKYAKEGLIRKPIFDNFRPPPLTPEDVGFASGFSASGTAASARLFSPL
HSGTRFDMHKRSPLLRAPRFTPSEAHSRIFESVTLPSNRTSAGTSSSGVSNRKRKRKV
FSPIRSEPRSPSHSMRTRSGRLSSSELSPLTPPSSVSSSLSISVSPLATSALNPTFTF
PSHSLTQSGESAEKNQRPRKQTSAPAEPFSSSSPTPLFPWFTPGSQTERGRNKDKAPE
ELSKDRDADKSVEKDKSRERDREREKENKRESRKEKRKKGSEIQSSSALYPVGRVSKE
KVVGEDVATSSSAKKATGRKKSSSHDSGTDITSVTLGDTTAVKTKILIKKGRGNLEKT
NLDLGPTAPSLEKEKTLCLSTPSSSTVKHSTSSIGSMLAQADKLPMTDKRVASLLKKA
KAQLCKIEKSKSLKQTDQPKAQGQESDSSETSVRGPRIKHVCRRAAVALGRKRAVFPD
DMPTLSALPWEEREKILSSMGNDDKSSIAGSEDAEPLAPPIKPIKPVTRNKAPQEPPV
KKGRRSRRCGQCPGCQVPEDCGVCTNCLDKPKFGGRNIKKQCCKMRKCQNLQWMPSKA
YLQKQAKAVKKKEKKSKTSEKKDSKESSVVKNVVDSSQKPTPSAREDPAPKKSSSEPP
PRKPVEEKSEEGNVSAPGPESKQATTPASRKSSKQVSQPALVIPPQPPTTGPPRKEVP
KTTPSEPKKKQPPPPESGPEQSKQKKVAPRPSIPVKQKPKEKEKPPPVNKQENAGTLN
ILSTLSNGNSSKQKIPADGVHRIRVDFKEDCEAENVWEMGGLGILTSVPITPRVVCFL
CASSGHVEFVYCQVCCEPFHKFCLEENERPLEDQLENWCCRRCKFCHVCGRQHQATKQ
LLECNKCRNSYHPECLGPNYPTKPTKKKKVWICTKCVRCKSCGSTTPGKGWDAQWSHD
FSLCHDCAKLFAKGNFCPLCDKCYDDDDYESKMMQCGKCDRWVHSKCENLSGTEDEMY
EILSNLPESVAYTCVNCTERHPAEWRLALEKELQISLKQVLTALLNSRTTSHLLRYRQ

*FIG. 5*

AAKPPDLNPETEESIPSRSSPEGPDPPVLTEVSKQDDQQPLDLEGVKRKMDQGNYTSV

LEFSDDIVKIIQAAINSDGGQPEIKKANSMVKSFFIRQMERVFPWFSVKKSRFWEPNK

VSSNSGMLPNAVLPPSLDHNYAQWQEREENSHTEQPPLMKKIIPAPKPKGPGEPDSPT

PLHPPTPPILSTDRSREDSPELNPPPGIEDNRQCALCLTYGDDSANDAGRLLYIGQNE

WTHVNCALWSAEVFEDDDGSLKNVHMAVIRGKQLRCEFCQKPGATVGCCLTSCTSNYH

FMCSRAKNCVFLDDKKVYCQRHRDLIKGEVVPENGFEVFRRVFVDFEGISLRRKFLNG

LEPENIHMMIGSMTIDCLGILNDLSDCEDKLFPIGYQCSRVYWSTTDARKRCVYTCKI

VECRPPVVEPDINSTVEHDENRTIAHSPTSFTESSSKESQNTAEIISPPSPDRPPHSQ

TSGSCYYHVISKVPRIRTPSYSPTQRSPGCRPLPSAGSPTPTTHEIVTVGDPLLSSGL

RSIGSRRHSTSSLSPQRSKLRIMSPMRTGNTYSRNNVSSVSTTGTATDLESSAKVVDH

VLGPLNSSTSLGQNTSTSSNLQRTVVTVGNKNSHLDGSSSSEMKQSSASDLVSKSSSL

KGEKTKVLSSKSSEGSAHNVAYPGIPKLAPQVHNTTSRELNVSKIGSFAEPSSVSFSS

KEALSFPHLHLRGQRNDRDQHTDSTQSANSSPDEDTEVKTLKLSGMSNRSSIINEHMG

SSSRDRRQKGKKSCKETFKEKHSSKSFLEPGQVTTGEEGNLKPEFMDEVLTPEYMGQR

*FIG. 5 (cont.)*

KSSIMYFEPAPLLPQSVGGTAATAAGTSTISQDTSHLTSGSVSGLASSSSVLNVVSMQ

TTTTPTSSASVPGHVTLTNPRLLGTPDIGSISNLLIKASQQSLGIQDQPVALPPSSGM

FPQLGTSQTPSTAAITAASSICVLPSTQTTGITAASPSGEADEHYQLQHVNQLLASKT

GIHSSQRDLDSASGPQVSNFTQTVDAPNSMGLEQNKALSSAVQASPTSPGGSPSSPSS

GQRSASPSVPGPTKPKPKTKRFQLPLDKGNGKKHKVSHLRTSSSEAHIPDQETTSLTS

GTGTPGAEAEQQDTASVEQSSQKECGQPAGQVAVLPEVQVTQNPANEQESAEPKTVEE

EESNFSSPLMLWLQQEQKRKESITEKKPKKGLVFEISSDDGFQICAESIEDAWKSLTD

KVQEARSNARLKQLSFAGVNGLRMLGILHDAVVFLIEQLSGAKHCRNYKFRFHKPEEA

NEPPLNPHGSARAEVHLRKSAFDMFNFLASKHRQPPEYNPNDEEEEEVQLKSARRATS

MDLPMPMRFRHLKKTSKEAVGVYRSPIHGRGLFCKRNIDAGEMVIEYAGNVIRSIQTD

KREKYYDSKGIGCYMFRIDDSEVVDATMHGNAARFINHSCEPNCYSRVINIDGQKHIV

IFAMRKIYRGEELTYDYKFPIEDASNKLPCNCGAKKCRKFLN MASSCAVQVK LELGHRAQVR KKPTVEGFTH

DWMVFVRGPE HSNIQHFVEK VVFHLHESFP RPKRVCKDPP YKVEESGYAG FILPIEVYFK NKEEPRKVRF

DYDLFLHLEG HPPVNHLRCE KLTFNNPTED FRRKLLKAGG DPNRSIHTSS SSSSSSSSSS SSSSSSSSSS

SSSSSSSSSS SSSSSSSSSS TSFSKPHKLM KEHKEKPSKD SREHKSAFKE PSRDHNKSSK ESSKKPKENK

PLKEEKIVPK MAFKEPKPMS KEPKPDSNLL TITSGQDKKA PSKRPPISDS EELSAKKRKK

SSSEALFKSF SSAPPLILTC SADKKQIKDK SHVKMGKVKI ESETSEKKKS TLPPFDDIVD

PNDSDVEENI SSKSDSEQPS PASSSSSSSS SFTPSQTRQQ GPLRSIMKDL HSDDNEEESD

EVEDNDNDSE MERPVNRGGS RSRRVSLSDG SDSESSSASS PLHHEPPPPL LKTNNNQILE

VKSPIKQSKS DKQIKNGECD KAYLDELVEL HRRLMTLRER HILQQIVNLI EETGHFHITN

TTFDFDLCSL DKTTVRKLQS YLETSGTS

Bold, underlined=TAT SEQUENCE
Italicized = =LINKER
Normal text=MLL
Underlined, not bolded =AF9

*FIG. 5 (cont.)*

YGRKKRRQRRR*GGGGS*MSSYFVNSLFSKYKTGESLRPNYYDCGFAQDLGGRPTVVY
GPSSGGSFQHPSQIQEFYHGPSSLSTAPYQQNPCAVACHGDPGNFYGYDPLQRQSLFGAQ
DPDLVQYADCKLAAASGLGEEAEGSEQSPSPTQLFPWMRPQAAAGRRRGRQTYSRYQTLE
LEKEFLFNPYLTRKRRIEVSHALGLTERQVKIWFQNRRMKWKKENNKDKFPSSKCEQEEL
EKQKLERAPEAADEGDAQKGDKK

Bold, underlined = TAT SEQUENCE
Italicized =LINKER
Normal text =HOXB8

*FIG. 6*

| | Input | Taxon | Gene ID | Gene Symbol | Transcript | Clone ID | Target Seq | Vector | PAM Seq | Cut Position | Cut % of Trans. Length | Exon | On Target Score | Other Matching Genes | Orig. Target Gene[?] |
|---|---|---|---|---|---|---|---|---|---|---|---|---|---|---|---|
| 1 | 567 | human | 567 | B2M | NM_004048.2 | BRDN0001483722 | CTGAATCTTTGGAGTACCTG | pXPR_BRD003 | AGG | 68 | 19% | 2 | 0.6292 | | B2M |
| 2 | 567 | human | 567 | B2M | NM_004048.2 | BRDN0001487814 | AAGTCAACTTCAATGTCGGA | pXPR_BRD003 | TGG | 160 | 44% | 2 | 0.5825 | | B2M |
| 3 | 567 | human | 567 | B2M | NM_004048.2 | BRDN0001488916 | TTCAGACTTGTCTTTCAGCA | pXPR_BRD003 | AGG | 230 | 64% | 2 | 0.5635 | | B2M |
| 4 | 567 | human | 567 | B2M | NM_004048.2 | BRDN0001485558 | TCACGTCATCCAGCAGAGAA | pXPR_BRD003 | TGG | 108 | 30% | 2 | 0.5309 | | B2M |
| 5 | 567 | human | 567 | B2M | NM_004048.2 | BRDN0001480934 | GAGTAGCGCGAGCACAGCTA | pXPR_BRD003 | AGG | 23 | 6% | 1 | 0.4812 | | B2M |
| 6 | 567 | human | 567 | B2M | NM_004048.2 | BRDN0001479750 | ACCCAGACACATAGCAATTC | pXPR_BRD003 | AGG | 132 | 37% | 2 | 0.3563 | | B2M |

*FIG. 7*

| | Input | Taxon | Gene ID | Gene Symbol | Transcript | Clone ID | Target Seq | Vector | PAM Seq | Cut Position | Cut % of Trans. Length | Exon | On Target Score | Other Matching Genes | Orig. Target Gene[?] |
|---|---|---|---|---|---|---|---|---|---|---|---|---|---|---|---|
| 1 | 972 | human | 972 | CD74 | NM_001025159.2 | BRDN0001582378 | CAAGTATGGCAACATGACAG | pXPR_BRD050 | AGG | 411 | 46% | 4 | 0.7337 | | CD74 |
| 2 | 972 | human | 972 | CD74 | NM_001025159.2 | BRDN0001584188 | GAGACACCTTAAGAACACCA | pXPR_BRD050 | TGG | 513 | 58% | 5 | 0.6895 | | CD74 |
| 3 | 972 | human | 972 | CD74 | NM_001025159.2 | BRDN0001583317 | AGCCGCGGAGCCCTGTACAC | pXPR_BRD050 | AGG | 148 | 17% | 2 | 0.6166 | | CD74 |

FIG. 8

METHODS FOR GENERATING UNIVERSAL AND CUSTOM MHC/HLA-COMPATIBLE HEMATOPOIETIC PROGENITOR CELLS

CROSS-REFERENCE TO RELATED APPLICATIONS

This application is a 35 U.S.C. § 371 National Phase Entry Application of International Application No. PCT/US2017/018401 filed Feb. 17, 2017, which designates the U.S. and claims benefit under 35 U.S.C. § 119(e) of U.S. Provisional Application No. 62/297,303 filed Feb. 19, 2016 and 62/440,823 filed Dec. 30, 2016, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Feb. 17, 2017, is named 030258-087332_SL.txt and is 331,643 bytes in size.

FIELD OF THE DISCLOSURE

This invention relates to methods of generating universal and custom patient specific MHC/HLA compatible hematopoietic progenitor cells and compositions comprising thereof for use in treatment of patients who are deficient in these cells and/or require augmented immune response.

BACKGROUND

Infections are one of the most common inpatient diagnoses. Depending on the patient's age and existing co-morbidities, clinical outcomes can vary drastically. Adding to this complexity is a growing population of elderly and immunocompromised patients. This immunocompromised population can be further subdivided into a few main categories including (a) patients who are receiving chemotherapy, (b) patients who are bone-marrow or solid organ transplant recipients, (c) patients whose immune system is compromised because they are receiving immune modulatory treatment (e.g. steroids or biological immunosuppressant medications) and (d) patients with diabetes, a very common condition that results in significantly higher infection risk.

Patients admitted with a suspected infection undergo a battery of testing in an attempt to determine the type of infection, and whether the infection is localized or widespread. Our ability to identify a specific pathogen as the cause of infection is limited, and depending on the type of infection can take hours to weeks. Because of these limitations, treating physicians will make their best guess as to whether the infection is bacterial, viral, or fungal, and initiate empiric anti-microbial therapy while awaiting the results of the diagnostic testing.

Despite this approach, a large majority of patients will succumb to their infection or will suffer permanent complications as a result of the infection or the treatment itself. Common complications of the infection as well as the anti-microbial therapy include: allergic reactions, rash, temporary or permanent kidney damage, temporary or permanent liver damage, temporary or permanent damage to the bone marrow, and of course the physical destruction of whatever tissue the infection is residing. There are currently no therapies capable of augmenting and/or amplifying the critical cellular response to assist with controlling and eliminating the offending pathogen. The current approach to the diagnosis and treatment of patients with infectious complications such as bacterial pneumonia, septic shock, skin and soft tissue infection, fungal infections, etc. is modular and reactive. Currently, if one is capable of identifying the causative pathogen, laboratory-based testing for optimal antimicrobial susceptibility helps to guide the best choice of anti-microbial agent. The remainder of the care remains strictly supportive. The ability to augment a patient's immune response with additional cellular immunotherapy represents a large unmet need in the area of infectious diseases therapy.

Neutrophils are the most abundant circulating white blood cell and serve as the first line of defense to a variety of infections. In fact, the state of neutropenia (lack of an adequate number of functional neutrophils) is one of the highest risk factors for serious infection. Once patients with neutropenia acquire an infection, the risk of death can be in excess of 40%. While there are multiple causes of neutropenia, one of the most common causes is the use of chemotherapy in the treatment of malignancies, especially in patients who have leukemia or lymphoma.

In patients with aggressive leukemias or lymphomas, the only curative therapy remains an allogeneic stem cell transplant. In the allo-SCT, high-dose chemotherapy is given prior to the infusion of the donor stem cells. This high-dose chemotherapy is termed 'ablative' because its goes is to permanently eliminate all (leukemic/malignant and normal) of the host hematopoietic cells. The donated stem cells repopulate the bone marrow (a process called engraftment) and generate all the new white blood cells, red blood cells, and platelets in the stem cell recipient. Unfortunately, there is a period of 2-4 weeks between the high-dose chemotherapy and the engraftment of the donor stem cells when the patient's blood counts are all very low.

During this vulnerable period, patients receive red blood cell transfusions and platelet transfusions. However, there is currently no means of boosting the white blood cell count, and therefore these patients remain extremely susceptible to infection. Over the last thirty years, many centers have attempted the transfusion of mature neutrophils from a variety of donors (usually family members). These granulocyte transfusions (granulocyte=neutrophil) have unfortunately not been effective despite years of clinical trials. Currently, granulocyte transfusions remain a controversial topic and are not considered the standard of care given their risks and unproven benefit. Accordingly, there is an unmet need for effective therapeutic options in subjects suffering from low neutrophil count for e.g. due to an infection.

SUMMARY

The technology herein provides methods for generation and expansion, ex vivo, of immune cells progenitors, for example neutrophilic progenitors for transfusion in patients who are deficient in these cells and/or require augmented immune response. Aspects of the technology disclosed herein relate to the ability to (1) generate and expand, ex vivo, hematopoietic progenitors such that the cells can be administered in clinically relevant manner and (2) to transfuse these cells as progenitors, rather than mature cells into patients. The transfusion at the progenitor stage is a critical improvement upon previous technologies, as it provides a source of cells that are safer to transfuse, undergo their final development in vivo, and undergo exponential expansion in vivo, providing even greater number of terminal effector cells, for example, neutrophils. Accordingly, provided herein are methods to generate universal MHC/HLA-compatible hematopoietic progenitors and methods to generate, custom patient-specific MHC/HLA-compatible hematopoietic progenitors. Compositions comprising the universal or patient specific hematopoietic progenitors are also disclosed.

In one aspect, the technology herein relates to an in vitro method for generating universal MHC/HLA-compatible hematopoietic progenitor cells, said method comprising the steps of, (a) contacting isolated progenitor cells with a fusion protein selected from a homeotic (HOX) oncoprotein or a mixed-lineage leukemia (MLL) oncoprotein, wherein said isolated progenitor cells are progenitor cells that give rise to subsets of mature blood cells, (b) disrupting antigen presentation by the cell by down-regulating a major histocompatibility complex (MHC, also called the human leukocyte antigen (HLA)) gene expression in the cell; and (c) culturing the progenitor cells of step b) with a combination of multilineage cytokines comprising stem-cell factor (SCF), Flt3 ligand, IL-3, TPO and IL-6, whereupon culturing, the progenitor cells become immortalized and exhibit commitment to neutrophil, macrophage, and/or dendritic lineage or exhibit multi-lineage blood cell differentiation potential.

In some embodiments, the contacting of step (a) comprises, (i) co-culture in vitro with a fusion protein comprising a HOX oncoprotein and a TAT domain, wherein the TAT is fused to the N-terminus of the HOX oncoprotein; (ii) co-culture in vitro with a fusion protein comprising a (MLL) oncoprotein and a TAT domain, wherein the TAT is fused to the N-terminus of the HOX oncoprotein; infecting the progenitor cells with a vector comprising a nucleic acid sequence which encodes the fusion protein comprising a HOX oncoprotein and an estrogen receptor binding domain (ERBD), wherein the ERBD is fused to the N-terminus of the HOX oncoprotein; or (iv) infecting the progenitor cells with a vector comprising a nucleic acid sequence which encodes the fusion protein comprising a MLL oncoprotein and an estrogen receptor binding domain (ERBD), wherein the ERBD is fused to the N-terminus of the MLL oncoprotein.

In some embodiments the HOX oncoprotein is HoxB4 or HoxB8. In some embodiments, the fusion HOX oncoprotein is a recombinant TAT-HoxB8, a recombinant TAT-HoxB4, recombinant ERBD-HoxB8, or a recombinant ERBD-HoxB4.

In some embodiments, the vector for the fusion protein is a retroviral vector.

In some embodiments, the methods of any one of the foregoing aspects further comprise a step of culturing the cells in the presence in an estrogen agonist when the fusion oncoprotein is an ERBD fusion oncoprotein.

In some embodiments, the downregulation of a MHC gene expression comprises infecting the progenitor cells with a second vector comprising a nucleic acid sequence that inhibits the MHC gene expression.

In some embodiments, the targeted gene that is inhibited or disrupted from expressing is a MHC/HLA class I gene or β2 microglobulin gene. In some embodiments, the MHC/HLA class I gene encodes HLA-A, HLA-B or HLA-C.

In some embodiments, the nucleic acid sequence is an RNA interference (RNAi) molecule or a CRISPR-mediated guide RNA (gRNA) molecule.

In some embodiments, the RNAi or gRNA molecule corresponds to a gene encoding a MHC class I gene or β2 microglobulin gene, wherein the RNAi or gRNA molecule is expressed and initiates RNA interference of expression of the MHC/HLA class I gene or β2 microglobulin gene, thereby down-regulating expression of the MHC gene and disrupting antigen presentation. In some embodiments, the gRNA molecule corresponds to a gene encoding a MHC class I gene or β2 microglobulin gene, wherein the gRNA molecule is expressed and initiates gene editing to disrupt the MHC class I gene or β2 microglobulin gene, thereby down-regulating expression of the MHC gene and disrupting antigen presentation.

In some embodiments, the second vector is a retroviral vector. In some embodiments, the promoter of the second vector is a U6 Pol III promoter.

In some embodiments, the RNAi molecule comprises a DNA sequence selected from SEQ ID NOs: 22-30. In some embodiments, the gRNA molecule comprises DNA sequence selected from SEQ ID NOs: 7-21.

In some embodiments, the isolated progenitor cells are granulocyte-macrophage progenitor cells (GMP). In some embodiments, the isolated progenitor cells are mononuclear cells (MN). In some embodiments, the isolated progenitor cells are isolated from bone marrow, peripheral blood, placenta, or umbilical cord of a donor subject.

In another aspect, the technology disclosed herein relates to a composition comprising universal MHC/HLA-compatible hematopoietic progenitor cells produced by the methods herein.

In another aspect, the technology disclosed herein relates to a method of treating a pathogen infection in a subject, said method comprising administering a composition disclosed herein.

In another aspect, the technology disclosed herein relates to an in vitro method for generating custom MHC/HLA-compatible hematopoietic progenitor cells for a recipient subject, said method comprising the steps of: (a) contacting isolated MHC/HLA-compatible progenitor cells with a fusion protein selected from a homeotic (HOX) oncoprotein or a mixed-lineage leukemia (MLL) oncoprotein, wherein said isolated progenitor cells are progenitor cells that give rise to subsets of mature blood cells; and (b) culturing the progenitor cells of step a) with a combination of multilineage cytokines comprising of stem-cell factor (SCF), Flt3 ligand, IL-3 TPO and IL-6, whereupon culturing, the progenitor cells become immortalized and exhibit commitment to neutrophil, macrophage, and/or dendritic lineage or exhibit multi-lineage blood cell differentiation potential.

In some embodiments, the contacting of step a) comprises: i) co-culture in vitro with a fusion protein comprising a HOX oncoprotein and a TAT domain, wherein the TAT is fused to the N-terminus of the HOX oncoprotein; ii) co-culture in vitro with a fusion protein comprising a (MLL) oncoprotein and a TAT domain, wherein the TAT is fused to the N-terminus of the HOX oncoprotein; infecting the progenitor cells with a vector comprising a nucleic acid sequence which encodes the fusion protein comprising a HOX oncoprotein and an estrogen receptor binding domain (ERBD), wherein the ERBD is fused to the N-terminus of the HOX oncoprotein; or iv) infecting the progenitor cells with a vector comprising a nucleic acid sequence which encodes the fusion protein comprising a MLL oncoprotein and an estrogen receptor binding domain (ERBD), wherein the ERBD is fused to the N-terminus of the MLL oncoprotein.

In some embodiments, the HOX oncoprotein is HOXB4 or HOXB8.

In some embodiments, the fusion HOX oncoprotein is a recombinant TAT-HoxB8, a recombinant TAT-HoxB4, recombinant ERBD-HoxB8, or a recombinant ERBD-HoxB4.

In some embodiments, the vector for the fusion protein is a retroviral vector.

In some embodiments, the method of the foregoing aspects further comprises a step of culturing the cells in the presence in an estrogen agonist when the fusion oncoprotein is a ERBD fusion oncoprotein.

In some embodiments the isolated MHC/HLA-compatible progenitor cells are granulocyte-macrophage progenitor cells (GMP).

In some embodiments, the isolated MHC/HLA-compatible progenitor cells are mononuclear cells (MN).

In some embodiments, the isolated MHC/HLA-compatible progenitor cells are isolated from bone marrow, peripheral blood, placenta, or umbilical cord of a donor subject.

In another aspect, a composition as disclosed herein relates to a composition comprising customized, patient-specific MHC/HLA-compatible hematopoietic progenitor cells produced by the methods herein.

In another aspect, the methods and compositions disclosed herein, relate to a method of treating neutropenia in a subject, said method comprising administering a composition as described herein.

Definitions:

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

The term "proliferation" as used herein, refers to expansion of a cell or population of cells by the continuous division of single cells into identical daughter cells.

The term "neutrophils" or "polymorphonuclear neutrophils (PMNs)" as used herein, refers to the most abundant type of white blood cells in mammals, which form an essential part of the innate immune system. They form part of the polymorphonuclear cell family (PMNs) together with basophils and eosinophils. Neutrophils are normally found in the blood stream. During the beginning (acute) phase of inflammation, particularly as a result of bacterial infection and some cancers, neutrophils are one of the first-responders of inflammatory cells to migrate toward the site of inflammation. They migrate through the blood vessels, then through interstitial tissue, following chemical signals such as interleukin-8 (IL-8) and C5a in a process called chemotaxis, the directed motion of a motile cell or part along a chemical concentration gradient toward environmental conditions it deems attractive and/or away from surroundings it finds repellent.

The term "Allogeneic" as used herein, refers to deriving from, originating in, or being members of the same species, where the members are genetically related or genetically unrelated but genetically similar. An "allogeneic transplant" refers to transfer of cells or organs from a donor to a recipient, where the recipient is the same species as the donor.

As used herein, the term "Autologous" refers to deriving from or originating from the same subject or patient. An "autologous transplant" refers to the harvesting and reinfusion or transplant of a subject's own cells or organs. Exclusive or supplemental use of autologous cells can eliminate or reduce many adverse effects of administration.

As used herein, the term "Mismatched allogeneic" refers to deriving from, originating in, or being members of the same species having non-identical major histocompatibility complex (MHC) antigens (i.e., proteins) as typically determined by standard assays used in the art, such as serological or molecular analysis of a defined number of MHC antigens. A "partial mismatch" refers to partial match of the MHC antigens tested between members, typically between a donor and recipient. For instance, a "half mismatch" refers to 50% of the MHC antigens tested as showing different MHC antigen type between two members. A "full" or "complete" mismatch refers to all MHC antigens tested as being different between two members.

As used herein, the term "Syngeneic" refers to deriving from, originating in, or being members of the same species that are genetically identical, particularly with respect to antigens or immunological reactions. These include identical twins having matching MHC types. Thus, a "syngeneic transplant" refers to transfer of cells or organs from a donor to a recipient who is genetically identical to the donor.

As used herein, the term "Congenic" refers to deriving from, originating in, or being members of the same species, where the members are genetically identical except for a small genetic region, typically a single genetic locus (i.e., a single gene). A "congenic transplant" refers to transfer of cells or organs from a donor to a recipient, where the recipient is genetically identical to the donor except for a single genetic locus.

As used herein, the term "Committed myeloid progenitor cell" or "myeloid progenitor cell" refers to a multipotent or unipotent progenitor cell capable of ultimately developing into any of the terminally differentiated cells of the myeloid lineage, but which do not typically differentiate into cells of the lymphoid lineage. Hence, "myeloid progenitor cell" refers to any progenitor cell in the myeloid lineage. Committed progenitor cells of the myeloid lineage include oligopotent CMP, GMP, and MEP as defined herein, but also encompass unipotent erythroid progenitor, megakaryocyte progenitor, granulocyte progenitor, and macrophage progenitor cells. Different cell populations of myeloid progenitor cells are distinguishable from other cells by their differentiation potential, and the presence of a characteristic set of cell markers well known in the art.

As used herein, the term "Common myeloid progenitor cell" or "CMP" refers to a cell characterized by its capacity to give rise to granulocyte/monocyte (GMP) progenitor cells and megakaryocyte/erythroid (MEP) progenitor cells. These progenitor cells have limited or no self-renewing capacity, but are capable of giving rise to myeloid dendritic, myeloid erythroid, erythroid, megakaryocytes, granulocyte/macrophage, granulocyte, and macrophage cells.

As used herein, the term "Granulocyte/macrophage progenitor cell" or "GMP" refers to a cell derived from common myeloid progenitor cells, and characterized by its capacity to give rise to granulocyte and macrophage cells, but which does not typically give rise to erythroid cells or megakaryocytes of the myeloid lineage. GMPs are characterized as $CD10^-$, $CD45RA^+$, $CD123^+$, $CD135^+$.

As used herein, "mononuclear cell" or "MN cell" refers to undifferentiated cells whose nuclei are unilobulated or rounded and which lack granules in the cytoplasm. Mononuclear cells can be derived from, for example, mononuclear fraction of normal adult Bone marrow (Bone marrow derived mononuclear cell) or peripheral blood (PBMC).

As used herein, the term "Cytokine" refers to compounds or compositions that in the natural state are made by cells and affect physiological states of the cells that produce the cytokine (i.e., autocrine factors) or other cells. Cytokine also encompasses any compounds or compositions made by recombinant or synthetic processes, where the products of those processes have identical or similar structure and biological activity as the naturally occurring forms. Lymphokines refer to natural, synthetic, or recombinant forms of cytokines naturally produced by lymphocytes, including, but not limited to, IL-1, IL-3, IL-4, IL-6, IL-11, and the like.

As used herein, the term "Growth factor" refers to a compound or composition that in the natural state affects cell proliferation, cell survival, and/or differentiation. A growth factor, while having the indicated effect on the cell, may also affect other physiological process, such as secretion, adhesion, response to external stimuli, and the like. Although many growth factors are made by cells, growth factors as used herein also encompass any compound or composition made by recombinant or synthetic processes, where the product of those processes have identical or similar structure and biological activity as the naturally occurring growth factor. Examples of growth factors include epidermal growth factor (EGF), fibroblast growth factor (FGF), erythropoietin (EPO), thromobopoietin (TPO), stem cell factor (SCF), and flt-3 ligand (FL), and analogs thereof.

"Expansion" in the context of cells refers to an increase in the number of a characteristic cell type, or cell types, from an initial population of cells, which may or may not be identical. The initial cells used for expansion need not be the same as the cells generated from expansion. For instance, the cells generated from expansion may be produced by growth and differentiation of the initial population of cells. Excluded from the term expansion are limiting dilution assays used to characterize the differentiation potential of cells.

As used herein, the term "Isolated" refers to a product, compound, or composition which is separated from at least one other product, compound, or composition with which it is associated in its naturally occurring state, whether in nature or as made synthetically.

As used herein, the term "Hematopoietic stem cell" or "HSC" refers to a clonogenic, self-renewing pluripotent cell capable of ultimately differentiating into all cell types of the hematopoietic system, including B cells T cells, NK cells, lymphoid dendritic cells, myeloid dendritic cells, granulocytes, macrophages, megakaryocytes, and erythroid cells. As with other cells of the hematopoietic system, HSCs are typically defined by the presence of a characteristic set of cell markers. "Enriched" when used in the context of HSC refers to a cell population selected based on the presence of a single cell marker, generally CD34+, while "purified" in the context of HSC refers to a cell population resulting from a selection on the basis of two or more markers, preferably CD34+CD90+.

As used herein, the term "Myeloablative" or "myeloablation" refers to impairment or destruction of the hematopoietic system, typically by exposure to a cytotoxic agent or radiation. Myeloablation encompasses complete myeloablation brought on by high doses of cytotoxic agent or total body irradiation that destroys the hematopoietic system. It also includes a less than complete myeloablated state caused by non-myeloablative conditioning. Thus, non-myeloablative conditioning is treatment that does not completely destroy the subject's hematopoietic system.

As used herein, the term "Neutropenia" refers to a lower than normal number of neutrophils and other polymorphonuclear leukocytes in the peripheral blood. Typically, a neutropenic condition is diagnosed based on the absolute neutrophil count (ANC), which is determined by multiplying the percentage of bands and neutrophils on a differential by the total white blood cell count. Typical accepted reference range for absolute neutrophil count (ANC) in adults is 1500 to 8000 cells per microliter (μl) of blood. Clinically, an abnormal ANC is fewer than about 1500 cells per ml of peripheral blood. The severity of neutropenia is categorized as mild for an ANC of 1000-1500 cells per ml, moderate for an ANC of 500-1000 cells per ml, and severe for an ANC of fewer than 500 cells per ml.

As used herein, the term "Thrombocytopenia" refers to a lower than normal platelet count, generally less than about $100\times10^9$/L, which gives rise to increased clotting time and increased risk of spontaneous bleeding, particularly at platelet levels of about 10-$50\times10^9$/L or lower. The condition occurs when platelets are lost from circulation at a faster rate than their replenishment by megakaryocytes. Thrombocytopenia may result from either failure of platelet synthesis and/or increased rate of platelet destruction.

As used herein, the term "Self renewal" refers to the ability of a cell to divide and generate at least one daughter cell with the identical (e.g., self-renewing) characteristics of the parent cell. The second daughter cell may commit to a particular differentiation pathway. For example, a self-renewing hematopoietic stem cell divides and forms one daughter stem cell and another daughter cell committed to differentiation in the myeloid or lymphoid pathway. A committed progenitor cell has typically lost the self-renewal capacity, and upon cell division produces two daughter cells that display a more differentiated (i.e., restricted) phenotype.

As used herein, the term "Substantially pure cell population" refers to a population of cells having a specified cell marker characteristic and differentiation potential that is at least about 50%, at least about 75-80%, at least about 85-90%, or at least about 95% of the cells making up the total cell population. Thus, a "substantially pure cell population" refers to a population of cells that contain fewer than about 50%, less than about 20-25%, less than about 10-15%, and less than about 5% of cells that do not display a specified marker characteristic and differentiation potential under designated assay conditions.

As used herein, the term "immortalized" refers to a cell population changed from having a finite life span to one possessing an infinite life span.

As used herein, the term "differentiation" refers to a process whereby relatively unspecialized cells acquire specialized structure and/or functional features that characterize the cells, tissues, or organs of the mature organism or some other relatively stable phase of the organism's life history.

As used herein, the term "progenitors" refers to a more differentiated progeny of stem cells that give rise to distinct subsets of mature blood cells and lack the capacity for self-renewal possessed by true stem cells.

Mature blood cells are fully differentiated cells of the hematopoietic lineage, e.g, monocytes, macrophages, dendritic cells, neutrophils, eosinophils, basophils, mast cells, T cells, B cells, NK cell, erythrocytes, megakaryocytes, platelets, and the like. A subset of mature blood cells refers to a group of 1 or more types of mature blood cells. Cells that can give rise to a subset of mature blood cells are progenitor cells that have no fully differentiated but which have the potential to terminally differentiate or produce daughter cells which can terminally differentiate.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art.

Contacting can be continuous or intermittent in nature. Contacting can be performed once, or repeated in order to, e.g., maintain a minimum level of the agent or to maintain an effect of the agent.

As used herein, the term "oncoprotein" refers to any protein associated with the causation of cancer.

As used herein, the term "multi-lineage differentiation potential" refers to a progenitor cell having the capability of development into a neutrophil, macrophage/dendritic, biphenotypic neutrophil/macrophage/dendritic, and/or eosinophil/mast cell. Multi-lineage differentiation potential can be measured and/or determined by determining if the cell displays the phenotype of a known progenitor cell type with the specified differentiation potential and/or by culturing the cell(s) under conditions that promote the specified differentiation and determining if they display proper differentiation (e.g. by morphological and/or cell maker analysis).

As used herein, "exhibiting commitment" to a particular lineage as used herein, e.g, the neutrophil, macrophage, and/or dendritic lineage, indicates a cell that has begun to express markers and/or exhibit morphology, structure, potency (e.g., the ability to differentiate along a particular lineage(s)) and/or other characteristics associated with the particular lineage.

The term "fusion protein", as used herein refers to a single polypeptide chain having at least two polypeptide domains that are not normally present in a single, natural polypeptide. Thus, naturally occurring proteins are not "fusion proteins", as used herein. Preferably, a polypeptide of interest is fused with at least one polypeptide domain via a peptide bond and the fusion protein may also include the linking regions of amino acids between amino acid portions derived from separate proteins. The polypeptide domain fused to the polypeptide of interest may enhance solubility and/or expression of the polypeptide of interest, may also provide a purification tag to allow purification of the recombinant fusion protein from the host cell or culture supernatant, or both, or allow delivery into the cell or subject for example when the protein of interest is fused with a cell penetrating peptide. In some embodiments the fusion protein can comprise protein of interest fused with polypeptide domain of a ligand binding domain for example estrogen receptor binding domain. The expression or biological activity of the polypeptide of interest is conditional to the presence of ligand of ligand binding domain (e.g., ligand estrogen for estrogen receptor binding domain). The polypeptide domain fused to the polypeptide of interest may be fused at the N-terminus or at the C-terminus of the polypeptide of interest. The term "recombinant" refers to an artificial combination of two otherwise separated segments of sequence, e.g., by chemical synthesis or by the manipulation of isolated segments of amino acids or of nucleic acids by genetic engineering techniques.

The term "cell penetrating peptide" (also referred to as "CPP," "protein transduction domain," "PTD", "Trojan peptide", "membrane translocating sequence", and "cell permeable protein") as used herein refers to a class of peptides generally capable of penetrating the plasma membrane of mammalian cells. CPPs generally are 10-16 amino acids in length and are capable of transporting compounds of many types and molecular weights across mammalian cells. Such compounds include, but are not limited to, effector molecules, such as proteins, DNA, conjugated peptides, oligonucleotides, and small particles such as liposomes. CPPs chemically linked or fused to other proteins ("fusion proteins") still are able to penetrate the plasma membrane and enter cells. The TAT sequence can be used as membrane penetrating fusion protein. TAT and other CPPs are known in the art, see, e.g, Brooks et al. 2005 Advanced Drug Reviews 559-577 and Bechara et al. 2013 FEBS Letters 587:1693-1702 and can include the sequence of SEQ ID NO: 36. The foregoing references are incorporated by reference herein in their entireties.

SEQ ID NO: 36—TAT polypeptide YGRKKRRQRRR

As used herein, the term "administering," or "delivering" refers to the placement of a compound as disclosed herein into a subject by a method or route that results in at least partial delivery of the agent at a desired site. Pharmaceutical compositions comprising the compounds disclosed herein can be administered by any appropriate route which results in an effective treatment in the subject, e.g., intracerebroventricular ("icv") administration, intranasal administration, subcutaneous administration, intraperitoneal administration, intravenous administration, intracranial administration, intracelial administration, intracerebellar administration, or intrathecal administration.

As used herein, the term "comprising" or "comprises" is used in reference to compositions, methods, and respective component(s) thereof, that are useful to an embodiment, yet open to the inclusion of unspecified elements, whether useful or not.

As used herein, the term "consisting essentially of" refers to those elements required for a given embodiment. The term permits the presence of elements that do not materially affect the basic and novel or functional characteristic(s) of that embodiment of the invention.

As used herein, the term "consisting of" refers to compositions, methods, and respective components thereof as described herein, which are exclusive of any element not recited in that description of the embodiment.

The terms "disease", "disorder", or "condition" are used interchangeably herein, refer to any alteration in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

As used herein, the term "gene expression" includes both gene transcription, whereby DNA (or RNA in the case of some RNA-containing viruses) corresponding to a gene is transcribed to generate an RNA molecule and RNA translation, whereby an RNA molecule is translated to generate a protein encoded by the gene. As used herein, the term "protein expression" is used to refer both to gene expression comprising transcription of DNA (or RNA) to form an RNA molecule and subsequent processing and translation of the RNA molecule to form protein and to gene expression comprising translation of mRNA to form protein.

As used herein, the term "inhibition of expression of gene" means inhibition of DNA transcription (or RNA transcription in the ease of some RNA-containing viruses), inhibition of RNA translation, inhibition of RNA processing, or some combination of these. "inhibition of expression of gene" in reference to an inhibitor of said expression (for example a RNAi inhibitor molecule such as siRNA or miRNA) refers to a decrease in mRNA level in a cell for a target gene (e.g. MHC/HLA class I gene) by at least about 5%, at least about 10%, at least about 20%, at least about 30%, at least about 40%, at least about 50%, at least about 60%, at least about 70%, at least about 80%, at least about 90%, at least about 95%, at least about 99%, at least about 100% of the mRNA level found in the cell without the presence of the inhibitor. In one preferred embodiment, the mRNA levels are decreased by at least about 70%, at least about 80%, at least about 90%, at least about 95%, at least about 99%, at least about 100%. “Inhibition of expression of gene”, in reference to an inhibitor of said expression (for example a RNAi inhibitor molecule such as siRNA or mina) refers to a decrease in protein or polypeptide level in a cell encoded by the gene by at least about 5%, at least about 10%, at least about 20%, at least about 30%, at least about 40%, at least about 50%, at least about 60%, at least about 70%, at least about 80%, at least about 90%, at least about 95%, at least about 99%, at least about 100% of the protein level found in the cell without the presence of the inhibitor. As used herein, the phrase “effective inhibition of expression of gene” will result in decrease in gene product to a level sufficient to allow progenitor cells generated using the methods herein to have a negative phenotype for MHC surface antigens.

As used herein, the term “RNAi” refers to any type of interfering RNA, including but not limited to, siRNA, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term “RNAi” can include both gene silencing RNAi molecules, and also RNAi effector molecules which activate the expression of a gene. By way of an example only, in some embodiments RNAi agents which serve to inhibit expression of MHC gene are useful in the methods, kits and compositions disclosed herein to inhibit a MHC gene (for example, MHC/HLA class I gene or MHC gene encoding HLA ABC).

In yet another embodiment, the RNA of an RNAi or sgRNA molecule as described herein, or a nucleic acid encoding a fusion protein or protein as described herein, is chemically modified to enhance stability or other beneficial characteristics. The nucleic acids featured in the invention may be synthesized and/or modified by methods well established in the art, such as those described in “Current protocols in nucleic acid chemistry,” Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone. RNA molecules comprising one or more such modifications are referred to as modified RNA or modRNA.

As used herein, “in vitro” used interchangeably with “ex vivo”, refers to events that which occur outside an organism, e.g., in an artificial environment outside the organism. The artificial environment can be, e.g., in a test tube or reaction vessel, in cell culture, in a Petri dish, etc., rather than within an organism (e.g., animal, plant, or microbe).

The term “major histocompatibility complex”, or “MHC”, as used herein is defined as a specific cluster of genes, many of which encode evolutionarily related cell surface proteins involved in antigen presentation also called major histocompatibility antigens, which are among the most important determinants of histocompatibility. Class I MHC, or MHC-I, function mainly in antigen presentation to CD8 T lymphocytes. Class II MHC, or MHC-II, function mainly in antigen presentation to CD4 T lymphocytes. The term “HLA” as used herein will be understood to refer to Human Leukocyte Antigens, which is defined as the histocompatibility antigens found in humans. As used herein, “HLA” is the human form of “MHC”. MHC class I molecules are heterodimers that consist of two polypeptide chains, α and β2-microglobulin. Class II molecules are also heterodimers, but in this case consist of two homogenous peptides, α and β chain, both of which are encoded in the MHC and does not comprise of β2-microglobulin.

Definitions of common terms in cell biology and molecular biology can be found in “The Merck Manual of Diagnosis and Therapy”, 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other than in the operating examples, or where otherwise indicated, all numbers expressing quantities of ingredients or reaction conditions used herein should be understood as modified in all instances by the term “about.” The term “about” when used in connection with percentages means ±1% of the value being referred to. For example, about 100 means from 99 to 101.

Although methods and materials similar or equivalent to those described herein can be used in the practice or testing of this disclosure, suitable methods and materials are described below. The abbreviation, “e.g.,” is derived from the Latin exempli gratia, and is used herein to indicate a non-limiting example. Thus, the abbreviation “e.g.,” is synonymous with the term “for example.”

As used in this specification and appended claims, the singular forms “a,” “an”, and “the” include plural references unless the context clearly dictates otherwise. Thus for example, reference to “the method” included one or more methods, and/or steps of the type described herein and/or which will become apparent to those persons skilled in the art upon reading this disclosure and so forth.

In this application and the claims, the use of the singular includes the plural unless specifically stated otherwise. In addition, use of “or” means “and/or” unless stated otherwise. Moreover, the use of the term “including”, as well as other forms, such as “includes” and “included”, is not limiting. Also, terms such as “element” or “component” encompass both elements and components comprising one unit and elements and components that comprise more than one unit unless specifically stated otherwise.

BRIEF DESCRIPTION OF THE DRAWINGS

FIG. 5 shows an exemplary sequence for an MLL oncoprotein fused with TAT at the N-terminus, provided herein as SEQ ID NO: 1. TAT sequence is represented in bold underlined text, the linker amino acid sequence is represented in italics, MLL and AF9 amino acid sequences are represented in normal and underlined text respectively.

FIG. 6 shows an exemplary sequence for a HoxB8 protein fused with TAT at the N-terminus, provided herein as SEQ ID NO: 2. TAT sequence is represented in bold underlined text, the linker amino acid sequence is represented in italics and a HoxB8 amino acid sequence represented in normal text.

FIG. 7 depicts sgRNA constructs for elimination of beta-2 microglobulin (gene ID:567) using CRISPR/Cas9. The column labeled “Target Seq” presents SEQ ID NOs: 37-42, respectively.

FIG. 8 depicts sgRNA constructs for elimination of Invariant chain (gene ID:972) using CRISPR/Cas9. The column labeled “Target Seq” presents SEQ ID NOs: 43-45, respectively.

DETAILED DESCRIPTION

Figure 1:
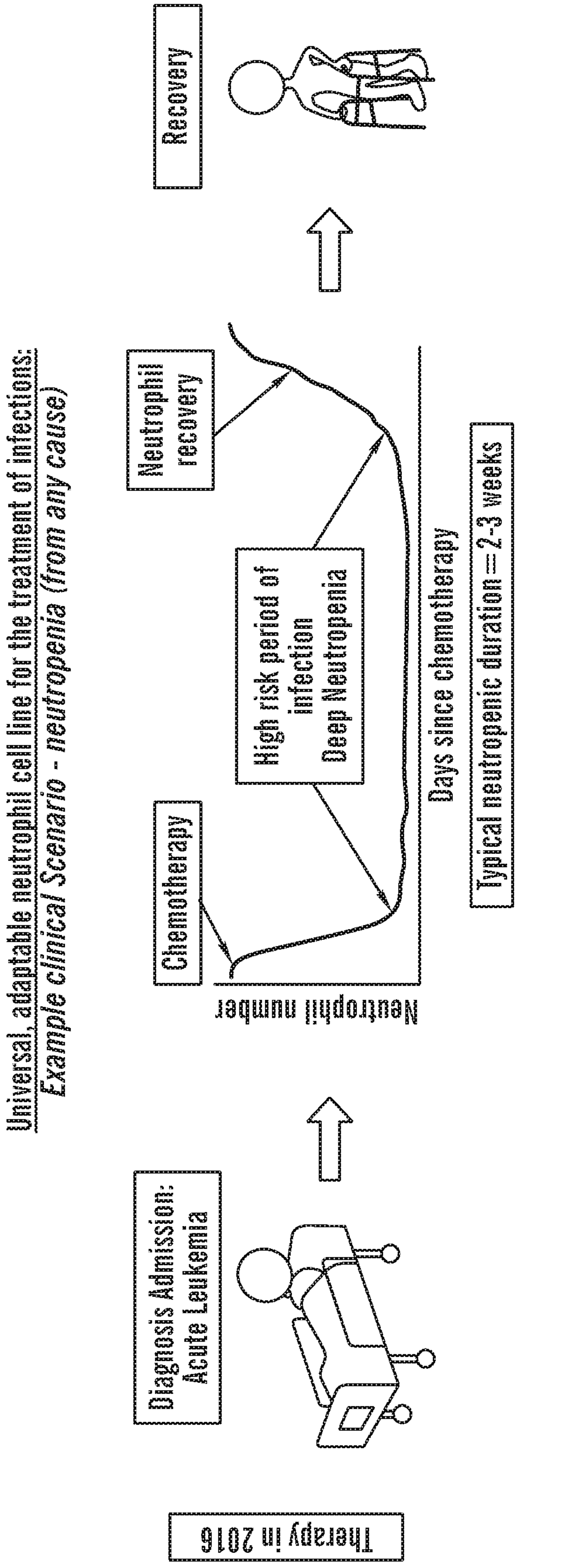
FIG. 1 shows an example clinical scenario wherein a patient suffers from deep neutropenia for example due to chemotherapeutic treatment. During the time period required for recovery of the hematopoietic system following neutropenia, the patient has low levels of circulating neutrophils and is susceptible to infections.
Figure 2:
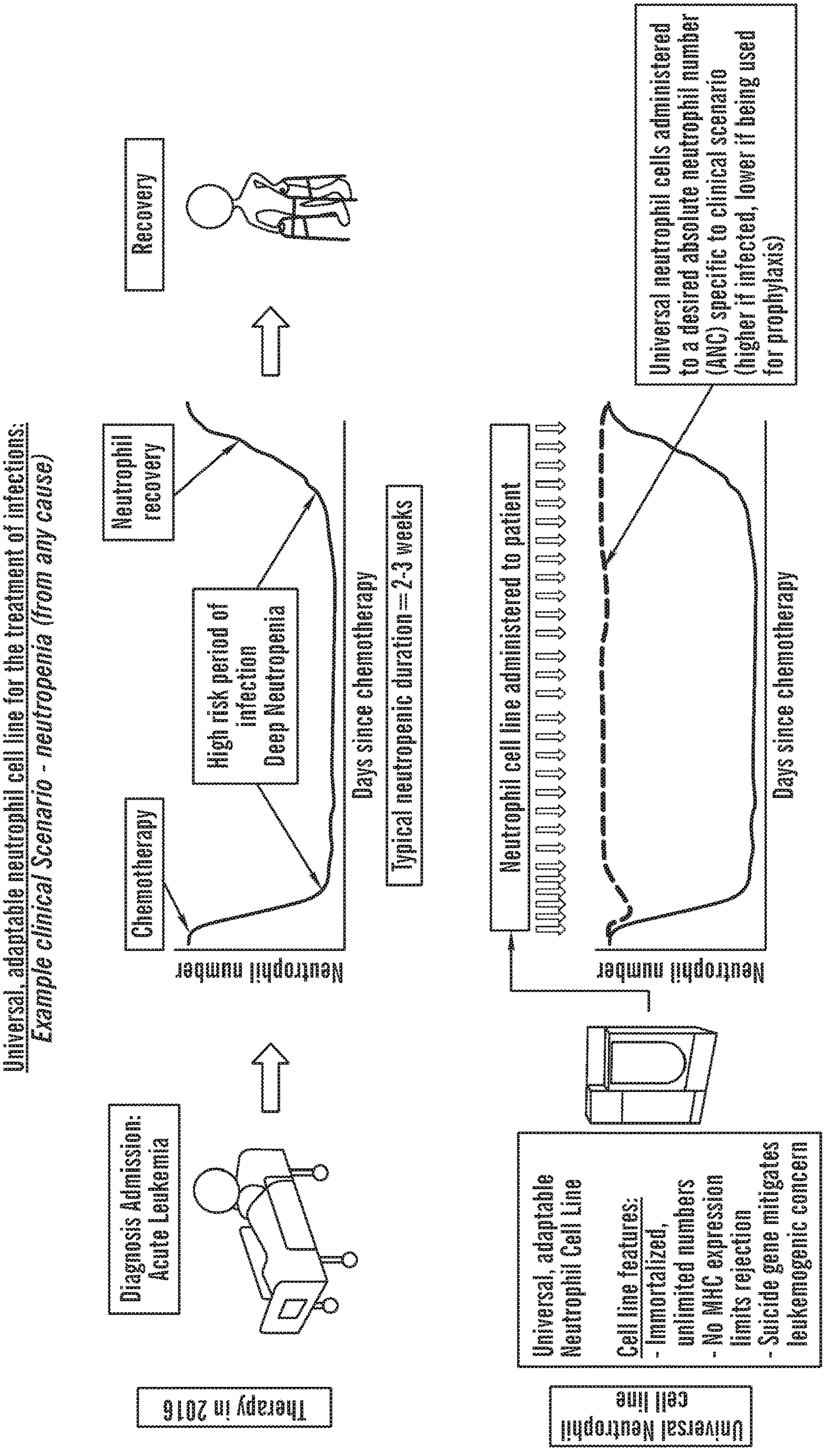
FIG. 2 shows an exemplary outline of the generation and expansion of Universal MHC/HLA compatible neutrophil cell line and treatment therewith. The Universal MHC/HLA compatible neutrophil cell line comprises features such as immortalized, unlimited numbers, no MHC expression to limit rejection and expression of a suicide gene to mitigate leukemogenic concern. The Universal MHC/HLA compatible neutrophil cell line can be administered to the patient with deep neutropenia to a desired absolute neutrophil number (ANC) specific to clinical scenario (high if infected, lower if being used for prophylaxis. Administration of the Universal MHC/HLA compatible neutrophil cell line can augment the immune response while the patient’s hematopoietic cells repopulate and recover, a period which can take more than 2-3 weeks. The details of generation and expansion of the Universal, adaptable neutrophil cell line are described in the working Examples and detailed description herein.
Figure 3:
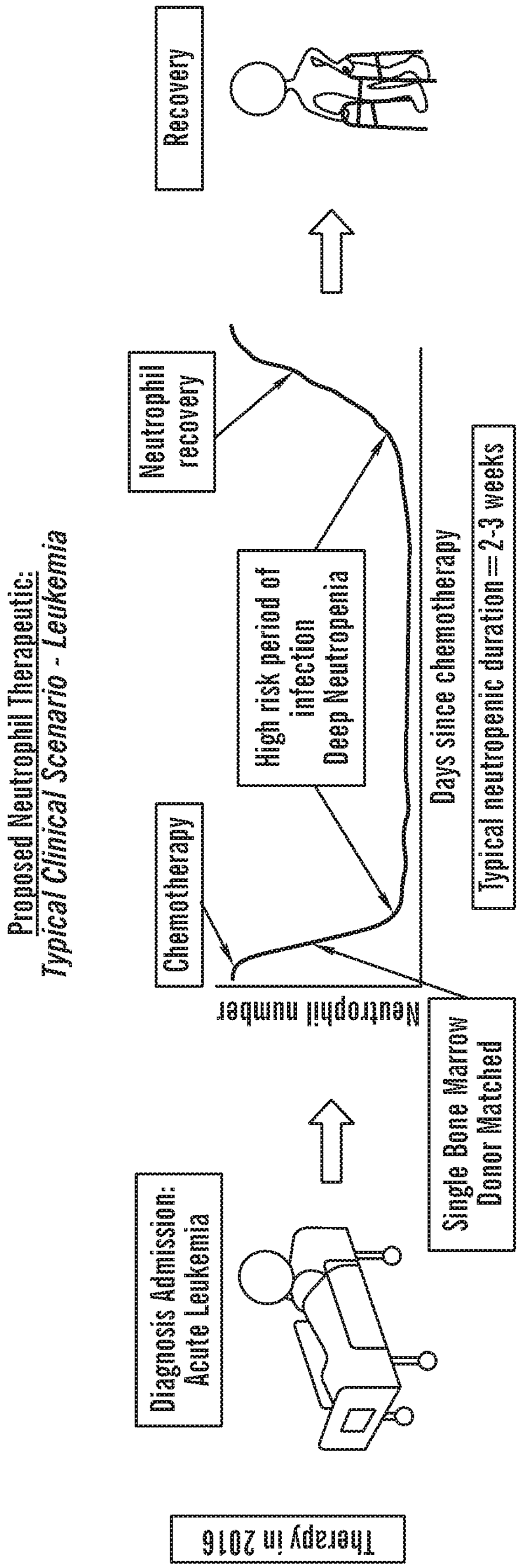
FIG. 3 shows an example clinical scenario wherein a patient suffers from deficiency of neutrophils (neutropenia), for example, due to chemotherapeutic treatment. In a typical clinical scenario hematopoietic stem cells obtained from a single bone marrow donor match for the patient are then transplanted in the patient for repopulation of the hematopoietic cells. During the time period required for recovery of the hematopoietic system following transplant, the transplant recipient has low levels of circulating neutrophils and is susceptible to infections. Prolonged neutropenia, particularly those resulting from delayed engraftment of donor HSCs, increases the probability of infection.
Figure 4:
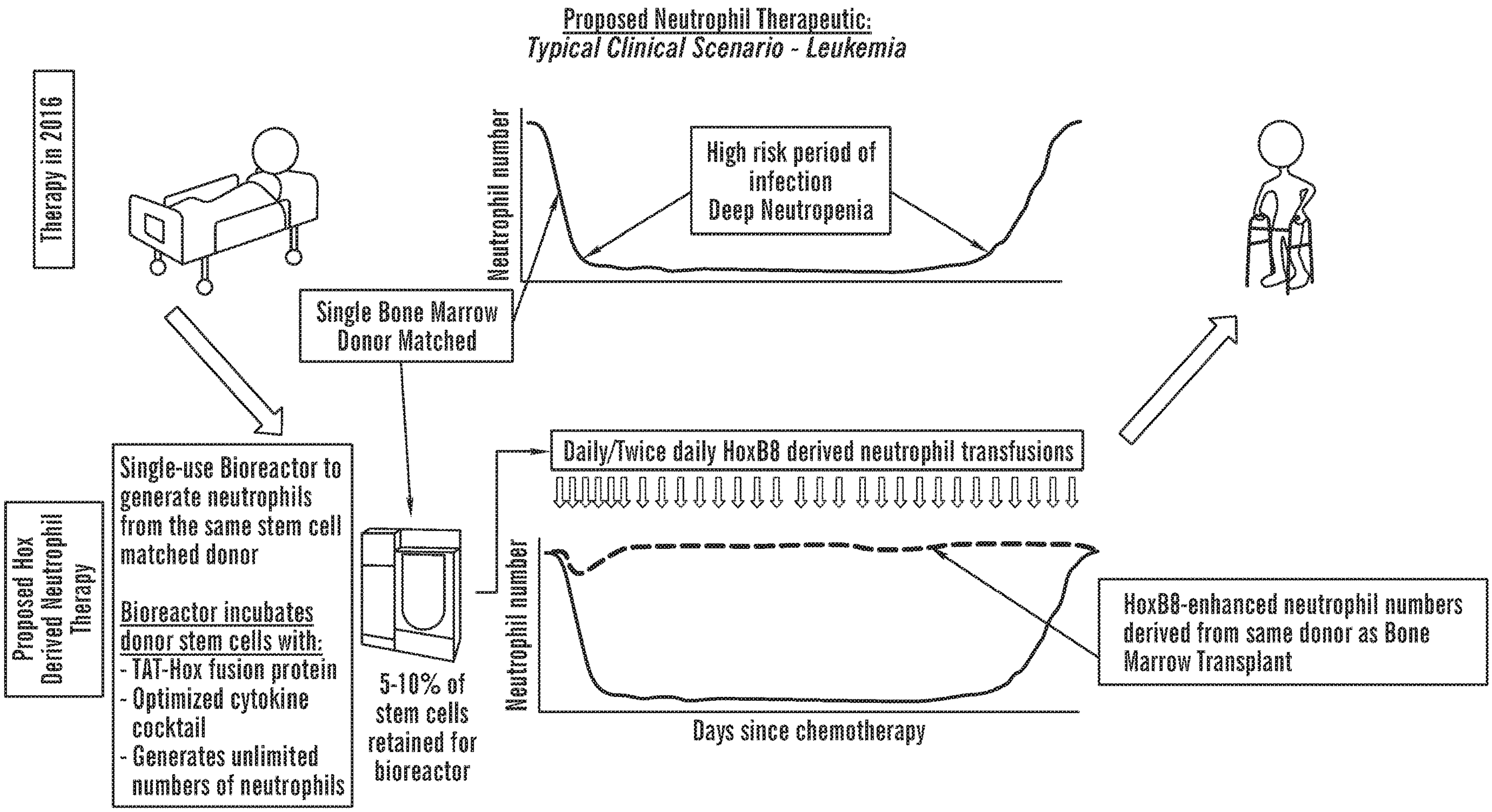
FIG. 4 shows exemplary outline of the generation and expansion of custom patient specific neutrophil progenitor cells and treatment therewith. About 5-10% of the stem cells from the same donor identified for the patient for hematopoietic stem cell transplantation are incubated in a bioreactor with TAT-Hox fusion protein and optimized cytokine cocktail to generate unlimited numbers of neutrophil progenitors. The cells can be administered, for example, daily or twice daily to the patient at an early stage after induction of neutropenia.

Provided herein are methods to generate universal MHC/HLA-compatible hematopoietic progenitors and methods to generate custom patient-specific MHC/HLA-compatible hematopoietic progenitors from isolated progenitor cells. Compositions comprising the universal or patient specific hematopoietic progenitors are also disclosed. The methods and compositions described herein relate to methods for generation and expansion, ex vivo, of universal and custom patient-specific hematopoietic progenitors, for example, neutrophilic progenitors for transfusion in patients who are deficient in these cells and/or require augmented immune response. Aspects of the technology disclosed herein relate to the ability to (1) generate and expand, ex vivo, universal and custom patient specific hematopoietic progenitors such that the cells can be administered in a clinically relevant manner and (2) to transfuse these cells as progenitors, rather than mature cells, into patients. The transfusion at the progenitor stage is a critical improvement upon previous technologies, as it provides a source of cells that are safer to transfuse, that undergo their final development in vivo, and that undergo exponential expansion in vivo, providing even greater number of terminal effector cells for example neutrophils.

Aspects of the invention relate to using the ability of HOX oncoprotein or MLL/AF9 or MLL fusion protein to block differentiation in order to control cell differentiation and immortalize specific types of progenitor cells, for example, myeloid progenitor cells. In some embodiments, a recombinant or conditional form of HOX or MLL oncoproteins is used as a means for generating unlimited numbers of multi-lineage committed progenitors (e.g., myeloid progeny that can differentiate into neutrophil, macrophage and/or dendritic cells upon in vivo administration into a subject).

Hox proteins are transcription factors that are normally required during hematopoiesis for the control of marrow development. The presence of high-levels of HoxB8, one of the 39 members, halts development of stem cells at the granulocyte-macrophage progenitor stage (GMP). Within the body, one GMP will generally give rise to 16-32 functional and mature neutrophils. MLL/AF9 or MLL is an oncogene upstream of Hox resulting in controlled growth of the isolated progenitor until the multi-lineage committed progenitor stage.

The methods disclosed herein comprise a step of contacting isolated progenitor cells, for example, embryonic stem (ES) cells, induced pluripotent stem cell (iPSC), myeloid progenitor cells, GMP, CMP; with a fusion protein comprising a HOX oncoprotein and/or a fusion protein comprising MLL oncoprotein. When matched with appropriate cytokine and growth factor culture conditions, the contacting results in growth and expansion of the isolated hematopoietic cells to hematopoietic progenitor cells which exhibit commitment to neutrophil, macrophage, and/or dendritic lineage or exhibit multi-lineage blood cell differentiation potential. The generated hematopoietic progenitor cells do not undergo further differentiation until the expression and/or activity of the HOX and/or MLL oncoproteins is inactivated due to their ability to block differentiation at the committed stage, thereby resulting in immortalization of the hematopoietic progenitor cells. Subsequent to contacting of the isolated progenitor cells with fusion HOX or MLL oncoprotein and culturing them in a growth permissive environment comprising cytokines and growth factors, populations of immortalized hematopoietic progenitors emerge. These progenitors proliferate indefinitely.

In some embodiments, the fusion protein comprises HOX oncoprotein and/or MLL oncoprotein and a cell penetrating peptide, for example, TAT domain. In related embodiments, the isolated progenitor cells can be contacted by co-culturing the cells with a recombinant form of fusion HOX oncoprotein and TAT domain or a MLL oncoprotein and TAT domain. In related embodiments, the isolated progenitor cells can be contacted by co-culturing the cells with a recombinant fusion protein comprising 1) HOX oncoprotein and TAT domain and/or 2) MLL oncoprotein and TAT domain. In such embodiments, for example, the absence of the TAT-fusion protein upon administration of cells in a subject, will trigger maturation of the administered immortalized hematopoietic progenitors into differentiated cell type, for example, neutrophil, macrophage and/or dendritic cell type. In some embodiments, the cell penetrating peptide (e.g., TAT domain) is fused to the N-terminus of the HOX oncoprotein and/or MLL oncoprotein. The polypeptide and coding nucleic acid sequences of HOX, MLL/AF9 and TAT of human origin and those of a number of animals are known in the art and are publically available, for example, from GenBank. An exemplary sequence for an MLL oncoprotein fused with TAT at the N-terminus can be as provided in SEQ ID NO: 1 below.

In some embodiments, a HOX oncoprotein is a full-length HOX oncoprotein, e.g., the HOX oncoprotein comprises the sequence of SEQ ID NO: 4 or a sequence corresponding to the sequence of SEQ ID NO: 4 (e.g., a sequence including one or more alleles or variants of SEQ ID NO: 4). In some embodiments, a HOX oncoprotein is a full-length HOX oncoprotein, e.g., HOXB4 (e.g., NCBI Gene ID: 3214) or HOXB8 (NCBI Gene ID: 3218), or a sequence corresponding thereto (e.g. an allele or variant thereof). In some embodiments, a MLL oncoprotein is a full-length MLL oncoprotein, e.g., the MLL oncoprotein comprises the sequence of SEQ ID NO: 5 or a sequence corresponding to the sequence of SEQ ID NO: 5 (e.g., a sequence including one or more alleles or variants of SEQ ID NO: 5).

MLL sequence=see NCBI Reference Sequence: NG_027813.1 (SEQ ID NO: 46), which is incorporated herein by reference in its entirety. AF9 sequence=see NCBI Reference Sequence: NP_004520.2 (SEQ ID NO: 47), which is incorporated herein by reference in its entirety.

```
TAT-MLLAF9 sequence
                                                   SEQ ID NO: 1
YGRKERRQRRRGGGGSMAHSCRWRFPARPGTTGGGGGGGRRGLGGAPRQRVPALLLPPGP

PVGGGGPGAPPSPPAVAAAAAAAGSSGAGVPGGAAAASTASSSSASSSSSSSSSASSG

PALLRVGPGFDAALQVSAAIGTNLRRFRAVFGESGGGGGSGEDEQFLGEGSDEEVRVR

SPTRSPSVKTSPRKPRGRPRSGSDRNSAILSDPSVESPLNKSETKSGDKIKKKDSKSI

EKKRGRPPTFPGVKIKITHGKDISELPKGNKEDSLKKIKRTPSATFQQATKIKKLRAG

KLSPLKSKFKTGKLQIGRKGVQIVRRRGRPPSTERIKTPSGLLINSELEKPQKVRKDK

EGTPPLTKEDKTVVRQSPRRIKPVRIIPSSKRTDATIAKQLLQRAKKGAQKKIEKEAA

QLQGRKVKTQVKNIRQFIMPVVSAISSRIIKTPRRFIEDEDYDPPIKIARLESTPNSR

FSAPSCGSSEKSSAASQHSSQMSSDSSRSSSPSVDTSTDSQASEEIQVLPEERSDTPE

VHPPLPISQSPENESNDRRSRRYSVSERSFGSRTTKKLSTLQSAPQQQTSSSPPPPLL

TPPPPLQPASSISDHTPWLMPPTIPLASPFLPASTAPMQGKRKSILREPTFRWTSLKH

SRSEPQYFSSAKYAKEGLIRKPIFDNFRPPPLTPEDVGFASGFSASGTAASARLFSPL

HSGTRFDMHKRSPLLRAPRFTPSEAHSRIFESVTLPSNRTSAGTSSSGVSNRKRKRKV

FSPIRSEPRSPSHSMRTRSGRLSSSELSPLTPPSSVSSSLSISVSPLATSALNPTFTF

PSHSLTQSGESAEKNQRPRKQTSAPAEPFSSSSPTPLFPWFTPGSQTERGRNKDKAPE

ELSKDRDADKSVEKDKSRERDREREKENKRESRKEKRKKGSEIQSSSALYPVGRVSKE

KVVGEDVATSSSAKKATGRKKSSSHDSGTDITSVTLGDTTAVKTKILIKKGRGNLEKT

NLDLGPTAPSLEKEKTLCLSTPSSSTVKHSTSSIGSMLAQADKLPMTDKRVASLLKKA

KAQLCKIEKSKSLKQTDQPKAQGQESDSSETSVRGPRIKHVCRRAAVALGRKRAVFPD

DMPTLSALPWEEREKILSSMGNDDKSSIAGSEDAEPLAPPIKPIKPVTRNKAPQEPPV

KKGRRSRRCGQCPGCQVPEDCGVCTNCLDKPKFGGRNIKKQCCKMRKCQNLQWMPSKA

YLQKQAKAVKKKEKKSKTSEKKDSKESSVVKNVVDSSQKPTPSAREDPAPKKSSSEPP

PRKPVEEKSEEGNVSAPGPESKQATTPASRKSSKQVSQPALVIPPQPPTTGPPRKEVP

KTTPSEPKKKQPPPPESGPEQSKQKKVAPRPSIPVKQKPKEKEKPPPVNKQENAGTLN

ILSTLSNGNSSKQKIPADGVHRIRVDFKEDCEAENVWEMGGLGILTSVPITPRVVCFL

CASSGHVEFVYCQVCCEPFHKFCLEENERPLEDQLENWCCRRCKFCHVCGRQHQATKQ

LLECNKCRNSYHPECLGPNYPTKPTKKKKVWICTKCVRCKSCGSTTPGKGWDAQWSHD

FSLCHDCAKLFAKGNFCPLCDKCYDDDDYESKMMQCGKCDRWVHSKCENLSGTEDEMY

EILSNLPESVAYTCVNCTERHPAEWRLALEKELQISLKQVLTALLNSRTTSHLLRYRQ

AAKPPDLNPETEESIPSRSSPEGPDPPVLTEVSKQDDQQPLDLEGVKRKMDQGNYTSV

LEFSDDIVKIIQAAINSDGGQPEIKKANSMVKSFFIRQMERVFPWFSVKKSRFWEPNK

VSSNSGMLPNAVLPPSLDHNYAQWQEREENSHTEQPPLMKKIIPAPKPKGPGEPDSPT

PLHPPTPPILSTDRSREDSPELNPPPGIEDNRQCALCLTYGDDSANDAGRLLYIGQNE

WTHVNCALWSAEVFEDDDGSLKNVHMAVIRGKQLRCEFCQKPGATVGCCLTSCTSNYH
```

-continued

FMCSRAKNCVFLDDKKVYCQRHRDLIKGEVVPENGFEVFRRVFVDFEGISLRRKFLNG

LEPENIHMMIGSMTIDCLGILNDLSDCEDKLFPIGYQCSRVYWSTTDARKRCVYTCKI

VECRPPVVEPDINSTVEHDENRTIAHSPTSFTESSSKESQNTAEIISPPSPDRPPHSQ

TSGSCYYHVISKVPRIRTPSYSPTQRSPGCRPLPSAGSPTPTTHEIVTVGDPLLSSGL

RSIGSRRHSTSSLSPQRSKLRIMSPMRTGNTYSRNNVSSVSTTGTATDLESSAKVVDH

VLGPLNSSTSLGQNTSTSSNLQRTVVTVGNKNSHLDGSSSSEMKQSSASDLVSKSSSL

KGEKTKVLSSKSSEGSAHNVAYPGIPKLAPQVHNTTSRELNVSKIGSFAEPSSVSFSS

KEALSFPHLHLRGQRNDRDQHTDSTQSANSSPDEDTEVKTLKLSGMSNRSSIINEHMG

SSSRDRRQKGKKSCKETFKEKHSSKSFLEPGQVTTGEEGNLKPEFMDEVLTPEYMGQR

PCNNVSSDKIGDKGLSMPGVPKAPPMQVEGSAKELQAPRKRTVKVTLTPLKMENESQS

KNALKESSPASPLQIESTSPTEPISASENPGDGPVAQPSPNNTSCQDSQSNNYQNLPV

QDRNLMLPDGPKPQEDGSFKRRYPRRSARARSNMFFGLTPLYGVRSYGEEDIPFYSSS

TGKKRGKRSAEGQVDGADDLSTSDEDDLYYYNFTRTVISSGGEERLASHNLFREEEQC

DLPKISQLDGVDDGTESDTSVTATTRKSSQIPKRNGKENGTENLKIDEPEDAGEKEFV

TKSSVGHKNEPKMDNCHSVSRVKTQGQDSLEAQLSSLESSRRVHTSTPSDKNLLDTYN

TELLKSDSDNNNSDDCGNILPSDIMDFVLKNTPSMQALGESPESSSSELLNLGEGLGL

DSNREKDMGLFEVFSQQLPTTEPVDSSVSSSISAEEQFELPLELPSDLSVLTTRSPTV

PSQNPSRLAVISDSGEKRVTITEKSVASSESDPALLSPGVDPTPEGHMTPDHFIQGHM

DADHISSPPCGSVEQGHGNNQDLTRNSSTPGLQVPVSPTVPIQNQKYVPNSTDSPGPS

QISNAAVQTTPPHLKPATEKLIVVNQNMQPLYVLQTLPNGVTQKIQLTSSVSSTPSVM

ETNTSVLGPMGGGLTLTTGLNPSLPTSQSLFPSASKGLLPMSHHQHLHSFPAATQSSF

PPNISNPPSGLLIGVQPPPDPQLLVSESSQRTDLSTTVATPSSGLKKRPISRLQTRKN

KKLAPSSTPSNIAPSDVVSNMTLINFTPSQLPNHPSLLDLGSLNTSSHRTVPNIIKRS

KSSIMYFEPAPLLPQSVGGTAATAAGTSTISQDTSHLTSGSVSGLASSSSVLNVVSMQ

TTTTPTSSASVPGHVTLTNPRLLGTPDIGSISNLLIKASQQSLGIQDQPVALPPSSGM

FPQLGTSQTPSTAAITAASSICVLPSTQTTGITAASPSGEADEHYQLQHVNQLLASKT

GIHSSQRDLDSASGPQVSNFTQTVDAPNSMGLEQNKALSSAVQASPTSPGGSPSSPSS

GQRSASPSVPGPTKPKPKTKRFQLPLDKGNGKKHKVSHLRTSSSEAHIPDQETTSLTS

GTGTPGAEAEQQDTASVEQSSQKECGQPAGQVAVLPEVQVTQNPANEQESAEPKTVEF

EESNFSSPLMLWLQQEQKRKESITEKKPKKGLVFEISSDDGFQICAESIEDAWKSLTD

KVQEARSNARLKQLSFAGVNGLRMLGILHDAVVFLIEQLSGAKHCRNYKFRFHKPEEA

NEPPLNPHGSARAEVHLRKSAFDMFNFLASKHRQPPEYNPNDEEEEEVQLKSARRATS

MDLPMPMRFRHLKKTSKEAVGVYRSPIHGRGLFCKRNIDAGEMVIEYAGNVIRSIQTD

KREKYYDSKGIGCYMFRIDDSEVVDATMHGNAARFINHSCEPNCYSRVINIDGQKHIV

IFAMRKIYRGEELTYDYKFPIEDASNKLPCNCGAKKCRKFLN MASSCAVQVK LELGHRAQVR

KKPTVEGFTH DWMVFVRGPE HSNIQHFVEK VVFHLHESFP RPKRVCKDPP YKVEESGYAG

FILPIEVYFK NKEEPRKVRF DYDLFLHLEG HPPVNHLRCE KLTFNNPTED FRRKLLKAGG

DPNRSIHTSS SSSSSSSSSS SSSSSSSSSS SSSSSSSSSS SSSSSSSSSS TSFSKPHKLM

KEHKEKPSKD SREHKSAFKE PSRDHNKSSK ESSKKPKENK

PLKEEKIVPK MAFKEPKPMS KEPKPDSNLL TITSGQDKKA PSKRPPISDS EELSAKKRKK

```
SSSEALFKSF SSAPPLILTC SADKKQIKDK SHVKMGKVKI ESETSEKKKS TLPPFDDIVD

PNDSDVEENI SSKSDSEQPS PASSSSSSSS SFTPSQTRQQ GPLRSIMKDL HSDDNEEESD

EVEDNDNDSE MERPVNRGGS RSRRVSLSDG SDSESSSASS PLHHEPPPPL LKTNNNQILE

VKSPIKQSKS DKQIKNGECD KAYLDELVEL HRRLMTLRER HILQQIVNLI EETGEFHITN

TTFDFDLCSL DKTTVRKLQS YLETSGTS
```

The TAT sequence is amino acids 1-11 of SEQ ID NO: 1. The linker is amino acids 12-16 of SEQ ID NO: 1. The MLL portion of SEQ ID NO: 1 is amino acids 17-3946 and the AF9 portion of SEQ ID NO: 1 is amino acids 3950-4556.

An exemplary sequence for a HoxB8 fused with TAT at the N-terminus can be as provided in SEQ ID NO: 2 below.

HOXB8 nucleotide sequence=see NCBI Reference Sequence: AH010084.2 (SEQ ID NO 48), which is incorporated herein by reference in its entirety. HoxB8 polypeptide sequence=see NCBI Reference Sequence: AAG42143.1 (SEQ ID NO 4), which is incorporated herein by reference in its entirety.

```
TAT-HoxB8 sequence
                                          SEQ ID NO: 2
YGRKKRRQRRRGGGGSMSSYFVNSLF SKYKTGESLR PNYYDCGFAQ

DLGGRPTVVY GPSSGGSFQH PSQIQEFYHG PSSLSTAPYQ

QNPCAVACHG DPGNFYGYDP LQRQSLFGAQ DPDLVQYADC

KLAAASGLGE EAEGSEQSPS PTQLFPWMRP QAAAGRRRGR

QTYSRYQTLE LEKEFLFNPY LTRKRRIEVS HALGLTERQV

KIWFQNRRMK WKKENNKDKF PSSKCEQEEL EKQKLERAPE

AADEGDAQKG DKK
```

The TAT sequence is amino acids 1-11 of SEQ ID NO: 2. The linker is amino acids 12-16 of SEQ ID NO: 2. The HOXB8 portion of SEQ ID NO: 12 is amino acids 17-259.

In some embodiments, the isolated progenitor cells can be contacted with a conditional form of HOX oncoprotein or MLL oncoprotein as a means of generating unlimited numbers of immortalized progenitor cells, for example, myeloid progenitors. The expression and/or activity of HOX oncoprotein or MLL oncoprotein can be made conditional on the presence of a ligand when fused with a ligand binding receptor (e.g., the estrogen receptor binding domain where biological activity of HOX or MLL oncoprotein requires the presence of, e.g., supratherapeutic estradiol) or ligand binding promoter sequence (e.g. tetracycline-dependent promoter, where all biological activity including expression of oncoproteins occurs only in the presence of tetracycline). Accordingly, in some embodiments, progenitor cells can be contacted with the HOX oncoprotein or the MLL oncoprotein fused with an estrogen receptor binding domain (ERBD) or fused with a tetracycline dependent promoter. In some embodiments, the fusion protein, for example, ERBD can be fused to the N-terminus of the HOX oncoprotein or the MLL oncoprotein. In some embodiments, the cells can be in contact with the recombinant form of fusion HOX oncoprotein or MLL oncoprotein. In a related aspect the isolated progenitor cells to be immortalized can be infected with a vector comprising a nucleic acid sequence, which encodes the fusion protein comprising a HOX oncoprotein and an ERBD. In some embodiments, the progenitor cells to be immortalized can be infected with a vector comprising a nucleic acid sequence, which encodes the fusion protein comprising a MLL oncoprotein and an ERBD. In some embodiments, the ERBD is fused to the N-terminus of a HOX oncoprotein. In some embodiments, the ERBD is fused to the N-terminus of a MLL oncoprotein.

In some embodiments, the progenitor cells can be contacted with a nucleic acid encoding the fusion protein, wherein the nucleic acid is translated and/or transcribed in the progenitor cell to provide the fusion protein. In some embodiments, the nucleic acid can be a modified RNA molecule. In some embodiments, the progenitor cell can be contacted with a modified RNA comprising a nucleic acid sequence which encodes the fusion protein comprising a HOX oncoprotein and an estrogen receptor binding domain (ERBD), wherein the ERBD is fused to the N-terminus of the HOX oncoprotein. In some embodiments, the progenitor cell can be contacted with a modified RNA comprising a nucleic acid sequence which encodes the fusion protein comprising a MLL oncoprotein and an estrogen receptor binding domain (ERBD), wherein the ERBD is fused to the N-terminus of the MLL oncoprotein.

As used herein, "estrogen receptor binding domain" or "ERBD" refers to a polypeptide that can bind to estrogen (and/or related compounds, e.g, estrogen agonists) and subsequent to the binding, undergoes a conformational change. In native polypeptides, this conformational change permits the rest of the native polypeptide to bind to target DNA sequences and regulate gene expression. When used in fusion proteins as described herein, the binding of an ERBD to an estrogen agonist permits the remainder of the fusion protein to carry out its activity. Accordingly, an ERBD can be included in a fusion protein in order to provide conditional control of the fusion protein, e.g, the fusion protein's activity can be limited to when an estrogen agonist is provided. The polypeptide and coding nucleic acid sequences of ERBD of human origin and those of a number of animals are publically available, e.g., from the NCBI website and are described in the art, e.g., Mueller-Farhnow et al. 1999 Current Opinion in Biotechnology 10:550-556 and Klinge 2001 Nucleic Acids Research 29:2905-2919; which are incorporated by reference herein in their entireties. Further discussion of ERBD fusion proteins is also discussed at U.S. Pat. No. 8,795,650; which is incorporated by reference herein in its entirety.

An exemplary sequence for an ERBD polypeptide can be as provided in SEQ ID NO: 3 below;

```
TADQMVSALLDAEPPILYSEYDPTRPFSEASMMGLLTNLADRELVHMINW

AKRVPGFVDLTLHDQVHLLECAWLEILMIGLVWRSMEHPGKLLFAPNLLL

DRNQGKCVEGMVEIFDMLLATSSRFRMMNLQGEEFVCLKSIILLNSGVYT

FLSSTLKSLEEKDHIHRVLDKITDTLIHLMAKAGLTLQQQHQRLAQLLLI

LSHIRHMSNKGMEHLYSMKCKNVVPLYDLLLEMLDAHRLHAPTSRGGASV

EETDQSHLATAGSTSSHSLQKYYITGEAEGFPATV
```

Additional ERBD sequences are known in the art and can be readily identified by one of skill in the art, e.g. by searching sequence databases for sequences homologous to SEQ ID NO: 3. In some embodiments, the ERBD polypeptide can be at least 90% identical to, e.g., at least 95% identical to, or at least 98% identical to, SEQ ID NO: 3. In some embodiments, the ERBD polypeptide can have a sequence with no more than 20 substitutions relative to SEQ ID NO: 3, e.g., no more than 20, no more than 15, no more than 10, no more than 5, or fewer substitutions.

As used herein "estrogen agonist" refers to an agent that can bind to ERBD and cause a conformational change. Estrogen agonists are known in the art and can include, by way of non-limiting example, estrogen, 17β-estradiol, estrone, raloxifene, estriol, and genistein.

In some embodiments, the HOX oncoprotein can be HoxB4 or HoxB8. In a further aspect, the fusion HOX oncoprotein is a recombinant TAT-HoxB8, a recombinant TAT-HoxB4, recombinant ERBD-HoxB8, or a recombinant ERBD-HoxB4.

An exemplary sequence of HoxB8 polypeptide can be as provided in SEQ ID NO: 4 below. HOXB8=see NCBI nucleic acid Reference Sequence: AH010084.2 (SEQ ID NO 48), which is incorporated herein by reference in its entirety. HoxB8=NCBI polypeptide reference number: AAG42143.1 (SEQ ID NO 4), which is incorporated herein by reference in its entirety.

permits the activity of the oncoprotein to be regulated by controlling the level and/or presence of an exogenous factor, e.g, an estrogen agonist. In some embodiments, the conditional control domain can be a ERBD domain.

In some embodiments, a linker sequence can be provided between the N-terminal domain and the oncoprotein. As used herein, "linker" refers to refers to an amino acid sequence that serves the structural purpose of separating two other sequences in the same peptide chain. Linker design, selection, and exemplary linkers are well-known in the art and described, e.g., in Chen, X., et al, "Fusion protein linkers: proterty, design and functionality" Adv. Drug Deliv. Rev. (2013); which is incorporated by reference herein in its entirety.

In some embodiments of any of the aspects described herein, the linker sequence can be a flexible peptide sequence. In some embodiments of any of the aspects described herein, a linker can comprise glycine and serine residues. In some embodiments of any of the aspects described herein, a linker can consist essentially of glycine and serine residues. In some embodiments of any of the aspects described herein, a linker can consist of glycine and serine residues.

```
HoxB8 protein
                                                        SEQ ID NO: 4
  1 mssyfvnslf skykVtgeslr pnyydcgfaq dlggrptvvy gpssggsfqh psqiqefyhg

 61 psslstapyq qnpcavachg dpgnfygydp lqrqslfgaq dpdlvqyadc klaaasglge

121 eaegseqsps ptqlfpwmrp qaaagrrrgr qtysryqtle lekeflfnpy ltrkrrievs

181 halglterqv kiwfqnrrmk wkkennkdkf psskceqeel ekqklerape aadegdaqkg

241 dkk
```

An exemplary sequence of MLL polypeptide can be as provided in SEQ ID NO: 5 below. MLL=NCBI nucleic acid Reference Sequence: AF036405.1 (SEQ ID NO 49), which is incorporated herein by reference in its entirety. NCBI polypeptide reference number: AAC95283.1 (SEQ ID NO 5), which is incorporated herein by reference in its entirety In some embodiments of any of the aspects described herein, the linker sequence can comprise the sequence GGGGS (SEQ ID NO: 35). In some embodiments of any of the aspects described herein, the linker sequence can consist of the sequence GGGGS (SEQ ID NO: 35). In some embodiments of any of the aspects described herein, the linker sequence can consist essentially of the sequence GGGGS (SEQ ID NO: 35).

```
MLL protein
                                                        SEQ ID NO: 5
  1 mahscrwrfp arpgttgggg gggrrglgga prqrvpalll ppgppvgggg pgappsppav

 61 aaaaaaagss gagvpggaaa asaassssas sssssssas sgpallrvgp gfdaalqvsa

121 aigtnlrrfr avfgesgggg gsgedeqflg fgsdeevrvr sptrspsvkt sprkprgrpr

181 sgsdrnsail sdpsvfspln ksetksadki kkkdsksiek krgrpptfpg vkikithgkd

241 iselpkgnke dslkkikrtp satfqqatki kklragklsp lkskfktgkl qigrkgvqiv

301 rrrgrppste riktpsglii nselekpqkv rkdkegtppl tkedktvvrq sprrikpvri

361 ipsskrtdat iakqllqrak kgaqkkieke aaqlqgrkvk tqvknirqfi mpvvsaissr

421 iiktprrfie dedydppiki arlestpnsr fsapscgsse kssaasqhss qmssdssrs
```

In some embodiments, the fusion protein can comprise an N-terminal cell-penetrating peptide and either a C-terminal MLL oncoprotein and/or a C-terminal HOX oncoprotein. In some embodiments, the cell-penetrating peptide can be a TAT domain.

In some embodiments, the fusion protein can comprise an N-terminal conditional control domain and either a C-terminal MLL oncoprotein and/or a C-terminal HOX oncoprotein. The conditional control domain can be a domain that In some embodiments, the contacting step can comprise contacting a cell with any embodiment of the fusion protein as described herein, e.g., expressing the fusion protein in a recombinant cell or ex vivo, or synthesizing the fusion protein, and then providing the fusion protein to the cell as a polypeptide molecule. In some embodiments, the contacting step can comprise contacting a cell with a vector comprising a nucleic acid sequence encoding any embodiment of the fusion protein as described herein, e.g., providing a vector which will express the fusion protein in the contacted cell.

Those of skill in the art can generate an expression construct encoding for the fusion proteins described herein (e.g., ERBD-MLL, ERBD-HoxB8) by using conventional DNA cloning or subcloning methods. Standard procedures for molecular DNA cloning is described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons. Inc). DNA cloning refers to a process whereby an origin of replication is operably linked to a double-stranded DNA fragment, and propagated in *E. coli*, or other suitable host. DNA subcloning refers to the process whereby a double-stranded DNA fragment (e.g., cDNA) is taken from a DNA molecule that has already been amplified, either in vitro, for example by PCR, or in vivo by propagation in *E. coli* or other suitable host, and is then linked to an operable origin of replication. Cloning and subcloning is typically performed by ligating the ends of a DNA fragment to the ends of a linearized vector containing an origin of replication and a selectable marker. The selectable marker is included in the vector to ensure that the newly cloned product, the plasmid containing the insert, is retained and propagated when introduced into its host cell.

The nucleic acid comprising a sequence encoding the fusion protein, e.g., a fusion protein comprising HOX oncoprotein and ERBD or MLL oncoprotein and ERBD can be delivered in the cell using a viral or non-viral delivery vector. Methods of using a viral or non-viral vector as a nucleic acid delivery vehicle are well known in the art. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. A wide variety of host/expression vector combinations can be used to express the nucleic acid sequences described herein. Suitable expression vectors include, without limitation, plasmids and viral vectors derived from, for example, bacteriophage, baculoviruses, and retroviruses. Numerous vectors and expression systems are commercially available from such corporations as Novagen™ (Madison, Wis.), Clontech™ (Palo Alto, Calif.), Stratagene™ (La Jolla, Calif.), and Invitrogen/Life Technologies™ (Carlsbad, Calif.).

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

Vectors include, for example, viral vectors (such as adenoviruses ("Ad"), adeno-associated viruses (AAV), and vesicular stomatitis virus (VSV) and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; BioTechniques, 34: 167-171 (2003). Large varieties of such vectors are known in the art and are generally available.

A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function (s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel, D T, et al. PNAS 88: 8850-8854, 1991). Suitable nucleic acid delivery systems include recombinant viral vector, typically sequence from at least one of an adenovirus, adenovirus-associated virus (AAV), helper dependent adenovirus, retrovirus, or hemagglutinating virus of Japan-liposome (HVJ) complex. In such cases, the viral vector comprises a strong eukaryotic promoter operably linked to the polynucleotide e.g., a cytomegalovirus (CMV) promoter. The recombinant viral vector can include one or more of the polynucleotides therein, preferably about one polynucleotide.

Viral vectors may include retroviruses, lentiviruses, adenoviruses, and adeno-associated viruses (AAV). It should be appreciated that any viral vector can be used with the methods and compositions described herein to introduce a nucleic acid sequence encoding a fusion protein comprising a HOX oncoprotein and an ERBD or nucleic acid sequence which encodes the fusion protein comprising a MLL oncoprotein and an ERBD. Use of viral vectors as delivery vectors are known in the art. See for example U.S. Pub. 2009/0017543 to Wilkes et al., the contents of which are incorporated by reference.

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™).

The ERBD-HOX or ERBD-MLL cDNA is inserted into a retroviral vector used to infect isolated progenitors, by culturing in one or more multi-lineage cytokines (e.g., stem cell factor, Flt3 ligand, IL-6, TPO and IL-3). In one aspect, the viral vector is a herpes simplex viral vector, an adenoviral vector, or an adeno-associated viral vector (AAV). In another aspect, the viral vector is a retroviral vector, for example, an HIV retroviral vector, a VL 30 vector, a MSCV retroviral vector, or a Harvey Murine Sarcoma Vector. In a related aspect, an isolated progenitor cell is transduced by being co-cultured with a retroviral producer cell line. In another aspect, transducing an isolated progenitor cell with ERBD-HOX or ERBD-MLL is performed with a DNA vector (i.e., a naked DNA) that comprises a nucleic acid encoding the fusion protein.

Infected/transfected progenitors can then be cultured in the presence of tissue culture medium containing an estrogen agonist (to keep the fusion protein active) and a myeloid specific cytokine (e.g., GM-CSF, G-CSF and Flt-3), which maintains proliferation of progenitors committed to the neutrophil or macrophage/dendritic lineage. In one aspect, the agonist can be β-estradiol, raloxifene, tamoxifen, toremifene, and clomiphene. Such agonists can be present at about 0.1 to about 0.5, about 0.5 to about 1.0, about 1 to about 5 micromolar, about 5 to about 10 micromolar, about 10 to about 20 micromolar, about 20 to about 30 micromolar, about 30 to about 40 micromolar, about 40 to about 50 micromolar, about 50 to about 60 micromolar, about 60 to about 70 micromolar, about 70 to about 80 micromolar, about 80 to about 90 micromolar, about 90 to about 100 micromolar.

Subsequent to infection, populations of immortalized hematopoietic progenitors emerge. These progenitors proliferate indefinitely.

The cells contacted with HOX or MLL oncoprotein fusion proteins are further cultured with a combination of one or more multi-lineage cytokines, a myeloid specific cytokine and in some embodiments, an estrogen agonist, upon culturing the progenitor cells become immortalized and exhibit commitment to neutrophil, macrophage, and/or dendritic lineage or exhibit multi-lineage blood cell differentiation potential. The proliferation of the immortalized progenitors can be ceased by controlling the expression of the HOX oncoprotein or MLL oncoprotein. For example, in some embodiments, the progenitor cells are cultured with HOX oncoprotein or MLL oncoprotein fused with cell penetrating peptide e.g., Tat domain; the cells can be cultured or administered to the subjects in the absence of the HOX oncoprotein or MLL oncoprotein fused with cell penetrating peptide leading to cessation of the proliferation and differentiation of the immortalized committed progenitors (e.g., myeloid progenitors into neutrophils, macrophages and/or dendritic cells). In some embodiments, the progenitor cells are infected with vectors comprising a nucleic acid sequence of HOX oncoprotein or MLL oncoprotein operably linked to ERBD or tetracycline-dependent promoter for controlled expression of oncoproteins, proliferation can be ceased and differentiation is induced by culturing the cells or administering the cells to a subject in absence of estrogen agonist or tetracycline.

Disclosed herein are methods for generating universal hematopoietic progenitor cells and custom patient-specific progenitor cells. In the methods described herein, isolated progenitor cells are cultured with a culture medium comprising a cytokine and growth factor mixture that supports growth and expansion of isolated progenitor cells into immortalized isolated progenitor cells e.g. cells committed to myeloid lineage, while limiting or minimizing growth and expansion of other cell types that are not committed myeloid progenitors. Suitable cytokines for ex vivo expansion purposes are selected from IL-1 (i.e., IL-1β), IL-3, IL-6, IL-11, G-CSF, GM-CSF, and analogs thereof. Suitable growth factors for ex vivo expansion purposes are selected from c-kit ligand (SCF or SF), FLT-3 ligand (FL), thrombopoietin (TPO), erythropoietin (EPO), and analogs thereof. As used herein, analogs include variants of the cytokines and growth factors having the characteristic biological activity of the naturally occurring forms.

In one embodiment, the cytokine and growth factor mixture in its base composition comprises stem cell factor (SCF), FLT-3 ligand (FL), and thromobopoietin (TPO). In some embodiments, a combination of multi-lineage cytokines comprising SCF, Flt3, IL-3, TPO and IL-6 is used. Source of the cytokines are those chosen to be active on the cells used for expansion, and thus will generally reflect the origin of the initial cells used for expansion. For example, if the progenitor cells are of human origin, human forms of the cytokine, either natural or recombinant, are used. Accordingly, in one embodiment, the cytokines are recombinant human rhuIL-1, (i.e., rhuIL-1β), rhuIL-3, rhuIL-6, rhuIL-11, rhuG-CSF, rhuGM-CST, and analogs thereof. However, the association between the form of the cytokine and the origin of cells need not be rigorous. As a general guide, the mixture of cytokines and growth factors will emphasize growth of myeloid progenitor cells while limiting the expansion of hematopoietic stem cells. Expansion is performed from about 2 days to about 14 days, from about 4 days to 10 days, about 4 days to 8 days and/or until the indicated fold expansion and the characteristic cell populations are obtained.

As used herein, "maintaining" or "culturing" refers to continuing the viability of cell and/or population of cells. A maintained or cultured population of cells will have a population of metabolically active cells.

In one embodiment, the final cell culture preparation is characterized by a CMP cell population that is expanded at least about 0.5 fold, at least about 1 fold, at least about 5 fold, at least about 10 fold, at least about 20 fold, or at least about 30 fold. In the final culture, the myeloid cell population will comprise CMPs, which are at least about 0.5%, at least about 1%, at least about 2%, at least about 5%, and at least about 10% of the total cells in the culture.

In another embodiment, the final cell culture preparation is characterized by a GMP cell population that is expanded at least about 10 fold, at least about 20 fold, at least about 40 fold, and at least about 80 fold. In the final culture, the myeloid cell population can comprise GMPs which are at least about 10%, at least about 20%, at least about 30%, and preferably at least about 50% of total cells in the culture. Thus, in preferred embodiments, the cell populations are expanded to preferentially enrich for GMP cells.

Disclosed herein are methods for generating universal hematopoietic progenitor cells and custom patient-specific hematopoietic progenitor cell from isolated progenitor cells. The isolated progenitor cells are cultured in presence of HOX or MLL oncoproteins to halt the development of isolated progenitors at the GMP stage, resulting in immortalized indefinite numbers of progenitor cells, which can then be transplanted in patients of need for further differentiation into neutrophils, macrophages, dendritic cells etc. Accordingly, the isolated cells as described herein can be cells that give rise to cells of the myeloid origin. The isolated progenitor cells are cells that can give rise to subsets of mature blood cells. In some embodiments, the isolated progenitor cells can comprise, for example, HSC, embryonic stem cells, induced-pluripotent stem cells, CMP, GMP or mononuclear cells.

The cell types relevant to the methods and composition described herein are those of the hematopoietic system, particularly hematopoietic stem cells and cells of the myeloid lineage.

The hematopoietic stem cells (HSC) are pluripotent stem cells capable of self-renewal and are characterized by their ability to give rise under permissive conditions to all cell types of the hematopoietic system. HSC self-renewal refers to the ability of an HSC cell to divide and produce at least one daughter cell with the same self-renewal and differentiation potential of a HSC; that is, cell division gives rise to additional HSCs. Self-renewal provides a continual source of undifferentiated stem cells for replenishment of the hematopoietic system. The marker phenotypes useful for identifying and isolating HSCs will be those commonly known in the art. For human HSCs, the cell marker phenotypes preferably include CD34+CD38−CD90(Thy1)+Lin−. For mouse HSCs, an exemplary cell marker phenotype is Sca-1+CD90+ (see, e.g., Spangrude, G. J. et al., Science 1:661-673 (1988)) or c-kit+Thylo Lin−Sca-1+ (see, Uchida, N. et at., J. Clin. Invest. 101(5):961-966 (1998)). Alternative HSC markers include e.g., aldehyde dehydrogenase (see Storms et al., Proc. Nat'l Acad. Sci. 96:9118-23 (1999) and AC133 (see Yin et al., Blood 90:5002-12 (1997).

HSCs give rise to committed lymphoid or myeloid progenitor cells. As used herein committed myeloid progenitor cells refer to cell populations capable of differentiating into any of the terminally differentiated cells of the myeloid lineage. Encompassed within the myeloid progenitor cells are the common myeloid progenitor cells (CMP), a cell population characterized by limited or non-self-renewal capacity but which is capable of cell division to form granulocyte/macrophage progenitor cells (GMP) and megakaryocyte/erythroid progenitor cells (MEP). A non-self renewing cell refers to cells that undergo cell division to produce daughter cells, neither of which have the differentiation potential of the parent cell type, but instead generates differentiated daughter cells. The marker phenotypes useful for identifying CMPs include those commonly known in the art. For CMP cells of marine origin, the cell population is characterized by the marker phenotype c-Kit$^{high}$ (CD117) CD16$^{low}$ CD34$^{low}$ Sca-1$^{neg}$ Lin$^{neg}$ and further characterized by the marker phenotypes FcyR$^{low}$ IL-7Rα$^{neg}$ (CD127). The murine CMP cell population is also characterized by the absence of expression of markers that include B220, CD4, CD8, CD3, Ter119, Gr-1 and Mac-1. For CMP cells of human origin, the cell population is characterized by CD34±CD38÷ and further characterized by the marker phenotypes CD123+ (IL-3Rα) CD45RA$^{neg}$. The human CMP cell population is also characterized by the absence of cell markers CD3, CD4, CD7, CD8, CD10, CD11b, CD14, CD19, CD20, CD56, and CD234a. Descriptions of marker phenotypes for various myeloid progenitor cells are described in, for example, U.S. Pat. Nos. 6,465,247 and 6,761,883; Akashi, Nature 404: 193-197 (2000); all publications incorporated herein by reference in their entirety.

Another committed progenitor cell of the myeloid lineage is the granulocyte/macrophage progenitor cell (GMP). The cells of this progenitor cell population are characterized by their capacity to give rise to granulocytes (e.g., basophils, eosinophil, and neutrophils) and macrophages. Similar to other committed progenitor cells, GMPs lack self-renewal capacity. Murine GMPs are characterized by the marker phenotype c-Kit$^{hi}$ (CD117) Sca-1$^{neg}$FcγR1$^{hi}$ (CD16) IL-7Rα$^{neg}$CD34$^{pos}$. Murine GMPs also lack expression of markers B220, CD4, CD8, CD3, Gr-1, Mac-1, and CD90. Human GMPs are characterized by the marker phenotype CD34+CD38+CD123+CD45RA+. Human GMP cell populations are also characterized by the absence of markers CD3, CD4, CD7, CD8, CD10, CD11b, CD14, CD19, CD20, CD56, and CD235a.

Where relevant to the discussion, the megakaryocyte/erythroid progenitor cells (MEP), which are derived from the CMPs, are characterized by their capability of differentiating into committed megakaryocyte progenitor and erythroid progenitor cells. Mature megakaryocytes are polyploid cells that are precursors for formation of platelets, a developmental process regulated by thrombopoietin. Erythroid cells are formed from the committed erythroid progenitor cells through a process regulated by erythropoietin, and ultimately differentiate into mature red blood cells. Murine MEPs are characterized by cell marker phenotype c-Kit$^{hi}$ and IL-7Rα$^{neg}$ and further characterized by marker phenotypes FcγR$^{lo}$ and CD34$^{low}$. Murine MEP cell populations are also characterized by the absence of markers B220, CD4, CD8, CD3, Gr-1, and CD90. Another exemplary marker phenotype for mouse MEPs is c-kit$^{high}$Sca-1$^{neg}$Lin$^{neg/low}$CD16$^{low}$CD34$^{low}$. Human MEPs are characterized by marker phenotypes CD34$^{+}$CD38$^{+}$CD123$^{neg}$CD45RA$^{neg}$. Human MEP cell populations are also characterized by the absence of markers CD3, CD4, CD7, CD8, CD10, CD11b, CD14, CD19, CD20, CD56, and CD235a.

Further restricted progenitor cells in the myeloid lineage are the granulocyte progenitor, macrophage progenitor, megakaryocyte progenitor, and erythroid progenitor. Granulocyte progenitor cells are characterized by their capability to differentiate into terminally differentiated granulocytes, including eosinophils, basophils, and neutrophils. The GPs typically do not differentiate into other cells of the myeloid lineage. With regards to the megakaryocyte progenitor cell (MKP), these cells are characterized by their capability to differentiate into terminally differentiated megakaryocytes but generally not other cells of the myeloid lineage (see, e.g., WO 2004/024875).

In a further aspect, the initial cells for expansion are isolated progenitor cells. These include isolated HSCs, which under the presence of the indicated mixture of cytokines and growth factors, develop into CMPs that further expand into other progenitor cells of the myeloid lineage. In another embodiment, the initial isolated progenitor cells are CMPs with the characteristic differentiation potential and cell marker phenotypes as described above. CMPs may have limited self-renewal capacity, and thus can expand to generate additional CMPs for a limited number of cells divisions while also differentiating into GMPs and MEPs. In another embodiment, the isolated progenitor cells are GMPs committed to differentiation for example to neutrophils.

Hematopoietic progenitor cells can include any progenitor cell in the hematopoietic lineage, e.g. HSCs, CMPs, or GMPs.

In some embodiments, the isolated progenitor cells are isolated from bone marrow, peripheral blood, placenta, or umbilical cord of a donor subject. Cells for expansion can be obtained from a variety of sources, including bone marrow, peripheral blood, cord blood, and other sources known to harbor hematopoietic and myeloid progenitor cells, including liver, particularly fetal liver. Peripheral and cord blood is a rich source of HSCs and progenitor cells. Cells are obtained using methods known and commonly practiced in the art. For example, methods for preparing bone marrow cells are described in Sutherland et al., Bone Marrow Processing and Purging: A Practical Guide (Gee, A. P. ed.), CRC Press Inc. (1991)). Umbilical cord blood or placental cord blood is typically obtained by puncture of the umbilical vein, in both term or preterm, before or after placental detachment (see, e.g., Turner, C. W. et al., Bone Marrow Transplant. 10:89 (1992); Bertolini, F. et al., J. Hematother. 4:29 (1995)). HSCs and myeloid progenitor cells can also be obtained from peripheral blood by leukapheresis, a procedure in which blood drawn from a suitable subject is processed by continuous flow centrifugation (e.g., Cobe B C T Spectra blood cell separators) to remove white blood cells while the other blood components are returned to the donor. Another type of isolation procedure is centrifugation through a medium of varying density, such as Ficoll-Hypaque (Amersham Pharmacia Biotech, Piscataway, N.J.).

Where applicable, stem cells and progenitor cells can be mobilized from the bone marrow into the peripheral blood by prior administration of cytokines or drugs to the subject (see, e.g., Lapidot, T. et al., Exp. Hematol. 30:973-981 (2002)). Cytokines and chemokines capable of inducing mobilization include, by way of example and not limitation, granulocyte colony stimulating factor (G-CSF), granulocyte macrophage colony stimulating factor (GM-CSF), erythropoietin (Kiessinger, A. et al., Exp. Hematol. 23:609-612 (1995)), stem cell factor (SCF), AMD3100 (AnorMed, Vancouver, Canada), interleukin-8 (IL-8), and variants of these factors (e.g., pegfilgastrim, darbopoietin). Combinations of cytokines and/or chemokines, such as G-CSF and SCF or GM-CSF and G-CSF, can act synergistically to promote mobilization and can be used to increase the number of HSC and progenitor cells in the peripheral blood, particularly for subjects who do not show efficient mobilization with a single cytokine or chemokine (Morris, C. et al., J. Haematol. 120:413-423 (2003)).

The initial populations of cells obtained by the methods above can be used directly for expansion or frozen for use at a later date. A variety of mediums and protocols for freezing cells are known in the art. Generally, the freezing medium will comprise DMSO from about 5-10%, 10-90% serum albumin, and 50-90% culture medium. Other additives useful for preserving cells include, by way of example and not disaccharides such as trehalose (Scheinkonig, C. et al., Bone Marrow Transplant. 34(6):531-6 (2004)), or a plasma volume expander, such as hetastarch (i.e., hydroxyethyl starch). In some embodiments, isotonic buffer solutions, such as phosphate-buffered saline, can be used. An exemplary cryopreservative composition has cell-culture medium with 4% HSA, 7.5% dimethyl sulfoxide (DMSO), and 2% hetastarch. Other compositions and methods for cryopreservation are well known and described in the art (see, e.g., Broxmeyer, H. E. et al., Proc. Natl. Acad. Sci. USA 100(2):645-650 (2003)). Cells are preserved at a final temperature of less than about −135° C.

The cells are derived from any animal species with a hematopoietic system, as generally described herein. Suitable animals include mammals, including, by way of example and not limitation, rodents, rabbits, canines, felines, pigs, horses, cows, primates (e.g., human), and the like. In one embodiment, the cells are derived from a human donor or human subject. The cells for expansion can be obtained from a single subject, or a plurality of subjects. A plurality refers to at least two (e.g., more than one) donors. When cells obtained are from a plurality of donors, their relationships can be syngeneic, allogenenic, or xenogeneic, as defined herein. In some embodiments, the isolated progenitor cells are obtained from an autologous or allogeneic donor matched with the recipient subject by HLA serotyping. Thus in some embodiments, the isolated cells for generating a custom-patient specific progenitor cells are MHC/HLA compatible. The isolated cells for use in the methods and compositions described herein comprise generation of a universal MHC/HLA compatible hematopoietic cell line; the cells need not be from a allogeneic donor matched to a recipient. The isolated cells for example can be from a mismatched allogeneic donor.

In one aspect disclosed herein is a method of generating custom MHC/HLA-compatible hematopoietic progenitor cells for a recipient subject. "Custom" as used herein refers to MHC/HLA-compatible hematopoietic progenitor cells generated for transplant in a specific recipient subject, such that the generated cells have negative phenotype for MHC surface antigens (protein) in the specific recipient subject. Alternatively, the cells are not alloreactive in the recipient subject.

The method comprises contacting isolated MHC/HLA-compatible progenitor cells with a fusion protein selected from HOX or MLL oncoprotein and culturing the cells with a combination of multi-lineage cytokines. In some embodiments, the method comprises contacting isolated MHC/HLA-compatible progenitor cells with a fusion protein comprising a HOX and/or MLL oncoprotein and culturing the cells with a combination of multi-lineage cytokines. Subsequent to contacting and culturing progenitors, cells emerge which are immortalized and exhibit commitment to neutrophil, macrophage, and/or dendritic lineage or exhibit multilineage blood cells differentiation potential. The isolated progenitor cells for use in this aspect are detailed above and can, for example, comprise myeloid progenitors or cells capable of differentiating into myeloid progenitors for e.g., HSC, ES, iPSC, GMP, CMP etc.

As used herein, "isolated MHC/HLA-compatible hematopoietic progenitor cells" are cells which do not induce alloreactivity directed to the major histocompatibility complex (MHC) antigens (proteins) on the transplanted hematopoietic progenitor cells, upon transplant in a recipient subject. "Alloreactivity" as used herein refers to the immune reaction in response to alloantigens i.e. non-self antigens (e.g., MHC/HLA antigens) from members of the same species. As it relates to generation of custom MHC/HLA-compatible hematopoietic progenitor cells for a recipient subject, the "isolated MHC/HLA-compatible hematopoietic progenitor cells" as that term is used herein refers to cells having identical Major histocompatibility complex (MHC) antigens as a recipient subject. "Isolated MHC/HLA-compatible hematopoietic progenitor cells" can be obtained, for example, from an autologous donor i.e. the recipient subject itself or allogeneic donor matched with the recipient subject. "Custom MHC/HLA-compatible hematopoietic progenitor cells" for a recipient subject can be isolated MHC/HLA-compatible progenitor cells obtained from a recipient subject or a matched allogeneic donor for the recipient subject, which are immortalized and exhibit commitment to neutrophil, macrophage, and/or dendritic lineage or exhibit multilineage blood cell differentiation potential and have negative phenotype for MHC surface antigens in the recipient subject. "Custom MHC/HLA-compatible hematopoietic progenitor cells" for a recipient subject can exhibit positive alloreactivity in recipients other than the recipient subject for whom the cells are generated.

The use of a "mismatched allogeneic" donor increases the risk of graft rejection or graft-versus-host disease. "Mismatched allogeneic" refers to cells derived from, originated in, or donor members of the same species having non-identical major histocompatibility complex (MHC) antigens (i.e., proteins) as typically determined by standard assays used in the art, such as serological or molecular analysis of a defined number of MHC antigens. A "partial mismatch" refers to a partial match of the MHC antigens tested between members, typically between a donor and recipient. For instance, a "half mismatch" refers to 50% of the MHC antigens tested as showing different MHC antigen type between two members. A "full" or "complete" mismatch refers to all MHC antigens tested as being different between two members. Determining the degree of MHC mismatch will employ standard tests known and used in the art.

For instance, there are at least six major categories of MHC genes in humans, identified as being important in transplant biology. HLA-A, HLA-B, HLA-C encode the HLA class I proteins while HLA-DR, HLA-DQ, and HLA-DP encode the HLA class II proteins. Genes within each of these groups are highly polymorphic, as reflected in the numerous HLA alleles or variants found in the human population, and differences in these groups between individuals is associated with the strength of the immune response against transplanted cells. Standard methods for determining the degree of MHC match examine alleles within HLA-B and HLA-DR, or HLA-A, HLA-B and HLA-DR groups. Thus, tests are made of at least 4, and preferably at least 6 MHC antigens within the two or three HLA groups, respectively.

In serological MHC tests, antibodies directed against each HLA antigen type are reacted with cells from one subject (e.g., donor) to determine the presence or absence of certain MHC antigens that react with the antibodies. This is compared to the reactivity profile of the other subject (e.g., recipient). Reaction of the antibody with an MHC antigen is typically determined by incubating the antibody with cells, and then adding complement to induce cell lysis (lymphocytotoxicity testing). The reaction is examined and graded according to the amount of cells lysed in the reaction (Mickelson, E. and Petersdorf, E. W., Hematopoietic Cell Transplantation, Thomas, E. D. et al. eds., pg. 28-37, Blackwell Scientific, Malden, Mass. (1999). Other cell-based assays include flow cytometry using labeled antibodies or enzyme linked immuno assays (ELISA).

Molecular methods for determining MHC type generally employ synthetic probes and/or primers to detect specific gene sequences that encode the HLA protein. Synthetic oligonucleotides can be used as hybridization probes to detect restriction fragment length polymorphisms associated with particular HLA types (Vaughn, R. W., Methods in Molecular Biology: MHC Protocols 210:45-60 (2002)). Alternatively, primers can be used for amplifying the HLA sequences (e.g., by polymerase chain reaction or ligation chain reaction), the products of which can be further examined by direct DNA sequencing, restriction fragment polymorphism analysis (RFLP), or hydridization with a series of sequence specific oligonucleotide primers (SSOP) (Petersdorf, E. W. et al., Blood 92(10):3515-20 (1998); Morishima, Y. et al., Blood 99(11):4200-6 (2002); and Middleton, D. and Williams, F., Methods in Molecular Biology: MHC Protocols 210:67-112 (2002)).

While description of "matched allogeneic" or mismatched allogeneic" is given for human MHC, it is to be understood that a similar analysis can be conducted for MHCs for various animal species. These include, by way of example and not limitation, mouse, rat (Gill, T. J. et al., Transplant Proc. 27(2):1495-500 (1995)), cow (Lewin, H. A, et al., Immunol Rev. 167:145-58 (1999), canine (Wagner, J. L. et al., J. Hered. 90(1):35-8 (1999)), feline (O'Brien, S. J. and Yuhki, N., Immunol Rev. 167:133-44 (1999)), swine (Chardon, P. et al., Genet Sel Evol. 32(2):109-28 (2000)), horses (Kydd, J. et al., Vet Immunol Immunopathol. 42(1):3-60 (1994), and primates (Heise, E. R. et al., Genetica 73(1-2): 53-68 (1987)).

Typically MHC/HLA-compatible hematopoietic progenitor cells are sought for prevention of rejection of the transplanted cells by the recipient subjects', immune system.

In one aspect, provided herein are methods for generating universal MHC/HLA-compatible progenitor cells. "Universal MHC/HLA compatible progenitor cells" as used herein refers to progenitor cells having negative phenotype for MHC surface antigens (proteins), thereby preventing their rejection upon transplant in any recipient subject in need of such treatment. In some embodiments, the isolated progenitor cells for generation of universal MHC/HLA-compatible hematopoietic cells can be obtained from a mismatched allogenic donor. In some embodiments, methods for generating a universal MHC/HLA compatible hematopoietic progenitor cells further comprises disrupting antigen presentation by the cell by down-regulating a major histocompatibility complex gene expression in the progenitor cells. MHC class I molecules are heterodimers that consist of two polypeptide chains, α and β2-microglobulin. The two chains are linked noncovalently via interaction of β2-microglobulin and the α3 domain. Only the α chain is polymorphic and encoded by a HLA gene (e.g. HLA-A, HLA-B, HLA-C), while the β2-microglobulin subunit is not polymorphic and encoded by the Beta-2 microglobulin gene. Classical MHC class I present antigens to the T-cell receptors of CD8+ T lymphocytes. Class II MHC comprises no β2 microglobulin. Class II molecules are also heterodimers, but in this case consist of two homogenous peptides, α and β chain, both of which are encoded in the MHC. The subdesignation α1, α2, etc. refers to separate domains within the HLA gene (e.g., HLA-DR, HLA-DQ, HLA-DP). Classical MHC class II molecules present antigens to CD4+ lymphocytes. Accordingly, aspects related to disruption of antigen presentation by a cell can comprise inhibition or downregulation of HLA genes and/or that of gene coding for β2 microglobulin.

In some embodiments, subsequent to the downregulation of MHC complex in the immortalized progenitor cells, the universal MHC/HLA compatible progenitor cells emerge. In some embodiments, the MHC gene whose expression is inhibited or downregulated is a MHC/HLA class I gene. In some embodiments, the MHC/HLA class I gene whose expression is inhibited encodes HLA ABC. In some embodiments, the MHC complex is downregulated by inhibition or downregulation of $\beta_2$ microglobulin gene. Methods for inhibition of gene expression are well known in the art. In some embodiments, the isolated progenitor cells are also contacted with a vector comprising a nucleic acid sequence that inhibits expression of MHC gene or $\beta_2$ microglobulin gene. In some embodiments, the nucleic acid sequence that inhibits gene expression can be an RNAi molecule or gRNA molecule, wherein the RNAi molecule or CRISPR-mediated gRNA molecule corresponds to a gene encoding a MHC class I gene or gene encoding $\beta_2$ microglobulin, wherein the RNAi and gRNA molecule is expressed and initiates inhibition or disruption of MHC class I gene. In some embodiments, the MHC class I gene can be gene encoding for HLA-A, HLA-B or HLA-C. Nucleases such as TALEN, Zinc fingers etc. can also be used for inhibition of gene expression.

As used herein, the term "guide RNA" or "gRNA" refers to a polynucleotide sequence that is complementary to a target sequence in a cell and associates with a Cas nuclease, thereby directing the Cas nuclease to the target sequence. The target sequence as it relates to the methods and composition described herein comprises a sequence within the MHC gene. In some embodiments, the target sequence is a sequence within the MHC/HLA class I gene. In some embodiments, the target sequence is a sequence within the β2 microglobulin gene. In some embodiments, a gRNA ranges between 1 and 30 nucleotides in length. In some embodiments, a gRN ranges between 5 and 25 nucleotides in length. In some embodiments, a gRNA ranges between 10 and 20 nucleotides in length. In some embodiments, a gRNA ranges between 14 and 18 nucleotides in length.

As used herein, the term "corresponds", when used in reference to an RNAi or gRNA molecule and its target (e.g., a MHC and/or β2 microglobulin gene), indicates that the RNAi or gRNA molecule has a sequence which permits it to specifically hybridize with the target gene and/or target gene expression product under conditions found in a cell comprising the target. As used herein, the term "specific hybridization" refers to a polynucleotide interaction between two polynucleotide molecules wherein the at least part of the first molecule's nucleotide sequence hybridizes (base-pairs) to at least part of the second molecule's nucleotide sequence with greater specificity and affinity than it binds to a third entity which is a non-target. In some embodiments, specific hybridization can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific hybridization for that target under the conditions of the assay being utilized.

The polypeptide and coding nucleic acid sequences of MHC/HLA class I (e.g. HLA-A, HLA-B, HLA-C) and that of β2 microglobulin of human origin and those of a number of animals are publican); available, e.g., from the NCBI website.

An exemplary sequence of β2 microglobulin gene can be as provided in SEQ ID NO: 6 below; (see NCBI Reference Sequence: NM_0041048.2 (SEQ ID NO 50), which is incorporated herein by reference in its entirety).

```
   1 aatataagtg gaggcgtcgc gctggcgggc attcctgaag ctgacagcat tcgggccgag
  61 atgtctcgct ccgtggcctt agctgtgctc gcgctactct ctctttctgg cctggaggct
 121 atccagcgtg agtctctcct accctcccgc tctggtcctt cctctcccgc tctgcaccct
 181 ctgtggccct cgctgtgctc tctcgctccg tgacttccct tctccaagtt ctccttggtg
 241 gcccgccgtg gggctagtcc agggctggat ctcggggaag cggcggggtg gcctgggagt
 301 ggggaagggg gtgcgcaccc gggacgcgcg ctacttgccc ctttcggcgg ggagcagggg
 361 agacctttgg cctacggcga cgggagggtc gggacaaagt ttagggcgtc gataagcgtc
 421 agagcgccga ggttggggga gggtttctct tccgctcttt cgcggggcct ctggctcccc
 481 cagcgcagct ggagtggggg acgggtaggc tcgtcccaaa ggcgcggcgc tgaggtttgt
 541 gaacgcgtgg aggggcgctt ggggtctggg ggaggcgtcg cccgggtaag cctgtctgct
 601 gcggctctgc ttcccttaga ctggagagct gtggacttcg tctaggcgcc cgctaagttc
 661 gcatgtccta gcacctctgg gtctatgtgg ggccacaccg tggggaggaa acagcacgcg
 721 acgtttgtag aatgcttggc tgtgatacaa agcggtttcg aataattaac ttatttgttc
 781 ccatcacatg tcacttttaa aaaattataa gaactacccg ttattgacat ctttctgtgt
 841 gccaaggact ttatgtgctt tgcgtcattt aattttgaaa acagttatct tccgccatag
 901 ataactacta tggttatctt ctgcctctca cagatgaaga aactaaggca ccgagatttt
 961 aagaaactta attacacagg ggataaatgg cagcaatcga gattgaagtc aagcctaacc
1021 agggcttttg cgggagcgca tgccttttgg ctgtaattcg tgcatttttt tttaagaaaa
1081 acgcctgcct tctgcgtgag attctccaga gcaaactggg cggcatgggc cctgtggtct
1141 tttcgtacag agggcttcct ctttggctct ttgcctggtt gtttccaaga tgtactgtgc
1201 ctcttacttt cggttttgaa aacatgaggg ggttgggcgt ggtagcttac gcctgtaatc
1261 ccagcactta gggaggccga ggcgggagga tggcttgagg tccgtagttg agaccagcct
1321 ggccaacatg gtgaagcctg gtctctacaa aaaataataa caaaaattag ccgggtgtgg
1381 tggctcgtgc ctgtggtccc agctgctccg gtggctgagg cgggaggatc tcttgagctt
```

-continued 1441 aggcttttga gctatcatgg cgccagtgca ctccagcgtg ggcaacagag cgagaccctg 1501 tctctcaaaa aagaaaaaaa aaaaaaaaga aagagaaaag aaaagaaaga aagaagtgaa 1561 ggtttgtcag tcaggggagc tgtaaaacca ttaataaaga taatccaaga tggttaccaa 1621 gactgttgag gacgccagag atcttgagca ctttctaagt acctggcaat acactaagcg 1681 cgctcacctt ttcctctggc aaaacatgat cgaaagcaga atgttttgat catgagaaaa 1741 ttgcatttaa tttgaataca atttatttac aacataaagg ataatgtata tatcaccacc 1801 attactggta tttgctggtt atgttagatg tcattttaaa aaataacaat ctgatattta 1861 aaaaaaaatc ttattttgaa aatttccaaa gtaatacatg ccatgcatag accatttctg 1921 gaagatacca caagaaacat gtaatgatga ttgcctctga aggtctattt tcctcctctg 1981 acctgtgtgt gggttttgtt ttgttttac tgtggggcata aattaatttt tcagttaagt 2041 tttggaagct taaataactc tccaaaagtc ataaagccag taactggttg agcccaaatt 2101 caaacccagc ctgtctgata cttgtcctct tcttagaaaa gattacagtg atgctctcac 2161 aaaatcttgc cgccttccct caaacagaga gttccaggca ggatgaatct gtgctctgat 2221 ccctgaggca tttaatatgt tcttattatt agaagctcag atgcaaagag ctctcttagc 2281 ttttaatgtt atgaaaaaaa tcagstettc attagattcc ccaatccacc tcttgatggg 2341 gctagtagcc tttccttaat gatagggtgt ttctagagag atatatctgg tcaaggtggc 2401 ctggtactcc tccttctccc cacagcctcc cagacaagga ggagtagctg catttttgtg 2461 atcatgtacc ctgaatataa gtgtatttaa aagaatttta tacacatata tttagtgtca 2521 atctgtatat ttagtagcac taacacttct cttcattttc aatgaaaaat atagagttta 2581 taatattttc ttcccacttc cccatggatg gtctaatcat gcctctcatt ttggaaagta 2641 ctgtttctga aacattaggc aatatattcc caacctggct agtttacagc aatcacctgt 2701 ggatgctaat taaaacgcaa atcccactgt cacatgcatt actccatttg atcataatgg 2761 aaagtatgtt ctgtcccatt tgccatagtc ctcacctatc cctgttgtat tttatcgggt 2821 ccaactcaac catttaaggt atttgccagc tcttgtatgc atttaggttt tgtttctttg 2881 ttttttagct catgaaatta ggtacaaagt cagagagggg tctggcatat aaaacctcag 2941 cagaaataaa gaggttttgt tgtttggtaa gaacatacct tgggttggtt gggcacggtg 3001 gctcgtgcct gtaatcccaa cactttggga ggccaaggca ggctgatcac ttgaagttgg 3061 gagttcaaga ccagcctggc caacatggtg aaatcccgtc tctactgaaa atacaaaaat 3121 taaccaggca tggtggtgtg tgcctgtagt cccaggaatc acttgaaccc aggaggcgga 3181 ggttgcagtg agctgagatc tcaccactgc acactgcact ccagcctggg caatggaatg 3241 agattccatc ccaaaaaaata aaaaaataaa aaaataaaga acataccttg ggttgatcca 3301 cttaggaacc tcagataata acatctgcca cgtatagagc aattgctatg tcccaggcac 3361 tctactagac acttcataca gtttagaaaa tcagatgggt gtagatcaag gcaggagcag 3421 gaaccaaaaa gaaaggcata aacataagaa aaaaaatgga aggggtggaa acagagtaca 3481 ataacatgag taatttgatg ggggctatta tgaactgaga aatgaacttt gaaaagtatc 3541 ttggggccaa atcatgtaga ctcttgagtg atgtgttaag gaatgctatg agtgctgaga 3601 gggcatcaga agtccttgag agcctccaga gaaaggctct taaaaatgca gcgcaatctc 3661 cagtgacaga agatactgct agaaatctgc tagaaaaaaa acaaaaaaagg catgtataga 3721 ggaattatga gggaaagata ccaagtcacg gtttattctt caaaatggag gtggcttgtt 3781 gggaaggtgg aagctcattt ggccagagtg gaaatggaat tgggagaaat cgatgaccaa 3841 atgtaaacac ttggtgcctg atatagcttg acaccaagtt agccccaagt gaaataccct -continued 3901 ggcaatatta atgtgtcttt tcccgatatt cctcaggtac tccaaagatt caggtttact 3961 cacgtcatcc agcagagaat ggaaagtcaa atttcctgaa ttgctatgtg tctgggtttc 4021 atcaatccga cattgaagtt gacttactga agaatggaga gagaattgaa aaagtggagc 4081 attcagactt gtctttcagc aaggactggt ctttctatct cttgtactac actgaattca 4141 cccccactga aaaagatgag tatgcctgcc gtgtgaacca tgtgactttg tcacagccca 4201 agatagttaa gtggggtaag tcttacattc ttttgtaagc tgctgaaagt tgtgtatgag 4261 tagtcatatc ataaagctgc tttgatataa aaaaggtcta tggccatact accctgaatg 4321 agtcccatcc catctgatat aaacaatctg catattggga ttgtcaggga atgttcttaa 4381 agatcagatt agtggcacct gctgagatac tgatgcacag catggtttct gaaccagtag 4441 tttccctgca gttgagcagg gagcagcagc agcacttgca caaatacata tacactctta 4501 acacttctta cctactggct tcctctagct tttgtggcag cttcaggtat atttagcact 4561 gaacgaacat ctcaagaagg tataggcctt tgtttgtaag tcctgctgtc ctagcatcct 4621 ataatcctgg acttctccag tactttctgg ctggattggt atctgaggct agtaggaagg 4681 gcttgttcct gctgggtagc tctaaacaat gtattcatgg gtaggaacag cagcctattc 4741 tgccagcctt atttctaacc attttagaca tttgttagta catggtattt taaaagtaaa 4801 acttaatgtc ttcctttttt ttctccactg tctttttcat agatcgagac atgtaagcag 4861 catcatggag gtaagttttt gaccttgaga aaatgttttt gtttcactgt cctgaggact 4921 atttatagac agctctaaca tgataaccct cactatgtgg agaacattga cagagtaaca 4981 ttttagcagg gaaagaagaa tcctacaggg tcatgttccc ttctcctgtg gagtggcatg 5041 aagaaggtgt atggccccag gtatggccat attactgacc ctctacagag agggcaaagg 5101 aactgccagt atggtattgc aggataaagg caggtggtta cccacattac ctgcaaggct 5161 ttgatctttc ttctgccatt tccacattgg acatctctgc tgaggagaga aaatgaacca 5221 ctcttttcct ttgtataatg ttgttttatt cttcagacag aagagaggag ttatacagct 5281 ctgcagacat cccattcctg tatggggact gtgtttgcct cttagaggtt cccaggccac 5341 tagaggagat aaagggaaac agattgttat aacttgatat aatgatacta taatagatgt 5401 aactacaagg agctccagaa gcaagagaga gggaggaact tggacttctc tgcatcttta 5461 gttggagtcc aaaggctttt caatgaaatt ctactgccca gggtacattg atgctgaaac 5521 cccattcaaa tctcctgtta tattctagaa cagggaattg atttgggaga gcatcaggaa 5581 ggtggatgat ctgcccagtc acactgttag taaattgtag agccaggacc tgaactctaa 5641 tatagtcatg tgttacttaa tgacggggac atgttctgag aaatgcttac acaaacctag 5701 gtgttgtagc ctactacacg cataggctac atggtatagc ctattgctcc tagactacaa 5761 acctgtacag cctgttactg tactgaatac tgtgggcagt tgtaacacaa tggtaagtat 5821 ttgtgtatct aaacatagaa gttgcagtaa aaatatgcta ttttaatctt atgagaccac 5881 tgtcatatat acagtccatc attgaccaaa acatcatatc agcatttttt cttctaagat 5941 tttgggagca ccaaagggat acactaacag gatatactct ttataatggg tttggagaac 6001 tgtctgcagc tacttctttt aaaaaggtga tctacacagt agaaattaga caagtttggt 6061 aatgagatct gcaatccaaa taaaataaat tcattgctaa ccttttttctt ttcttttcag 6121 gtttgaagat gccgcatttg gattggatga attccaaatt ctgcttgctt gctttttaat 6181 attgatatgc ttatacactt acactttatg cacaaaatgt agggttataa taatgttaac 6241 atggacatga tcttctttat aattctactt tgagtgctgt ctccatgttt gatgtatctg -continued

```
6301 agcaggttgc tccacaggta gctctaggag ggctggcaac ttagaggtgg ggagcagaga
6361 attctcttat ccaacatcaa catcttggtc agatttgaac tcttcaatct cttgcactca
6421 aagcttgtta agatagttaa gcgtgcataa gttaacttcc aatttacata ctctgcttag
6481 aatttggggg aaaatttaga aatataattg acaggattat tggaaatttg ttataatgaa
6541 tgaaacattt tgtcatataa gattcatatt tacttcttat acatttgata aagtaaggca
6601 tgaaacattt tgtcatataa gattcatatt tacttcttat acatttgata aagtaaggca
6661 gtgttatctc tta
```

The polypeptide and coding nucleic acid sequences of MHC/HLA class I (e.g. HLA-A, HLA-B, HLA-C) of human origin and those of a number of animals are publically available, e.g., from the NCBI website. For coding sequences examples include, but not limited to, for HLA-A, see accession No. NG_029217.2 (SEQ ID NO: 51); for HLA-B, see accession No. 1. NG_023187.1 (SEQ ID NO: 52); for HLA-C, see accession No. NG_029422.2 (SEQ ID NO: 53) (the contents of which are incorporated herein by reference in their entireties).

For polypeptide sequences, examples include, but not limited to, for HLA-A, see accession No. NP_001229687 (SEQ ID NO: 54); for HLA-B, see accession No. NP_005505.2 (SEQ ID NO: 55); for HLA-C, see accession No. NP_001229971.1 (SEQ ID NO: 56) (the contents of which are incorporated herein by reference in their entireties).

Those of skill in the art can design gRNA targeting the MHC/HLA class I genes (e.g., HLA-A, HLA-B and HLA-C) or β2 microglobulin gene using the publically available nucleic acid sequences and one of many publically available gRNA design softwares. Non-limiting examples of publically available gRNA design softwares include; sgRNA Scorer 1.0, Quilt Universal guide RNA designer, Cas-OFFinder & Cas-Designer, CRISPR-ERA, CRISPR/Cas9 target online predictor, Off-Spotter—for designing gRNAs, CRISPR MultiTargeter, ZiFiT Targeter, CRISPRdirect, CRISPR design from crispr.mit.edu/, E-CRISP etc.

An exemplary software to design gRNA is available at portals.broadinstitute.org/gpp/public/analysis-tools/sgrna-design. One of skill in the art can design gRNAs targeting a gene of interest, for example, MHC/HLA class I gene (e.g., HLA-A, HLA-B or HLA-C) or β2-microglobulin, upon input of their respective nucleic acid sequences into the software. Non-limiting exemplary sequences of gRNA targeting the β2 microglobulin gene can be as provided in SEQ ID NOs: 7-21 below;

| gRNA-PAM sequence (NGG) | SEQ ID NO: |
|---|---|
| CAGCCCAAGATAGTTAAGTG-GGG | SEQ ID NO: 7 |
| TGGGCTGTGACAAAGTCACA-TGG | SEQ ID NO: 8 |
| AAGTCAACTTCAATGTCGGA-TGG | SEQ ID NO: 9 |
| CAGTAAGTCAACTTCAATGT-CGG | SEQ ID NO: 10 |
| CTGAATCTTTGGAGTACCTG-AGG | SEQ ID NO: 11 |
| ACAGCCCAAGATAGTTAAGT-GGG | SEQ ID NO: 12 |
| ACAAAGTCACATGGTTCACA-CGG | SEQ ID NO: 13 |
| GGCCGAGATGTCTCGCTCCG-TGG | SEQ ID NO: 14 |
| AGTCACATGGTTCACACGGC-AGG | SEQ ID NO: 15 |
| CATACTCATCTTTTTCAGTG-GGG | SEQ ID NO: 16 |
| TTACCCCACTTAACTATCTT-GGG | SEQ ID NO: 17 |
| ACCCAGACACATAGCAATTC-AGG | SEQ ID NO: 18 |
| CTCAGGTACTCCAAAGATTC-AGG | SEQ ID NO: 19 |
| ACTCTCTCTTTCTGGCCTGG-AGG | SEQ ID NO: 20 |
| GAGTAGCGCGAGCACAGCTA-AGG | SEQ ID NO: 21 |

In some embodiments, the gRNA can comprise the sequence of one or more of SEQ ID NOs: 7-21. In some embodiments, the gRNA can consist essentially of the sequence of one or more of SEQ ID NOs: 7-21. In some embodiments, the gRNA can consist of the sequence of one or more of SEQ ID NOs: 7-21.

Those of skill in the art can design RNAi targeting the MHC/HLA class I genes (e.g., HLA-A, HLA-B and HLA-C) or β2 microglobulin gene using the publically available nucleic acid sequences and one of many publically available RNAi design softwares. Non-limiting examples of publically available RNAi design softwares include; AsiDesigner (Bioinformatics Research Center, KRIBB), Block-iT RNAi Designer (Invitrogen), Gene specific siRNA selector (bioinformatics Facility, The Wistar Institute), siDESIGN Center (Dharmaeon), siRNA Design (IDT), siRNA Target Finder (Ambion), siRNA Target Finder (GeneScript) etc.

An exemplary software to design gRNA is available at rnaidesigner.thermofisher.com/maiexpress/design.do. One of skill in the art can design RNAi (e.g., siRNA, shRNA) targeting a gene of interest, for example. MHC/HLA class I gene (e.g., HLA-A, HLA-B or HLA-C) or β2-microglobulin, upon input of their respective nucleic acid sequences into the software. Non-limiting exemplary sequences of siRNA targeting the β2 microglobulin gene can be as provided in SEQ ID NOs: 22-30 below;

| siRNA sequences | SEQ ID NO: |
|---|---|
| GCTATCCAGCGTACTCCAA | SEQ ID NO: 22 |
| TCCAGCGTACTCCAAAGAT | SEQ ID NO: 23 |
| CCAGCGTACTCCAAAGATT | SEQ ID NO: 24 |
| CCAAAGATTCAGGTTTACT | SEQ ID NO: 25 |

-continued

| siRNA sequences | SEQ ID NO: |
|---|---|
| TCAGGTTTACTCACGTCAT | SEQ ID NO: 26 |
| GCAGAGAATGGAAAGTCAA | SEQ ID NO: 27 |
| GGTTTCATCCATCCGACAT | SEQ ID NO: 28 |
| TCATCCATCCGACATTGAA | SEQ ID NO: 29 |
| CCGACATTGAAGTTGACTT | SEQ ID NO: 30 |

In some embodiments, RNAi molecule can comprise the sequence of one or more of SEQ ID NOs: 22-30. In some embodiments, RNAi molecule can consist essentially of the sequence of one or more of SEQ ID NOs: 22-30. In some embodiments, RNAi molecule can consist of the sequence of one or more of SEQ ID NOs: 22-30.

In some embodiments, the methods and compositions described herein can relate to inhibiting expression of all MHC class I and/or class II molecules, e.g., by deleting sequences from the genome. In some embodiments, the invariant chain (Ii, CD74) can be deleted from the genome to eliminate all MHC class II expression, e.g, by deleting the sequence of SEQ ID NO: 33 from the genome. In some embodiments, MHC class II expression can be inhibited or eliminated by contacting the cell with a sgRNA comprising the sequence of one of SEQ ID NOs: 43-45. In some embodiments, MHC class II expression can be inhibited or eliminated by contacting the cell with a sgRNA consisting essentially of the sequence of one of SEQ NOs: 43-45. In some embodiments, MHC class II expression can be inhibited or eliminated by contacting the cell with a sgRNA consisting of the sequence of one of SEQ ID NOs: 43-45.

In some embodiments, the beta-2 microglobulin can be deleted from the genome to eliminate all MHC class I expression, e.g, by deleting the sequence of SEQ ID NO: 34 from the genome. In some embodiments, MHC class I expression can be inhibited or eliminated by contacting the cell with a sgRNA comprising the sequence of one of SEQ NOs: 37-42, In some embodiments, MHC class I expression can be inhibited or eliminated by contacting the cell with a sgRNA consisting essentially of the sequence of one of SEQ ID NOs: 37-42. In some embodiments, MHC class I expression can be inhibited or eliminated by contacting the cell with a sgRNA consisting of the sequence of one of SEQ ID NOs: 37-42.

SEQ ID NO: 33 Amino acid sequence for deletion of invariant chain (Ii, CD74) to eliminate all MHC class II mhrrrsrscr cdqkpvmddq rdlisnneql pmlgrrpgap eskcsrgaly tgfsilvtll lagqattayf lyqqqgrldk ltvtsqnlql enlrmklpkp pkpv-skmrma tpllmqalpm galpqgpmqn atkygnmted hvmhllqnad plkvypplkg sfpenlrhlk ntmetidwkv feswmhhwll femsrhsleq kptdappkes leledpssgl gvtkqdlgpg kglaeghlvt sssspagpap lwagegv SEQ ID NO: 34 Amino acid sequence for deletion of beta-2 microglobulin to eliminate all MHC class I msrsva-lavl allslsglea iqrtpkiqvy srhpaengks nflncyvsgf hpsdievdll kngeriekve hsdlsfskdw sfyllyytef tptekdeyac rvnhvtlsqp kivkwdrdm In some embodiments, the vector used to deliver a gRNA or a RNAi molecule can be retroviral vector. In some embodiments, the vector comprises a U6 Pol III promoter. In related embodiments, the RNAi molecule comprises the sequence selected from SEQ ID NOs: 22-30. In related embodiments, the nRNA molecule comprises the sequence selected from SEQ ID NOs: 7-21.

As used herein, a "subject", "patient", "individual" and like terms are used interchangeably and refers to a vertebrate, preferably a mammal. In some embodiments, the mammal is a human, primates, rodents, wild or domesticated animals, including feral animals, farm animals, sport animals, and pets. Primates include, for example, chimpanzees, cynomologous monkeys, spicier monkeys, and macaques, e.g., Rhesus. In one embodiment, the subject is a human. Rodents include, for example, mice, rats, woodchucks, ferrets, rabbits and hamsters. Domestic and game animals include, for example, cows, horses, pigs, deer, bison, buffalo, feline species, e.g., domestic cat, and canine species, e.g., dog, fox, wolf, avian species, e.g., chicken, emu, ostrich, and fish, e.g., trout, catfish and salmon. The term, "Subject" can include worms e.g., *C. elegans*. A subject can be male or female. In some embodiments, the subject is a pregnant female. Mammals other than humans can be advantageously used as subjects that represent animal models of diseases or disorders described herein, for example, pathogenic infection, leukemia, neutropenia. Subject amenable to treatment with the compositions disclosed herein can be one suffering, from, diagnosed with or at a risk of suffering from deficiency of immune cell e.g., neutrophils. Accordingly, in some embodiments, the subject can be one suffering from neutropenia. In some embodiments, the subject can be one in need of augmenting their immune response. For example, a subject undergoing radiation or chemotherapy that requires augmentation of immune response while their bone marrow repopulates by their own residual stem and progenitor cells or bone marrow is repopulated. In some embodiments, the subject can be one who needs augmentation of immune response to prevent risk of infection or treat an infection during post hematopoietic stem cell transplantation. In some embodiments, the subject can be one suffering from disorder known to cause neutropenia.

A "subject in need" of treatment for a particular condition can be a subject having that condition, diagnosed as having that condition, or at risk of developing that condition.

Disclosed herein are compositions comprising the universal MHC/HLA-compatible hematopoietic progenitor cells. In another aspect, disclosed herein are compositions comprising the customized, patient-specific MHC/HLA compatible hematopoietic progenitor cells. The compositions disclosed herein can be used for treatment of disease and infection associated with deficiency of immune cells e.g., neutrophils. The compositions as described herein can include substantially purified populations and pharmaceutical compositions of such. In one embodiment, the compositions disclosed herein can be frozen for later use. The pharmaceutical compositions will generally comprise a pharmaceutically acceptable carrier and a pharmacologically effective amount of the progenitor cells generated herein. The pharmaceutical composition can be formulated as cell suspension, powders, granules, solutions, suspensions, aerosols, solids, pills, tablets, capsules, gels, topical cremes, suppositories, transdermal patches, and other formulations known in the art.

As used herein, the term "pharmaceutically acceptable carrier" comprises any standard pharmaceutically accepted carriers known to those of ordinary skill in the art in formulating pharmaceutical compositions. Thus, the compounds, by themselves, such as being present as pharmaceutically acceptable salts, or as conjugates, can be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients.

Pharmaceutical compositions can further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, solutes that render the formulation isotonic, hypotonic or weakly hypertonic with the blood of a recipient, suspending agents, thickening agents, preservatives, flavoring agents, sweetening agents, and coloring compounds as appropriate.

While any suitable carrier known to those of ordinary skill in the art can be employed in the compositions, the type of carrier will typically vary depending on the mode of administration. The therapeutic compositions can be formulated for any appropriate manner of administration, including for example, oral, nasal, mucosal, rectal, vaginal, topical, intravenous, intraperitoneal, intradermal, subcutaneous, and intramuscular administration. In some embodiments, the therapeutic composition can be administered as a formulation adapted for systemic delivery. In some embodiments, the therapeutic composition can be administered as a formulation adapted for delivery to specific organs, for example but not limited to, the liver, spleen, the bone marrow, and the skin.

The compositions described herein can be administered therapeutically to a subject prior to, simultaneously with (in the same or different compositions) or sequentially with the administration of at least one other cancer therapy. For example, the additional cancer therapy is radiation, chemotherapy, or proton therapy.

For parenteral administration, the compositions can be administered as injectable dosages of a solution or suspension of the substance in a physiologically acceptable diluent with a pharmaceutical carrier that can be a sterile liquid such as sterile pyrogen free water, oils, saline, glycerol, polyethylene glycol or ethanol. Additionally, auxiliary substances, such as wetting or emulsifying agents, surfactants, pH buffering substances and the like can be present in compositions described herein. Other components of pharmaceutical compositions can include petroleum, animal, vegetable, or synthetic origin, for example, non-aqueous solutions of peanut oil, soybean oil, corn oil, cottonseed oil, ethyl oleate, and isopropyl myristate.

The pharmaceutical compositions described herein can be presented in unit-dose or multi-dose containers, such as sealed ampoules or vials. Such containers are typically sealed in such a way to preserve the sterility and stability of the formulation until use. In general, formulations can be stored as suspensions, solutions or emulsions in oily or aqueous vehicles, as indicated above. Alternatively, a pharmaceutical composition can be stored in a freeze-dried condition requiring only the addition of a sterile liquid carrier immediately prior to use. In one embodiment, a pharmaceutical composition is provided comprising the subject expanded myeloid progenitor cells cryopreserved in a suitable cryopreservation medium, which can then be thawed and resuspended as needed for administration to a patient.

The amount of the cells needed for achieving a therapeutic effect can be determined empirically in accordance with conventional procedures for the particular purpose. Generally, for administering the cells for therapeutic purposes, the cells are given at a pharmacologically effective dose. By "pharmacologically effective amount" or "pharmacologically effective dose" is an amount sufficient to produce the desired physiological effect or amount capable of achieving the desired result, particularly for treating the disorder or disease condition, including reducing or eliminating one or more symptoms or manifestations of the disorder or disease. As an illustration, administration of cells to a patient suffering from a neutropenia provides a therapeutic benefit not only when the underlying condition is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

Pharmacologically effective dose, as defined above, will also apply to therapeutic compounds used in combination with the cells, as further described below. Transplantation of cells into an appropriate host is accomplished by methods generally used in the art. The preferred method of administration is intravenous infusion. The number of cells transfused will take into consideration factors such as sex, age, weight, the types of disease or disorder, stage of the disorder, the percentage of the desired cells in the cell population (e.g., purity of cell population), and the cell number needed to produce a therapeutic benefit. In some embodiments, the number of cells transfused can be, for example, at least about 100 billion cells, at least about 100-110 billion cells, at least about 110-120 billion cells, at least about 120-130 billion cells per infusion, at least about 130-140 billion cells per infusion, at least about 140-150 billion cells per infusion, at least about 150-160 billion cells per infusion, at least about 160-170 billion cells per infusion, at least about 170-180 billion cells per infusion, at least about 180-190 billion cells per infusion, at least about 190-200 billion cells per infusion. In some embodiments, the number of cells transfused can be 100-200 billion cells per infusion per patient. In some embodiments, the cells are administered to a desired absolute neutrophil number specific to clinical scenario, for example, higher if the patient is infected or lower if the cells are transfused for prophylaxis. A variety of adjunctive treatments can be used with the compositions, described above. For treating neutropenia and related conditions, the compositions can be used in combination with other agents and compounds that enhance the therapeutic effect of the infused cells or treat complications arising from neutropenia. In one aspect, the adjunctive treatments include, among others, anti-fungal agents, anti-bacterial agents, and anti-viral agents.

In a further embodiment, the adjunctively administered agent is a cytokine or growth factor that enhances differentiation and mobilization of terminally differentiated myeloid cells, particularly granulocytes, macrophages, megakaryocytes and erythroid cells. For enhancing granulocyte development, the cytokines C-CSF and GM-CSF can be used. G-CSF is effective in accelerating engraftment and production of neutrophils in HSCT. In another embodiment, the cytokine or growth factor is thrombopoietin. Administration of TPO enhances engraftment of transplanted progenitor cells and promotes development of megakaryocytes and platelets (Fox, N et al., J. Clin. Invest. 110:389-394 (2002); Akahori, H. et al., Stem Cells 14(6):678-689 (1996)).

A variety of vehicles and excipients and routes of administration can be used for adjunctive therapy, as will be apparent to the skilled artisan. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A, H. ed., Washington D.C., American Pharmaceutical Association (2000); hereby incorporated by reference in their entirety.

The amount administered to the host will vary depending upon what is being administered, the purpose of the administration, such as prophylaxis or therapy, the state of the host, the manner of administration, the number of administrations, interval between administrations, and the like. These can be determined empirically by those skilled in the art and can be adjusted for the extent of the therapeutic response. Factors to consider in determining an appropriate dose include, but is not limited to, size and weight of the subject, the age and sex of the subject, the severity of the symptom, the stage of the disease, method of delivery of the agent, half-life of the agents, and efficacy of the agents. Stage of the disease to consider includes whether the disease is acute or chronic, relapsing or remitting phase, and the progressiveness of the disease.

Determining the dosages and times of administration for a therapeutically effective amount are well within the skill of the ordinary person in the art. For example, an initial effective dose can be estimated from cell culture or other in vitro assays. A dose can then be formulated in animal models to generate a circulating concentration or tissue concentration, including that of the IC50 as determined by the cell culture assays.

In addition, toxicity and therapeutic efficacy are generally determined by cell culture assays and/or using experimental animals, typically by determining a LD50 (lethal dose to 50% of the test population) and ED50 (therapeutically effectiveness in 50% of the test population). Guidance is found in standard reference works, for example, Goodman & Gilman's The Pharmacological Basis of Therapeutics, 10th Ed. (Hardman, J. G. et al., eds.) McGraw-Hill, New York, N.Y. (2001).

The compositions may be administered once per clay,a few or several times per day, or even multiple times per day, depending upon, among other things, the indication being treated and the judgement of the prescribing physician.

In some embodiments, the compositions disclosed herein (e.g., composition comprising universal MHC/HLA-compatible hematopoietic progenitor cells can be used to treat a pathogen infection in a subject. In one aspect, disclosed herein are methods of treating a pathogen infection in a subject. In some embodiments, the compositions disclosed herein (e.g., composition comprising custom patient-specific MHC/HLA-compatible hematopoietic progenitor cells) can be used to treat neutropenia in a subject. In one aspect, disclosed herein are methods of treating neutropenia in a subject.

Cells prepared by the methods described herein are used for treatment of various disorders related to deficiencies in hematopoiesis caused by disease or myeloablative treatments. As used herein, "treatment" refers to therapeutic or prophylactic treatment, or a suppressive measure for the disease, disorder or undesirable condition. Treatment encompasses administration of the subject cells in an appropriate form prior to the onset of disease symptoms and/or after clinical manifestations, or other manifestations of the disease or condition to reduce disease severity, halt disease progression, or eliminate the disease. Prevention of the disease includes prolonging or delaying the onset of symptoms of the disorder or disease, preferably in a subject with increased susceptibility to the disorder.

Conditions suitable for treatment with the cells described herein include neutropenia, a condition characterized by decrease in the amount of circulating neutrophils, and thromobocytopenia, a condition characterized by less than normal levels of platelets in the peripheral blood. Both conditions may be a result of acquired or inherited disorder. Defective hematopoietic stem cell development known to create low neutrophil numbers include, among others, reticular dysgenesis, Fanconis's anemia, Chediak-Higashi syndrome, and cyclic neutropenia. For thrombocytopenia, low platelet levels are manifested in, among others, Wiskott-Aldrich Syndrome, thrombocytopenia with absent radii (TAR), and systemic lupus erythematosus. Acquired forms of neutropenia and thrombocytopenia occur under similar circumstances, such as with hematological malignancies, vitamin deficiency, exposure to ionizing radiation, viral infections (e.g., mononucleosis, CMV, HIV, etc.), and following treatment with various cytotoxic drugs. For the present purposes, the cells can be used prophylactically to reduce the occurrence of neutropenia and thrombocytopenia, and their associated complications, particularly to lessen infection by opportunistic pathogens in patients that have been treated with myeloablative agents or have undergone HSCT. In the transplant setting, myeloid cells can be used concurrently or subsequent to stem cell transplantation until the recipients own HSCs or transplanted HSCs begin to restore hematopoiesis and raise neutrophil and platelet levels sufficiently. Infusion of myeloid progenitor cells increases the number of neutrophils and megakaryocytes in the treated subject, thereby providing temporary but needed protection during the neutropenic or thrombocytopenic period. Use of myeloid progenitor cell populations e.g., GMP, as opposed to more differentiated neutrophils and platelets, provides for longer lasting protection because of the temporary engraftment of myeloid progenitors and their differentiation in vivo. It is to be noted that while treatments may provide a detectable increase in peripheral cell count or ANC, this increase is not a reliable indicator of successful, transient engraftment or efficacy. Thus other measures, such as reduced infection rate and/or increased survival can be used for determining effectiveness of the treatment.

As an example universal MHC/HLA compatible progenitor cells can be used to augment a subject's own neutrophil number for an elevated effector function to treat a pathogenic infection in the subject. In some embodiments, the universal MHC/HLA compatible progenitor cells can be used to augment a subject's nuetrophil number to prevent a pathogenic infection. In some embodiments, the subject may have undergone a myeloablative therapy. In some embodiments, the subject is diagnosed with neutropenia.

In one embodiment, the methods and compositions disclosed herein can be applied to the leukemic treatment scheme. All leukemic patients have long durations of neutropenia. In one embodiment, the methods and compositions described herein can become standard of care for leukemia treatment, especially those with signs of infection. In some embodiments, the methods and compositions disclosed herein can be used to treat disorders that can include, but not limited to, sepsis/shock, drug-induced neutropenia (marrow toxic agents) or neutrophil dysfunction (immune modulators), autoimmune diseases (lupus, etc) that can result in neutropenia, congenital disorders with abnormal neutropenia following, severe infection in setting of comorbid diseases such as advanced diabetes, radiation injury, which can result in marrow failure, any clinical syndrome that results in neutropenia.

In addition, toxicity and therapeutic efficacy are generally determined by cell culture assays and/or using experimental animals, typically by determining a LD50 (lethal dose to 50% of the test population) and ED50 (therapeutically effectiveness in 50% of the test population). Guidance is found in standard reference works, for example, Goodman & Gilman's The Pharmacological Basis of Therapeutics, 10th Ed. (Hardman, J. G. et al., eds.) McGraw-Hill, New York, N.Y. (2001). The effects of any particular dosage can be monitored by a suitable bioassay, e.g., absolute blood count or absolute neutrophil count, among others. The dosage can be determined by a physician and adjusted, as necessary, to suit observed effects of the treatment.

The efficacy of compositions as described herein in, e.g., the treatment of a condition described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g., absolute neutrophil count. Efficacy can also be measured by a failure of an individual to worsen as assessed by hospitalization, or need for medical interventions (i.e., progression of the disease is halted). Methods of measuring these indicators are known to those of skill in the art and/or are described herein.

Treatment includes any treatment of a disease in an individual or an animal (some non-limiting examples include a human or an animal) and includes: (1) inhibiting the disease, e.g., preventing a worsening of symptoms (e.g. pathogenic infection, pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example, mouse model of cancer, leukemia, pathogenic infection model, neutropenia or related disorders or in immunocompromised animals. When using an experimental animal model, efficacy of treatment is evidenced when a statistically significant change in a marker is observed, e.g. absolute count of neutrophils. In some embodiments, in humans, for example, successful treatment can be determined, by measurement of absolute counts for individual blood cell types (white blood cells, red blood cells and platelets) in the peripheral blood, reaching a number of cells accepted by those of skill in the art as within the normal range for the subject.

Methods of conducting a complete blood count, differential leukocyte count i.e. including counts of each type of white blood cell, for e.g., neutrophils, eosinophils, basophils, monocytes, and lymphocytes, and platelet counts are known to those skilled in the art. Briefly, post-administration of an effective dosage of the compositions described herein, the blood can be collected at regular intervals in a tube containing an anti-coagulant like the EDTA, the cells can be counted using an automated blood count analyzer or manually using a hemocytometer. Neutrophils are a type of white blood cell that are a marker of engraftment; the absolute neutrophil count (ANC) must be at least within the typical normal range for the treatment to be effective. The efficacy of a given therapeutic regimen involving methods and compositions described herein, may be monitored, for example by convention FACS assays for phenotypes of cells in the blood circulation of the subject under treatment. Such analysis is useful to monitor changes in the numbers of cells of various lineages e.g., cells of the myeloid lineage.

Summary of Current Barriers that are Addressed by the Proposed Invention:

- Donor neutrophils have a half-life of less than 24 hours.
- Donor neutrophils are not matched to the patient.
- Donor neutrophils may not be able to home to the site of active infection.
- Granulocyte transfusion trials including the recent RING trial (reference 1) demonstrate that there continues to be intense interest in neutrophil transfusions for this population, but the current process of seeking out donors for neutrophil transfusion is very far from perfect (reference 1 and 2).

In one aspect, described herein is a kit comprising a composition as described herein, e.g., a fusion protein or a nucleic acid encoding the fusion protein, according to any of the aspects of embodiments described herein. A kit is any manufacture (e.g., a package or container) comprising at least one reagent, e.g., a fusion protein, the manufacture being promoted, distributed, or sold as a unit for performing the methods described herein.

The kits described herein can optionally comprise additional components useful for performing the methods described herein. By way of example, the kit can comprise fluids (e.g., buffers) suitable for a composition comprising a fusion protein as described herein, an instructional material which describes performance of a method as described herein, vectors, a nucleic acid sequence that inhibits MHC gene expression (e.g., a RANi or gRNA molecule), progenitor cells, means for isolating progenitor cells (e.g., marked antibodies specific for progenitor cell surface markers), cytokines, growth factors, and/or estrogen agonists, and the like. A kit can further comprise devices and/or reagents for delivery of the composition as described herein. Additionally, the kit may comprise an instruction leaflet and/or may provide information as to the relevance of the obtained results.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphatylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. the activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M), (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the invention. Further, all patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1. An in vitro method for generating universal MHC/HLA-compatible hematopoietic progenitor cells, said method comprising the steps of:
   a) contacting isolated progenitor cells with a fusion protein selected from a homeotic (HOX) oncoprotein or a mixed-lineage leukemia (MLL) oncoprotein, wherein said isolated progenitor cells are progenitor cells that give rise to subsets of mature blood cells,
   b) disrupting antigen presentation by the cell by down-regulating gene expression of a major histocompatibility complex (MHC, also called the human leukocyte antigen (HLA)) gene expression in the cell; and
   c) culturing the progenitor cells of step b) with a combination of multilineage cytokines comprising steal-cell factor (SCF), Flt3 ligand, IL-3, TPO and IL-6, whereupon culturing, the progenitor cells become immortalized and exhibit commitment to neutrophil, macrophage, and/or dendritic lineage or exhibit multi-lineage blood cell differentiation potential.
2. The in vitro method of paragraph 1, wherein the contacting of step a) comprises:
   i) co-culture in in vitro with a fusion protein comprising a HOX oncoprotein and a TAT domain, wherein the TAT is fused to the N-terminus of the HOX oncoprotein;
   ii) co-culture in in vitro with a fusion protein comprising a (MLL) oncoprotein and a TAT domain, wherein the TAT is fused to the N-terminus of the HOX oncoprotein;
   iii) infecting the progenitor cells with a vector comprising a nucleic acid sequence which encodes the fusion protein comprising a HOX oncoprotein and an estrogen receptor binding domain (ERBD), wherein the ERBD is fused to the N-terminus of the HOX oncoprotein; or
   iv) infecting the progenitor cells with a vector comprising a nucleic acid sequence which encodes the fusion protein comprising a MLL oncoprotein and an estrogen receptor binding domain (ERBD), wherein the ERBD is fused to the N-terminus of the MLL oncoprotein.
3. The in vitro method of paragraph 1 or 2, wherein the HOX oncoprotein is 1HoxB4 or HoxB8.
4. The in vitro method of paragraph 1, 2 or 3, wherein the fusion HOX oncoprotein is a recombinant TAT-HoxB8, a recombinant TAT-HoxB4, recombinant ERBD-HoxB8, or a recombinant ERBD-HoxB4.
5. The in vitro method of any one of paragraphs 1-4, wherein the vector for the fusion protein is a retroviral vector.
6. The in vitro method of any one of paragraphs 1-5, further culturing the cells in the presence in an estrogen agonist when the fusion oncoprotein is an ERBD fusion oncoprotein.
7. The in vitro method of any one of paragraphs 1-6, wherein the down-regulation of a MHC gene expression comprises infecting the progenitor cells with a second vector comprising a nucleic acid sequence that inhibits the MHC gene expression.
8. The in vitro method of any one of paragraphs 1-7, wherein the targeted gene that is inhibited or disrupted from expressing is a MHC/HLA class I gene or β2 microglobulin gene.
9. The in vitro method of paragraph 8, wherein the MHC/HLA class I gene encodes HLA-A, HLA-B, HLA-C.
10. The in vitro method of any one of paragraph 7-9, wherein the nucleic acid sequence is an RNA interference (RNAi) molecule or a CRISPR-mediated guide RNA (gRNA) molecule.
11. The in vitro method of paragraph 10, wherein the RNAi or gRNA molecule corresponding to a gene encoding a MHC class I gene or β2 microglobulin gene, wherein the RNAi or gRNA molecule is expressed and initiates RNA interference of expression of the MHC/HLA class I gene or β2 microglobulin gene, thereby down-regulating expression of the MHC/HLA class I gene or β2 microglobulin gene and disrupting antigen presentation.
12. The in vitro method of paragraph 10, wherein the gRNA molecule corresponding to a gene encoding a MHC class I gene or β2 microglobulin gene, wherein the gRNA molecule is expressed and initiates gene editing to disrupt the MHC class I gene or β2 microglobulin gene, thereby down-regulating expression of the MHC gene and disrupting antigen presentation.
13. The in vitro method of any of paragraphs 7-12, wherein the second vector is a retroviral vector.
14. The in vitro method of any of paragraphs 7-12, wherein the promoter of the second vector is a U6 Pol III promoter.
15. The in vitro method of any of paragraphs 10-14, wherein the RNAi molecule comprises a DNA sequence selected from SEQ ID NOs: 22-30.
16. The in vitro method of any of paragraphs 10-14, wherein the gRNA molecule comprises DNA sequence selected from SEQ ID NOs: 7-21.
17. The in vitro method of any of paragraphs 1-16, wherein the isolated progenitor cells are granulocyte-macrophage progenitor cells (GMP).
18. The in vitro method of any of paragraphs 1-16, wherein the isolated progenitor cells are mononuclear cells (MN).
19. The in vitro method of any of paragraphs 1-18, wherein the isolated progenitor cells are isolated from bone marrow, peripheral blood, placenta, or umbilical cord of a donor subject.
20. A composition comprising universal MHC/HLA-compatible hematopoietic progenitor cells produced by the method of paragraph 1.
21. A method of treating a pathogen infection in a subject, said method comprising administering a composition of paragraph 20.
22. An in vitro method for generating custom MHC/HLA-compatible hematopoietic progenitor cells for a recipient subject, said method comprising the steps of:
   a) contacting isolated MHC/HLA-compatible progenitor cells with a fusion protein selected from a homeotic (HOX) oncoprotein or a mixed-lineage leukemia (MLL) oncoprotein, wherein said isolated progenitor cells are progenitor cells that give rise to subsets of mature blood cells; and
   b) culturing the progenitor cells of step a) with a combination of multilineage cytokines comprising of stem-cell factor (SCF), Flt3 ligand, IL-3, TPO and IL-6, whereupon culturing, the progenitor cells become immortalized and exhibit commitment to neutrophil, macrophage, and/or dendritic lineage or exhibit multi lineage blood cell differentiation potential.

23. The in vitro method of paragraph 22, wherein the contacting of step a) comprises:
 i) co-culture in in vitro with a fusion protein comprising a HOX oncoprotein and a TAT domain, wherein the TAT is fused to the N-terminus of the HOX oncoprotein,
 ii) co-culture in in vitro with a fusion protein comprising a (MLL) oncoprotein and a TAT domain, wherein the TAT is fused to the N-terminus of the HOX oncoprotein;
 iii) infecting the progenitor cells with a vector comprising a nucleic acid sequence which encodes the fusion protein comprising a HOX oncoprotein and an estrogen receptor binding domain (ERBD), wherein the ERBD is fused to the N-terminus of the HOX oncoprotein; or
 iv) infecting the progenitor cells with a vector comprising a nucleic acid sequence which encodes the fusion protein comprising a MLL oncoprotein and an estrogen receptor binding domain (ERBD), wherein the ERBD is fused to the N-terminus of the MLL oncoprotein.
24. The in vitro method of paragraph 22 or 23, wherein the HOX oncoprotein is HoxB4 or HoxB8.
25. The in vitro method of paragraph 22, 23 or 24, wherein the fusion HOX oncoprotein is a recombinant TAT-HoxB8, a recombinant TAT-HoxB4, recombinant ERBD-HoxB8, or a recombinant ERBD-HoxB4.
26. The in vitro method of any one of paragraphs 22-25, wherein the vector for the fusion protein is a retroviral vector.
27. The in vitro method of any one of paragraphs 22-26, further culturing the cells in the presence in an estrogen agonist when the fusion oncoprotein is an ERBD fusion oncoprotein.
28. The in vitro method of any of paragraphs 22-27, wherein the isolated MHC/HLA-compatible progenitor cells are granulocyte-macrophage progenitor cells (GMP).
29. The in vitro method of any of paragraphs 22-27, wherein the isolated MHC/HLA-compatible progenitor cells are mononuclear cells (MN).
30. The in vitro method of any of paragraphs 22-29, wherein the isolated MHC/HLA-compatible progenitor cells are isolated from bone marrow, peripheral blood, placenta, or umbilical cord of a donor subject.
31. A composition comprising customized, patient-specific MHC/HLA-compatible hematopoietic progenitor cells produced by the method of paragraph 30.
32. A method of treating neutropenia in a subject, said method comprising administering a composition of paragraph 31.

Some embodiments of the technology described herein can be defined according to any of the following numbered paragraphs:

1. An in vitro method for generating universal MHC/HLA-compatible hematopoietic progenitor cells, said method comprising the steps of:
 a) contacting isolated progenitor cells with a fusion protein comprising a homeotic (HOX) oncoprotein and/or a mixed-lineage leukemia (MLL) oncoprotein, wherein said isolated progenitor cells are progenitor cells that give rise to subsets of mature blood cells,
 b) disrupting antigen presentation by the cell by downregulating gene expression of a major histocompatibility complex (MHC, also called the human leukocyte antigen (HLA)) gene expression in the cell; and
 c) culturing the progenitor cells of step b) with a combination of multilineage cytokines comprising stem-cell factor (SCF), Flt3 ligand, IL-3, TPO and IL-6, whereupon culturing, the progenitor cells become immortalized and exhibit commitment to neutrophil, macrophage, and/or dendritic lineage or exhibit multi-lineage blood cell differentiation potential.
2. The method of paragraph 1, wherein the fusion protein comprises:
 an N-terminal cell-penetration peptide or an N-terminal conditional control domain; and
 a C-terminal homeotic (HOX) oncoprotein and/or a mixed-lineage leukemia (MLL) oncoprotein.
3. The in vitro method of paragraph 1, wherein the contacting of step a) comprises:
 i) co-culture in in vitro with a fusion protein comprising a HOX oncoprotein and a TAT domain, wherein the TAT is fused to the N-terminus of the HOX oncoprotein;
 ii) co-culture in in vitro with a fusion protein comprising a MLL oncoprotein and a TAT domain, wherein the TAT is fused to the N-terminus of the MLL oncoprotein;
 iii) infecting the progenitor cells with a vector comprising a nucleic acid sequence which encodes the fusion protein comprising a HOX oncoprotein and an estrogen receptor binding domain (ERBD), wherein the ERBD is fused to the N-terminus of the HOX oncoprotein;
 iv) infecting the progenitor cells with a vector comprising a nucleic acid sequence which encodes the fusion protein comprising a MLL oncoprotein and an estrogen receptor binding domain (ERBD), wherein the ERBD is fused to the N-terminus of the MLL oncoprotein;
 v) contacting the progenitor cells with a modified RNA comprising a nucleic acid sequence which encodes the fusion protein comprising a HOX oncoprotein and an estrogen receptor binding domain (ERBD), wherein the ERBD is fused to the N-terminus of the HOX oncoprotein; or
 vi) contacting the progenitor cells with a modified RNA comprising a nucleic acid sequence which encodes the fusion protein comprising a MLL oncoprotein and an estrogen receptor binding domain (ERBD), wherein the ERBD is fused to the N-terminus of the MLL oncoprotein.
4. The in vitro method of any of paragraphs 1-3, wherein the HOX oncoprotein is HoxB4 or HoxB8.
5. The in vitro method of any of paragraphs 1-4 wherein the fusion HOX oncoprotein is a recombinant TAT-HoxB8, a recombinant TAT-HoxB4, recombinant ERBD-HoxB8, or a recombinant ERBD-HoxB4.
6. The in vitro method of any one of paragraphs 1-5, wherein the vector for the fusion protein is a retroviral vector.

7. The in vitro method of any one of paragraphs 1-6, wherein the fusion protein has the sequence of one of SEQ ID NO:s 1 or 2.
8. The in vitro method of any one of paragraphs 1-7, further culturing the cells in the presence of an estrogen agonist when the fusion oncoprotein is an ERBD fusion oncoprotein.
9. The in vitro method of any one of paragraphs 1-8, wherein the down-regulation of a MHC gene expression comprises infecting the progenitor cells with a second vector comprising a nucleic acid sequence that inhibits the MHC gene expression.
10. The in vitro method of any one of paragraphs 1-9, wherein the targeted gene that is inhibited or disrupted from expressing is a MHC/HLA class I gene or β2 microglobulin gene.
11. The in vitro method of paragraph 8, wherein the MHC/HLA class I gene encodes HLA-A, HLA-B, HLA-C.
12. The in vitro method of any one of paragraph 9-11, wherein the nucleic acid sequence is an RNA interference (RNAi) molecule or a CRISPR-mediated guide RNA (gRNA) molecule.
13. The in vitro method of paragraph 12, wherein the RNAi or gRNA molecule corresponds to a gene encoding a MHC class I gene or β2 microglobulin gene,
    wherein the RNAi or gRNA molecule is expressed and initiates RNA interference of expression of the MHC/HLA class I gene or β2 microglobulin gene, thereby down-regulating expression of the MHC/HLA class I gene or β2 microglobulin gene and disrupting antigen presentation.
14. The in vitro method of paragraph 121, wherein the gRNA molecule corresponds to a gene encoding a MHC class I gene or β2 microglobulin gene,
    wherein the gRNA molecule is expressed and initiates gene editing to disrupt the MHC class I gene or β2 microglobulin gene, thereby down-regulating expression of the MHC gene and disrupting antigen presentation.
15. The in vitro method of any of paragraphs 9-14, wherein the second vector is a retroviral vector.
16. The in vitro method of any of paragraphs 9-14, wherein the promoter of the second vector is a U6 Pol III promoter.
17. The in vitro method of any of paragraphs 12-16, wherein the RNAi molecule comprises a DNA sequence selected from SEQ ID NOs: 22-30.
18. The in vitro method of any of paragraphs 12-16, wherein the sRNA molecule comprises DNA sequence selected from SEQ ID NOs: 7-21 and 37-45.
19. The in vitro method of any of paragraphs 1-18, wherein the isolated progenitor cells are granulocyte-macrophage progenitor cells (GMP).
20. The in vitro method of any of paragraphs 1-18, wherein the isolated progenitor cells are mononuclear cells (MN).
21. The in vitro method of any of paragraphs 1-20, wherein the isolated progenitor cells are isolated from hone marrow, peripheral blood, placenta, or umbilical cord of a donor subject.
22. A composition comprising universal MHC/HLA-compatible hematopoietic progenitor cells produced by the method of any of paragraphs 1-21.
23. The composition of paragraph 22, further comprising a pharmaceutically acceptable carrier.
24. A method of treating a pathogen infection in a subject in need thereof, said method comprising administering a composition of any of paragraphs 22-23.
25. The use of a composition of any of paragraphs 22-23 in the treatment of a pathogen infection in a subject in need thereof.
26. A kit comprising:
    a fusion protein comprising a homeotic (HOX) oncoprotein and/or a mixed-lineage leukemia (MLL) oncoprotein or a nucleic acid sequence encoding said fusion protein.
27. The kit of paragraph 26, wherein the fusion protein comprises:
    an N-terminal cell-penetration peptide or an N-terminal conditional control domain; and
    a C-terminal homeotic (HOX) oncoprotein and/or a mixed-lineage leukemia (MLL) oncoprotein.
28. The kit of paragraph 26, wherein the fusion protein is selected from:
    i) a fusion protein comprising a HOX oncoprotein and a TAT domain, wherein the TAT is fused to the N-terminus of the HOX oncoprotein;
    ii) a fusion protein comprising a MLL oncoprotein and a TAT domain, wherein the TAT is fused to the N-terminus of the MLL oncoprotein;
    iii) a fusion protein comprising a HOX oncoprotein and an estrogen receptor binding domain (ERBD), wherein the ERBD is fused to the N-terminus of the HOX oncoprotein;
    iv) a fusion protein comprising a MLL oncoprotein and an estrogen receptor binding domain (ERBD), wherein the ERBD is fused to the N-terminus of the MLL oncoprotein
    v) a modified RNA comprising a nucleic acid sequence which encodes the fusion protein comprising a HOX oncoprotein and an estrogen receptor binding domain (ERBD), wherein the ERBD is fused to the N-terminus of the HOX oncoprotein; or
    vi) a modified RNA comprising a nucleic acid sequence which encodes the fusion protein comprising a MLL oncoprotein and an estrogen receptor binding domain (ERBD), wherein the ERBD is fused to the N-terminus of the MLL oncoprotein.
29. The kit of any of paragraphs 26-28, wherein the HOX oncoprotein is HoxB4 or HoxB8.
30. The kit of any of paragraphs 26-29, wherein the fusion protein has the sequence of one of SEQ ID NO:s 1 or 2.
31. The kit of any of paragraphs 26-30, wherein a vector comprises the nucleic acid sequence encoding said fusion protein.
32. The kit of paragraph 31, wherein the vector is a retroviral vector.
33. The kit of any of paragraphs 26-32, further comprising a vector comprising a nucleic acid sequence that inhibits MHC gene expression.
34. The kit of paragraph 33, wherein the nucleic acid sequence that inhibits MHC gene expression is a RNAi molecule or gRNA molecule.
35. The kit of any of paragraphs 33-34, wherein the RNAi molecule comprises a DNA sequence selected from SEQ ID NOs: 22-30.
36. The kit of any of paragraphs 33-35, wherein the gRNA molecule comprises DNA sequence selected from SEQ ID NOs: 7-21 and 37-45.

37. The kit of any of paragraphs 33-36, wherein the vector comprising a nucleic acid sequence that inhibits MHC gene expression is a retroviral vector.
38. The kit of any of paragraphs 26-37, further comprising one or more progenitor cells or means for isolating one or more progenitor cells.
39. The kit of paragraph 368, wherein the progenitor cells are granulocyte-macrophage progenitor cells (GMP) or mononuclear cells (MN).
40. The kit of any of paragraphs 26-39, further comprising one or more multilineage cytokines selected from stem-cell factor (SCF), Flt3 ligand, IL-3, TPO and IL-6.
41. The kit of any of paragraphs 26-40, further comprising an estrogen agonist.
42. An in vitro method for generating custom MHC/HLA-compatible hematopoietic progenitor cells for a recipient subject, said method comprising the steps of:
 a) contacting isolated MHC/HLA-compatible progenitor cells with a fusion protein comprising a homeotic (HOX) oncoprotein and/or a mixed-lineage leukemia (MLL) oncoprotein, wherein said isolated progenitor cells are progenitor cells that give rise to subsets of mature blood cells; and
 b) culturing the progenitor cells of step b) with a combination of multilineage cytokines comprising stem-cell factor (SCF), Flt3 ligand, IL-3, TPO and IL-6, whereupon culturing, the progenitor cells become immortalized and exhibit commitment to neutrophil, macrophage, and/or dendritic lineage or exhibit multi-lineage blood cell differentiation potential.
43. The method of paragraph 42, wherein the fusion protein comprises:
 an N-terminal cell-penetration peptide or an N-terminal conditional control domain; and
 a C-terminal homeotic (HOX) oncoprotein and/or a mixed-lineage leukemia (MLL) oncoprotein.
44. The in vitro method of paragraph 42, wherein the contacting of step a) comprises:
 i) co-culture in in vitro with a fusion protein comprising a HOX oncoprotein and a TAT domain, wherein the TAT is fused to the N-terminus of the HOX oncoprotein;
 ii) co-culture in in vitro with a fusion protein comprising a MLL oncoprotein and a TAT domain, wherein the TAT is fused to the N-terminus of the MLL oncoprotein;
 iii) infecting the progenitor cells with a vector comprising a nucleic acid sequence which encodes the fusion protein comprising a HOX oncoprotein and an estrogen receptor binding domain (ERBD), wherein the ERBD is fused to the N-terminus of the HOX oncoprotein;
 iv) infecting the progenitor cells with a vector comprising, a nucleic acid sequence which encodes the fusion protein comprising a MLL oncoprotein and an estrogen receptor binding domain (ERBD), wherein the ERBD is fused to the N-terminus of the MLL oncoprotein;
 v) contacting the progenitor cells with a modified RNA comprising a nucleic acid sequence which encodes the fusion protein comprising a HOX oncoprotein and an estrogen receptor binding domain (ERBD), wherein the ERBD is fused to the N-terminus of the HOX oncoprotein; or
 vi) contacting the progenitor cells with a modified RNA comprising a nucleic acid sequence which encodes the fusion protein comprising a MLL oncoprotein and an estrogen receptor binding domain (ERBD), wherein the ERBD is fused to the N-terminus of the MLL oncoprotein.
45. The in vitro method of any of paragraphs 42-44, wherein the HOX oncoprotein is HoxB4 or HoxB8.
46. The in vitro method of any of paragraphs 42-45, wherein the fusion HOX oncoprotein is a recombinant TAT-HoxB8, a recombinant TAT-HoxB4, recombinant ERBD-HoxB8, or a recombinant ERBD-HoxB4.
47. The in vitro method of any one of paragraphs 42-46, wherein the vector for the fusion protein is a retroviral vector.
48. The in vitro method of any one of paragraphs 42-47, wherein the fusion protein has the sequence of one of SEQ ID NO:s 1 or 2.
49. The in vitro method of any one of paragraphs 42-48, further culturing the cells in the presence of an estrogen agonist when the fusion oncoprotein is an ERBD fusion oncoprotein.
50. The in vitro method of any of paragraphs 42-49, wherein the isolated progenitor cells are granulocyte-macrophage progenitor cells (GMP).
51. The in vitro method of any of paragraphs 42-50, wherein the isolated progenitor cells are mononuclear cells (MN).
52. The in vitro method of any of paragraphs 42-51, wherein the isolated progenitor cells are isolated from hone marrow, peripheral blood, placenta, or umbilical cord of a donor subject.
53. A composition comprising customized, patient-specific MHC/HLA-compatible hematopoietic progenitor cells produced by the method of any of paragraphs 42-52.
54. The composition of paragraph 53, further comprising a pharmaceutically acceptable carrier.
55. A method of treating a pathogen infection in a subject in need thereof, said method comprising administering a composition of any of paragraphs 53-54.
56. The use of a composition of any of paragraphs 53-54 in the treatment of a pathogen infection in a subject in need thereof.
57. A method of treating neutropenia in a subject in need thereof, said method comprising administering a composition of any of paragraphs 22-23 or 53-54.
58. The use of a composition of any of paragraphs 22-23 or 53-54 in the treatment of neutropenia in a subject in need thereof.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology described herein is further illustrated by the following examples which in no way should be construed as being further limiting.

Example 1

Overview:

There are currently no therapies capable of augmenting and/or amplifying the critical cellular response to assist with controlling and eliminating the offending pathogen. The technology described in this application describes the formation of a universal and adaptable neutrophil cell line that can be administered to any patient for the enhanced elimination of pathogens. The use of this cellular immunotherapy will translate into (a) a more rapid patient recovery, (b) decreased exposure to anti-microbials, and (c) decreased need for advanced life-support.

State-of-the-Art Treatment of Infectious Diseases:

Our current approach to the diagnosis and treatment of patients with infectious complications such as bacterial pneumonia, septic shock, skin and soft tissue infection, fungal infections, etc. is modular and reactive. Currently, if one is capable of identifying the causative pathogen, laboratory-based testing for optimal antimicrobial susceptibility helps to guide the best choice of anti-microbial agent. The remainder of our care remains strictly supportive.

This application outlines a technology to supply a universal neutrophil cell line that can be applied to any patient with infectious diseases to improve clearance and elimination of invasive pathogens. In this manner, one could combine anti-microbial therapy with an enhanced immune response to achieve a more rapid recovery, reduce side effects, and prevent permanent complications. The ability to augment a patient's immune response with additional cellular immunotherapy in the form of a universal neutrophil cell line represents a large unmet need in the area of infectious diseases therapy.

Moreover, the rising burden of multi-drug resistant pathogens often leaves patients without any drug treatment options. An augmented, universal and adaptable neutrophil cell line has the possibility of offering a last resort, life-saving option in those critically ill with multi-drug resistant bacteria or fungal infections.

Barriers to Generating a Universal, Adaptable Neutrophil Cell Line:

Several reasons exist that currently hinder the ability to create a universal neutrophil cell line. These include:

Inability to genetically alter innate immune cells. The most abundant first-responder immune cell to infection is the neutrophil. Unfortunately, these cells are short-lived in the patient as well as in vitro following isolation. For these reasons, there has been very limited success in genetically or functionally modifying neutrophils. This application describes technology that permits immortalization of neutrophils.

Rejection of foreign cells. Host immune systems will not tolerate mis-matched cellular sources due to the recognition of major histocompatibility complexes (MHC) and other major antigens on transferred cells and tissue. This application describes technology that adapts a neutrophil cell line universally by removing major MHC antigens, thus limiting recognition of allo-antigens and subsequent rejection.

Concern for leukemogenic potential of transferred, immortalized neutrophil cells. To mitigate possible leukemogenic potential, this application describes use of suicide gene technology to ensure that all transfused neutrophil cells can be completely eliminated.

Sufficient numbers of cells for treatment. Based on estimates from animal modeling, the numbers of neutrophils required to treat a single patient are in the order of 100-200 billion cells per infusion. For these reasons, a universal cell line that is capable of unlimited growth is optimal to achieve this cell number range.

How Pathogens are Recognized by Neutrophils:

Pathogens (including viruses, bacteria, and fungi) possess unique patterns on their surface. These patterns are termed pathogen-associated molecular patterns or PAMPs. Neutrophils and immune cells have evolved to express a large variety of receptors on their surface that recognize PAMPs; these receptors are termed pattern-recognition receptors or PRRs. The patterns that PRRs recognize are PAMPs.

Once a PRR on a host immune cells recognizes a PAMP, several responses take place. Neutrophils activate, and develop the capacity of phagocytosing or "eating" the pathogen resulting in pathogen degradation and elimination. This activated neutrophil also secretes cytokines and chemokines as a "beacon" to attract and activate additional immune cells. These processes are essential for the clearance of pathogens by immune cells, and all innate immune cells use processes to recognize and remove pathogens.

Process of Generating a Universal Neutrophil Cell Line:

To address these barriers, a technology is described that permits the successful production of a universal, adaptable neutrophil cell line. This builds upon previous work where the inventors have shown the ability to expand, ex vivo, functional immune cells for the purpose of transfusion into patients who are deficient in these cells. The features of this proposal involve the ability to (1) expand, ex vivo, myeloid progenitors to the necessary numbers required to be clinically relevant in patients and (2) to transfuse these cells as progenitors, rather than mature cells into patients. The transfusion at the progenitor stage is an improvement upon previous technologies, as it provides a source of cells that are safer to transfuse, that undergo their final development in vivo, and that undergo exponential expansion in vivo, providing even greater number of terminal effector cells.

1. Immortalized neutrophil cell line
    - a. Myeloid progenitors are immortalized through expression of Hox family protein or MLL fusion protein in GMP or CMP progenitors, ES cells, or iPSC:
        - i. HoxB8—transcriptional factor producing differentiation arrest
        - ii. MLL/AF9 or MLL fusion protein—oncogene resulting in immortalization (upstream of HoxB8)
    - b. Administration of Hox fusion protein (ie. HoxB8) or MLL fusion protein (ie. MLL/AF9)
        - i. Transduction by lentivirus.
        - ii. Stable integrase site. An engineered, stably transfected integrase site allows for integration of HoxB8 or MLL/AF9.
        - iii. TAT-fusion protein as a direct tissue culture supplement (TAT sequence used as a membrane penetrating fusion protein)
    - c. Control of HoxB8 or MLL/AF9 expression
        - i. If used as a TAT-fusion protein, the absence of supplemented TAT-fusion protein will trigger maturation to differentiated neutrophils.
        - ii. if applied through lentiviral transduction or through the stable integrase site, HoxB8 or MLL/AF9 expression will be conditional under the control of the estrogen receptor, where biological activity requires supratherapeutic estradiol or the tetracycline-dependent promoter, where all biological activity only in the presence of tetracycline.

2. Rejection of foreign cells
   a. To avoid rejection of the universal neutrophil cell line, the neutrophil cell line will be adapted to any patient's immune system by removal of MHC and major allo-antigens.
      i. CRISPR/Cas9 elimination of major alto-antigens.
         1. Lentivirus. Cas9 can be transiently expressed by lentiviral transduction and guide-RNA targeting MHC and other major alloantigens for elimination. Given the short-life span in the patient, loss of MHC will have a very limited impact on function.
         2. T-Cas9. Cas9 can be transiently introduced as recombinant TAT-Cas9 fusion protein. Guide-RNA directs endonuclease activity to eliminate alto-antigen.
         3. Either method results in stable, permanent elimination of MHC.
3. Concern for leukemogenic potential
   a. Using suicide gene technology, all generated cells can be completely eliminated by suicide gene inducible activation.
      i. Universal neutrophil cell line is engineered to express herpes thymidine kinase. Administration of ganciclovir will result in the production of toxic metabolites only in cells with herpes thymidine kinase such as the universal neutrophil cell line, which results in complete elimination of any neutrophil cell.
      ii. If ganciclovir cannot be used, the universal neutrophil cell line can undergo radiation exposure at the point of care, which will establish a finite, terminal lifespan of the cell line.
4. In vivo tracking system. For determining the amount of universal neutrophil cell line remaining in patients both PCR and flow cytometry can be used.
   a. PCR of HoxB8 or MLL/AF9 or herpes thymidine kinase will provide a percentage of circulating universal cells that are remaining.
   b. Using flow cytometry, all neutrophils can be isolated using Gr-1+, Mac-1+; of those, universal neutrophil cells are MHC negative whereas a patient's native neutrophils will be MHC positive.

Summary of Current Barriers that are Addressed by the Proposed Invention:

- Despite antimicrobial therapy, infectious complications result in acceptably high rates of mortality and morbidity
- Many patients have a loss of neutrophil effectors or dysfunction neutrophils due to comorbid conditions such as diabetes or the administration of immune modulators such as corticosteroids, which incapacitate their neutrophil activity
- Augmenting neutrophil numbers through the use of a universal, adaptable neutrophil cell line will result in improved survival and rapid elimination of pathogens
- Through the removal of MHC and major alloantigen, the described neutrophil cell line will have minimal alloreactivity and no rejection.
- Concern for leukemogenic potential is mitigated through the expression of a suicide gene, which can eliminate all transfused neutrophil cells.
- The universal, adaptable neutrophil cell line generated by the methods described herein to be applied to any patient with infectious complications.

Proposed Infected Patient Populations to be Treated with Universal Neutrophil Cell Line:

- Sepsis/shock
- Drug-induced neutropenia (marrow toxic agents) or neutrophil dysfunction (immune modulators)
- Autoimmune diseases (lupus, etc) that can result in neutropenia
- Congenital disorders with abnormal neutropenia following
- Severe infection in setting of comorbid diseases such as advanced diabetes
- Radiation injury, which can result in marrow failure
- Any clinical syndrome that results in neutropenia
- Chemotherapy-related neutropenia
- Bone marrow or solid-organ transplant recipients
- Individuals with resistant organisms with limited antimicrobial options
- Any clinical infectious syndrome that can be alleviated by targeted cellular immune therapy Example Therapeutic Scenarios with Universal Neutrophil Cell Line:

- An patient with drug-resistant *Pseudomonas* (grain-negative bacteria) pneumonia is admitted to the intensive care unit (ICU) for respiratory arrest and shock despite antimicrobial therapy (>80% mortality). Universal neutrophils are infused to augment the patient's endogenous cells permitting a more rapid recovery. This scenario augments the patient's own neutrophils numbers by using the universal neutrophil cells for an elevated effector function to clear the offending pathogen.
- A patient with leukemia undergoing bone-marrow transplant currently with no neutrophils (severe neutropenia) is admitted with fevers found to have positive blood cultures with *Candida albicans* (50-70% mortality). Universal neutrophils are infused to an absolute neutrophil number to ensure elimination of the invasive pathogen. This scenario supplements a neutropenic patient with neutrophils to a sufficient number capable of clearing the infecting pathogen.
- A patient drug-induced neutropenia without signs or symptoms of an infection is transfused with universal neutrophils to a minimal absolute number of 500 to prevent infectious complications. This scenario uses supplemented universal neutrophils to raise the numbers to a minimum value for the prevention of infections.

Current State of Leukemia Treatment:

Neutrophils are the most abundant circulating white blood cell and serve as the first line of defense to a variety of infections. In fact, the state of neutropenia (lack of an adequate number of functional neutrophils) is one of the highest risk factors for serious infection. Once patients with neutropenia acquire an infection, the risk of death can be in excess of 40%. While there are multiple causes of neutropenia, one of the most common causes is the use of chemotherapy in the treatment of malignancies, especially in patients who have leukemia or lymphoma.

In patients with aggressive leukemias or lymphomas, the only curative therapy remains an allogeneic stem cell transplant. In the allo-SCT, high-dose chemotherapy is given prior to the infusion of the donor stem cells. This high-dose chemotherapy is termed 'ablative' because its goes is to permanently eliminate all (leukemic/malignant and normal) of the host hem atopoietic cells. The donated stem cells repopulate the bone marrow (a process called engraftment) and generate all the new white blood cells, red blood cells, and platelets in the stem cell recipient. Unfortunately, there is a period of 2-4 weeks between the high-dose chemotherapy and the engraftment of the donor stem cells when the patient's blood counts are all very low.

During this vulnerable period, patients receive red blood cell transfusions and platelet transfusions. However, there is currently means of boosting the white blood cell count, and therefore these patients remain extremely susceptible to infection. Over the last thirty years, many centers have attempted the transfusion of mature neutrophils from a variety of donors (usually family members). These granulocyte transfusions (granulocyte=neutrophil) have unfortunately not been effective despite years of clinical trials. Currently, granulocyte transfusions remain a controversial topic and are not considered the standard of care given their risks and unproven benefit.

Neutrophil Transfusions:

There are several possible reasons why conventional neutrophil transfusions have not been successful. First, neutrophils are very short-lived cells; life span is measured in hours (6-12 hours). Following collection, isolation of neutrophils and transfusion, it is likely that donated neutrophils are functional for a very short period of time. Second, their ability to identify, migrate towards the site of infection, and functionally eliminate pathogens is compromised at the end of their lifespan. Third, to generate a large number of neutrophils, multiple donors are required; neutropenic patients have been reported to receive neutrophil transfusion from over 30 donors. The exposure of immune molecule on the surface of neutrophils from so many donors results in frequent allergic reactions, and, more seriously, "alto-immunization". Allo-immunization leads to difficulties with future transfusions (red blood cell, platelet), and also reduces the likelihood of finding another bone marrow donor if the first stem cell transplant should fail.

Ex vivo Hox-protein generated neutrophil progenitors. The methods and compositions described herein addresses ALL the above issues. Furthermore, the methods and compositions described herein allow one to replace a patient's neutrophils at an early stage, reducing the risk of infection during the period of engraftment.

Process of generating and administrating Hox neutrophil progenitors. Hox proteins are transcription factors that are nominally required during hematopoiesis for the control of marrow development. The presence of high-levels of HoxB8, one of the 39 members, halts development of stem cells at the granulocyte-macrophage progenitor stage (GMP). Within the body, one GMP will generally give rise to 16-32 functional and mature neutrophils.

The proposed process involves taking a very small percentage of the stem cell unit that has been reserved for the stem cell transplant recipient. By using the same stem cell unit—and therefore the same donor—for the process, the risk of additional alloimmunization is eliminated (there is no need for other neutrophil donors other than the already matched bone marrow donor).

These donated stem cells are placed into a bioreactor, a device that circulates warmed media through a lattice structure to support cell growth. The media for the stem cells can be supplemented with cytokines including stem-cell factor (SCF), Flt3 ligand, IL-3, TPO and IL-6. In order to safely increase the levels of HoxB8, the media can be supplemented with recombinant TAT-HoxB8, a fusion protein coupling the TAT penetrating peptide to HoxB8. By increasing intracellular HoxB8 protein levels, stem cells within the bioreactor continue to grow and expand at the GMP stage. At set time points, GMP cells are collected from the bioreactor and prepared for transfusion into the patient. These GMP cells, now in the absence of exogenous TAT-HoxB8, continue to differentiate within the patient into mature neutrophils capable of homing and eliminating pathogens. GMP cells can be transfused for the purpose of reducing infection rates, and can even be administered at higher frequency (even twice or three times per day) if there are signs of active infection, a condition that may require a higher neutrophil number.

The method and compositions described herein can be utilized in treating any clinical syndrome that results in neutropenia. All neutropenia results in a high risk infectious period (high mortality). Leukemia, which a common cause of neutropenia, is specifically contemplated herein as a condition that can be treated according to the methods described herein. Other neutropenic or neutrophil dysfunction conditions include, but not limited to:

- Sepsis/shock
- Drug-induced neutropenia (marrow toxic agents) or neutrophil dysfunction (immune modulators)
- Autoimmune diseases (lupus, etc) that can result in neutropenia
- Congenital disorders with abnormal neutropenia following
- Severe infection in setting of comorbid diseases such as advanced diabetes
- Radiation injury, which can result in marrow failure Highlights and Advantages of the custom patient-specific progenitor cells described herein include the fact that in certain embodiments, alloimmunization is not necessary and/or included. The neutrophil cells derived from the bioreactor can come from the same donor selected for the bone marrow transplant. Because of this single donor scenario, no further "alloimmunization" is required, meaning the chances of matching to another donor in the future remains unlimited. In contrast, other methods that relate to transfusing neutrophils from multiple donors end up alloimmunizing patients making a future bone marrow donor match very difficult. For patients with diabetes who would need their own neutrophils generated, there is no alloimmunization since patient's own neutrophils are expanded.

Furthermore, the neutrophils are longer lived. Transfusion of mature circulating neutrophils from many donors is involved in prior art methods and these cells are very short lived, on the order of hours. Probably for this reason, there is only a modest protective effect. Disclosed herein is transfusion of maturing cells; the cells described herein continue to divide in the patient for a short time increasing the cell number as they become neutrophils therefore provided are higher number and longer lived cells.

Example 2

Figure 9:
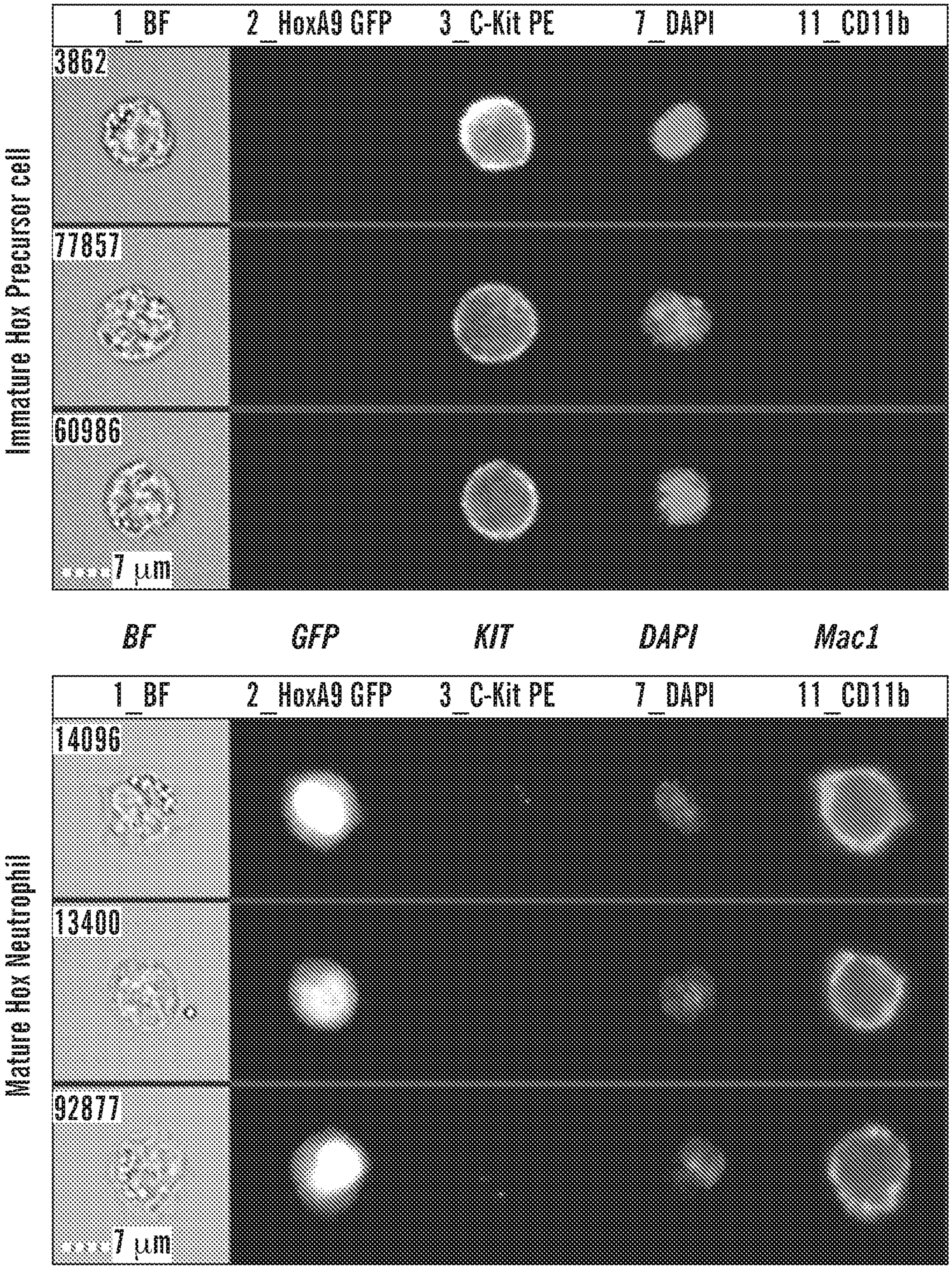
FIG. 9 demonstrates that Hox-derived neutrophils can mature into neutrophils. Depicted is Imagestream™ analysis of Hox cells demonstrating Kit receptor positivity on immature cells (top panel). Kit is a receptor on early precursor cells. Following maturation, the precursor cells now mature into Mac-1 (CD11b) positive cells and have lost Kit expression. This specific Hox cell line also expresses GFP (lower panel) upon maturation into a neutrophil. DAPI is a marker of the nucleus present in both immature and mature cells.

The Hox-derived neutrophils described herein have been demonstrated to mature into neutrophils (FIG. 9). The early Hox-derived neutrophil precursor cells express Kit, but mature into cells which express Mac-1 (CD11b) and which do not express Kit.

Figure 10:
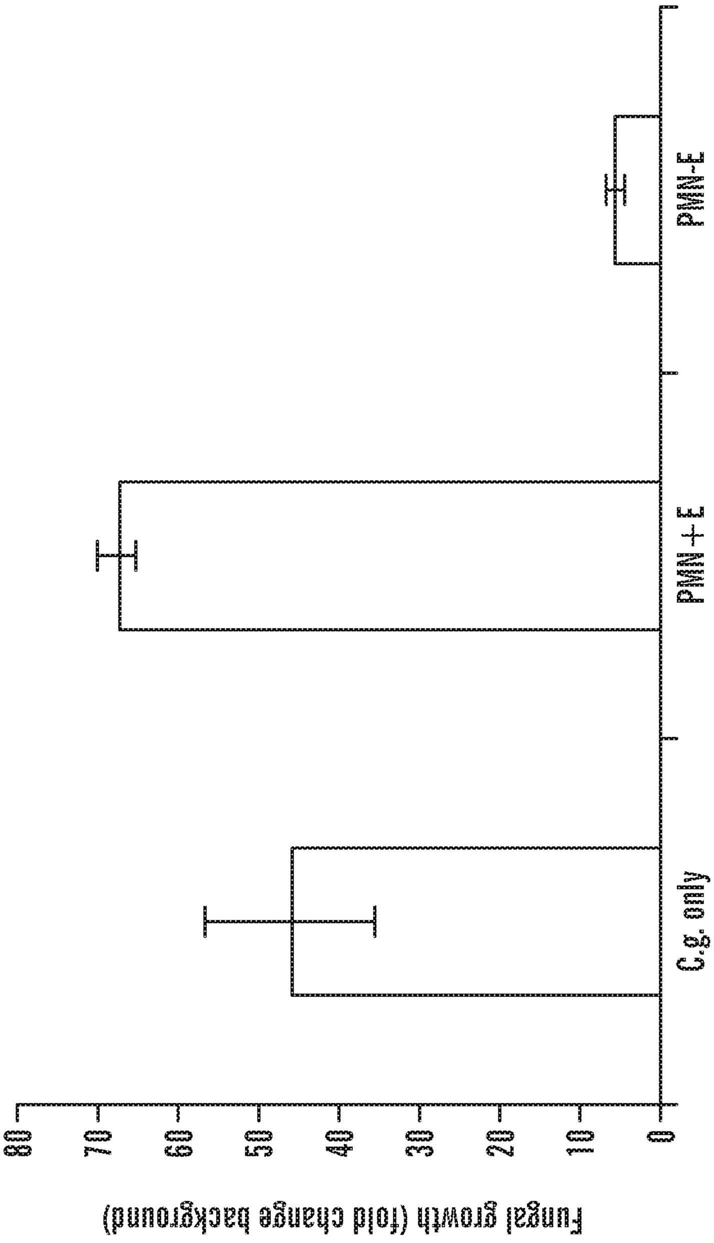
FIG. 10 demonstrates that HoxB8-derived neutrophils are capable of inhibiting the human pathogenic human yeast, *C. glabrata*. The graph depicts the results of a PrestoBlue™ assay measuring fungal metabolic growth and activity. C.g. only=growth of yeast only. PMN+E=immature HoxB8 neutrophil cell line (no killing capacity). PMN−E=matured neutrophil cell line (active killing capacity).
Figure 11:
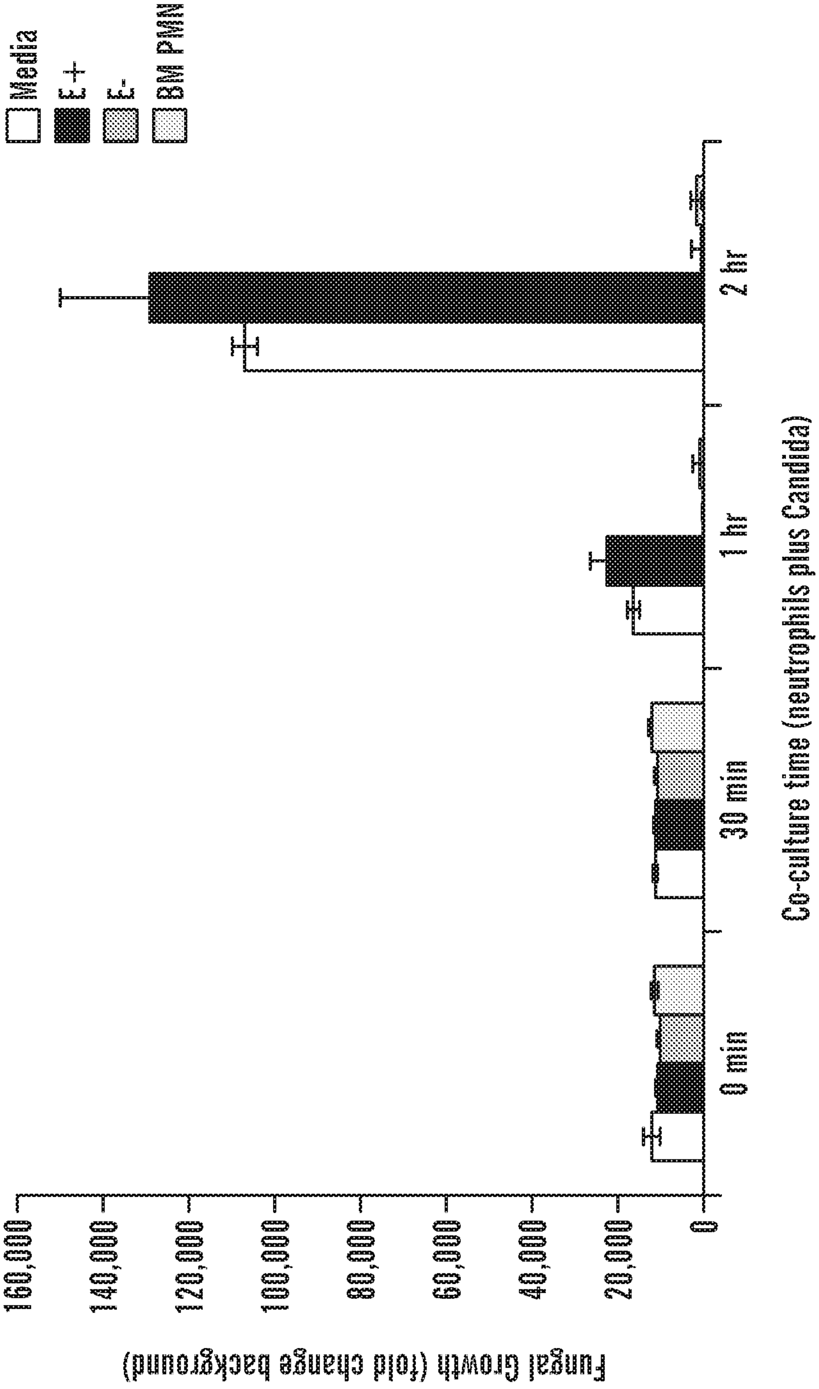
FIG. 11 demonstrates that HoxB8-derived neutrophils are capable of inhibiting the human pathogenic human yeast, *C. albicans*. The graph depicts the results of a PrestoBlue™ assay measuring fungal metabolic growth and activity. Media=yeast only in media. +E=immature HoxB8 neutrophil cell line (no killing capacity). −E=matured neutrophil cell line (active killing capacity). BM PMN=primary bone marrow neutrophils.
Figure 12:
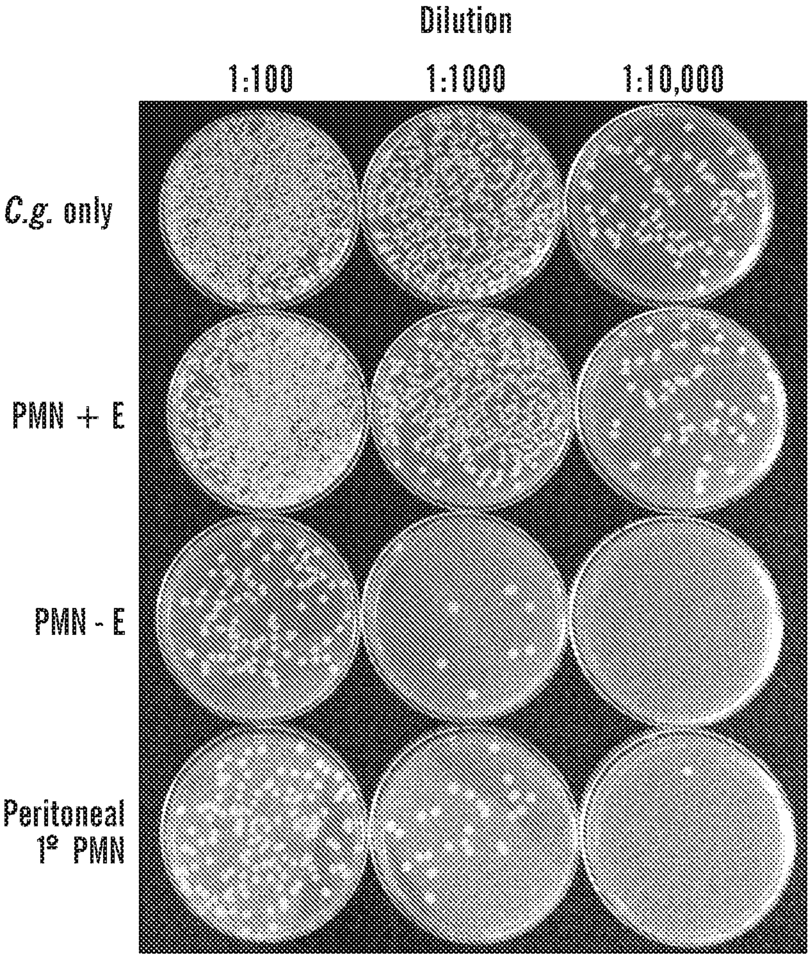
FIG. 12 demonstrates that HoxB8-derived neutrophils are capable of killing the human pathogenic human yeast, *C. glabrata*. Cells were incubated with *C. glabrata* for 24 hours at 37° C., MOI 0.1 followed by lysis of neutrophils. Remaining yeast were diluted and plated on YPD agar. The image shows the number of viable yeast that grew into colonies (each white dot represents a viable yeast). Primary neutrophils and matured HoxB8 neutrophils are capable of fungal killing. C.g. only=growth of yeast only; PMN+E=immature HoxB8 neutrophil cell line (no killing capacity); PMN−E=matured neutrophil cell line (active killing capacity); Peritoneal 1PMN=primary peritoneal neutrophil.
Figure 13:
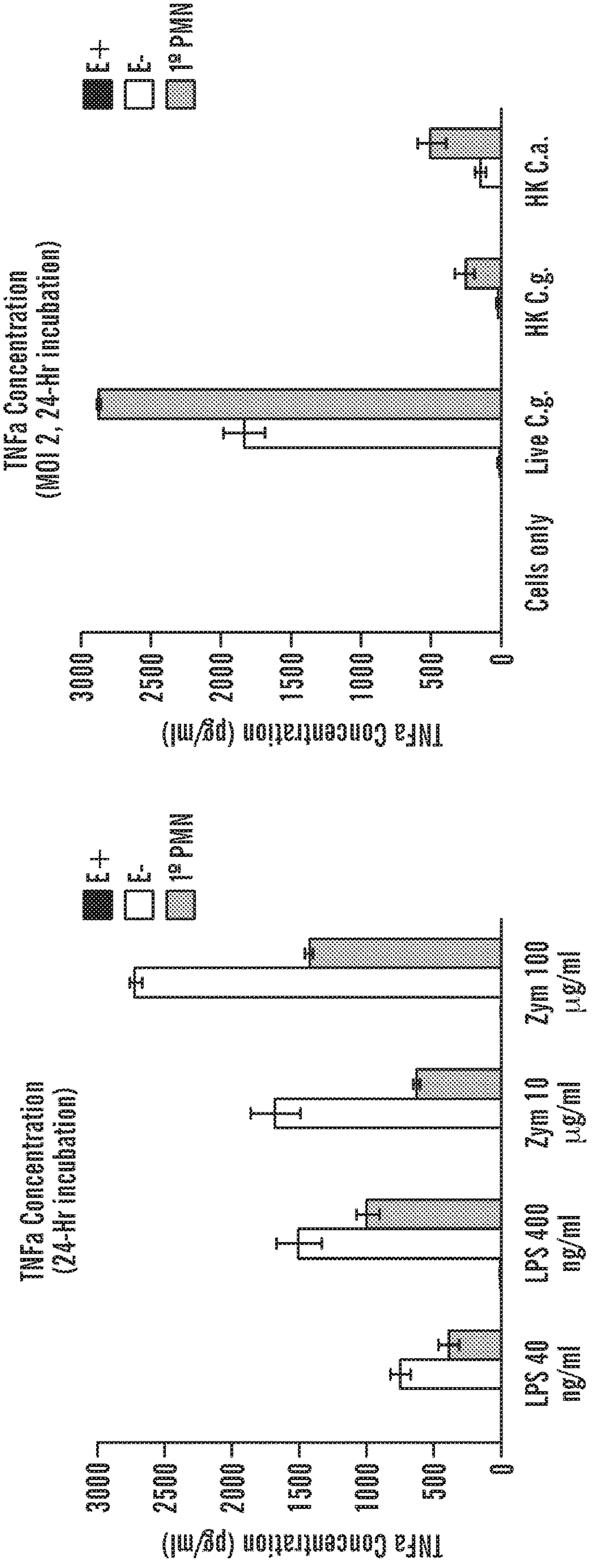
FIG. 13 demonstrates that HoxB8-derived neutrophil can produce the pro-inflammatory cytokine, tumor necrosis factor. LPS=lipopolysaccharide (positive control). Zym=zymosan (crude fungal wall extract), Live C.g.=live *Candida glabrata*, HK C.g.=heat killed *Candida glabrata*, HK C.a.=heat killed *Candida albicans*, MOI=multiplicity of infection (the ratio of pathogen to neutrophil). E+=immature HoxB8 neutrophil cell line (no killing capacity); E−=matured neutrophil cell line (active killing capacity); 1° PMN=primary bone marrow neutrophil.
Figure 14:
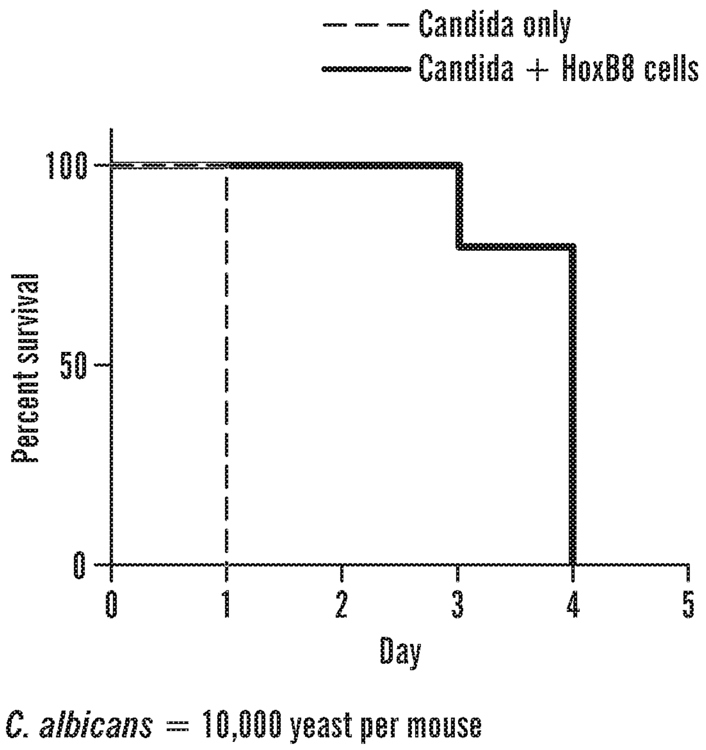
FIG. 14 demonstrates that HoxB8-derived neutrophils are capable prolonging survival in a mouse model of lethal *Candida albicans* challenge. To mimic the neutropenic state, mice were exposed to gamma radiation eliminating all neutrophils. One group did not receive cellular therapy, the other was transfused with 20 million HoxB8 cells 4 days prior to challenge. On day 0 (of the x-axis), all mice were challenged with live *C. albicans* intravenously to model disseminated candidemia. Mice were followed clinically. Mice were rendered neutropenic through the use of gamma radiation (an accepted model of neutropenia). The radiation results in bone marrow failure and given that neutrophils are very short lived, they are eliminated quite quickly. These neutropenic mice are highly susceptible to infection and even 10,000 *candida* yeast injected intravenously results in rapid disease. In group 1, the mice are challenged with *candida* intravenously. Within 24 hrs, there is rapid disease onset, and multi organ failure. In group 2, the mice have been injected intravenously with the HoxB8 cells 4 days prior to challenge. These HoxB8 cells have now matured into neutrophils within the mouse itself. They are challenged intravenously with *candida* at the same time as group 1. There is marked improvement in survival and overall health. For both groups, n=5.

It is further demonstrated herein that the Hox-derived neutrophils display normal neutrophils phagocytosis activity. Using confocal microscopy, it was demonstrated that matured Hox-derived neutrophils recognize and phagocytose pathogenic *E. coli* and pathogenic *C. albicans* (data not shown). Additionally, the matured Hox-derived neutrophils inhibit the growth of *C. albicans* (FIG. 11) and *C. glabrata* (FIG. 10; FIG. 12). The HoxB8-derived neutrophils can also produce TNF (tumor necrosis factor) (FIG. 13).

Finally, the activity of the HoxB8-derived neutrophils was tested in an in vivo survival model. Mice were rendered neutropenic through the use of gamma radiation (an accepted model of neutropenia). The radiation results in bone marrow failure and given that neutrophils are very short lived, they are eliminated quite quickly. These neutropenic mice are highly susceptible to infection and even 10,000 *candida* yeast injected intravenously results in rapid disease. In group 1, the mice were challenged with *candida* intravenously. Within 24 hrs, there was rapid disease onset, and multi organ failure. In group 2, the mice were injected intravenously with the HoxB8 cells 4 days prior to challenge. By the time of challenge with *candida*, the HoxB8 cells have matured into neutrophils within the mouse itself. The group 2 mice were then challenged intravenously with *candida* at the same time as group 1. There is marked improvement in survival and overall health in the mice receiving HoxB8-derived neutrophils. These results demonstrate that HoxB8-derived neutrophils are capable prolonging survival in a mouse model of lethal *Candida albicans* challenge.

The references cited herein and throughout the specification are incorporated herein by reference.

REFERENCES

1. Price T H et. al. Efficacy of transfusion with granulocytes from G-CSF/dexamethasone-treated donors in neutropenic patients with infection. The American Society of Hematology, 61. doi: 10.1182/blood-2015-05-645986. Epub 2015 Sep. 2.
2. Estcourt L J et. al. Granulocyte transfusions for preventing infections in people with neutropenia or neutrophil dysfunction. Cochrane Database Syst Rev. 2015 Jun. 29; 6:CD005341, doi; 10.1002/14651858.CD005341.pub3.

Amino acid sequence for MLL/AF9

SEQ ID NO: 31

MAHSCRWRFPARPGTTGGGGGGGRRGLGGAPRQRVPALLLPPGPPVGGGG

PGAPPSPPAVAAAAAAAGSSGAGVPGGAAAASAASSSSASSSSSSSSSAS

SGPALLRVGPGFDAALQVSAAIGTNLRRFRAVFGESGGGGGSGEDEQFLG

FGSDEEVRVRSPTRSPSVKTSPRKPRGRPRSGSDRNSAILSDPSVFSPLN

KSETKSGDKIKKKDSKSIEKKRGRPPTFPGVKIKITHGKDISELPKGNKE

DSLKKIKRTPSATFQQATKIKKLRAGKLSPLKSKFKTGKLQIGRKGVQIV

RRRGRPPSTERIKTPSGLLINSELEKPQKVRKDKEGTPPLTKEDKTVVRQ

-continued

SPRRIKPVRIIPSSKRTDATIAKQLLQRAKKGAQKKIEKEAAQLQGRKVK

TQVKNIRQFIMPVVSAISSRIIKTPRRFIEDEDYDPPIKIARLESTPNSR

FSAPSCGSSEKSSAASQHSSQMSSDSSRSSSPSVDTSTDSQASEEIQVLP

EERSDTPEVHPPLPLSQSPENESNDRRSRRYSVSERSFGSRTTKKLSTLQ

SAPQQQTSSSPPPPLLTPPPPLQPASSISDHTPWLMPPTIPLASPFLPAS

TAPMQGKRKSILREPTFRWTSLKHSRSEPQYFSSAKYAKEGLIRKPIFDN

FRPPPLTPEDVGFASGFSASGTAASARLFSPLHSGTRFDMHKRSPLLRAP

RFTPSEAHSRIFESVTLPSNRTSAGTSSSGVSNRKRKRKVFSPIRSEPRS

PSHSMRTRSGRLSSSELSPLTPPSSVSSSLSISVSPLATSALNPTFTFPS

HSLTQSGESAEKNQRPRKQTSAPAEPFSSSSPTPLFPWFTPGSQTERGRN

KDKAPEELSKDRDADKSVEKDKSRERDREREKENKRESRKEKRKKGSEIQ

SSSALYPVGRVSKEKVVGEDVATSSSAKKATGRKKSSSHDSGTDITSVTL

GDTTAVKTKILIKKGRGNLEKTNLDLGPTAPSLEKEKTLCLSTPSSSTVK

HSTSSIGSMLAQADKLPMTDKRVASLLKKAKAQLCKIEKSKSLKQTDQPK

AQGQESDSSETSVRGPRIKHVCRRAAVALGRKRAVFPDDMPTLSALPWEE

REKILSSMGNDDKSSIAGSEDAEPLAPPIKPIKPVTRNKAPQEPPVKKGR

RSRRCGQCPGCQVPEDCGVCTNCLDKPKFGGRNIKKQCCKMRKCQNLQWM

PSKAYLQKQAKAVKKKEKKSKTSEKKDSKESSVVKNVVDSSQKPTPSARE

DPAPKKSSSEPPPRKPVEEKSEEGNVSAPGPESKQATTPASRKSSKQNSQ

PALVIPPQPPTTGPPRKEVPKTTPSEPKKKQPPPPESGPEQSKQKKVAPR

PSIPVKQKPKEKEKPPPVNKQENAGTLNILSTLSNGNSSKQKIPADGVHR

IRVDFKEDCEAENVWEMGGLGILEVKSPIKQSKSDKQIKNGECDKAYLDE

LVELHRRLMTLRERHILQQIVNLIEETGHFHITNTTFDFDLCSLDKTTVR

KLQSYLETSGTS

Amino acid sequence for HoxB8

SEQ ID NO: 32

MSSYFVNSLFSKYKTGESLRPNYYDCGFAQDLGGRPTVVYGPSSGGSFQH

PSQIQEFYHGPSSLSTAPYQQNPCAVACHGDPGNFYGYDPLQRQSLFGAQ

DPDLVQYADCKLAAASGLGEEAEGSEQSPSPTQLFPWMRPQAAAGRRRGR

QTYSRYQTLELEKEFLFNPYLTRKRRIEVSHALGLTERQVKIWFQNRRMK

WKKENNKDKFPSSKCEQEELEKQKLERAPEAADEGDAQKGDKK

What is claimed is:

1. A method of treating a pathogen infection in a subject in need thereof, said method comprising:

a) generating custom MHC/HLA-compatible hematopoietic progenitor cells for the subject, said generating comprising the steps of:

i) a contacting step, wherein the contacting step consists of contacting isolated MHC/HLA-compatible progenitor cells with a fusion protein consisting of a N-terminal cell-penetration peptide and a C-terminal a mixed-lineage leukemia (MLL) oncoprotein, the fusion protein having the sequence of SEQ ID NO: 1;

wherein said isolated progenitor cells are:

progenitor cells that give rise to subsets of mature blood cells; and isolated from bone marrow, peripheral blood, placenta, or umbilical cord of a donor subject; and ii) a culturing step, wherein the culturing step comprises the progenitor cells of step i) with a combination of multilineage cytokines comprising stem-cell factor (SCF), Flt3 ligand, IL-3, TPO and IL-6, whereupon culturing, the progenitor cells become immortalized and exhibit commitment to neutrophil, macrophage, and/or dendritic lineage or exhibit multi-lineage blood cell differentiation potential;

b) administering the cells resulting from step a) to the subject.

2. The method of claim 1, wherein the isolated progenitor cells are granulocyte-macrophage progenitor cells (GMP).

3. The method of claim 1, wherein the isolated progenitor cells are mononuclear cells (MN).

* * * * *

UNITED STATES PATENT AND TRADEMARK OFFICE

CERTIFICATE OF CORRECTION

PATENT NO. : 11,564,942 B2
APPLICATION NO. : 15/999463
DATED : January 31, 2023
INVENTOR(S) : Michael K. Mansour, David B. Sykes and David T. Scadden It is certified that error appears in the above-identified patent and that said Letters Patent is hereby corrected as shown below:

In the Specification

Column 1, immediately following Line 15 and preceding Line 16, insert the following new heading and paragraph:
-- STATEMENT REGARDING FEDERALLY SPONSORED RESEARCH OR DEVELOPMENT
This invention was made with government support under AI110655 awarded by the National Institutes of Health. The government has certain rights in the invention. --

Signed and Sealed this
Twenty-eighth Day of February, 2023

Katherine Kelly Vidal

Katherine Kelly Vidal
*Director of the United States Patent and Trademark Office*

SEQUENCE LISTING

```
<160> NUMBER OF SEQ ID NOS: 56

<210> SEQ ID NO 1
<211> LENGTH: 4556
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Tyr Gly Arg Lys Lys Arg Arg Gln Arg Arg Arg Gly Gly Gly Gly Ser
1               5                   10                  15
```

-continued

```
Met Ala His Ser Cys Arg Trp Arg Phe Pro Ala Arg Pro Gly Thr Thr
            20                  25                  30

Gly Gly Gly Gly Gly Gly Gly Arg Arg Gly Leu Gly Gly Ala Pro Arg
        35                  40                  45

Gln Arg Val Pro Ala Leu Leu Leu Pro Pro Gly Pro Pro Val Gly Gly
    50                  55                  60

Gly Gly Pro Gly Ala Pro Pro Ser Pro Pro Ala Val Ala Ala Ala Ala
65                  70                  75                  80

Ala Ala Ala Gly Ser Ser Gly Ala Gly Val Pro Gly Gly Ala Ala Ala
                85                  90                  95

Ala Ser Ala Ala Ser Ser Ser Ser Ala Ser Ser Ser Ser Ser Ser Ser
            100                 105                 110

Ser Ser Ala Ser Ser Gly Pro Ala Leu Leu Arg Val Gly Pro Gly Phe
        115                 120                 125

Asp Ala Ala Leu Gln Val Ser Ala Ala Ile Gly Thr Asn Leu Arg Arg
    130                 135                 140

Phe Arg Ala Val Phe Gly Glu Ser Gly Gly Gly Gly Gly Ser Gly Glu
145                 150                 155                 160

Asp Glu Gln Phe Leu Gly Phe Gly Ser Asp Glu Glu Val Arg Val Arg
                165                 170                 175

Ser Pro Thr Arg Ser Pro Ser Val Lys Thr Ser Pro Arg Lys Pro Arg
            180                 185                 190

Gly Arg Pro Arg Ser Gly Ser Asp Arg Asn Ser Ala Ile Leu Ser Asp
        195                 200                 205

Pro Ser Val Phe Ser Pro Leu Asn Lys Ser Glu Thr Lys Ser Gly Asp
    210                 215                 220

Lys Ile Lys Lys Lys Asp Ser Lys Ser Ile Glu Lys Lys Arg Gly Arg
225                 230                 235                 240

Pro Pro Thr Phe Pro Gly Val Lys Ile Lys Ile Thr His Gly Lys Asp
                245                 250                 255

Ile Ser Glu Leu Pro Lys Gly Asn Lys Glu Asp Ser Leu Lys Lys Ile
            260                 265                 270

Lys Arg Thr Pro Ser Ala Thr Phe Gln Gln Ala Thr Lys Ile Lys Lys
        275                 280                 285

Leu Arg Ala Gly Lys Leu Ser Pro Leu Lys Ser Lys Phe Lys Thr Gly
    290                 295                 300

Lys Leu Gln Ile Gly Arg Lys Gly Val Gln Ile Val Arg Arg Arg Gly
305                 310                 315                 320

Arg Pro Pro Ser Thr Glu Arg Ile Lys Thr Pro Ser Gly Leu Leu Ile
                325                 330                 335

Asn Ser Glu Leu Glu Lys Pro Gln Lys Val Arg Lys Asp Lys Glu Gly
            340                 345                 350

Thr Pro Pro Leu Thr Lys Glu Asp Lys Thr Val Val Arg Gln Ser Pro
        355                 360                 365

Arg Arg Ile Lys Pro Val Arg Ile Ile Pro Ser Ser Lys Arg Thr Asp
    370                 375                 380

Ala Thr Ile Ala Lys Gln Leu Leu Gln Arg Ala Lys Lys Gly Ala Gln
385                 390                 395                 400

Lys Lys Ile Glu Lys Glu Ala Ala Gln Leu Gln Gly Arg Lys Val Lys
                405                 410                 415

Thr Gln Val Lys Asn Ile Arg Gln Phe Ile Met Pro Val Val Ser Ala
            420                 425                 430
```

-continued

```
Ile Ser Ser Arg Ile Ile Lys Thr Pro Arg Arg Phe Ile Glu Asp Glu
        435                 440                 445

Asp Tyr Asp Pro Pro Ile Lys Ile Ala Arg Leu Glu Ser Thr Pro Asn
    450                 455                 460

Ser Arg Phe Ser Ala Pro Ser Cys Gly Ser Ser Glu Lys Ser Ser Ala
465                 470                 475                 480

Ala Ser Gln His Ser Ser Gln Met Ser Ser Asp Ser Ser Arg Ser Ser
                485                 490                 495

Ser Pro Ser Val Asp Thr Ser Thr Asp Ser Gln Ala Ser Glu Glu Ile
            500                 505                 510

Gln Val Leu Pro Glu Glu Arg Ser Asp Thr Pro Glu Val His Pro Pro
        515                 520                 525

Leu Pro Ile Ser Gln Ser Pro Glu Asn Glu Ser Asn Asp Arg Arg Ser
    530                 535                 540

Arg Arg Tyr Ser Val Ser Glu Arg Ser Phe Gly Ser Arg Thr Thr Lys
545                 550                 555                 560

Lys Leu Ser Thr Leu Gln Ser Ala Pro Gln Gln Gln Thr Ser Ser Ser
                565                 570                 575

Pro Pro Pro Pro Leu Leu Thr Pro Pro Pro Pro Leu Gln Pro Ala Ser
            580                 585                 590

Ser Ile Ser Asp His Thr Pro Trp Leu Met Pro Pro Thr Ile Pro Leu
        595                 600                 605

Ala Ser Pro Phe Leu Pro Ala Ser Thr Ala Pro Met Gln Gly Lys Arg
    610                 615                 620

Lys Ser Ile Leu Arg Glu Pro Thr Phe Arg Trp Thr Ser Leu Lys His
625                 630                 635                 640

Ser Arg Ser Glu Pro Gln Tyr Phe Ser Ser Ala Lys Tyr Ala Lys Glu
                645                 650                 655

Gly Leu Ile Arg Lys Pro Ile Phe Asp Asn Phe Arg Pro Pro Pro Leu
            660                 665                 670

Thr Pro Glu Asp Val Gly Phe Ala Ser Gly Phe Ser Ala Ser Gly Thr
        675                 680                 685

Ala Ala Ser Ala Arg Leu Phe Ser Pro Leu His Ser Gly Thr Arg Phe
    690                 695                 700

Asp Met His Lys Arg Ser Pro Leu Leu Arg Ala Pro Arg Phe Thr Pro
705                 710                 715                 720

Ser Glu Ala His Ser Arg Ile Phe Glu Ser Val Thr Leu Pro Ser Asn
                725                 730                 735

Arg Thr Ser Ala Gly Thr Ser Ser Ser Gly Val Ser Asn Arg Lys Arg
            740                 745                 750

Lys Arg Lys Val Phe Ser Pro Ile Arg Ser Glu Pro Arg Ser Pro Ser
        755                 760                 765

His Ser Met Arg Thr Arg Ser Gly Arg Leu Ser Ser Ser Glu Leu Ser
    770                 775                 780

Pro Leu Thr Pro Pro Ser Ser Val Ser Ser Ser Leu Ser Ile Ser Val
785                 790                 795                 800

Ser Pro Leu Ala Thr Ser Ala Leu Asn Pro Thr Phe Thr Phe Pro Ser
                805                 810                 815

His Ser Leu Thr Gln Ser Gly Glu Ser Ala Glu Lys Asn Gln Arg Pro
            820                 825                 830

Arg Lys Gln Thr Ser Ala Pro Ala Glu Pro Phe Ser Ser Ser Ser Pro
        835                 840                 845

Thr Pro Leu Phe Pro Trp Phe Thr Pro Gly Ser Gln Thr Glu Arg Gly
```

-continued

```
    850                 855                 860

Arg Asn Lys Asp Lys Ala Pro Glu Glu Leu Ser Lys Asp Arg Asp Ala
865                 870                 875                 880

Asp Lys Ser Val Glu Lys Asp Lys Ser Arg Glu Arg Asp Arg Glu Arg
                885                 890                 895

Glu Lys Glu Asn Lys Arg Glu Ser Arg Lys Glu Lys Arg Lys Lys Gly
            900                 905                 910

Ser Glu Ile Gln Ser Ser Ser Ala Leu Tyr Pro Val Gly Arg Val Ser
        915                 920                 925

Lys Glu Lys Val Val Gly Glu Asp Val Ala Thr Ser Ser Ser Ala Lys
    930                 935                 940

Lys Ala Thr Gly Arg Lys Lys Ser Ser Ser His Asp Ser Gly Thr Asp
945                 950                 955                 960

Ile Thr Ser Val Thr Leu Gly Asp Thr Thr Ala Val Lys Thr Lys Ile
                965                 970                 975

Leu Ile Lys Lys Gly Arg Gly Asn Leu Glu Lys Thr Asn Leu Asp Leu
            980                 985                 990

Gly Pro Thr Ala Pro Ser Leu Glu  Lys Glu Lys Thr Leu  Cys Leu Ser
        995                 1000                1005

Thr Pro  Ser Ser Ser Thr Val  Lys His Ser Thr Ser  Ser Ile Gly
    1010                1015                1020

Ser Met  Leu Ala Gln Ala Asp  Lys Leu Pro Met Thr  Asp Lys Arg
    1025                1030                1035

Val Ala  Ser Leu Leu Lys Lys  Ala Lys Ala Gln Leu  Cys Lys Ile
    1040                1045                1050

Glu Lys  Ser Lys Ser Leu Lys  Gln Thr Asp Gln Pro  Lys Ala Gln
    1055                1060                1065

Gly Gln  Glu Ser Asp Ser Ser  Glu Thr Ser Val Arg  Gly Pro Arg
    1070                1075                1080

Ile Lys  His Val Cys Arg Arg  Ala Ala Val Ala Leu  Gly Arg Lys
    1085                1090                1095

Arg Ala  Val Phe Pro Asp Asp  Met Pro Thr Leu Ser  Ala Leu Pro
    1100                1105                1110

Trp Glu  Glu Arg Glu Lys Ile  Leu Ser Ser Met Gly  Asn Asp Asp
    1115                1120                1125

Lys Ser  Ser Ile Ala Gly Ser  Glu Asp Ala Glu Pro  Leu Ala Pro
    1130                1135                1140

Pro Ile  Lys Pro Ile Lys Pro  Val Thr Arg Asn Lys  Ala Pro Gln
    1145                1150                1155

Glu Pro  Pro Val Lys Lys Gly  Arg Arg Ser Arg Arg  Cys Gly Gln
    1160                1165                1170

Cys Pro  Gly Cys Gln Val Pro  Glu Asp Cys Gly Val  Cys Thr Asn
    1175                1180                1185

Cys Leu  Asp Lys Pro Lys Phe  Gly Gly Arg Asn Ile  Lys Lys Gln
    1190                1195                1200

Cys Cys  Lys Met Arg Lys Cys  Gln Asn Leu Gln Trp  Met Pro Ser
    1205                1210                1215

Lys Ala  Tyr Leu Gln Lys Gln  Ala Lys Ala Val Lys  Lys Lys Glu
    1220                1225                1230

Lys Lys  Ser Lys Thr Ser Glu  Lys Lys Asp Ser Lys  Glu Ser Ser
    1235                1240                1245

Val Val  Lys Asn Val Val Asp  Ser Ser Gln Lys Pro  Thr Pro Ser
    1250                1255                1260
```

```
Ala Arg Glu Asp Pro Ala Pro Lys Lys Ser Ser Ser Glu Pro Pro
    1265                1270                1275

Pro Arg Lys Pro Val Glu Glu Lys Ser Glu Glu Gly Asn Val Ser
    1280                1285                1290

Ala Pro Gly Pro Glu Ser Lys Gln Ala Thr Thr Pro Ala Ser Arg
    1295                1300                1305

Lys Ser Ser Lys Gln Val Ser Gln Pro Ala Leu Val Ile Pro Pro
    1310                1315                1320

Gln Pro Pro Thr Thr Gly Pro Pro Arg Lys Glu Val Pro Lys Thr
    1325                1330                1335

Thr Pro Ser Glu Pro Lys Lys Lys Gln Pro Pro Pro Pro Glu Ser
    1340                1345                1350

Gly Pro Glu Gln Ser Lys Gln Lys Lys Val Ala Pro Arg Pro Ser
    1355                1360                1365

Ile Pro Val Lys Gln Lys Pro Lys Glu Lys Glu Lys Pro Pro Pro
    1370                1375                1380

Val Asn Lys Gln Glu Asn Ala Gly Thr Leu Asn Ile Leu Ser Thr
    1385                1390                1395

Leu Ser Asn Gly Asn Ser Ser Lys Gln Lys Ile Pro Ala Asp Gly
    1400                1405                1410

Val His Arg Ile Arg Val Asp Phe Lys Glu Asp Cys Glu Ala Glu
    1415                1420                1425

Asn Val Trp Glu Met Gly Gly Leu Gly Ile Leu Thr Ser Val Pro
    1430                1435                1440

Ile Thr Pro Arg Val Val Cys Phe Leu Cys Ala Ser Ser Gly His
    1445                1450                1455

Val Glu Phe Val Tyr Cys Gln Val Cys Cys Glu Pro Phe His Lys
    1460                1465                1470

Phe Cys Leu Glu Glu Asn Glu Arg Pro Leu Glu Asp Gln Leu Glu
    1475                1480                1485

Asn Trp Cys Cys Arg Arg Cys Lys Phe Cys His Val Cys Gly Arg
    1490                1495                1500

Gln His Gln Ala Thr Lys Gln Leu Leu Glu Cys Asn Lys Cys Arg
    1505                1510                1515

Asn Ser Tyr His Pro Glu Cys Leu Gly Pro Asn Tyr Pro Thr Lys
    1520                1525                1530

Pro Thr Lys Lys Lys Lys Val Trp Ile Cys Thr Lys Cys Val Arg
    1535                1540                1545

Cys Lys Ser Cys Gly Ser Thr Thr Pro Gly Lys Gly Trp Asp Ala
    1550                1555                1560

Gln Trp Ser His Asp Phe Ser Leu Cys His Asp Cys Ala Lys Leu
    1565                1570                1575

Phe Ala Lys Gly Asn Phe Cys Pro Leu Cys Asp Lys Cys Tyr Asp
    1580                1585                1590

Asp Asp Asp Tyr Glu Ser Lys Met Met Gln Cys Gly Lys Cys Asp
    1595                1600                1605

Arg Trp Val His Ser Lys Cys Glu Asn Leu Ser Gly Thr Glu Asp
    1610                1615                1620

Glu Met Tyr Glu Ile Leu Ser Asn Leu Pro Glu Ser Val Ala Tyr
    1625                1630                1635

Thr Cys Val Asn Cys Thr Glu Arg His Pro Ala Glu Trp Arg Leu
    1640                1645                1650
```

-continued

```
Ala Leu  Glu Lys Glu Leu Gln  Ile Ser Leu Lys Gln  Val Leu Thr
    1655                 1660                 1665

Ala Leu  Leu Asn Ser Arg Thr  Thr Ser His Leu Leu  Arg Tyr Arg
    1670                 1675                 1680

Gln Ala  Ala Lys Pro Pro Asp  Leu Asn Pro Glu Thr  Glu Glu Ser
    1685                 1690                 1695

Ile Pro  Ser Arg Ser Ser Pro  Glu Gly Pro Asp Pro  Pro Val Leu
    1700                 1705                 1710

Thr Glu  Val Ser Lys Gln Asp  Asp Gln Gln Pro Leu  Asp Leu Glu
    1715                 1720                 1725

Gly Val  Lys Arg Lys Met Asp  Gln Gly Asn Tyr Thr  Ser Val Leu
    1730                 1735                 1740

Glu Phe  Ser Asp Asp Ile Val  Lys Ile Ile Gln Ala  Ala Ile Asn
    1745                 1750                 1755

Ser Asp  Gly Gly Gln Pro Glu  Ile Lys Lys Ala Asn  Ser Met Val
    1760                 1765                 1770

Lys Ser  Phe Phe Ile Arg Gln  Met Glu Arg Val Phe  Pro Trp Phe
    1775                 1780                 1785

Ser Val  Lys Lys Ser Arg Phe  Trp Glu Pro Asn Lys  Val Ser Ser
    1790                 1795                 1800

Asn Ser  Gly Met Leu Pro Asn  Ala Val Leu Pro Pro  Ser Leu Asp
    1805                 1810                 1815

His Asn  Tyr Ala Gln Trp Gln  Glu Arg Glu Glu Asn  Ser His Thr
    1820                 1825                 1830

Glu Gln  Pro Pro Leu Met Lys  Lys Ile Ile Pro Ala  Pro Lys Pro
    1835                 1840                 1845

Lys Gly  Pro Gly Glu Pro Asp  Ser Pro Thr Pro Leu  His Pro Pro
    1850                 1855                 1860

Thr Pro  Pro Ile Leu Ser Thr  Asp Arg Ser Arg Glu  Asp Ser Pro
    1865                 1870                 1875

Glu Leu  Asn Pro Pro Pro Gly  Ile Glu Asp Asn Arg  Gln Cys Ala
    1880                 1885                 1890

Leu Cys  Leu Thr Tyr Gly Asp  Asp Ser Ala Asn Asp  Ala Gly Arg
    1895                 1900                 1905

Leu Leu  Tyr Ile Gly Gln Asn  Glu Trp Thr His Val  Asn Cys Ala
    1910                 1915                 1920

Leu Trp  Ser Ala Glu Val Phe  Glu Asp Asp Asp Gly  Ser Leu Lys
    1925                 1930                 1935

Asn Val  His Met Ala Val Ile  Arg Gly Lys Gln Leu  Arg Cys Glu
    1940                 1945                 1950

Phe Cys  Gln Lys Pro Gly Ala  Thr Val Gly Cys Cys  Leu Thr Ser
    1955                 1960                 1965

Cys Thr  Ser Asn Tyr His Phe  Met Cys Ser Arg Ala  Lys Asn Cys
    1970                 1975                 1980

Val Phe  Leu Asp Asp Lys Lys  Val Tyr Cys Gln Arg  His Arg Asp
    1985                 1990                 1995

Leu Ile  Lys Gly Glu Val Val  Pro Glu Asn Gly Phe  Glu Val Phe
    2000                 2005                 2010

Arg Arg  Val Phe Val Asp Phe  Glu Gly Ile Ser Leu  Arg Arg Lys
    2015                 2020                 2025

Phe Leu  Asn Gly Leu Glu Pro  Glu Asn Ile His Met  Met Ile Gly
    2030                 2035                 2040

Ser Met  Thr Ile Asp Cys Leu  Gly Ile Leu Asn Asp  Leu Ser Asp
```

```
    2045                2050                2055

Cys Glu  Asp Lys Leu Phe Pro  Ile Gly Tyr Gln Cys  Ser Arg Val
    2060                2065                2070

Tyr Trp  Ser Thr Thr Asp Ala  Arg Lys Arg Cys Val  Tyr Thr Cys
    2075                2080                2085

Lys Ile  Val Glu Cys Arg Pro  Pro Val Val Glu Pro  Asp Ile Asn
    2090                2095                2100

Ser Thr  Val Glu His Asp Glu  Asn Arg Thr Ile Ala  His Ser Pro
    2105                2110                2115

Thr Ser  Phe Thr Glu Ser Ser  Ser Lys Glu Ser Gln  Asn Thr Ala
    2120                2125                2130

Glu Ile  Ile Ser Pro Pro Ser  Pro Asp Arg Pro Pro  His Ser Gln
    2135                2140                2145

Thr Ser  Gly Ser Cys Tyr Tyr  His Val Ile Ser Lys  Val Pro Arg
    2150                2155                2160

Ile Arg  Thr Pro Ser Tyr Ser  Pro Thr Gln Arg Ser  Pro Gly Cys
    2165                2170                2175

Arg Pro  Leu Pro Ser Ala Gly  Ser Pro Thr Pro Thr  Thr His Glu
    2180                2185                2190

Ile Val  Thr Val Gly Asp Pro  Leu Leu Ser Ser Gly  Leu Arg Ser
    2195                2200                2205

Ile Gly  Ser Arg Arg His Ser  Thr Ser Ser Leu Ser  Pro Gln Arg
    2210                2215                2220

Ser Lys  Leu Arg Ile Met Ser  Pro Met Arg Thr Gly  Asn Thr Tyr
    2225                2230                2235

Ser Arg  Asn Asn Val Ser Ser  Val Ser Thr Thr Gly  Thr Ala Thr
    2240                2245                2250

Asp Leu  Glu Ser Ser Ala Lys  Val Val Asp His Val  Leu Gly Pro
    2255                2260                2265

Leu Asn  Ser Ser Thr Ser Leu  Gly Gln Asn Thr Ser  Thr Ser Ser
    2270                2275                2280

Asn Leu  Gln Arg Thr Val Val  Thr Val Gly Asn Lys  Asn Ser His
    2285                2290                2295

Leu Asp  Gly Ser Ser Ser Ser  Glu Met Lys Gln Ser  Ser Ala Ser
    2300                2305                2310

Asp Leu  Val Ser Lys Ser Ser  Ser Leu Lys Gly Glu  Lys Thr Lys
    2315                2320                2325

Val Leu  Ser Ser Lys Ser Ser  Glu Gly Ser Ala His  Asn Val Ala
    2330                2335                2340

Tyr Pro  Gly Ile Pro Lys Leu  Ala Pro Gln Val His  Asn Thr Thr
    2345                2350                2355

Ser Arg  Glu Leu Asn Val Ser  Lys Ile Gly Ser Phe  Ala Glu Pro
    2360                2365                2370

Ser Ser  Val Ser Phe Ser Ser  Lys Glu Ala Leu Ser  Phe Pro His
    2375                2380                2385

Leu His  Leu Arg Gly Gln Arg  Asn Asp Arg Asp Gln  His Thr Asp
    2390                2395                2400

Ser Thr  Gln Ser Ala Asn Ser  Ser Pro Asp Glu Asp  Thr Glu Val
    2405                2410                2415

Lys Thr  Leu Lys Leu Ser Gly  Met Ser Asn Arg Ser  Ser Ile Ile
    2420                2425                2430

Asn Glu  His Met Gly Ser Ser  Ser Arg Asp Arg Arg  Gln Lys Gly
    2435                2440                2445
```

-continued

```
Lys Lys  Ser Cys Lys Glu Thr  Phe Lys Glu Lys His  Ser Ser Lys
    2450                 2455                 2460

Ser Phe  Leu Glu Pro Gly Gln  Val Thr Thr Gly Glu  Glu Gly Asn
    2465                 2470                 2475

Leu Lys  Pro Glu Phe Met Asp  Glu Val Leu Thr Pro  Glu Tyr Met
    2480                 2485                 2490

Gly Gln  Arg Pro Cys Asn Asn  Val Ser Ser Asp Lys  Ile Gly Asp
    2495                 2500                 2505

Lys Gly  Leu Ser Met Pro Gly  Val Pro Lys Ala Pro  Pro Met Gln
    2510                 2515                 2520

Val Glu  Gly Ser Ala Lys Glu  Leu Gln Ala Pro Arg  Lys Arg Thr
    2525                 2530                 2535

Val Lys  Val Thr Leu Thr Pro  Leu Lys Met Glu Asn  Glu Ser Gln
    2540                 2545                 2550

Ser Lys  Asn Ala Leu Lys Glu  Ser Ser Pro Ala Ser  Pro Leu Gln
    2555                 2560                 2565

Ile Glu  Ser Thr Ser Pro Thr  Glu Pro Ile Ser Ala  Ser Glu Asn
    2570                 2575                 2580

Pro Gly  Asp Gly Pro Val Ala  Gln Pro Ser Pro Asn  Asn Thr Ser
    2585                 2590                 2595

Cys Gln  Asp Ser Gln Ser Asn  Asn Tyr Gln Asn Leu  Pro Val Gln
    2600                 2605                 2610

Asp Arg  Asn Leu Met Leu Pro  Asp Gly Pro Lys Pro  Gln Glu Asp
    2615                 2620                 2625

Gly Ser  Phe Lys Arg Arg Tyr  Pro Arg Arg Ser Ala  Arg Ala Arg
    2630                 2635                 2640

Ser Asn  Met Phe Phe Gly Leu  Thr Pro Leu Tyr Gly  Val Arg Ser
    2645                 2650                 2655

Tyr Gly  Glu Glu Asp Ile Pro  Phe Tyr Ser Ser Ser  Thr Gly Lys
    2660                 2665                 2670

Lys Arg  Gly Lys Arg Ser Ala  Glu Gly Gln Val Asp  Gly Ala Asp
    2675                 2680                 2685

Asp Leu  Ser Thr Ser Asp Glu  Asp Asp Leu Tyr Tyr  Tyr Asn Phe
    2690                 2695                 2700

Thr Arg  Thr Val Ile Ser Ser  Gly Gly Glu Glu Arg  Leu Ala Ser
    2705                 2710                 2715

His Asn  Leu Phe Arg Glu Glu  Glu Gln Cys Asp Leu  Pro Lys Ile
    2720                 2725                 2730

Ser Gln  Leu Asp Gly Val Asp  Asp Gly Thr Glu Ser  Asp Thr Ser
    2735                 2740                 2745

Val Thr  Ala Thr Thr Arg Lys  Ser Ser Gln Ile Pro  Lys Arg Asn
    2750                 2755                 2760

Gly Lys  Glu Asn Gly Thr Glu  Asn Leu Lys Ile Asp  Arg Pro Glu
    2765                 2770                 2775

Asp Ala  Gly Glu Lys Glu His  Val Thr Lys Ser Ser  Val Gly His
    2780                 2785                 2790

Lys Asn  Glu Pro Lys Met Asp  Asn Cys His Ser Val  Ser Arg Val
    2795                 2800                 2805

Lys Thr  Gln Gly Gln Asp Ser  Leu Glu Ala Gln Leu  Ser Ser Leu
    2810                 2815                 2820

Glu Ser  Ser Arg Arg Val His  Thr Ser Thr Pro Ser  Asp Lys Asn
    2825                 2830                 2835
```

-continued

```
Leu Leu  Asp Thr Tyr Asn Thr  Glu Leu Leu Lys Ser  Asp Ser Asp
    2840                 2845                 2850

Asn Asn  Asn Ser Asp Asp Cys  Gly Asn Ile Leu Pro  Ser Asp Ile
    2855                 2860                 2865

Met Asp  Phe Val Leu Lys Asn  Thr Pro Ser Met Gln  Ala Leu Gly
    2870                 2875                 2880

Glu Ser  Pro Glu Ser Ser Ser  Ser Glu Leu Leu Asn  Leu Gly Glu
    2885                 2890                 2895

Gly Leu  Gly Leu Asp Ser Asn  Arg Glu Lys Asp Met  Gly Leu Phe
    2900                 2905                 2910

Glu Val  Phe Ser Gln Gln Leu  Pro Thr Thr Glu Pro  Val Asp Ser
    2915                 2920                 2925

Ser Val  Ser Ser Ser Ile Ser  Ala Glu Glu Gln Phe  Glu Leu Pro
    2930                 2935                 2940

Leu Glu  Leu Pro Ser Asp Leu  Ser Val Leu Thr Thr  Arg Ser Pro
    2945                 2950                 2955

Thr Val  Pro Ser Gln Asn Pro  Ser Arg Leu Ala Val  Ile Ser Asp
    2960                 2965                 2970

Ser Gly  Glu Lys Arg Val Thr  Ile Thr Glu Lys Ser  Val Ala Ser
    2975                 2980                 2985

Ser Glu  Ser Asp Pro Ala Leu  Leu Ser Pro Gly Val  Asp Pro Thr
    2990                 2995                 3000

Pro Glu  Gly His Met Thr Pro  Asp His Phe Ile Gln  Gly His Met
    3005                 3010                 3015

Asp Ala  Asp His Ile Ser Ser  Pro Pro Cys Gly Ser  Val Glu Gln
    3020                 3025                 3030

Gly His  Gly Asn Asn Gln Asp  Leu Thr Arg Asn Ser  Ser Thr Pro
    3035                 3040                 3045

Gly Leu  Gln Val Pro Val Ser  Pro Thr Val Pro Ile  Gln Asn Gln
    3050                 3055                 3060

Lys Tyr  Val Pro Asn Ser Thr  Asp Ser Pro Gly Pro  Ser Gln Ile
    3065                 3070                 3075

Ser Asn  Ala Ala Val Gln Thr  Thr Pro Pro His Leu  Lys Pro Ala
    3080                 3085                 3090

Thr Glu  Lys Leu Ile Val Val  Asn Gln Asn Met Gln  Pro Leu Tyr
    3095                 3100                 3105

Val Leu  Gln Thr Leu Pro Asn  Gly Val Thr Gln Lys  Ile Gln Leu
    3110                 3115                 3120

Thr Ser  Ser Val Ser Ser Thr  Pro Ser Val Met Glu  Thr Asn Thr
    3125                 3130                 3135

Ser Val  Leu Gly Pro Met Gly  Gly Gly Leu Thr Leu  Thr Thr Gly
    3140                 3145                 3150

Leu Asn  Pro Ser Leu Pro Thr  Ser Gln Ser Leu Phe  Pro Ser Ala
    3155                 3160                 3165

Ser Lys  Gly Leu Leu Pro Met  Ser His His Gln His  Leu His Ser
    3170                 3175                 3180

Phe Pro  Ala Ala Thr Gln Ser  Ser Phe Pro Pro Asn  Ile Ser Asn
    3185                 3190                 3195

Pro Pro  Ser Gly Leu Leu Ile  Gly Val Gln Pro Pro  Pro Asp Pro
    3200                 3205                 3210

Gln Leu  Leu Val Ser Glu Ser  Ser Gln Arg Thr Asp  Leu Ser Thr
    3215                 3220                 3225

Thr Val  Ala Thr Pro Ser Ser  Gly Leu Lys Lys Arg  Pro Ile Ser
```

3230 3235 3240

Arg Leu Gln Thr Arg Lys Asn Lys Lys Leu Ala Pro Ser Ser Thr
3245 3250 3255

Pro Ser Asn Ile Ala Pro Ser Asp Val Val Ser Asn Met Thr Leu
3260 3265 3270

Ile Asn Phe Thr Pro Ser Gln Leu Pro Asn His Pro Ser Leu Leu
3275 3280 3285

Asp Leu Gly Ser Leu Asn Thr Ser Ser His Arg Thr Val Pro Asn
3290 3295 3300

Ile Ile Lys Arg Ser Lys Ser Ser Ile Met Tyr Phe Glu Pro Ala
3305 3310 3315

Pro Leu Leu Pro Gln Ser Val Gly Gly Thr Ala Ala Thr Ala Ala
3320 3325 3330

Gly Thr Ser Thr Ile Ser Gln Asp Thr Ser His Leu Thr Ser Gly
3335 3340 3345

Ser Val Ser Gly Leu Ala Ser Ser Ser Ser Val Leu Asn Val Val
3350 3355 3360

Ser Met Gln Thr Thr Thr Thr Pro Thr Ser Ser Ala Ser Val Pro
3365 3370 3375

Gly His Val Thr Leu Thr Asn Pro Arg Leu Leu Gly Thr Pro Asp
3380 3385 3390

Ile Gly Ser Ile Ser Asn Leu Leu Ile Lys Ala Ser Gln Gln Ser
3395 3400 3405

Leu Gly Ile Gln Asp Gln Pro Val Ala Leu Pro Pro Ser Ser Gly
3410 3415 3420

Met Phe Pro Gln Leu Gly Thr Ser Gln Thr Pro Ser Thr Ala Ala
3425 3430 3435

Ile Thr Ala Ala Ser Ser Ile Cys Val Leu Pro Ser Thr Gln Thr
3440 3445 3450

Thr Gly Ile Thr Ala Ala Ser Pro Ser Gly Glu Ala Asp Glu His
3455 3460 3465

Tyr Gln Leu Gln His Val Asn Gln Leu Leu Ala Ser Lys Thr Gly
3470 3475 3480

Ile His Ser Ser Gln Arg Asp Leu Asp Ser Ala Ser Gly Pro Gln
3485 3490 3495

Val Ser Asn Phe Thr Gln Thr Val Asp Ala Pro Asn Ser Met Gly
3500 3505 3510

Leu Glu Gln Asn Lys Ala Leu Ser Ser Ala Val Gln Ala Ser Pro
3515 3520 3525

Thr Ser Pro Gly Gly Ser Pro Ser Ser Pro Ser Ser Gly Gln Arg
3530 3535 3540

Ser Ala Ser Pro Ser Val Pro Gly Pro Thr Lys Pro Lys Pro Lys
3545 3550 3555

Thr Lys Arg Phe Gln Leu Pro Leu Asp Lys Gly Asn Gly Lys Lys
3560 3565 3570

His Lys Val Ser His Leu Arg Thr Ser Ser Ser Glu Ala His Ile
3575 3580 3585

Pro Asp Gln Glu Thr Thr Ser Leu Thr Ser Gly Thr Gly Thr Pro
3590 3595 3600

Gly Ala Glu Ala Glu Gln Gln Asp Thr Ala Ser Val Glu Gln Ser
3605 3610 3615

Ser Gln Lys Glu Cys Gly Gln Pro Ala Gly Gln Val Ala Val Leu
3620 3625 3630

-continued

```
Pro Glu  Val Gln Val Thr Gln  Asn Pro Ala Asn Glu  Gln Glu Ser
    3635                 3640                 3645

Ala Glu  Pro Lys Thr Val Glu  Glu Glu Glu Ser Asn  Phe Ser Ser
    3650                 3655                 3660

Pro Leu  Met Leu Trp Leu Gln  Gln Glu Gln Lys Arg  Lys Glu Ser
    3665                 3670                 3675

Ile Thr  Glu Lys Lys Pro Lys  Lys Gly Leu Val Phe  Glu Ile Ser
    3680                 3685                 3690

Ser Asp  Asp Gly Phe Gln Ile  Cys Ala Glu Ser Ile  Glu Asp Ala
    3695                 3700                 3705

Trp Lys  Ser Leu Thr Asp Lys  Val Gln Glu Ala Arg  Ser Asn Ala
    3710                 3715                 3720

Arg Leu  Lys Gln Leu Ser Phe  Ala Gly Val Asn Gly  Leu Arg Met
    3725                 3730                 3735

Leu Gly  Ile Leu His Asp Ala  Val Val Phe Leu Ile  Glu Gln Leu
    3740                 3745                 3750

Ser Gly  Ala Lys His Cys Arg  Asn Tyr Lys Phe Arg  Phe His Lys
    3755                 3760                 3765

Pro Glu  Glu Ala Asn Glu Pro  Pro Leu Asn Pro His  Gly Ser Ala
    3770                 3775                 3780

Arg Ala  Glu Val His Leu Arg  Lys Ser Ala Phe Asp  Met Phe Asn
    3785                 3790                 3795

Phe Leu  Ala Ser Lys His Arg  Gln Pro Pro Glu Tyr  Asn Pro Asn
    3800                 3805                 3810

Asp Glu  Glu Glu Glu Glu Val  Gln Leu Lys Ser Ala  Arg Arg Ala
    3815                 3820                 3825

Thr Ser  Met Asp Leu Pro Met  Pro Met Arg Phe Arg  His Leu Lys
    3830                 3835                 3840

Lys Thr  Ser Lys Glu Ala Val  Gly Val Tyr Arg Ser  Pro Ile His
    3845                 3850                 3855

Gly Arg  Gly Leu Phe Cys Lys  Arg Asn Ile Asp Ala  Gly Glu Met
    3860                 3865                 3870

Val Ile  Glu Tyr Ala Gly Asn  Val Ile Arg Ser Ile  Gln Thr Asp
    3875                 3880                 3885

Lys Arg  Glu Lys Tyr Tyr Asp  Ser Lys Gly Ile Gly  Cys Tyr Met
    3890                 3895                 3900

Phe Arg  Ile Asp Asp Ser Glu  Val Val Asp Ala Thr  Met His Gly
    3905                 3910                 3915

Asn Ala  Ala Arg Phe Ile Asn  His Ser Cys Glu Pro  Asn Cys Tyr
    3920                 3925                 3930

Ser Arg  Val Ile Asn Ile Asp  Gly Gln Lys His Ile  Val Ile Phe
    3935                 3940                 3945

Ala Met  Arg Lys Ile Tyr Arg  Gly Glu Glu Leu Thr  Tyr Asp Tyr
    3950                 3955                 3960

Lys Phe  Pro Ile Glu Asp Ala  Ser Asn Lys Leu Pro  Cys Asn Cys
    3965                 3970                 3975

Gly Ala  Lys Lys Cys Arg Lys  Phe Leu Asn Met Ala  Ser Ser Cys
    3980                 3985                 3990

Ala Val  Gln Val Lys Leu Glu  Leu Gly His Arg Ala  Gln Val Arg
    3995                 4000                 4005

Lys Lys  Pro Thr Val Glu Gly  Phe Thr His Asp Trp  Met Val Phe
    4010                 4015                 4020
```

-continued

```
Val Arg  Gly Pro Glu His Ser  Asn Ile Gln His Phe  Val Glu Lys
    4025                 4030                 4035

Val Val  Phe His Leu His Glu  Ser Phe Pro Arg Pro  Lys Arg Val
    4040                 4045                 4050

Cys Lys  Asp Pro Pro Tyr Lys  Val Glu Glu Ser Gly  Tyr Ala Gly
    4055                 4060                 4065

Phe Ile  Leu Pro Ile Glu Val  Tyr Phe Lys Asn Lys  Glu Glu Pro
    4070                 4075                 4080

Arg Lys  Val Arg Phe Asp Tyr  Asp Leu Phe Leu His  Leu Glu Gly
    4085                 4090                 4095

His Pro  Pro Val Asn His Leu  Arg Cys Glu Lys Leu  Thr Phe Asn
    4100                 4105                 4110

Asn Pro  Thr Glu Asp Phe Arg  Arg Lys Leu Leu Lys  Ala Gly Gly
    4115                 4120                 4125

Asp Pro  Asn Arg Ser Ile His  Thr Ser Ser Ser Ser  Ser Ser Ser
    4130                 4135                 4140

Ser Ser  Ser Ser Ser Ser Ser  Ser Ser Ser Ser Ser  Ser Ser Ser
    4145                 4150                 4155

Ser Ser  Ser Ser Ser Ser Ser  Ser Ser Ser Ser Ser  Ser Ser Ser
    4160                 4165                 4170

Ser Ser  Ser Ser Ser Thr Ser  Phe Ser Lys Pro His  Lys Leu Met
    4175                 4180                 4185

Lys Glu  His Lys Glu Lys Pro  Ser Lys Asp Ser Arg  Glu His Lys
    4190                 4195                 4200

Ser Ala  Phe Lys Glu Pro Ser  Arg Asp His Asn Lys  Ser Ser Lys
    4205                 4210                 4215

Glu Ser  Ser Lys Lys Pro Lys  Glu Asn Lys Pro Leu  Lys Glu Glu
    4220                 4225                 4230

Lys Ile  Val Pro Lys Met Ala  Phe Lys Glu Pro Lys  Pro Met Ser
    4235                 4240                 4245

Lys Glu  Pro Lys Pro Asp Ser  Asn Leu Leu Thr Ile  Thr Ser Gly
    4250                 4255                 4260

Gln Asp  Lys Lys Ala Pro Ser  Lys Arg Pro Pro Ile  Ser Asp Ser
    4265                 4270                 4275

Glu Glu  Leu Ser Ala Lys Lys  Arg Lys Lys Ser Ser  Ser Glu Ala
    4280                 4285                 4290

Leu Phe  Lys Ser Phe Ser Ser  Ala Pro Pro Leu Ile  Leu Thr Cys
    4295                 4300                 4305

Ser Ala  Asp Lys Lys Gln Ile  Lys Asp Lys Ser His  Val Lys Met
    4310                 4315                 4320

Gly Lys  Val Lys Ile Glu Ser  Glu Thr Ser Glu Lys  Lys Lys Ser
    4325                 4330                 4335

Thr Leu  Pro Pro Phe Asp Asp  Ile Val Asp Pro Asn  Asp Ser Asp
    4340                 4345                 4350

Val Glu  Glu Asn Ile Ser Ser  Lys Ser Asp Ser Glu  Gln Pro Ser
    4355                 4360                 4365

Pro Ala  Ser Ser Ser Ser Ser  Ser Ser Ser Ser Phe  Thr Pro Ser
    4370                 4375                 4380

Gln Thr  Arg Gln Gln Gly Pro  Leu Arg Ser Ile Met  Lys Asp Leu
    4385                 4390                 4395

His Ser  Asp Asp Asn Glu Glu  Glu Ser Asp Glu Val  Glu Asp Asn
    4400                 4405                 4410

Asp Asn  Asp Ser Glu Met Glu  Arg Pro Val Asn Arg  Gly Gly Ser
```

```
    4415                4420                4425

Arg Ser  Arg Arg Val Ser Leu  Ser Asp Gly Ser Asp  Ser Glu Ser
    4430                4435                4440

Ser Ser  Ala Ser Ser Pro Leu  His His Glu Pro Pro  Pro Pro Leu
    4445                4450                4455

Leu Lys  Thr Asn Asn Asn Gln  Ile Leu Glu Val Lys  Ser Pro Ile
    4460                4465                4470

Lys Gln  Ser Lys Ser Asp Lys  Gln Ile Lys Asn Gly  Glu Cys Asp
    4475                4480                4485

Lys Ala  Tyr Leu Asp Glu Leu  Val Glu Leu His Arg  Arg Leu Met
    4490                4495                4500

Thr Leu  Arg Glu Arg His Ile  Leu Gln Gln Ile Val  Asn Leu Ile
    4505                4510                4515

Glu Glu  Thr Gly His Phe His  Ile Thr Asn Thr Thr  Phe Asp Phe
    4520                4525                4530

Asp Leu  Cys Ser Leu Asp Lys  Thr Thr Val Arg Lys  Leu Gln Ser
    4535                4540                4545

Tyr Leu  Glu Thr Ser Gly Thr  Ser
    4550                4555


<210> SEQ ID NO 2
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Tyr Gly Arg Lys Lys Arg Arg Gln Arg Arg Arg Gly Gly Gly Gly Ser
1               5                   10                  15

Met Ser Ser Tyr Phe Val Asn Ser Leu Phe Ser Lys Tyr Lys Thr Gly
            20                  25                  30

Glu Ser Leu Arg Pro Asn Tyr Tyr Asp Cys Gly Phe Ala Gln Asp Leu
        35                  40                  45

Gly Gly Arg Pro Thr Val Val Tyr Gly Pro Ser Ser Gly Gly Ser Phe
    50                  55                  60

Gln His Pro Ser Gln Ile Gln Glu Phe Tyr His Gly Pro Ser Ser Leu
65                  70                  75                  80

Ser Thr Ala Pro Tyr Gln Gln Asn Pro Cys Ala Val Ala Cys His Gly
                85                  90                  95

Asp Pro Gly Asn Phe Tyr Gly Tyr Asp Pro Leu Gln Arg Gln Ser Leu
            100                 105                 110

Phe Gly Ala Gln Asp Pro Asp Leu Val Gln Tyr Ala Asp Cys Lys Leu
        115                 120                 125

Ala Ala Ala Ser Gly Leu Gly Glu Glu Ala Glu Gly Ser Glu Gln Ser
    130                 135                 140

Pro Ser Pro Thr Gln Leu Phe Pro Trp Met Arg Pro Gln Ala Ala Ala
145                 150                 155                 160

Gly Arg Arg Arg Gly Arg Gln Thr Tyr Ser Arg Tyr Gln Thr Leu Glu
                165                 170                 175

Leu Glu Lys Glu Phe Leu Phe Asn Pro Tyr Leu Thr Arg Lys Arg Arg
            180                 185                 190

Ile Glu Val Ser His Ala Leu Gly Leu Thr Glu Arg Gln Val Lys Ile
        195                 200                 205
```

```
Trp Phe Gln Asn Arg Arg Met Lys Trp Lys Lys Glu Asn Asn Lys Asp
    210                 215                 220

Lys Phe Pro Ser Ser Lys Cys Glu Gln Glu Glu Leu Glu Lys Gln Lys
225                 230                 235                 240

Leu Glu Arg Ala Pro Glu Ala Ala Asp Glu Gly Asp Ala Gln Lys Gly
                245                 250                 255

Asp Lys Lys


<210> SEQ ID NO 3
<211> LENGTH: 285
<212> TYPE: PRT
<213> ORGANISM: Homo sapiens

<400> SEQUENCE: 3

Thr Ala Asp Gln Met Val Ser Ala Leu Leu Asp Ala Glu Pro Pro Ile
1               5                   10                  15

Leu Tyr Ser Glu Tyr Asp Pro Thr Arg Pro Phe Ser Glu Ala Ser Met
            20                  25                  30

Met Gly Leu Leu Thr Asn Leu Ala Asp Arg Glu Leu Val His Met Ile
        35                  40                  45

Asn Trp Ala Lys Arg Val Pro Gly Phe Val Asp Leu Thr Leu His Asp
    50                  55                  60

Gln Val His Leu Leu Glu Cys Ala Trp Leu Glu Ile Leu Met Ile Gly
65                  70                  75                  80

Leu Val Trp Arg Ser Met Glu His Pro Gly Lys Leu Leu Phe Ala Pro
                85                  90                  95

Asn Leu Leu Leu Asp Arg Asn Gln Gly Lys Cys Val Glu Gly Met Val
            100                 105                 110

Glu Ile Phe Asp Met Leu Leu Ala Thr Ser Ser Arg Phe Arg Met Met
        115                 120                 125

Asn Leu Gln Gly Glu Glu Phe Val Cys Leu Lys Ser Ile Ile Leu Leu
    130                 135                 140

Asn Ser Gly Val Tyr Thr Phe Leu Ser Ser Thr Leu Lys Ser Leu Glu
145                 150                 155                 160

Glu Lys Asp His Ile His Arg Val Leu Asp Lys Ile Thr Asp Thr Leu
                165                 170                 175

Ile His Leu Met Ala Lys Ala Gly Leu Thr Leu Gln Gln Gln His Gln
            180                 185                 190

Arg Leu Ala Gln Leu Leu Leu Ile Leu Ser His Ile Arg His Met Ser
        195                 200                 205

Asn Lys Gly Met Glu His Leu Tyr Ser Met Lys Cys Lys Asn Val Val
    210                 215                 220

Pro Leu Tyr Asp Leu Leu Leu Glu Met Leu Asp Ala His Arg Leu His
225                 230                 235                 240

Ala Pro Thr Ser Arg Gly Gly Ala Ser Val Glu Glu Thr Asp Gln Ser
                245                 250                 255

His Leu Ala Thr Ala Gly Ser Thr Ser Ser His Ser Leu Gln Lys Tyr
            260                 265                 270

Tyr Ile Thr Gly Glu Ala Glu Gly Phe Pro Ala Thr Val
        275                 280                 285


<210> SEQ ID NO 4
<211> LENGTH: 243
<212> TYPE: PRT
<213> ORGANISM: Homo sapiens
```

<400> SEQUENCE: 4

Met Ser Ser Tyr Phe Val Asn Ser Leu Phe Ser Lys Tyr Lys Thr Gly
1               5                   10                  15

Glu Ser Leu Arg Pro Asn Tyr Tyr Asp Cys Gly Phe Ala Gln Asp Leu
            20                  25                  30

Gly Gly Arg Pro Thr Val Val Tyr Gly Pro Ser Ser Gly Gly Ser Phe
        35                  40                  45

Gln His Pro Ser Gln Ile Gln Glu Phe Tyr His Gly Pro Ser Ser Leu
    50                  55                  60

Ser Thr Ala Pro Tyr Gln Gln Asn Pro Cys Ala Val Ala Cys His Gly
65                  70                  75                  80

Asp Pro Gly Asn Phe Tyr Gly Tyr Asp Pro Leu Gln Arg Gln Ser Leu
                85                  90                  95

Phe Gly Ala Gln Asp Pro Asp Leu Val Gln Tyr Ala Asp Cys Lys Leu
            100                 105                 110

Ala Ala Ala Ser Gly Leu Gly Glu Glu Ala Glu Gly Ser Glu Gln Ser
        115                 120                 125

Pro Ser Pro Thr Gln Leu Phe Pro Trp Met Arg Pro Gln Ala Ala Ala
    130                 135                 140

Gly Arg Arg Arg Gly Arg Gln Thr Tyr Ser Arg Tyr Gln Thr Leu Glu
145                 150                 155                 160

Leu Glu Lys Glu Phe Leu Phe Asn Pro Tyr Leu Thr Arg Lys Arg Arg
                165                 170                 175

Ile Glu Val Ser His Ala Leu Gly Leu Thr Glu Arg Gln Val Lys Ile
            180                 185                 190

Trp Phe Gln Asn Arg Arg Met Lys Trp Lys Lys Glu Asn Asn Lys Asp
        195                 200                 205

Lys Phe Pro Ser Ser Lys Cys Glu Gln Glu Glu Leu Glu Lys Gln Lys
    210                 215                 220

Leu Glu Arg Ala Pro Glu Ala Ala Asp Glu Gly Asp Ala Gln Lys Gly
225                 230                 235                 240

Asp Lys Lys

<210> SEQ ID NO 5
<211> LENGTH: 479
<212> TYPE: PRT
<213> ORGANISM: Homo sapiens

<400> SEQUENCE: 5

Met Ala His Ser Cys Arg Trp Arg Phe Pro Ala Arg Pro Gly Thr Thr
1               5                   10                  15

Gly Gly Gly Gly Gly Gly Gly Arg Arg Gly Leu Gly Gly Ala Pro Arg
            20                  25                  30

Gln Arg Val Pro Ala Leu Leu Leu Pro Pro Gly Pro Pro Val Gly Gly
        35                  40                  45

Gly Gly Pro Gly Ala Pro Pro Ser Pro Pro Ala Val Ala Ala Ala Ala
    50                  55                  60

Ala Ala Ala Gly Ser Ser Gly Ala Gly Val Pro Gly Gly Ala Ala Ala
65                  70                  75                  80

Ala Ser Ala Ala Ser Ser Ser Ser Ala Ser Ser Ser Ser Ser Ser Ser
                85                  90                  95

Ser Ser Ala Ser Ser Gly Pro Ala Leu Leu Arg Val Gly Pro Gly Phe
            100                 105                 110

Asp Ala Ala Leu Gln Val Ser Ala Ala Ile Gly Thr Asn Leu Arg Arg

-continued

```
        115                 120                 125

Phe Arg Ala Val Phe Gly Glu Ser Gly Gly Gly Gly Gly Ser Gly Glu
    130                 135                 140

Asp Glu Gln Phe Leu Gly Phe Gly Ser Asp Glu Glu Val Arg Val Arg
145                 150                 155                 160

Ser Pro Thr Arg Ser Pro Ser Val Lys Thr Ser Pro Arg Lys Pro Arg
                165                 170                 175

Gly Arg Pro Arg Ser Gly Ser Asp Arg Asn Ser Ala Ile Leu Ser Asp
            180                 185                 190

Pro Ser Val Phe Ser Pro Leu Asn Lys Ser Glu Thr Lys Ser Gly Asp
        195                 200                 205

Lys Ile Lys Lys Lys Asp Ser Lys Ser Ile Glu Lys Lys Arg Gly Arg
    210                 215                 220

Pro Pro Thr Phe Pro Gly Val Lys Ile Lys Ile Thr His Gly Lys Asp
225                 230                 235                 240

Ile Ser Glu Leu Pro Lys Gly Asn Lys Glu Asp Ser Leu Lys Lys Ile
                245                 250                 255

Lys Arg Thr Pro Ser Ala Thr Phe Gln Gln Ala Thr Lys Ile Lys Lys
            260                 265                 270

Leu Arg Ala Gly Lys Leu Ser Pro Leu Lys Ser Lys Phe Lys Thr Gly
        275                 280                 285

Lys Leu Gln Ile Gly Arg Lys Gly Val Gln Ile Val Arg Arg Arg Gly
    290                 295                 300

Arg Pro Pro Ser Thr Glu Arg Ile Lys Thr Pro Ser Gly Leu Leu Ile
305                 310                 315                 320

Asn Ser Glu Leu Glu Lys Pro Gln Lys Val Arg Lys Asp Lys Glu Gly
                325                 330                 335

Thr Pro Pro Leu Thr Lys Glu Asp Lys Thr Val Val Arg Gln Ser Pro
            340                 345                 350

Arg Arg Ile Lys Pro Val Arg Ile Ile Pro Ser Ser Lys Arg Thr Asp
        355                 360                 365

Ala Thr Ile Ala Lys Gln Leu Leu Gln Arg Ala Lys Lys Gly Ala Gln
    370                 375                 380

Lys Lys Ile Glu Lys Glu Ala Ala Gln Leu Gln Gly Arg Lys Val Lys
385                 390                 395                 400

Thr Gln Val Lys Asn Ile Arg Gln Phe Ile Met Pro Val Val Ser Ala
                405                 410                 415

Ile Ser Ser Arg Ile Ile Lys Thr Pro Arg Arg Phe Ile Glu Asp Glu
            420                 425                 430

Asp Tyr Asp Pro Pro Ile Lys Ile Ala Arg Leu Glu Ser Thr Pro Asn
        435                 440                 445

Ser Arg Phe Ser Ala Pro Ser Cys Gly Ser Ser Glu Lys Ser Ser Ala
    450                 455                 460

Ala Ser Gln His Ser Ser Gln Met Ser Ser Asp Ser Ser Arg Ser
465                 470                 475


<210> SEQ ID NO 6
<211> LENGTH: 6673
<212> TYPE: DNA
<213> ORGANISM: Homo sapiens

<400> SEQUENCE: 6

aatataagtg gaggcgtcgc gctggcgggc attcctgaag ctgacagcat tcgggccgag      60

atgtctcgct ccgtggcctt agctgtgctc gcgctactct ctctttctgg cctggaggct     120
```

```
atccagcgtg agtctctcct accctcccgc tctggtcctt cctctcccgc tctgcaccct    180
ctgtggccct cgctgtgctc tctcgctccg tgacttccct tctccaagtt ctccttggtg    240
gcccgccgtg gggctagtcc agggctggat ctcggggaag cggcggggtg gcctgggagt    300
ggggaagggg gtgcgcaccc gggacgcgcg ctacttgccc ctttcggcgg ggagcagggg    360
agacctttgg cctacggcga cgggagggtc gggacaaagt ttagggcgtc gataagcgtc    420
agagcgccga ggttggggga gggtttctct tccgctcttt cgcggggcct ctggctcccc    480
cagcgcagct ggagtggggg acgggtaggc tcgtcccaaa ggcgcggcgc tgaggtttgt    540
gaacgcgtgg aggggcgctt ggggtctggg ggaggcgtcg cccgggtaag cctgtctgct    600
gcggctctgc ttcccttaga ctggagagct gtggacttcg tctaggcgcc cgctaagttc    660
gcatgtccta gcacctctgg gtctatgtgg ggccacaccg tggggaggaa acagcacgcg    720
acgtttgtag aatgcttggc tgtgatacaa agcggtttcg aataattaac ttatttgttc    780
ccatcacatg tcacttttaa aaaattataa gaactacccg ttattgacat ctttctgtgt    840
gccaaggact ttatgtgctt tgcgtcattt aattttgaaa acagttatct tccgccatag    900
ataactacta tggttatctt ctgcctctca cagatgaaga aactaaggca ccgagatttt    960
aagaaactta attacacagg ggataaatgg cagcaatcga gattgaagtc aagcctaacc   1020
agggcttttg cgggagcgca tgccttttgg ctgtaattcg tgcatttttt tttaagaaaa   1080
acgcctgcct tctgcgtgag attctccaga gcaaactggg cggcatgggc cctgtggtct   1140
tttcgtacag agggcttcct ctttggctct ttgcctggtt gtttccaaga tgtactgtgc   1200
ctcttacttt cggttttgaa aacatgaggg ggttgggcgt ggtagcttac gcctgtaatc   1260
ccagcactta gggaggccga ggcgggagga tggcttgagg tccgtagttg agaccagcct   1320
ggccaacatg gtgaagcctg gtctctacaa aaaataataa caaaaattag ccgggtgtgg   1380
tggctcgtgc ctgtggtccc agctgctccg gtggctgagg cgggaggatc tcttgagctt   1440
aggcttttga gctatcatgg cgccagtgca ctccagcgtg ggcaacagag cgagaccctg   1500
tctctcaaaa aagaaaaaaa aaaaaaaaga aagagaaaag aaaagaaaga aagaagtgaa   1560
ggtttgtcag tcaggggagc tgtaaaacca ttaataaaga taatccaaga tggttaccaa   1620
gactgttgag gacgccagag atcttgagca ctttctaagt acctggcaat acactaagcg   1680
cgctcacctt ttcctctggc aaaacatgat cgaaagcaga atgttttgat catgagaaaa   1740
ttgcatttaa tttgaataca atttatttac aacataaagg ataatgtata tatcaccacc   1800
attactggta tttgctggtt atgttagatg tcattttaaa aaataacaat ctgatattta   1860
aaaaaaaatc ttattttgaa aatttccaaa gtaatacatg ccatgcatag accatttctg   1920
gaagatacca caagaaacat gtaatgatga ttgcctctga aggtctattt tcctcctctg   1980
acctgtgtgt gggttttgtt tttgttttac tgtgggcata aattaatttt tcagttaagt   2040
tttggaagct taaataactc tccaaaagtc ataaagccag taactggttg agcccaaatt   2100
caaacccagc ctgtctgata cttgtcctct tcttagaaaa gattacagtg atgctctcac   2160
aaaatcttgc cgccttccct caaacagaga gttccaggca ggatgaatct gtgctctgat   2220
ccctgaggca tttaatatgt tcttattatt agaagctcag atgcaaagag ctctcttagc   2280
ttttaatgtt atgaaaaaaa tcaggtcttc attagattcc ccaatccacc tcttgatggg   2340
gctagtagcc tttccttaat gatagggtgt ttctagagag atatatctgg tcaaggtggc   2400
ctggtactcc tccttctccc cacagcctcc cagacaagga ggagtagctg ccttttagtg   2460
```

-continued

```
atcatgtacc ctgaatataa gtgtatttaa aagaatttta tacacatata tttagtgtca   2520
atctgtatat ttagtagcac taacacttct cttcattttc aatgaaaaat atagagttta   2580
taatattttc ttcccacttc cccatggatg gtctagtcat gcctctcatt ttggaaagta   2640
ctgtttctga aacattaggc aatatattcc caacctggct agtttacagc aatcacctgt   2700
ggatgctaat taaaacgcaa atcccactgt cacatgcatt actccatttg atcataatgg   2760
aaagtatgtt ctgtcccatt tgccatagtc ctcacctatc cctgttgtat tttatcgggt   2820
ccaactcaac catttaaggt atttgccagc tcttgtatgc atttaggttt tgtttctttg   2880
ttttttagct catgaaatta ggtacaaagt cagagagggg tctggcatat aaaacctcag   2940
cagaaataaa gaggttttgt tgtttggtaa gaacatacct tgggttggtt gggcacggtg   3000
gctcgtgcct gtaatcccaa cactttggga ggccaaggca ggctgatcac ttgaagttgg   3060
gagttcaaga ccagcctggc caacatggtg aaatcccgtc tctactgaaa atacaaaaat   3120
taaccaggca tggtggtgtg tgcctgtagt cccaggaatc acttgaaccc aggaggcgga   3180
ggttgcagtg agctgagatc tcaccactgc acactgcact ccagcctggg caatggaatg   3240
agattccatc ccaaaaaata aaaaaataaa aaaataaaga acataccttg ggttgatcca   3300
cttaggaacc tcagataata acatctgcca cgtatagagc aattgctatg tcccaggcac   3360
tctactagac acttcataca gtttagaaaa tcagatgggt gtagatcaag gcaggagcag   3420
gaaccaaaaa gaaaggcata aacataagaa aaaaaatgga aggggtggaa acagagtaca   3480
ataacatgag taatttgatg ggggctatta tgaactgaga aatgaacttt gaaaagtatc   3540
ttggggccaa atcatgtaga ctcttgagtg atgtgttaag gaatgctatg agtgctgaga   3600
gggcatcaga agtccttgag agcctccaga gaaaggctct taaaaatgca gcgcaatctc   3660
cagtgacaga agatactgct agaaatctgc tagaaaaaaa acaaaaaagg catgtataga   3720
ggaattatga gggaaagata ccaagtcacg gtttattctt caaaatggag gtggcttgtt   3780
gggaaggtgg aagctcattt ggccagagtg gaaatggaat tgggagaaat cgatgaccaa   3840
atgtaaacac ttggtgcctg atatagcttg acaccaagtt agccccaagt gaaataccct   3900
ggcaatatta atgtgtcttt tcccgatatt cctcaggtac tccaaagatt caggtttact   3960
cacgtcatcc agcagagaat ggaaagtcaa atttcctgaa ttgctatgtg tctgggtttc   4020
atccatccga cattgaagtt gacttactga agaatggaga gagaattgaa aaagtggagc   4080
attcagactt gtctttcagc aaggactggt ctttctatct cttgtactac actgaattca   4140
cccccactga aaaagatgag tatgcctgcc gtgtgaacca tgtgactttg tcacagccca   4200
agatagttaa gtggggtaag tcttacattc ttttgtaagc tgctgaaagt tgtgtatgag   4260
tagtcatatc ataaagctgc tttgatataa aaaaggtcta tggccatact accctgaatg   4320
agtcccatcc catctgatat aaacaatctg catattggga ttgtcaggga atgttcttaa   4380
agatcagatt agtggcacct gctgagatac tgatgcacag catggtttct gaaccagtag   4440
tttccctgca gttgagcagg gagcagcagc agcacttgca caaatacata tacactctta   4500
acacttctta cctactggct tcctctagct tttgtggcag cttcaggtat atttagcact   4560
gaacgaacat ctcaagaagg tataggcctt tgtttgtaag tcctgctgtc ctagcatcct   4620
ataatcctgg acttctccag tactttctgg ctggattggt atctgaggct agtaggaagg   4680
gcttgttcct gctgggtagc tctaaacaat gtattcatgg gtaggaacag cagcctattc   4740
tgccagcctt atttctaacc attttagaca tttgttagta catggtattt taaaagtaaa   4800
acttaatgtc ttcctttttt ttctccactg tctttttcat agatcgagac atgtaagcag   4860
```

```
catcatggag gtaagttttt gaccttgaga aaatgttttt gtttcactgt cctgaggact   4920

atttatagac agctctaaca tgataaccct cactatgtgg agaacattga cagagtaaca   4980

ttttagcagg gaaagaagaa tcctacaggg tcatgttccc ttctcctgtg gagtggcatg   5040

aagaaggtgt atggccccag gtatggccat attactgacc ctctacagag agggcaaagg   5100

aactgccagt atggtattgc aggataaagg caggtggtta cccacattac ctgcaaggct   5160

ttgatctttc ttctgccatt tccacattgg acatctctgc tgaggagaga aaatgaacca   5220

ctcttttcct ttgtataatg ttgttttatt cttcagacag aagagaggag ttatacagct   5280

ctgcagacat cccattcctg tatggggact gtgtttgcct cttagaggtt cccaggccac   5340

tagaggagat aaagggaaac agattgttat aacttgatat aatgatacta taatagatgt   5400

aactacaagg agctccagaa gcaagagaga gggaggaact tggacttctc tgcatcttta   5460

gttggagtcc aaaggctttt caatgaaatt ctactgccca gggtacattg atgctgaaac   5520

cccattcaaa tctcctgtta tattctagaa cagggaattg atttgggaga gcatcaggaa   5580

ggtggatgat ctgcccagtc acactgttag taaattgtag agccaggacc tgaactctaa   5640

tatagtcatg tgttacttaa tgacggggac atgttctgag aaatgcttac acaaacctag   5700

gtgttgtagc ctactacacg cataggctac atggtatagc ctattgctcc tagactacaa   5760

acctgtacag cctgttactg tactgaatac tgtgggcagt tgtaacacaa tggtaagtat   5820

ttgtgtatct aaacatagaa gttgcagtaa aaatatgcta ttttaatctt atgagaccac   5880

tgtcatatat acagtccatc attgaccaaa acatcatatc agcatttttt cttctaagat   5940

tttgggagca ccaaagggat acactaacag gatatactct ttataatggg tttggagaac   6000

tgtctgcagc tacttctttt aaaaaggtga tctacacagt agaaattaga caagtttggt   6060

aatgagatct gcaatccaaa taaaataaat tcattgctaa ccttttttctt ttcttttcag   6120

gtttgaagat gccgcatttg gattggatga attccaaatt ctgcttgctt gctttttaat   6180

attgatatgc ttatacactt acactttatg cacaaaatgt agggttataa taatgttaac   6240

atggacatga tcttctttat aattctactt tgagtgctgt ctccatgttt gatgtatctg   6300

agcaggttgc tccacaggta gctctaggag ggctggcaac ttagaggtgg ggagcagaga   6360

attctcttat ccaacatcaa catcttggtc agatttgaac tcttcaatct cttgcactca   6420

aagcttgtta agatagttaa gcgtgcataa gttaacttcc aatttacata ctctgcttag   6480

aatttggggg aaaatttaga aatataattg acaggattat tggaaatttg ttataatgaa   6540

tgaaacattt tgtcatataa gattcatatt tacttcttat acatttgata aagtaaggca   6600

tggttgtggt taatctggtt tatttttgtt ccacaagtta aataaatcat aaaacttgat   6660

gtgttatctc tta                                                     6673
```

```
<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

cagcccaaga tagttaagtg ggg                                           23


<210> SEQ ID NO 8
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

tgggctgtga caaagtcaca tgg                                             23


<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

aagtcaactt caatgtcgga tgg                                             23


<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

cagtaagtca acttcaatgt cgg                                             23


<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

ctgaatcttt ggagtacctg agg                                             23


<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

acagcccaag atagttaagt ggg                                             23


<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

acaaagtcac atggttcaca cgg                                             23


<210> SEQ ID NO 14
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 14
ggccgagatg tctcgctccg tgg 23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agtcacatgg ttcacacggc agg 23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
catactcatc tttttcagtg ggg 23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ttaccccact taactatctt ggg 23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
acccagacac atagcaattc agg 23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ctcaggtact ccaaagattc agg 23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
actctctctt tctggcctgg agg 23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
gagtagcgcg agcacagcta agg 23

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
gctatccagc gtactccaa 19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
tccagcgtac tccaaagat 19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
ccagcgtact ccaaagatt 19

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
ccaaagattc aggtttact 19

<210> SEQ ID NO 26
<211> LENGTH: 19
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 26
tcaggtttac tcacgtcat 19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
gcagagaatg gaaagtcaa 19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 28
ggtttcatcc atccgacat 19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
tcatccatcc gacattgaa 19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
ccgacattga agttgactt 19

<210> SEQ ID NO 31
<211> LENGTH: 1512
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 31

```
Met Ala His Ser Cys Arg Trp Arg Phe Pro Ala Arg Pro Gly Thr Thr
1               5                   10                  15

Gly Gly Gly Gly Gly Gly Gly Arg Arg Gly Leu Gly Gly Ala Pro Arg
            20                  25                  30

Gln Arg Val Pro Ala Leu Leu Leu Pro Pro Gly Pro Pro Val Gly Gly
        35                  40                  45
```

-continued

```
Gly Gly Pro Gly Ala Pro Pro Ser Pro Pro Ala Val Ala Ala Ala Ala
    50                  55                  60

Ala Ala Ala Gly Ser Ser Gly Ala Gly Val Pro Gly Gly Ala Ala Ala
65                  70                  75                  80

Ala Ser Ala Ala Ser Ser Ser Ser Ala Ser Ser Ser Ser Ser Ser Ser
                85                  90                  95

Ser Ser Ala Ser Ser Gly Pro Ala Leu Leu Arg Val Gly Pro Gly Phe
            100                 105                 110

Asp Ala Ala Leu Gln Val Ser Ala Ala Ile Gly Thr Asn Leu Arg Arg
        115                 120                 125

Phe Arg Ala Val Phe Gly Glu Ser Gly Gly Gly Gly Gly Ser Gly Glu
    130                 135                 140

Asp Glu Gln Phe Leu Gly Phe Gly Ser Asp Glu Glu Val Arg Val Arg
145                 150                 155                 160

Ser Pro Thr Arg Ser Pro Ser Val Lys Thr Ser Pro Arg Lys Pro Arg
                165                 170                 175

Gly Arg Pro Arg Ser Gly Ser Asp Arg Asn Ser Ala Ile Leu Ser Asp
            180                 185                 190

Pro Ser Val Phe Ser Pro Leu Asn Lys Ser Glu Thr Lys Ser Gly Asp
        195                 200                 205

Lys Ile Lys Lys Lys Asp Ser Lys Ser Ile Glu Lys Lys Arg Gly Arg
    210                 215                 220

Pro Pro Thr Phe Pro Gly Val Lys Ile Lys Ile Thr His Gly Lys Asp
225                 230                 235                 240

Ile Ser Glu Leu Pro Lys Gly Asn Lys Glu Asp Ser Leu Lys Lys Ile
                245                 250                 255

Lys Arg Thr Pro Ser Ala Thr Phe Gln Gln Ala Thr Lys Ile Lys Lys
            260                 265                 270

Leu Arg Ala Gly Lys Leu Ser Pro Leu Lys Ser Lys Phe Lys Thr Gly
        275                 280                 285

Lys Leu Gln Ile Gly Arg Lys Gly Val Gln Ile Val Arg Arg Arg Gly
    290                 295                 300

Arg Pro Pro Ser Thr Glu Arg Ile Lys Thr Pro Ser Gly Leu Leu Ile
305                 310                 315                 320

Asn Ser Glu Leu Glu Lys Pro Gln Lys Val Arg Lys Asp Lys Glu Gly
                325                 330                 335

Thr Pro Pro Leu Thr Lys Glu Asp Lys Thr Val Val Arg Gln Ser Pro
            340                 345                 350

Arg Arg Ile Lys Pro Val Arg Ile Ile Pro Ser Ser Lys Arg Thr Asp
        355                 360                 365

Ala Thr Ile Ala Lys Gln Leu Leu Gln Arg Ala Lys Lys Gly Ala Gln
    370                 375                 380

Lys Lys Ile Glu Lys Glu Ala Ala Gln Leu Gln Gly Arg Lys Val Lys
385                 390                 395                 400

Thr Gln Val Lys Asn Ile Arg Gln Phe Ile Met Pro Val Val Ser Ala
                405                 410                 415

Ile Ser Ser Arg Ile Ile Lys Thr Pro Arg Arg Phe Ile Glu Asp Glu
            420                 425                 430

Asp Tyr Asp Pro Pro Ile Lys Ile Ala Arg Leu Glu Ser Thr Pro Asn
        435                 440                 445

Ser Arg Phe Ser Ala Pro Ser Cys Gly Ser Ser Glu Lys Ser Ser Ala
    450                 455                 460

Ala Ser Gln His Ser Ser Gln Met Ser Ser Asp Ser Ser Arg Ser Ser
```

-continued

```
465                 470                 475                 480

Ser Pro Ser Val Asp Thr Ser Thr Asp Ser Gln Ala Ser Glu Glu Ile
                485                 490                 495

Gln Val Leu Pro Glu Glu Arg Ser Asp Thr Pro Glu Val His Pro Pro
            500                 505                 510

Leu Pro Ile Ser Gln Ser Pro Glu Asn Glu Ser Asn Asp Arg Arg Ser
        515                 520                 525

Arg Arg Tyr Ser Val Ser Glu Arg Ser Phe Gly Ser Arg Thr Thr Lys
    530                 535                 540

Lys Leu Ser Thr Leu Gln Ser Ala Pro Gln Gln Gln Thr Ser Ser Ser
545                 550                 555                 560

Pro Pro Pro Pro Leu Leu Thr Pro Pro Pro Pro Leu Gln Pro Ala Ser
                565                 570                 575

Ser Ile Ser Asp His Thr Pro Trp Leu Met Pro Pro Thr Ile Pro Leu
            580                 585                 590

Ala Ser Pro Phe Leu Pro Ala Ser Thr Ala Pro Met Gln Gly Lys Arg
        595                 600                 605

Lys Ser Ile Leu Arg Glu Pro Thr Phe Arg Trp Thr Ser Leu Lys His
    610                 615                 620

Ser Arg Ser Glu Pro Gln Tyr Phe Ser Ser Ala Lys Tyr Ala Lys Glu
625                 630                 635                 640

Gly Leu Ile Arg Lys Pro Ile Phe Asp Asn Phe Arg Pro Pro Pro Leu
                645                 650                 655

Thr Pro Glu Asp Val Gly Phe Ala Ser Gly Phe Ser Ala Ser Gly Thr
            660                 665                 670

Ala Ala Ser Ala Arg Leu Phe Ser Pro Leu His Ser Gly Thr Arg Phe
        675                 680                 685

Asp Met His Lys Arg Ser Pro Leu Leu Arg Ala Pro Arg Phe Thr Pro
    690                 695                 700

Ser Glu Ala His Ser Arg Ile Phe Glu Ser Val Thr Leu Pro Ser Asn
705                 710                 715                 720

Arg Thr Ser Ala Gly Thr Ser Ser Ser Gly Val Ser Asn Arg Lys Arg
                725                 730                 735

Lys Arg Lys Val Phe Ser Pro Ile Arg Ser Glu Pro Arg Ser Pro Ser
            740                 745                 750

His Ser Met Arg Thr Arg Ser Gly Arg Leu Ser Ser Ser Glu Leu Ser
        755                 760                 765

Pro Leu Thr Pro Pro Ser Ser Val Ser Ser Ser Leu Ser Ile Ser Val
    770                 775                 780

Ser Pro Leu Ala Thr Ser Ala Leu Asn Pro Thr Phe Thr Phe Pro Ser
785                 790                 795                 800

His Ser Leu Thr Gln Ser Gly Glu Ser Ala Glu Lys Asn Gln Arg Pro
                805                 810                 815

Arg Lys Gln Thr Ser Ala Pro Ala Glu Pro Phe Ser Ser Ser Ser Pro
            820                 825                 830

Thr Pro Leu Phe Pro Trp Phe Thr Pro Gly Ser Gln Thr Glu Arg Gly
        835                 840                 845

Arg Asn Lys Asp Lys Ala Pro Glu Glu Leu Ser Lys Asp Arg Asp Ala
    850                 855                 860

Asp Lys Ser Val Glu Lys Asp Lys Ser Arg Glu Arg Asp Arg Glu Arg
865                 870                 875                 880

Glu Lys Glu Asn Lys Arg Glu Ser Arg Lys Glu Lys Arg Lys Lys Gly
                885                 890                 895
```

-continued

```
Ser Glu Ile Gln Ser Ser Ser Ala Leu Tyr Pro Val Gly Arg Val Ser
            900                 905                 910

Lys Glu Lys Val Val Gly Glu Asp Val Ala Thr Ser Ser Ser Ala Lys
        915                 920                 925

Lys Ala Thr Gly Arg Lys Lys Ser Ser Ser His Asp Ser Gly Thr Asp
    930                 935                 940

Ile Thr Ser Val Thr Leu Gly Asp Thr Thr Ala Val Lys Thr Lys Ile
945                 950                 955                 960

Leu Ile Lys Lys Gly Arg Gly Asn Leu Glu Lys Thr Asn Leu Asp Leu
                965                 970                 975

Gly Pro Thr Ala Pro Ser Leu Glu Lys Glu Lys Thr Leu Cys Leu Ser
            980                 985                 990

Thr Pro Ser Ser Ser Thr Val Lys  His Ser Thr Ser Ser  Ile Gly Ser
        995                 1000                1005

Met Leu  Ala Gln Ala Asp Lys  Leu Pro Met Thr Asp  Lys Arg Val
    1010                 1015                 1020

Ala Ser  Leu Leu Lys Lys Ala  Lys Ala Gln Leu Cys  Lys Ile Glu
    1025                 1030                 1035

Lys Ser  Lys Ser Leu Lys Gln  Thr Asp Gln Pro Lys  Ala Gln Gly
    1040                 1045                 1050

Gln Glu  Ser Asp Ser Ser Glu  Thr Ser Val Arg Gly  Pro Arg Ile
    1055                 1060                 1065

Lys His  Val Cys Arg Arg Ala  Ala Val Ala Leu Gly  Arg Lys Arg
    1070                 1075                 1080

Ala Val  Phe Pro Asp Asp Met  Pro Thr Leu Ser Ala  Leu Pro Trp
    1085                 1090                 1095

Glu Glu  Arg Glu Lys Ile Leu  Ser Ser Met Gly Asn  Asp Asp Lys
    1100                 1105                 1110

Ser Ser  Ile Ala Gly Ser Glu  Asp Ala Glu Pro Leu  Ala Pro Pro
    1115                 1120                 1125

Ile Lys  Pro Ile Lys Pro Val  Thr Arg Asn Lys Ala  Pro Gln Glu
    1130                 1135                 1140

Pro Pro  Val Lys Lys Gly Arg  Arg Ser Arg Arg Cys  Gly Gln Cys
    1145                 1150                 1155

Pro Gly  Cys Gln Val Pro Glu  Asp Cys Gly Val Cys  Thr Asn Cys
    1160                 1165                 1170

Leu Asp  Lys Pro Lys Phe Gly  Gly Arg Asn Ile Lys  Lys Gln Cys
    1175                 1180                 1185

Cys Lys  Met Arg Lys Cys Gln  Asn Leu Gln Trp Met  Pro Ser Lys
    1190                 1195                 1200

Ala Tyr  Leu Gln Lys Gln Ala  Lys Ala Val Lys Lys  Lys Glu Lys
    1205                 1210                 1215

Lys Ser  Lys Thr Ser Glu Lys  Lys Asp Ser Lys Glu  Ser Ser Val
    1220                 1225                 1230

Val Lys  Asn Val Val Asp Ser  Ser Gln Lys Pro Thr  Pro Ser Ala
    1235                 1240                 1245

Arg Glu  Asp Pro Ala Pro Lys  Lys Ser Ser Ser Glu  Pro Pro Pro
    1250                 1255                 1260

Arg Lys  Pro Val Glu Glu Lys  Ser Glu Glu Gly Asn  Val Ser Ala
    1265                 1270                 1275

Pro Gly  Pro Glu Ser Lys Gln  Ala Thr Thr Pro Ala  Ser Arg Lys
    1280                 1285                 1290
```

```
Ser Ser  Lys Gln Val Ser Gln  Pro Ala Leu Val Ile  Pro Pro Gln
    1295                 1300                 1305

Pro Pro  Thr Thr Gly Pro Pro  Arg Lys Glu Val Pro  Lys Thr Thr
    1310                 1315                 1320

Pro Ser  Glu Pro Lys Lys Lys  Gln Pro Pro Pro Pro  Glu Ser Gly
    1325                 1330                 1335

Pro Glu  Gln Ser Lys Gln Lys  Lys Val Ala Pro Arg  Pro Ser Ile
    1340                 1345                 1350

Pro Val  Lys Gln Lys Pro Lys  Glu Lys Glu Lys Pro  Pro Pro Val
    1355                 1360                 1365

Asn Lys  Gln Glu Asn Ala Gly  Thr Leu Asn Ile Leu  Ser Thr Leu
    1370                 1375                 1380

Ser Asn  Gly Asn Ser Ser Lys  Gln Lys Ile Pro Ala  Asp Gly Val
    1385                 1390                 1395

His Arg  Ile Arg Val Asp Phe  Lys Glu Asp Cys Glu  Ala Glu Asn
    1400                 1405                 1410

Val Trp  Glu Met Gly Gly Leu  Gly Ile Leu Glu Val  Lys Ser Pro
    1415                 1420                 1425

Ile Lys  Gln Ser Lys Ser Asp  Lys Gln Ile Lys Asn  Gly Glu Cys
    1430                 1435                 1440

Asp Lys  Ala Tyr Leu Asp Glu  Leu Val Glu Leu His  Arg Arg Leu
    1445                 1450                 1455

Met Thr  Leu Arg Glu Arg His  Ile Leu Gln Gln Ile  Val Asn Leu
    1460                 1465                 1470

Ile Glu  Glu Thr Gly His Phe  His Ile Thr Asn Thr  Thr Phe Asp
    1475                 1480                 1485

Phe Asp  Leu Cys Ser Leu Asp  Lys Thr Thr Val Arg  Lys Leu Gln
    1490                 1495                 1500

Ser Tyr  Leu Glu Thr Ser Gly  Thr Ser
    1505                 1510


<210> SEQ ID NO 32
<211> LENGTH: 243
<212> TYPE: PRT
<213> ORGANISM: Homo sapiens

<400> SEQUENCE: 32

Met Ser Ser Tyr Phe Val Asn Ser Leu Phe Ser Lys Tyr Lys Thr Gly
1               5                   10                  15

Glu Ser Leu Arg Pro Asn Tyr Tyr Asp Cys Gly Phe Ala Gln Asp Leu
            20                  25                  30

Gly Gly Arg Pro Thr Val Val Tyr Gly Pro Ser Ser Gly Gly Ser Phe
        35                  40                  45

Gln His Pro Ser Gln Ile Gln Glu Phe Tyr His Gly Pro Ser Ser Leu
    50                  55                  60

Ser Thr Ala Pro Tyr Gln Gln Asn Pro Cys Ala Val Ala Cys His Gly
65                  70                  75                  80

Asp Pro Gly Asn Phe Tyr Gly Tyr Asp Pro Leu Gln Arg Gln Ser Leu
                85                  90                  95

Phe Gly Ala Gln Asp Pro Asp Leu Val Gln Tyr Ala Asp Cys Lys Leu
            100                 105                 110

Ala Ala Ala Ser Gly Leu Gly Glu Glu Ala Glu Gly Ser Glu Gln Ser
        115                 120                 125

Pro Ser Pro Thr Gln Leu Phe Pro Trp Met Arg Pro Gln Ala Ala Ala
    130                 135                 140
```

Gly Arg Arg Arg Gly Arg Gln Thr Tyr Ser Arg Tyr Gln Thr Leu Glu
145 150 155 160

Leu Glu Lys Glu Phe Leu Phe Asn Pro Tyr Leu Thr Arg Lys Arg Arg
165 170 175

Ile Glu Val Ser His Ala Leu Gly Leu Thr Glu Arg Gln Val Lys Ile
180 185 190

Trp Phe Gln Asn Arg Arg Met Lys Trp Lys Lys Glu Asn Asn Lys Asp
195 200 205

Lys Phe Pro Ser Ser Lys Cys Glu Gln Glu Glu Leu Glu Lys Gln Lys
210 215 220

Leu Glu Arg Ala Pro Glu Ala Ala Asp Glu Gly Asp Ala Gln Lys Gly
225 230 235 240

Asp Lys Lys

<210> SEQ ID NO 33
<211> LENGTH: 257
<212> TYPE: PRT
<213> ORGANISM: Unknown
<220> FEATURE:
<223> OTHER INFORMATION: Description of Unknown:
Amino acid sequence for deletion of invariant chain
(Ii, CD74) to eliminate all MHC class II

<400> SEQUENCE: 33

Met His Arg Arg Arg Ser Arg Ser Cys Arg Glu Asp Gln Lys Pro Val
1 5 10 15

Met Asp Asp Gln Arg Asp Leu Ile Ser Asn Asn Glu Gln Leu Pro Met
20 25 30

Leu Gly Arg Arg Pro Gly Ala Pro Glu Ser Lys Cys Ser Arg Gly Ala
35 40 45

Leu Tyr Thr Gly Phe Ser Ile Leu Val Thr Leu Leu Leu Ala Gly Gln
50 55 60

Ala Thr Thr Ala Tyr Phe Leu Tyr Gln Gln Gln Gly Arg Leu Asp Lys
65 70 75 80

Leu Thr Val Thr Ser Gln Asn Leu Gln Leu Glu Asn Leu Arg Met Lys
85 90 95

Leu Pro Lys Pro Pro Lys Pro Val Ser Lys Met Arg Met Ala Thr Pro
100 105 110

Leu Leu Met Gln Ala Leu Pro Met Gly Ala Leu Pro Gln Gly Pro Met
115 120 125

Gln Asn Ala Thr Lys Tyr Gly Asn Met Thr Glu Asp His Val Met His
130 135 140

Leu Leu Gln Asn Ala Asp Pro Leu Lys Val Tyr Pro Pro Leu Lys Gly
145 150 155 160

Ser Phe Pro Glu Asn Leu Arg His Leu Lys Asn Thr Met Glu Thr Ile
165 170 175

Asp Trp Lys Val Phe Glu Ser Trp Met His His Trp Leu Leu Phe Glu
180 185 190

Met Ser Arg His Ser Leu Glu Gln Lys Pro Thr Asp Ala Pro Pro Lys
195 200 205

Glu Ser Leu Glu Leu Glu Asp Pro Ser Ser Gly Leu Gly Val Thr Lys
210 215 220

Gln Asp Leu Gly Pro Gly Lys Gly Leu Ala Glu Gly His Leu Val Thr
225 230 235 240

Ser Ser Ser Ser Pro Ala Gly Pro Ala Pro Leu Trp Ala Gly Glu Gly 245 250 255

Val

<210> SEQ ID NO 34
<211> LENGTH: 119
<212> TYPE: PRT
<213> ORGANISM: Unknown
<220> FEATURE:
<223> OTHER INFORMATION: Description of Unknown:
Amino acid sequence for deletion of beta-2 microglobulin
to eliminate all MHC class I

<400> SEQUENCE: 34

```
Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115
```

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

```
Gly Gly Gly Gly Ser
1               5
```

<210> SEQ ID NO 36
<211> LENGTH: 11
<212> TYPE: PRT
<213> ORGANISM: Human immunodeficiency virus

<400> SEQUENCE: 36

```
Tyr Gly Arg Lys Lys Arg Arg Gln Arg Arg Arg
1               5                   10
```

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
ctgaatcttt ggagtacctg 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
aagtcaactt caatgtcgga 20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
ttcagacttg tctttcagca 20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
tcacgtcatc cagcagagaa 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
gagtagcgcg agcacagcta 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
acccagacac atagcaattc 20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
caagtatggc aacatgacag 20

<210> SEQ ID NO 44

-continued

<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
gagacacctt aagaacacca 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
agccgcggag ccctgtacac 20

<210> SEQ ID NO 46
<211> LENGTH: 97335
<212> TYPE: DNA
<213> ORGANISM: Homo sapiens

<400> SEQUENCE: 46
aaagggaata aatatctaga agtcccctta aacagaagta attaattcgt ttgcagaaat 60
tggcaaaatt tggggttccc ttcttaaaag tttccttctg tcacttggaa aaaatttaaa 120
atatgtgcat taggttgaca aagatcaaaa aagttaaaaa aaaaaccctt tttggaatgc 180
tgtggagaaa ggagcacttt tatttatcta ttatttattt tattttattt tattttatta 240
attaattatt ttttttcttt ttctgagaca aggtctcatc tcactctctt gcccaggcta 300
gagtgcagtg gcctgatctc agctcactgc agcctcagcc acctcagctc cactagcagc 360
tgggactaca ggcacatgcc aagtttccca ggctggtctc aaactcctga gctcaagatc 420
ctcccatctc agcctcccga agtcctggaa ttatgaaaga ggcactcttt ttttcttctt 480
cttttttttt tttttttttg agacactctt ctccgtcttc caggttagag tgcagtgggg 540
tgattttggc tcattgcaac ctccacctcc ccggttcaag tgattctggt gcctcagcct 600
cctgagtagc taggactaca ggtgtgtgcc accacgccag gctaattttt ctatttttag 660
tagagacgga gttttgccat gttggccagg ttgatctcga acccctgacc tcaggtgatt 720
tgcccacctc tgcctcccag aagtgttgga attacagtca tgagccactg cacccagcca 780
aaaggcactc tagaacattg ctggtgggag tatgaattag cataaccttt accggggaca 840
acttggcact gtctattaaa actacaaatg tacatacctt ttgactcagc aactgctctt 900
ctagaaatct atactacaga tacatttgaa catttgcaaa atgacgtata ttaaaggtta 960
tgcactgcag cattgtgtga aatacatgca acagattgga aacaactcaa gtgcccaccg 1020
atagagaact gattaaagta agctctatct ctattccata cagccccaat aatgaggaaa 1080
ctgtctactt atagtaatat ttccaagata taagtgaaat aagcaagatt caggaaattg 1140
gtttgatatg cttttattta tgcaaaaact tctatatgtg tatgcttttg taggcataga 1200
ctatgtatgg aagaatatac aatagactga taacagttac tcctactaaa gggtaagtaa 1260
tattactgag gttggggaga ggatgattca gagcaaaaat aaagtgagga ctttaaggac 1320
tttaattcct ttaatttttt tttttttttt tttttttga gatggagtct tgctctgtcg 1380
cccaggctgg agtgcaatgg tgggatctaa gctccctgca acctctgcct cccaggttca 1440
agcgattctc ctgcttcaac ctcccaagta gctgggatta caggcacttg ccaccacacc 1500
cggctaattt ttgtattttt catagagatg gggtttcacc atgttagcca ggctggtttc 1560
aaactcctga cctcatgatt cgcccgcttt ggcctcccaa attacggagt gagccaccac 1620
gcccggcctc cttttaaatt ttttttttta attttttttt tttagagatg gagtctcact 1680
ctgtcgccca ggctggagtg cagtggtgcg atttcggctc actgcaacct ccgccccccg 1740
ggttcaagtg attcccctgc ctcagcctcc cgagtagctg attacaggca cccgccacca 1800
cacccgctaa tttttgtatt tttagtcgag acgggggttt caccatgttg gctaggctgt 1860
tcttgaactc ctgacctcag gtgatctgcc cagctcagcc tcccaaagta ctgggattac 1920
aggcgtgagc caccgtgccc ggccttaaat ttttaaccat atgaatgtat taggtattca 1980
agaaaaatat gttgaatgaa aatttaaaat aaaaaataag taaagcacat cgaatttaag 2040
gtacctaatg tgtaaggcac agaatgtctt tttttttttt tttttttttt tgagacggag 2100
tcttgctgtc gcccaggctg gagtgcagtg gcgcgatctc ggctcactgc aggctccacc 2160
ccccggggtt cacgccattc tcctgcctca gcctcccgag aagctgggaa tacaggcgcc 2220
cgccacctcg cccagctaat tttttgtatt tttagtagag acggggtttc agtgttagcc 2280
agaatggtct cgatctcctg acctcatgat ccgcctgcct cggcctccca aagtgctggg 2340
attacaggag tcgtaatgtc tttttatgat cagcaggatg gttaacggat atttgctgtc 2400
agaccccagt gagttttagc acttctactt actagctgtg tgactttaga cattattcta 2460
agcctcagtt tccccatatg taaaatcaaa cttatagaat tggagagaat tgagtgcaca 2520
taaagcactt aggctcacag aaagcactga aaaatgttat tattaatatt ttcgccctaa 2580
aatctccaac aataaaccaa attctgactt gctctggctc cttttggact agtctagagg 2640
caaagagaca aactatatga tttctcaagg agtttttctg ctcagaggct tgagtctggg 2700
gactccacac aatattcgaa gacattcttc cttctttctg ctgccttgca acctgcagac 2760
ctcccacctg tgttaaatga agaatgcttg aagtgaggtt actcagaacc cacccggttc 2820
atgttttctc aagggtagaa ggcgggaaga aatctgttga cacagttata taaagcctgt 2880
cattcagtcc cctgcctatt acctctgcag accgttatgc atattaaaga aggggggcg 2940 gcaaatacaa aagaaaaata agagagacga gagagagaga gaaagagaga gagagagaga 3000
gagaacgaac aaatcaggat gcttgaggga atccacgtgg tcgccaatct gtaactgatc 3060
agagcagcta cactgaagca aaaaccccag cgcccaacgc taaatatatt gcaatggaga 3120
aaccgtccac aatggggtgt ctctgtcctt agcagagcct tggggctgcc gtttaagacc 3180
ctcctgctac tcccaccctt ttagcatcta gtaaaccacg cgctgtaaca acggaatctt 3240
gttctgtgta ttgcgttgtg cgagtgtgcg ctttgcaaac catctgggcc ccatcctgcg 3300
cggttggaac gaagatcgat tcgggacgag ttgggggagt tgaggcttgc ctgtgtctcc 3360
tccctttcat tgctcctctc cagcccccat cccatcgtcc gctctgcaca aatgtttcgc 3420
cagtggaggg acgtaggttt tcagcaccag gaggctgtgg accttctctg gaggcgtgaa 3480
gtgcaccctc cggagggcca gagctgagtg caacctgctc acaacgaccc tctccctcct 3540
tcccaaattc gccgccccag gctgtaatat tacatgcagt gcgctgtacc ggtgcgggag 3600
tccaggaagg ctgcatgacc ttccagcgaa ctccccctcg gcttggggga tggaggctgc 3660
cccggggcct gcaggctgtg tatcgatccc ccagcctcag ccaacgcaag ttctcccgac 3720
acaaacccct ccctaccctc tcggctttcc cagccttgca ggcgtctaac gctatgctcg 3780

-continued aggcgccctc ccctctttcc cgcaataaag taaacccggt ggatattcat tcccctccct 3840
aactcgcctc cttctttccc cctcccccct cagcttacta accccgcgca cagagctcgc 3900
cgccggcggg ccccttccac ccagtgtatc ataatgccca acgctctcct cctcccccctc 3960 tcttaatcag aaacgtgctc gcgagccccc ctccctctgc gtgcatacat tagggtctgc 4020
tttgcatgca gcggcaggca gagaccggag gaagaagggg cgggggcgct tttgcccgcc 4080
tcttccctcc aggccccgtt agccacccag cttcagcttc gttgtaacac cgcgtcgtta 4140
gcggagcacg ccgtggcctc agtgcccggg ctggagaaac acaacccaac tccctgcaga 4200
agggcacgaa agccagacga gtgcacagta gagcgaggag gtggcaggag acctgccact 4260
cggtgtgtgc tttttggaaa gagctccagc atgaaaatgg gaggggctcc ttttttattt 4320
tttaaagtgc gttcattgag ggcctttctg ttttgcatat agtaaactgg gcagcgcttc 4380
tgttttgcat gtagtacaat aagggctctt ttattctaga agcgttcaat tcgggctaac 4440
ccatcttgta tccgtgccct ggggcggagg agaaggctca ctgctccccg acccagccgc 4500
cgcgttatac tggaagctgc tctcccgggc tgttcgattc ccagcgcgtc ccgggaacgt 4560
gtgtaatcgg cctctcggcg ctcaaggctg caggcggccc ggctccctac gcctccatcc 4620
tccgcgtagt cctcgccccc tccccctctc tccggaaccc gcgctctgct ccgggctccc 4680
gggcttcctt ccccctcct tttcccgagc aatgcctctc ccggagggcg gggcatgcag 4740
ttatccaggt tgcggggccg gcgggcgggc aggaggcggc ggcccgggcc tcgggatgga 4800
gttgcagcgc ccaggcgtca gaggcggagg cccgaggccg ctatacagat tgcggggctg 4860
gcgggcgcgg cccggcgctc tgcatagcgg ccggcagggt gcaggcggcc gggcggcgca 4920
gagctggtta ggcaggttcc ggggccccgt gcccccccct ccgcctcccc gccccccctgt 4980 gttgtcgcct ctccctctcg ctgcttcact tcacggggcg aacatggcgc acagctgtcg 5040
gtggcgcttc cccgcccgac ccgggaccac cgggggcggc ggcggcgggg ggcgccgggg 5100
cctagggggc gccccgcggc aacgcgtccc ggccctgctg cttcccccccg ggcccccggt 5160 cggcggtggc ggccccgggg cgccccccctc cccccggct gtggcggccg cggcggcggc 5220
ggcgggaagc agcggggctg ggttccagg gggagcggcc gccgcctcag cagcctcctc 5280
gtcgtccgcc tcgtcttcgt cttcgtcatc gtcctcagcc tcttcagggc cggccctgct 5340
ccgggtgggc ccgggcttcg acgcggcgct gcaggtctcg gccgccatcg gcaccaacct 5400
gcgccggttc cgggccgtgt ttggggagag cggcggggga ggcggcagcg gagaggtaag 5460
ggggcgagga acccccaggt ccggggtctc gaccctctgc ggagcccct cccctcccc 5520 atccgggatt gaggagcatc ccaattctgg gaccatctcg gggtccctga cccggggcga 5580
atggctctcc catcttggga cccccatgca gggctgcaga cccccaggcg cccccacccc 5640
ggggtttggg cccatctggc tgagggcgtt tgcccccgc tctcctcccc ctgacccttc 5700
cccaaatccc ttggcacaga cccccctcgcc ggggtttccc atcccgggac tgaacccctc 5760
ctccctttca cagattacct catccgagca agattcctcc ctccctccct cctagagacc 5820
tgatcccgcc acatccccgc ctccctctct gggcagatgt gttactccta gggcagtttt 5880
cctctcgggc gtctctcggg tgatggcctc atccagggcc acgttctcct ggcccttggg 5940
gatcgtgtcc cttccagcac cttgctttcg aaaacccgat gaaccctcgc gccatccccg 6000
ggccaggtcc ctatactgcc agccactccc ccttccttca cctccaccct ctaccccac 6060 cccaagcaga ccgatcctcc cccatcccgc cctaccccac cggggaaaat ctctcctctg 6120
caccttgcct ggtctcacct cctttccctc tgaagataac ggtgattcct catacagcag 6180
tctcttcccc cccccgcccc gtcttacagg gctacagttt ctagcctatt ggtagccggg 6240
aattactcta ccttcactcc accctttccc tcctttagaa tgaaggatta gtggcatctt 6300
ggaggggaaa atagtccact gtcccctagg cttagagaag agcagctttc caccactccc 6360
cttggagagg aggcaggctt tccctccagc tctggggaag gggccccctg tgaggggagg 6420
tgtttgttgg gggactgagg cagcatcctc ccaggggaag cagctgctct cctaccccac 6480
ccactgcgcc tgagagcacg cagtctccaa cccgagctcc ctcccgccct tctcttctcg 6540
tcatttcatt attgatccac cttttcctag gccaatcctg gggcttggaa ggggtggggg 6600
aagccaggtt ggggtgagga gagtagataa gggacagtta tactttagtg tggtggcggt 6660
ggttgctttg ggatgggaga aaaaggatta tcaagcaaag ttattcctta gaaaggactt 6720
ggggttgtct ctgattcttg taaggggacc caaggtggat gaagggtcag agcgttgccc 6780
cttccccatt agtactgggg caagaacgga gttgcttcta taaacattat tcggccccct 6840
tcagcaaaaa ggaaagttgc ccaaggaagg gaagttgagt tcaggttcag ccagtggcgt 6900
tgcgcatttg ttttccattg gatgcagaag gggggagttc gaattgtaga ggggggagga 6960
tggcatgggg gatgctagga ggaggaagag cagctgctag gggctgaagc gaagggggt 7020
agggggttgc tgctctggag tgctcttgat tgaaacagaa agggaaagat aacaaccagc 7080
cgtttcctgc gtgctctgcc gttggtgcac acaaaatatc ctgggcaaac cccttgtccc 7140
ctattgtgcc ccgcacccct ttagatttac ggaaagatcc tgggaagaag gggagggagg 7200
agatcccaag gaccctggcc cctcctttca aggagctggc attttttagt tgttagtctt 7260
cctgcctcct ttttttaat cgtttctaag gcagcctgat caggagactg acaacaaccc 7320
gccttctgac agagcaagga ggacatgatg ggggcgtgtt ccttgctatg tagctagctg 7380
cagcgtcccc tttccctgcc tctttctgct ctatctccac ctccttttcc cagccttcag 7440
aaggcagctg cagtcagcag ggttgtttga gactatttat tggttgctgt agattattat 7500
tttttttga aaggccaatt ctgtattttt taagctaaca acacagatcc catgtagttg 7560
gagaaccaaa ggccacatac atgacaaaaa gactgaaccg ttcaggttac ttgcatggag 7620
ttggtgctta aatgtgagtt gattttgctt ttttaaaaga tacagcagca aaaaaaaaaa 7680
aaaagaaaaa aaagaaaaaa ctgacatttc atttacctgc ttattttcaa aattgagact 7740
tgcctggtta tatgtagcat tttagcccca tgtatatttg agtttaataa gaaagtctct 7800
attaggagaa gttagtccat tttaagggga tcctaagaag cattttcttc ttgttcagta 7860
tgcttattta ttttgtatag aaggactaag cattcacatt ccaaatatta tcacatattc 7920
aaaagcaaag ttttatgctg acagcttcca atcatagttt ttcaagagac tggttagaaa 7980
gagagccacc tggattcagg gacctaatgt ctgggcacca gaatatttta tctgttggtc 8040
tttgacaaat cacttttaaa gttttaatca ggggctaaac gttttcttat ctactggcat 8100
tatgagataa ttgtaaacta ctgttttatt tttcttaaca ctagtatata atgtaaagcc 8160
tgtcaaggaa ttgcagttat ttcaaatagg atcatattta taaggggttt ttgtctttaa 8220
aactttttcc tgaacagtag ttgctgcttc attatgagaa gagtggttga ctccttacat 8280
taaacttgag tattttttct gaattggact tgaatgagct ctgttccatg ggtaagcttt 8340
ttatgtggtg tttgaggcaa tccagtatga gttgatggta tgcattgagt agtggtaaac 8400
ctctgagctg gtagttttca gtgtagaagc aagcactttt tttttttttt taacatagcc 8460
ttactaatca atgataaagt tccaaaaggg aagtttaggg ttcaccctgg gctgacatag 8520

-continued

```
aattctaaag actgcttctc agaactcact catagctctg tatcaagtct tatctggatt   8580
catgaagaaa tggttatatg atccaaaatg attctaacct ctttaaactc tggttcgcct   8640
tcagtgaata atgactataa cttgcctatg taacaacacc tatgttaata cttctaaaac   8700
taggtaacag aacttccaga tgactttgct gtttgaactc ccttagccat aggagacttg   8760
tccttcactg ctgttggttc ctaacttcct ttgtatgaca attaggaagt agaattgagg   8820
ttttgtttta ttgagcactg taagaaatca gaggtccatt ttttgccttt ccccttccct   8880
ctgtagtgtc agtatcccat ttttctaagg attctctcag gtaatgttca tactactgta   8940
ctttgccatc taaataaaca tagtacagca gcaccctttc tgttgactag aagttaggct   9000
gttgtaataa taaacccctg aaacagtgtg tttatcagta actagtcttc gtttattaat   9060
gtcataatcc agttaccttc cctactactt cacaaaatat taaaagcaaa atttccatcc   9120
tgatcataac atagcaaact ttaattagat acaaattgaa actgagttac agcattggtg   9180
tgtatttatt ttcacttgaa attgcagttt agttcatgtg gactgagaca ggcttttgga   9240
ttggacttga aaagatagta ctcctgcagc tgaaaggtag taggagagcg tgattttttt   9300
tttttttttt taatgtttac tggtcatgta tgtaccaaga gtgggagttg ctccttcgtt   9360
gccttcacag ctagtcctaa gattggcaga aggtaaatga aggagggaac acaagcagag   9420
tggagtgcac gaagcctccg agtagaagtc agtggatgtg ggctctcatc tccgttactg   9480
aacagttatg agaccctggg caaattcact tttaacctta aatttctgat ctgtaaaatg   9540
aaaagtttgg actaaatagc tcatgaatct gttctgtgtc agtattatga ttcctttctg   9600
ttgtattaaa cttttggtca aatcagaatt tcttattctg agtttatttc aaaagtcaga   9660
gtcaagtgag acgatttgat aatttttgtt tttttttga gtcagggtct cactatgttg   9720
cccaggtgca tcttgaactc ctgatcctcc tgccttagcc tcctgagtag ctgggattct   9780
gtttggtaat ttttaatatc agattataca tttgcctata taactggcat tattattagg   9840
aggagaaatt tcaacttgga aagttttcgt tgtgtggaaa aaacataagg actttgggga   9900
agttgaccag tttcatttat aagaaaaatg aggataaagt ttttacacat agttctgaga   9960
acctacagaa tcccaggcat tatctggtgt ttagaggccc tcttgtttgg ctaaatgtgt  10020
tgtcattgtt gtgaattcca gactatccaa aagagaagtt attttcagtc taggtggtat  10080
attcctgtag gtgtatgaat tttgaatgaa aagaaaaatc caatacatca atgtatttat  10140
aaatctgaag tgatagtacc tacttcatag gatgtagtta ttaatatgtt ctgaaatggt  10200
ttatactgag cattagaaat tcagtcttta gaacttttct tcctctgtga ctgaaaacca  10260
gatgacatgt ccccatcttt cacttccatt taattatctt aaggcacata ctcctggagg  10320
aaatcatcat tcacacaata gtgatccatc ttcttattgg aagttgagag aaactattcc  10380
catcttgact taattctcat ctctttgctc accttagagc tgtccttccg tggggcagct  10440
gtgcagactc tataccaatt gcctccctta ccctgtggct agagggggtg gcaacagtgc  10500
tttgcttgct cagaggcata acagactgca gtgcctctct cttttggaaa ctcgctgtgt  10560
tttaattgta ggtctcctaa ttaagatctc tttgtgcctg cccacattcc actagtgttg  10620
gcacagagct tcagcttcct tctagcactt aactgaaggc cttcaatcgg gccttttgtg  10680
aatatcttgt ctctttccat tcttcctctg ccaaggtgga gagcccagtg gcatagacct  10740
ttgagaaggg ggaagctttg tgactatcac tactttggga ggaatttatt cgaggattgc  10800
tgggatggga ccttcctttg tttgcatatg ttattttcag ggattaagaa aggttaaatt  10860
actaatgagt ctggcatgat gtacctacat tttaatcaga ttcttaaccc tgtaggcact  10920
```

```
agtaggaaag aggatgccac agagttcact gttacaaagt atttccttgg atcttatcta  10980
gactggttta tgaaacttga tgagtaaaat attgtcgtgg agtaaatctc agactcgtga  11040
tttttgtgga ctctgaggtt gttgaagaca agacaatcag atgaaattat tgattgctcc  11100
taagttgtat cggctttgag acacagactg aattaaagtt agctttcaga tctgagttaa  11160
cttttgatta gaaagacttt aggaggttct ggaaattgtt gagttaatta agaataccct  11220
tgtaggctcc actatttctt gagattttca ggaattgtct aggcttctag agtattttca  11280
gaataagata aaatagcttt tctggaaaaa gtagtttgac tttagtttcc aggaccttcg  11340
tattcaaaat acagtatgtt ctttactaga tctacatgtg gcatgctaga gaaaatgcta  11400
tcttttatta agaaaaagga atcttaagtc ctttacctgg acccagatgg cttcattgat  11460
cacatcagta tgaggttacg cagacaaagg gctatttttg ttgttgttat tgtcatttca  11520
ttggttgttg aagaaggcct gggagaagga agtacaggat cttttatggc atgcattaaa  11580
taaagctgga ggcctgcact cttatacctg agtgggtggt tttatggcct aattctctaa  11640
ttgctggcat ttatgacagt gtggatgcta ctggccctgt ggctgaggta gattatgctg  11700
ggaataggga ggaaaaaggg gtccttttgt tagccttttc attttgcccc tcaataaagt  11760
ctctgcaaaa accctgagga aatacagaga cacttggact gagggaatga cttcccataa  11820
aatggttctt tatgttttta aaatgatgag ccgcttttct tgacctatcc aaagaaatcc  11880
ataccaccac tgttaaatat ttcaatgagt tttttacctt gtcaggttac acaccagggg  11940
aagccaacca tgagactgta gctgctgcca aacattcgct tctaaagact taagacattt  12000
gaaagaagaa ttttgttacg tgatttgtaa ttgttgtgga tgatataaat ccccttgaag  12060
gattagtcca aaacttctaa gaggccaagc ttggtttaac ttttagatgt tgaattgaat  12120
gtattgccct aatgagtttt agttttaagg aaacaacaaa gatataagag ttagttggca  12180
gttttgtgtg cagtgtatga aaattcccct tcccttgaaa tgagtagttg tttttctatt  12240
tgacaaatag actgaaggga tttccccaga tatcttacct tcaattattg ctgcagcagt  12300
accctgtgaa gtaccagtgg gcagcatcgg tccagtagca tttatttcag gagctggagt  12360
ttcttccgta tatagtgttt tatccatttt cttgcatttc tggttttgtg ttttgttggg  12420
atgtttgggt atagatgttt tgatgtcttt cagcaacaaa agatatgaat ctttctaaca  12480
ttcatactgt tttagagaga tccacttgta ttatctatgc tttgctgaag catcattgtt  12540
tcattcttat tttacagcat caaggtaatg gtagctttct gtcttgaatt aggagagtga  12600
tattacttgt gagaagggtt ttggagaata gtttttttctt taggctgtcc tttatactat  12660
ctcagttcta aacactaggg aaaagttaat tcttatctct aataaatatc ctacacctag  12720
agaaagaaat atttacacat gcccatattc aacttctgtc catccatgag gattgaccac  12780
tttttagatc aaacacaaac attgtcccta gattattgcc tttaattata agcagtaaaa  12840
ccttgtggat aacatctctt taagcttagc taatgaggaa atccttttgt aatctctttg  12900
gctaggattt tttatttgtg catatataaa tacctttaca gaagaaaggg agaatctcat  12960
aatctaatct gtagtggtgt gagatcgttt agcatagtaa ttaagagttg ttaagaccat  13020
gggctctgga tttaaactgc ctgagttcaa atctaagctc agccatcttg aaaaagtttt  13080
ttttgtgttt tgtttggttt gtttgagaca ggatcttgct ttgttgccta ggctagagtg  13140
taatggcaca aacatttcat ttcagcctca acctccaggg ctcaagcaat cctcttgtct  13200
cagcctccta agtagctggg actacaggca tgcaccacca cactcagcta attgttttat  13260
```

-continued

```
ttgttgtaga gatgggagtc tcaccatgtt gcccaggttg gtcttgaact cctggcctca  13320
agtggtcccc ctacctcagc ctcccaaagt gttgggatta caaatgtgag gcactgcacc  13380
caaccagaaa agtttttgaa cctctccata cctctgtttc ttcatttgta actgagaggt  13440
actcatgctt catagtctca ttgtgaggct taagtgagat catgcatgta agcacttagc  13500
attttgcctg gcacatagga agccctaatt gttagaacca agagattgaa aggagagcag  13560
ggttataatc tttttttttc atcaaaataa ctggttttta ttacattaag ttatacctgt  13620
atatgtatgc atacatacac ctatttgagt gctataatct tagaatgttc ttgatattag  13680
tctgagtgtc aagttcttct ataaactagg tggaaccaaa ttgaaggcca gccacccgtc  13740
ttggtaacaa cattagtgtc caactaaagc atattaaaga taaggcaaaa aagaagaaag  13800
agaacaagat ggtaaatagg caagtaagat accgaggaac acagtgcctc catgagttgc  13860
taattatcag gccaaggcag ctataatggg gttgctacct gttgtctcta taactagtgt  13920
tcctgatatt tttatgagga ggcacttggt cgttccttat aacagctctg aggctcttca  13980
gggttcttgg gctccaggtt cagacccatt agtctatact tgatgacatt tgttcttaag  14040
tgtcagcttg aggagaatga gtgctggtct acagagatca atgcaagtaa ccatttaatt  14100
atagaagaaa tgctgaattg taggttgcaa tttctggggg ttggaacttg agcagaatgg  14160
tcaaaagcag attagagttt aagaataact agtaaagagt agtgtgttta aggaggaaaa  14220
gtacagtttt gggttgggcg cagtggctca cgcctataat cccagcactt tgggaggcca  14280
aggcgggaag attgcctgag gtcaggagtt cgagaccagc ctggctaaca tggtgaaacc  14340
ctgtctctac taaaaataca aaaattagct gggtgtggtg gttgcgcacc tgtatcccca  14400
gctactcggg aggctgaggc aggagaatcg cctgaaccca ggaggtggag gttgcagtaa  14460
gctgagattc cgccactaca ctccagcctg ggcgaaagag caagactctg tctccaaaaa  14520
aaagaaagaa aaaaagaaaa gtacagtttt gctgtactct ctttaaaaag atttgcaggc  14580
cgggtggggt ggctcaatcc tgtaatccca acactttgga aggccgaggc aggcagatca  14640
cttgaggtca ggagtttgag accagcctgg ccaacatggt ggaaccctgt ctctacttaa  14700
aatacaataa ttagctacat gtcgtggtgc acacctgcaa tcccagctac ttggggggct  14760
gaggcatgag aatcgcttga acccgggagg cagaggttgc agtgagctga gatcacacca  14820
ctgcattcca tcctggagga tagagtgaga ctgtgtctca aaagaaagaa aagaaaagaa  14880
aagaaaagat ttgctaacat actcagtaca ccatcagaaa ccatcaatac acctcagaaa  14940
ctgaggcaca gacaagttaa acagttttcc ttaagttata tggctagtaa gtggcagggc  15000
tagaatttaa atctgaacct acatctgttt gaaagttgat tcttgctctc tacactgtgc  15060
tgtctttaag tcctttctct tcccactcac atccaatcaa tttctgagtc ttgtccatta  15120
tattattgta gtgtttcttt catttgtccc tgctgttctg ttcctgctgt cctagtttaa  15180
atttccatta cttttggata gtttattgtg gtaatcttct cattggtctt cccacctatc  15240
ttttcaccct acacagtgct tcacaatatg atagttttct taaatacaga tcagagtatg  15300
tcactttatt cctaaaattc tttggcttct cactgaatat gaaataaaat ttcagattct  15360
cagcgctgca tgatcttgct agcctgtatt tctaaatttt gaaccgtgtc tcctgaatgt  15420
acatcgttac tgcttcaacc acattggact actgaactat taggtgttct ccacagtctt  15480
tgtttatctg cctttgtacc tttgctaaag cctctccttt gccttaaagt ctttcccatt  15540
ttgacctgtc ttgggcttat tattcgtctc ccatggttca actcagatcc ccagatccta  15600
actcttccat gaagttttca cagattgtac tgctagttga aactgaactt ctttcctgtt  15660
```

-continued

```
ttctttttgt gttttgtatg ttatccttaa aaaatttaac cccgtatacc ttatgtcgtg  15720
gtacttttga aatgtgtctg tctttgtccc attagatagt gactccctta agacacgggc  15780
catttctaag tcatcattta tgttttatgt tttttataat ggtgactttt tatatagtat  15840
ttgttgaatt gaaaatttga tgtccataca acttttagga atactttgct gggacacatt  15900
acataaacta ggagaactta agactacgaa cagaatattt ggactaatca ttaagaaata  15960
ctaatttaag tatggcaaag gaaagcacag gtgccatgat gcgacatttt tgtaaaggta  16020
ttgattgggg ttttgaaagc gatgttaggg tatcctgatg ggatggcatt atcttttatg  16080
tagataatac ttagcactga tcatcccctt acttgagtgt tgtttccatt tctaggttcc  16140
tcaacttaaa agggatgagg agaccttgga gacggttctg aggagactca aaagatgatt  16200
atatgattgg aagtcagtcc tatgaggaaa ggttgagaga atgaaaggtt aagaggcaac  16260
ttaataactc ttcaaaaaac atgaatggat ccattattag gaatggtaac cagcggtttc  16320
ccagctccac tgacagcaga ataagagaaa ataggtttaa accgaaatca ggagtagttg  16380
tgtaaagaac ttattggtaa tgatggttgt cattacagtc atggtaaaaa ggttaccaaa  16440
ataattttat tatcttctct ggaagtatat tttaaaagta cagtcctgcc tacatatgta  16500
taaaatgacc tcttaagcta ccttttcctt ctgtgaatca gtaaataaat tcttattcag  16560
ctcctcgaag caataattac tttccagtag gaagcttcca gagatatttc tttaggaagt  16620
aatggttttt gtagtggctt tataggagaa tacaaatttt taagtggagc taagagagaa  16680
atcttaaaca tcaagagaaa ccaaggaaaa cagtaggtgt ggtatcaata taggaaacaa  16740
ataagtattt gtagctttta tgtccatttt cagttgtcat ttaaagaggt atagttcaga  16800
atagctcttg ttaaggctgt cactgcttgt ggatacattg taacaaatgc ttataaatca  16860
tttccaaact aatagaagtt tgcttcatgt tagttagtat tataaaagcc tctgaccctt  16920
ggcttttgag gctgtgtaga gggcttgcat cactcagaat gaaacctttt tagatatgtt  16980
gggttgcaga aagcatttcc tgtacagtca gaatgaaaac ttgaattggg attattcata  17040
tagattacca aaagtctggg cagagctgat attaccacca gccagttttc ctactaactc  17100
ttaactccaa aaccttcatt gggttattga agctttagga cttttgaatt tcctactgga  17160
attgtgtatg aattccttct ttcaagtgaa ctgatactag atttatttaa gattagttat  17220
acatcttaag tattttttaa gtggcatata atgaatggtc tctactttta accagtctca  17280
taaaatgcct ggggttcata ggtgaagctg gattgttgca ggaattctgc aattgttggc  17340
aaagcgaagg gcagtttgac tccttaatta taaagttgga tgtcatttga gaaactctgg  17400
gaattggaag tagaacaaat tcatactttc cctataactt ttaatttctt gtcatacatt  17460
cagaaaacaa gagatgtaaa attcataaaa ctgcttgtat aaattcagaa aacgggatta  17520
taaaagcaaa gacaaattgt cttacgattc tttgttctac ttgagagatt caagtgttgg  17580
agtaataaaa aataccaggg actttctttt ttttaatagg ttaatgccac ctaatgtggg  17640
cttctcagaa tgtgatggca aacttccaaa tatgatgtgg gagccaaaag agaccaactg  17700
gttttacaaa atattaagaa cacaaaattt cccaactcat atatttgaat attcctaaaa  17760
aataataagt caaaattgtg ttggtgggct gggcacagtg gctcacaact gtaataccag  17820
cactgtggga ggctgaggtg ggaggattgc ttaaggccag gagttcaaga ctagcctggg  17880
caacttggta agacctgatc tctacaaaat aaaaatttta aatttaaaaa attaaaaaaa  17940
aaaaattagc caagcatggt ggcctggcgc cttgtagtcc cagctactca ggaagctgtg  18000
```

-continued atgggaggat tgcttgagcc caatgggtcg aggctgcagt gagccatgat catgacactg 18060
cactccagcc tgggcaacag agtgagactc catctcaaaa aaaaaaaaaa aaaagagaaa 18120
aaaaattgca ttggccaact tggaggcttc agtgttattt tgccaagaag aatgttcact 18180
tttgtcatct aattttacac tgctccttca gcaaactgac tttatggaga gataaccctg 18240
tttaccttta gaaagaagga agttgtggat tcctcagtct tactcccatt actattggtc 18300
attcaacagc ccatcttccc agaaggaaag atgtaacctg acttttgcgc cagaataaga 18360
acaacaaacg gaagaaaaaa actgagtttt atagtagaag tttgtagttg aatgagcatg 18420
tagctcaaaa tgaagttaac cacttaaact tgtcatatgg gggaccaaaa tttcttataa 18480
taaaaagaac tatatctgaa aataaagttg gtgtttgttt aatttttcta gcctattcaa 18540
atcaatctgg tcatttatgg tactttccta ttagagaaaa ataaaccctg tgattgtgat 18600
gcttaactta attttctaca gtgaatcagt taagtgggct tattttttct gctttagcaa 18660
gtagataaac cagttcagac ttggaacctg aggattctgg aaatacacct ttcttgagtt 18720
tttggttttt tttttaaag attctgcaga ataatttggg acattgccag gaatcagaat 18780
agtttactat ctgaagtagt gcattcattt tgctgttttt tgttttttg tttttaagac 18840 agataagcta ctttatgact acctcttttt ctgaagcagg gtgggtggag gtcacctgtc 18900
tcatttgctt tgctgttttc agcatctttg ctgcttattc ttgttgacat ggagtgggga 18960
tgaggggtac tacctatttc tctagttaca aagtgagtag catttgtgtt tcttaggtga 19020
cagttgctag gtagaattga attaaatatt tgaaaactgg acttcattct tgtgtgggtg 19080
aaatttttac cttctgttgt tattgaagaa cagagaatta ttgtcttagc gctctttaat 19140
cccaagtgac ctttttgtgt taacatttct caatatcagg cagagatcat atttaaacag 19200
tttcaatctc ttcctatctg ttatgcattc aaataatcat tgttctcttg atgcaccaat 19260
aaccagagag aatctgccct tgttcctgcc cctgacaatc tgttcacaag agaatatgat 19320
gtcagttcaa taacagcata catttcttga ctggttgaat ttcattaact atttggctta 19380
agaagtttgc cccttgatgt ctgtgtattt gactgtgctt gggtatatta tacttttctt 19440
actgattgag cagcattatt tttatattct gcttttggaa atgatttaca ggtgtcacta 19500 cattttttt ctactacaaa taatgaaaaa gtacctgcaa agaggctcat cttcctaaaa 19560
atggctatca taaatattgc attacaaagt aagaaataga aattgaaaaa tcgaattcat 19620
ttatcaaaga acatctttta tactctaggt ggatgaccag ctactggggc tctaccattg 19680
gagacgtccc ttccctcatg aaacttgcta tctaattctt tttttttt ttttttttta 19740 gagacaggtt tttgctcttc cacccaggct gggatgcagt ggcacaaaca cagctcactg 19800
cagcctcaaa ctcctgggct caagggatcc tccttcctca gcctcctgag tagctgggac 19860
cataggctca caacaccatg cctactaatt tttaattttc ttttctgttc tcttttgaga 19920
cagagtcttg ccctgtcacc caggctggag tgcagtggcg caatttcggc tcattgcaac 19980
ctccacctcc tgggctcaag tgattctcgt gcctcagcct cctgagtagc tgagactaca 20040
ggcacatgcc accacatctg gctaattttt tatgttttta gtagagacgg ggtttcacca 20100
tgttagccag gctggtctcg aactcctgac ctcaggtgat ccacccacct cggcctccca 20160
aagtgaattt tttttttt ttttgtagag atggggtctc accatcttat gtagctggtc 20220
tcgaactccc aggctcaagc agtcgtcctg ccttgacctc tcaaagtgct gggattatag 20280
gtgcgaccca ccatgcccag cctctcattc tttttaatga gctcagctta aaatgtagca 20340
ggaatataag tattcacatt tttaatactt tgcaagatac tttggaaatt gataatctga 20400
aggttgaagc tctcagaact aatgttaaca gaattgtcct tgggagcaat tcagctattc 20460
ttcatttacg gatttagtga ttcttgagtc agttgtctta caccaaatgt aatacatgaa 20520
tcaggagggt ttttctttgt ttgctttttg ttttttaag agacgaggtc tcactatgtt 20580
acctgcgctg gagggcagtg gctgttcaca ggcataatca tcatgtatta cagacttgaa 20640
atcctgagct taagcgattc tactccctca gcctccaaaa tagctgagac catagtgcac 20700
acaactacgt ctggctctga atcaggagat tttaaatgtt ctcaaagtat gtaatagctt 20760
tttcagtcag gcatggtggc tcacacctgt aatgccagca ctttgggagg ccaaagagga 20820
aggaccgcat gagctcagga gttcaagaca gtctgaacaa catagtgaga ccccttctct 20880
acaacagaat aagaataacc aggcatggtg gtgagcactg tagtcccagc tcctcaggag 20940
actgagatgg gagcatcact taagcccagg aataggaggc tgccgtgagg tatgatcata 21000
ccactgcact ccagcctggg cgacagaata agaccctgtc tcaaaaaaca aaactttttc 21060
cctcctgtta aaatggaact tagatgtgac tacatgctct gctgccttct accatcaaag 21120
aagtgccccc ttcttttttt ttttctttct tgtttttttt ttgagatgga gtctcactct 21180
gctgcccagg ctggagtgca gtggcgccat ctcggctcac agcaacctcc gcctcctggg 21240
ttcaagcgat tgttctgcct cagcctccca agtagctggg attacaggcg cccaccacca 21300
cgccctgcta atttttgtat ttttagtaga gatggggttt caccatattg gccaggctgg 21360
tctcgaactc ctgacctcgt gatctgccca cctcggcctc ccaaagtgct gggattgcag 21420
gcgtgagcca ctgtgcctgg cggaagtgcc cccttctatc taaggccaac ctctccattt 21480
gagctctgga tcccatctcc tctcatctag tcagggttgt acctgcagtt atctcatctc 21540
tcctgctgca taggtaattt ctctctcaca actagattgg tcccatcacc atataaaact 21600
atctgcctta atataatcct ttaaaaaaac gcttgacccc acgtccacct ctagctgcta 21660
cctgattctt ttctcccttt tcacagcaaa actccttgaa agtgctgtgt gtaattgcta 21720
tttctacttt ctcacctttc attctttcct caactactcc agttgggctt ttatccccat 21780
gatgcctctg aaatagctct tatcaaggtt ctcaaggagc tctattttac cagattgaat 21840
agataattct cagttctcat cttgttaaac cctttggcag cctttgaacc agctgaccac 21900
tcccttcttg gatttttttt tttaacattg tactcacctg tttttcttct taactcattg 21960
gctgttaatt ttcagtattc tgtatggctt ccctcctctg cttaactctc ctgaataagg 22020
ttcccaggag tctacttttc actgccttct ctgtctacac actcttccta ggtcatctca 22080
tccaggcctc atctatacgc tgacaactaa gaaatctttt tctctaacac tgactacttc 22140
tcagagttcc aggcttgtat agcctgctgc caatttgata tttccatttg gctaatattt 22200
actgagtgtt tattgtgggc caggctatat tctgagcact tcacatgaat tatctcacct 22260
aaccttcatg accattgtct gaagtatcac tagtattccc atttcatagg caaggaaaca 22320
catatacatt gaagcacttg gatacctaat aggtatctct tacttaccat atctaaaaag 22380
tcttgacttt cttcctcaaa ccttttccat tcccagtctc tttgtttctt aattattcca 22440
ccaaaaatcc agttgctcag gcctaacatg taagatttat cgtcgattta tctcttttat 22500
tcacatctca catctatccc atcagcaaat tctgtctgta ttacatccaa aataagccct 22560
aaattcaact acctctcaac aactttgcta ccaaaacctc agactctccc attatagtct 22620
cttggttgga gttgcttatg ttattacctc actaaagttt gtttctcaca tagcaacagt 22680
aaactctggt atcaaatcct attccttcac tttaaaccta tctgtgtctc cccacactgc 22740

-continued taggataaat ccagattcct tactatggcc aacaaagcca cacgtaagct ggcctctggt 22800
caagcctact tctcgagcat tgtctcttct catctcatcc attctgctat atagccacac 22860
tagccttttt ctgtctgtca tgcatgctgt gcctgttgct gtcttggggc ctttgcactt 22920
gctctcaggc tagaacacta ctccaccaag gtctttatat gtctgacttt ttctcattta 22980
ggcctaacca ggtttggcaa gttttttttct gcaaagggcc agatggcctc tgttgaaact 23040
actccactct gttgttgtaa gtgcaaaagc aaccataggc aatacagatg ctccccaact 23100
tacgaagggg ctacatcctg aaaaacccat acatcaaaaa tgtcataagt caaagatacg 23160
tttaatacac ttacaagctc gtcgtaaagt caaaaattgt aagtcagacc attgtaagtc 23220
agggactgtc tgtccattaa caactgaacg tggccatgtt ccaatacaat tttatttatg 23280
aacactgaaa tttgaatttc atatagtttt catgtacaca aaatattctt ttgactttaa 23340
aaaaatggtt aatttttttt ttttttaatt ttaacttgca gaacaattga tggtgggcca 23400
aattcggcct gtggcccata gttttccagt cttcggtaaa ctattgcctt agagaagcct 23460
ttcctgtcta ccctagcgaa tataacccca cagctaacac ctctccaccc cccactcctg 23520
tcaattctta ttgtcctagt gtcttttttc ttcttagaga cagggtttca ctctgtcacc 23580
caggttggag cgcagtggct cagtcagttc actgcagcct caaactcttg ggctcacatg 23640
aacctcctgc ctcagccttc ctggtagcta ggattacagg cgagagccac catgcccagc 23700
ccctagtgtc ttttatttat ttgttatatg tttattttct gtctctccat tagattgtag 23760
cttcatgggg caggaatttt gttagttctt tacatgtatc ttgagagtca aacagtacct 23820
ggcaatactc aataaatact tattgaatga ttgagtgaca gtcatatttg aattatgcct 23880
gtagcctgct atctggtccc cctttttaa gtctttctta ctctagttca ttatatatac 23940
catttccaga ataaacttca cagttaatgc cttctctaca tttgagaacc aatggtagca 24000
gtctgtattc attgcatttg ctttgaccat accatacaag aattaacaag gttctgatta 24060
tttcatttgt cttctatctt ggccctactc tggctacccc ttttcagcct aatcagtttt 24120
taccaatcct ccaatccttg catctgattt tcttccccct ctctgcccct tattattatt 24180
attttttttt atttttattt ttatttttat ttatttattt ttttttgagg cagggtctca 24240
ctctgttatc caggctggag ttcagtggcg caatcatggc tcactgcaac cttgacctcc 24300
tgggctctgg tgatcctccc atctcagact tctgagtagt tgagactaca ccacacccag 24360
ctaatttttg tgtttttcttt tgtagagatg gggtttcaca ttgttgccca ggctggtctt 24420
gaactgctgt ctcaagcaag ctgcctgctt cagcctccca aagtgctagg attacaggca 24480
tgagccactg tgcccagcct tggctacatt tttaatacat ttttaatttt tttttagaca 24540
agtcatctcc ctttgttgcc caggctgatc tcaaactcct ggaatatccc actgcctcag 24600
gcccccaaag tgctaggatt atagatgtga gccactgcac ctggcctctc cctgttactg 24660
ttaatcagcc attgctcatt accttcatga tctattttct tcagagctgc attctttaaa 24720
acttttaggg ccatgcatgg tggctaacac ctgtaatccc agcactttgg gaggattgct 24780
tgagctcagg agtttcagac cagcctgggc aatatagtga gacctcatct ctactaaaaa 24840
tttaaaaaat gaaccttttt tttttttgag acagagtctc acattgtcac ccgggctgga 24900
gtgcaatggc gtgaccttgg tttactgcaa cctccgcctc ctgggctcaa gcaattctct 24960
tgcttcagcc tcccaagtag ctgggattac aggcacctgc caccacgccc agctaatttt 25020
ttgtgttttt agtagagatg gggtttcact atgttggcca ggctggtctc aaactcctga 25080
cctcatgatt cgcccacctt ggcctcccaa agtgctagga ttacaggcat gagccgccgc 25140

-continued

```
gcctggcatg cctatatatt tctaagtatg taggtattcc tcagaactct gccatctacc  25200
ctccttttct ttcagtacta tattctttcc ctgggtgact gaattcatac acagtttcag  25260
cattcatata ttcattgagt cagatgtgtt ttcttcagat cattataccc tttagacaac  25320
gtggataaac atttcaaatt cagatgtcta aaatgatctc tcttcccact cctttaaacc  25380
tgtctccttt ctgtgttccc agtcttggta aataccacca taaacctaat caacctaagc  25440
cagacatcca caagtgtttt attgattctt tgcactccct taaaccttta tatcaaagtc  25500
ttgtccattt tgcctcctaa tgtctatagg atctgtcctt ttccccttaa tccgtatggc  25560
cactacagtc attttacaac tgttcttcct gcctctactt ctctactgct gtcatagctt  25620
ttggcagcaa aaatccaaat ctaatcatac ttctctccta ccagagtcac taatctgcta  25680
tagccttcag gatgaggtct acacgtcctc aaagataaac ttcaaactca tgaaggcata  25740
taagaccttt catgatacac ctcctgcctt tttttttttt tttttttttt tttttgaga  25800
cagagtcttg ctctgtcacc caggctggag tgcagtggca tgatcttagc tcactgcaac  25860
ctctgccttc tgggttcaag cgattctccg cctcagcctc ctgagtagct gggactacag  25920
gtgcccacca ccacgcctgg ctaatttttt ttttgtattt tttagtagag acagggtttc  25980
accatgttgg ccaagctggt ctcaaactcc tgacctcatg atccacctgc gttggcctcc  26040
caaagtgctg ggattacagg tgtgagccac catgcctgac cgcctttttt tcccttcaat  26100
atcttttgcc cctttcccac atcagctaag gcctcagtca tccagaacta tttttaattt  26160
cactccatgc cacattcttt tgtgtctctg tgcctttgta tgtgttattc tctctgcttg  26220
cactacactc ctcccccacc ccccaccagc tttatcatcc ttcgaaagat taagttttca  26280
tcctctctgc aatggccttc ccgatccttt ctccttgagt gggttaattg tctttctgct  26340
gtgctcctcc agcagtgtct tcctctagca tagcaggcaa catacgatac ttcattaatt  26400
tactcatctg tttttaagat tagcaggtcc ttaaagacag aagctgtcct ttatctctgt  26460
tttcataccg tagcctagga atggccgata tatattttaa tgagtgagtg aatgaatgaa  26520
ttggtacagt ctgtcctccc aacctgaggg cattctccct atgcattttt ttttgagatg  26580
ctttcaaatt tattttattt tggtttattt ttgagacagg atctcactct gtcacccagc  26640
ctggagtgca gtgtctcgat cacagttcac tgcagcctgt atcttctgga cttaagtgat  26700
tctcccacct caacctccca agtagctggg actacaggca cccaccacac ccagttaatt  26760
ttttctattt tttatagaaa gagggtttca ctatgttggt ctagaactag gctggtctac  26820
aactcctggg ctcaagccat cctccctcct cggcctccca ttgttaggat ttcaggtgtg  26880
agccacctcg tcctgcccct atacattctt aaaagtaaga atcatattgt gtaattcttt  26940
gaagtccctc agtattttct actatagtac tattaccaca gtaggtattt aatgttctta  27000
aaacaagttt attgcatttc ttttattttc attttacaaa catttattgg gtgccaaatt  27060
tgtgctagat attagaaata caaaaatgaa taggaaaact gtttctatcc tcagagtaca  27120
cactctaaag aagacaaatg tgtgaacaca ttttttaaaa ttccttctgc taatactagt  27180
aattatgtga gcatgtcttt aaggtgcaac attaagacct tggtattttg aagcttgtag  27240
cagtagccac aaggggaaat gtgccagctg aagtgatagc tacctggaat aaattcccaa  27300
aggggaagtg gtattctttt taaacttatc gctgccaaga tgcacagttt gcctcctgga  27360
tatttcttca actttagttg ttctcagtaa ttttgttagt tctcctgtgg cctcctcatt  27420
tgatggaatg atatataatg gtactagaag ccttcaaaac aaagtatttc aaaaaacaag  27480
```

-continued

```
tgcatcagga gtgattttga tactgtctat ggtattgatg ttattttcaa ttgattcatt  27540

gaaatttgtt ttgtaattga agggatttga tttttcaaac tctttttttt cccccctttg  27600

agacagagtc ttgctctgtt acccaggctg gagtgcagtg cacaatctca gctcactgca  27660

acctctgcct cctgggttca agtgattctt gtgcatcagc cacccaagaa gctgggatta  27720

aaggcatgta ccactatgcc caccaaattt ttatttttgg tagagacagg gtttcaccat  27780

gttggccagg ctgatcttga actctggcct caagtgatcc atccatctca gcctcccaaa  27840

gtgctgggat tacaggtgtg agccaccatg ccaggccctg atttttcata agactaaaaa  27900

ttttggaaac agaagaatgc taagatatag ctgctaaagg gcatgtttga gatgcctacc  27960

acttaattaa gtgctgtgaa gtacctagga gtctcttgct agaaaaggaa ggtgagggtg  28020

tgagcaaagt catcctaggc tgtattcatc tgaggccagg agtattggag cttattcaat  28080

agaggaattc tcaaagtagc tctggagcct ccatcttagc ctggtaggta aagaactcta  28140

ggcgggtgat ttttgctctg actatggtat attgaaaata attttttttt ttttgaaatg  28200

gagtcttgct ccgttgccca ggctggagta cagtggcatg agctcttggc tcactgcaac  28260

ctctacccgg ccctcccaac cccccgcccc gggttcaagc aattctcctt cctcagcctc  28320

ccgagtagct aggattacag gcgggcacta ccacgcccgg ctaatttttg tatttttggt  28380

agagacaggg tttcaccatg tctctggtca tgtcaggatg gtctcaaact cctgacctca  28440

agtgatctgc ctgccttggc ctcccaaagt gctgggatta caggcttgag ccactgcctc  28500

aggcccaatt gggaagaatt taagggagga actaaaagct atgcatttta gttggggata  28560

gggaagaaaa cattacagtt tatcagttga aattttatca gatcagtggt attactagaa  28620

actgtgtcac atctagttac tatagataat ttaggtcttg attgcctaaa ctctgatttc  28680

tagctctgga gtgcctagtt acaatactga ggaatggaga tatacattgc catcctttgg  28740

aagaattttg aaatttgaat atttctccat gaaccacata ctaatataga aggaagaata  28800

gactttttct tttttctgag atagggactt gctctgtcac ccaggctgga gtgcagtggc  28860

acgatctcag cccactgcaa cctccgtccc ccaggctcag ggatcctcct acctcagcct  28920

cccgagtagc tggaccacag gcatgcacca gcacacccag ctattttttt gtatttttag  28980

tggagatggg ggtctcacca tgttgcccag cctggtctca aactccctga gctcaagcaa  29040

tccacctgcc ttggcctcac aaaatgctgg gtttacagtc aggagacacc acacccagcc  29100

ttcaagagtt aagcaaaatt ttttattcca gaatatgaat atgaattaca catagtattt  29160

tatccttcag taacattgtt tttttagaga caggatctgg ctatgttgct caggctggag  29220

tgcagtggat tcacaggtgc aataataggg gaccacagcc ttgaactcct ggtctccagt  29280

gatccttctg tttcagcctc ccaaatagtt gggactacag gcgcacacca ccatacccag  29340

ctattcttta gtgacatttt aatgcaactg atttttaaaa ggaaggctga aattgcacac  29400

tgcctgtctg ccttagatac ttcttgggag caggaatcat gtcttactca atgttgtatc  29460

tggaacatat agccctaggg caagtgtata aatgtttttt gagtgaacaa atgaattaaa  29520

tattgctttg tttgaaaagt tgtcttagta gtacataatt ccttgaaaca cagaatttca  29580

tgtatttttc taatatacct tatattttat acacaaacat tatgtttaat acttatttag  29640

ggttcactta ggttcttttg tgggagaaat attcctattg cttcgtcact cacagaaata  29700

actggccact aaagaattaa agttttgcca ctaaaataaa atttctgaat attaagatat  29760

ttatgaataa cgtgaattta gtggtaaagg tatgcttgga agctctcaaa taactggtta  29820

ccccagagtg gagatgcagg ggtcagaaag aaattctaca tgtttattat ttttacaact  29880
```

-continued

```
agatttcact taggaagtga cattacatag cttaatttgc tgtcttaatc actggaagct  29940
aaatatgagt taacagtatt ttgcagtgct ctacttggca agggtgtttt tctatctttg  30000
ctggtaagaa aatgaaatat tggtgatcta gtctccaagg acatcagtgt cagcaaggtt  30060
taggttttgt ggctatactg tcttggaatg ctgtgctcat cagagtaggc caagttgaaa  30120
ggaaaagtgt gtgatgaatg gttgcctgag cccagttccc aggagtccct agtcatgtat  30180
agcatgatgt ctcctgtacc ctctctcttc agggctgtcc aggcttatga tgccacgatg  30240
ccaaatgtgg atttaattgt agcttctttt gtcttttta tacacatatt actgtagtct  30300
tttgatttct agataagttt aaatccttgg gaagccaaca ctcttacctt gtttccaacc  30360
tccagggatc ccatgtgctt aaggagagtg atggagcaag atgagaagcc tgttgctcat  30420
gatagtgcag tgaaaggagg actttttgc agcaccctct ttatttattt atttattttt  30480
gagacggagt tttgctttat cacccaggct ggagtgcagt ggcgtgagct tttggctcaa  30540
tgcaacctct gcctcccagg ttcaagtaat tctcgtgcct cagcctcccg agtagctggg  30600
actacaggcg cgtgccacca taactggata atttttgtat attttgtaga gacggggttt  30660
caccatgctg gccaggctga tctcgaactc ctggcctcag gtgacccacc catctctacc  30720
ttccaaagtg ctgggattac aggtgtgaac caccatgccc ggctgcagca ccctcttgta  30780
gccttctttc ccagtgcttt ctcaacttgg ctttacttag tttttttgtt ttgttttgtt  30840
ttgttttgtt ttgtttttta gggctcttac ataggcttgg aagttccaag ttagaagact  30900
ggagctcttt aacataacaa tgacagcttt tgtttttggc taagctgtcc ggattattta  30960
aacaatgggt acttattttt taaagcatgc ttcaagaaat caatcaatat ttcaagtgca  31020
aagaaagttc ttgggtaaaa gtatagttca ttttgactac ttatttttat ttatttattt  31080
attttttgag acagagtctc gctctgtcgc ccaggctgga gtgcagtggt gcgatctcgg  31140
ctcactgcag gctccgcctc ccgggttcac gccattctcc tgcctcagcc tcctgagtag  31200
ctgggactac aggcgcccgc catcacgccc ggctaatttt tttgtatttt ttttagtaga  31260
gacagggttt caccgtgtta gccaggatgg tctcgatctc ctgactttgt gatcctccca  31320
cgtcggcctc ctaaagtcct gggattacag gcgtgagcca ctgcacccgg cctgactact  31380
tattttttat ttccttattc caagtacaag accagaagga aaacgaatta atgcttcctg  31440
tcattttgga aagtacttag aaactttaaa tattggcagt taaactgcct gacagctcag  31500
tggaactctt gttttggaat acattgcagt taggattata tagttacatt ttgtaaaagt  31560
ttgaaatata taaaaatgac tcattaggtt gttaataatg aacctaacag tgtgtatctc  31620
ttacatttat ctttattttt ttttttaaa taaagatggg gtcttgctat gttgcccagg  31680
ctggtcttgc actcctgggg tcaagcaatc ctcctacctt gtcctcccaa agtgctggga  31740
ttacaggcat gagccactgc acccagccca tttcttttaa agattaataa ctttttatta  31800
cctgttgaat actttaccta ttgattatta tatgtatagt tgcttgagct gtcaatcatt  31860
gtagcatttg gaacataaaa tgcgtgtatt tagcaatgta gtcccctagt aagtgttggg  31920
aaatccccag atgtctttgt gaaatgcata gattagcagg ttgttccacg agtataattc  31980
aggaaaagaa tgaattaatc agaaatttga aggatctgaa aatggccatc atgtgacttt  32040
tacagtagct aaaagaatag caatttttgt actttagaca acttattcaa ttcctttaaa  32100
tatttattgt tttatattgt atctattatg gtaggaaaac tattctacag ccagtttaga  32160
cacttaggtt ctttgtagct aactgtgtga tcttgggcaa gtcatttggc cttttagagc  32220
```

-continued

```
ttcattttct tcaaacacaa caataagaac tactatgtga ggggacttca aagaaaactc  32280
atggaaaaat acatattatg aaaaaactgc agaatttcaa aattttgtat gcaccaaaat  32340
aaacttgcac taacttgtca taacatatct gaacaggatg tagtttgagg cactaagaag  32400
gataagacat cagtttgaaa agagccccta tcagagcaac ataagttctg ctaaaattga  32460
agcaaaaaca aacataaaat ttatggtgaa gctgggtgaa agaatggtga aatcattgat  32520
gctttacata aagtttatgg ggacaatgcc ccaaataaat aattggatgg ctcattttaa  32580
gaagggacaa gatgatgttg aagatgaagc ctgtagtagc agactgtcca gtttgcaagg  32640
aaaaaattca tcttgttcat gccgtaattg aagaggaatg atgattaaca gcacaaataa  32700
tagccaacac catagacatc tcaattggtt cagcttacac aattctgact gaaaaactaa  32760
agttggctgg gcgtggtggc tcacgcctgt tatcccagca ctttcagagg ccaaggtggg  32820
tggatcacct gaggtgagga gttcgagacc agcctggcca acatgacgaa accccatctc  32880
cactaaaaat acaaaaataa ccaggtgtag tagtgcatgc ctgtagtccc agctacttgg  32940
gaggttgaga caggagaatc acttgaaccc aagaggcaga ggttgcagtg agtgagccaa  33000
gattgtgcca ttgcactcca gcatgggtgg caagagggaa actctgtctc aaaaaaaaaa  33060
aaaaaaaacc taaagttgag caactttcta ccaaatgggt gccaaaacca ttgcacccaa  33120
atcagctgca gacaagtgta gagcattcaa tggaaatttt aaacaagtgg cagcaagatc  33180
ctgaagcatg tctttgaaga attgtaacag gagatgaaac atggctttac caatacgatc  33240
ctgaaaacaa agcacaatca aagtaatggc taccaggagg tagaagtggt ccagtcaaag  33300
caaaagcaga ctgtttaaga gcaaaggtca tggcaacagt tttttgggga tgctcaaggc  33360
attttgcttg ttgactttct ggaggaccaa agaatgatag catcagctta tttgaaagtg  33420
ttttgagaaa gttaaccaaa gctttagtag aaaaatgccc aggaaagctt caccagagtc  33480
ctgctccatc atggcaatgt ccctgctcat tcctctcatc aaacaagggc aactttgtga  33540
gaattttcat gagaagtcat tcagtatcat taagtatgct gatttgtctc ctttgccttt  33600
tttgtttccc aatcttaaaa atctatgaag gaggcggagc atctaggctg aggcaggaga  33660
atcgcttgaa cccaggagac ggaggttgca gtgagccaag attgtgccac tgcactatag  33720
ctaggtgaca gagtgaaact cttatcttaa aaagaaaaaa aagaaatcta tgaagggcac  33780
ccatttttct tcagttaata atgtaaaaaa gactgcatta aaatgtttca gttcccacga  33840
cccccagttc tttagggatg ggctaaatag ctggtatcat ggcttacaaa agtgtcttga  33900
ccttggagat tatgttgaga aataaaattt atatttttaa tttttatctt ttaattccat  33960
tttccatgaa ccttttgaag tcccatcata tgtatgttgc ctatagcttt ccaagtgatt  34020
tcacataaat tatttattcc ttacagtgct caaataaaaa atgaaattga gggatagata  34080
cagtaagtga gttgtctaag attacatagt ctgagagaat cagactgaga ccctaaacca  34140
acccttctct ccccacatcc agcactctcc tcactggcat cacgtatgag aagactggat  34200
tggccccctc tacaattata atattctatg atttttttgt ttctgaagtg atttgccatt  34260
acctatttta tttgcttttt cctcaaaata tattttaggg ttactatttt taatgtcttt  34320
tttttctgcc tgaaagtaca ttttaaaagt taacagtatg gaatttcatt attgtgataa  34380
gattttatat taattgtgct gttaggagtt ttggctgttt ttgttttgtt ttgttttttt  34440
ggtaacattg tagcctacaa gtgtaaaccc tgaaaatgat tccagaaatt tatttggggt  34500
tcagattcac atgttgtagg ttagttatat actaacttgt tttaagatga agagagataa  34560
ttttttttatt ttaaaattac ttttagattt tttttagatt gggaggccag tatgggagga  34620
```

-continued

```
tcacttgagc ccagaagttt gagaccagcc tgggcaacat agtgagaccc cgtctctgta  34680
aataatttta aaattagctg agtgctggta catgcctgta gtcccagctg cccaggaggc  34740
taaggcagga gcattgctag agcccaggag tttgaggctg cagtgagccg tgatcacacc  34800
actgcagtac agcctgagtg acagagtgag cactggcaaa ttttaaaatt ttctgtaaag  34860
actcactatg ttgcccaggc tagccttgaa ctcctggcct caagcagtcc tcccatattg  34920
gcctctcaag gcgctgggat tacaggtatg agctactgtg ctggccaaga gagaattttt  34980
cttattcaca aataatgttc acagtaagaa tttacttaaa attttttaa agtaaaaaga  35040
actggctggg cacagtggct cacgcctgta aatcccagca ctttgggaag ccaaggtggg  35100
tggatcactt gaggccagga gttcaagacc agcctggcca acattgcaaa agcccatctc  35160
tactaaaaat acaaaattag ccaggtgtgg tggcacacgc ctgtaattcc agctacttgg  35220
gagggtgagg tatgagaatc tcttgaacct gggaggctga ggtggcgcca ttgtactcca  35280
gcctgggcga cagagcaaga ctctgcctca aaaaaaacaa aacaaaacaa aacaaaaaca  35340
acaaaaaacc aacaaaaaaa gaacttacgt gtaagaattt aaattagtga tgaaagaaga  35400
aactgtaaaa agtactccag taagccaggc atagtggtgc atgtatgtag tccgagctat  35460
gcaggaggct gaggcaggag tatcacttga gaccaggaat taaagaccag cctgagcaaa  35520
atatgtaatt aaaaaaaaaa ttactgtagt ctgtgttcct taaatttagg tttcatacat  35580
tcttagaatt ataatacttt ttcatggctg ggcacagtgg tgcatgcctg taatcccagc  35640
actttgggag gccgaggtgg gcagatcact tgaggtcagg agtttgagac caacctgccc  35700
aacatggtaa aaccctgtct ctactaaaaa tacaaaaatg agctgagcat ggtgacaagg  35760
gcctctagtc ttagctattc aggaggctga ggcaagagaa tcgcttgaac ccaggaggcg  35820
gaggttgcag tgagctgaga tcgcgccact gcactccagc ctgggtgaca gagcaagact  35880
ccgtctcaaa aaaaaaaaaa aaattataat actttttcag atgtctttga agaggagaat  35940
ttcagccttt tcttaaatag tccaatactt taatcttagc aatctcagag caaaagcctt  36000
tttagatgcc agtaagactt ttctctcagt tgcctagtat gcaaaggctg ggccttaaat  36060
gttttgctcc tctaaagcat ttaaatttaa gagatgaacc tgctaatttg tcctaaaagt  36120
tatatatgtc ttttaatata gtcatggctg aaaaatggct aagacagtta gcacctgact  36180
ctagttttaa attaactgag aaaataatcc ttcagaaaat cattgatgtt gtccacatac  36240
atgtgttctt acctctcgag aggaaaatgt taatgctttt gtcattggaa ctcagtttgg  36300
gacttaccac tataaattgg aggttccaga atgtctgttc ttcattcctt attttgttct  36360
tgttttatgt ggattttgtt tctggaatct gaaattctat cattctgtgt ctgtctctgg  36420
aaagaactca atctctgaat cattgaattt ctattaatca gtttgtttaa atagaccatc  36480
tttcttgaga acttgtgcaa aataggttaa acaaatcctt ttttttttta tagagcaggt  36540
taaaattaga ggtaagcaga agcttttgct ttttgtcctt tccaactata actgaaaata  36600
ggatgcttcc ctaagtttta gtaaaggatt tcatcctata tgcagtcaat tcatgatccc  36660
tttcacaaac gctgctgccc accattaagt ctcttatcac aggcattttt aaaattatac  36720
cataaaatgc atgttgagac tctctggatc tcaaatgtac agaaatcaca tctaaatgtc  36780
aattcctgag ttaaggaact gacaattatg gcactttcag tctctattaa tatttagaag  36840
gcaagagatt attatattgt ttatattact ccttatgtgt ctgtagactt aaatactttt  36900
tgaaaagcat ttgtttgttg tattggggct gtatgtttct gccattatac ttatttgctt  36960
```

acctgattta aagttgtcct ttaattgttt tgggctgtat ctatagtttg aaattaggac 37020
tatcctctgt gtactatgca ccaaagatga catttcaatg cattgttcag ttactacaca 37080
gctcctattt gtctgtaata aagctgtatg gctgggtcca tttatttcaa tattagttat 37140
tttatagtat ccattggaat gatgataatt aatatataaa ggcaactttt ccaaattcat 37200
ttgtgtctcc tctgggcatt tctttgggat gtgtttgtat gcacgttttt gcttctgatt 37260
ttaaaataat tttcctttgt tgtaggatga gcaattctta ggttttggct cagatgaaga 37320
agtcagagtg cgaagtccca caaggtctcc ttcaggtacg gccaattaag tgcatggtgc 37380
cttttaagtt ttgtttgtta ggagattgtg gcttcctctt gccttcttta catgtaaagg 37440
atgctctacc atacttgggt taggaaatgg ctgatgagct agacttcttt ttatttattt 37500
atttatttat tattgttata ctttaagttt tagggtacat gtgcacaatg tgcaagttag 37560
ttacatatgt atacatgtgc catgctggtg cgctgcaccc actaactcgt catctagcat 37620
taggtatatc tcccaatgct atccctcccc cctcccccca gctagacttc tttatgggac 37680
tcttatctat caggccacat tgggtttatt ctttctctct gggaactact tggggcatgg 37740
gaagtaggtt tccacagaat tactgggaaa tctggtaggc aaagtgaagg taacctagta 37800
agagtatcct cagatttaca cattttgtgt tatgtggtag tgtatatgtc tttgggaata 37860
atttggccat tattttttttt ggatgaaatt tggtccacta ttgtcaaaga accaaaaaca 37920
aaatattggc attatgtgaa acatttttac ctgattcttg aaaggctgta ttaaaataaa 37980
aaaatggaaa attagcaata tttgtcatta ttctcaccaa caaaatatct agaatatctt 38040
gaaattctag acttacaagc agtttcctaa gagaagaccc tcaatggaaa taacatttaa 38100
tggcttgcct aattcagttc tgtataggag aaagctatgt atcttttgat gaaaatgcat 38160
tccccatctg tgctgccatt ctgacttcat atatggtttt ctttgatttt atgtggatag 38220
acactccagc taaatatgat attgttagct gtttctgctt tttgacattg acttagcttg 38280
tgatgtgtgc tagcattagg gtctcactta agagtcatca tatattatca tctaattcaa 38340
acatccaagt tgacagtttt tcttttctta aagaggagtg gtattgtcat tctagttggg 38400
ggcagttggc cagtagtgtc ccagtatctg tgctattcag acagtagcag tgttctcttt 38460
aacatgtgat gaagtcttaa aacttcatat aggaaaggaa ttagagagat catctgggat 38520
ttttgtttgt ttgtttatag atgaaaaaat gaggtccatg aaatacatga gtaatgattt 38580
ataaccagtt tgagagttct ttggatatgt tgtggatcag ggaagttagc agcagtgctg 38640
ggactcttct ctgttctgct gcttctactt atctaccaaa agagtttttt aaaaagtagg 38700
atagaagagg ttttcagaat tgataaagcc ctctgattgg ccaggttcaa gtctaccaca 38760
atggtaagga atcttttgat gtatttccgg gcaggagttg ttttgtttgt ttgttgtttt 38820
tgtttttgtt tttgagacgg agtctcactc tgtcacccag gctctgggca ggagttttat 38880
tttgttaatt cacaactttt tcatggtagt ttcctcttaa gttttttttc atgactacca 38940
gtctaccttg aatgttgtct tgttttctaa gaaaccatct cgatatgctt cattatttga 39000
gaaatgagac atggtttctc tgctgtctcc tagtttatta cctttgttgt aattaggata 39060
tgttgagaaa ggagctgtga atccttaatc tattaaagga agtctcataa attaattgat 39120
gaggaatgca tttatattta gaaagctcaa caataaaacc tttgttgact tctgttctgt 39180
tagcaagcag ttccattgta aaaatgttca tctcttttgg tgcctattaa gggaagtttt 39240
agtctcagaa gaatgttatc aaaagggaaa agaagatttg ataaaatagc ctagtcttac 39300
tactttttaa aatacaggtt tatacaaggt gttttagaaa cagtcttgtt ttcttgaatg 39360

-continued

```
gcttgaaaag cagcaaactg agcttattta taaattggca aattcctttt atttagaata  39420
gaactttgat ttaataagtt gtcattttgc tgttgacatc agttaaggtt aaatcttttt  39480
gcaacttgag actagctcaa gaacctctaa gcaggggagt agatttagtg gacacattat  39540
gtcacttcac tgattagttc acatgccact gagttcagtg gtcttattct gatgtgtcat  39600
aaatgaacat ttttctattc agtaaaactt tcttagtcta ctttggcaaa acagattgaa  39660
atatgggact ctgagctgcc caaggagttg gtatgttgat gattgaagag cagcgtattc  39720
aaatttgttc aaagccagaa ttctgaattg aaaagatggg atgactaact agaagcatat  39780
tcttaaatgt taatcttggt ggctaggata tggcgaggaa gttcagatgt tttttcttta  39840
caattccttt gaattcagaa aaaaccttct tgctcatcta aaattgtaag aaaatcagtt  39900
ttgtggatta attgttcaac tgaaaacttt ttattatctt tttgtatcaa aaaagtaatt  39960
aaatgttctt tcaggtggaa tgttatttgc tgacttcttt gaggcaaatt ttgggtgaaa  40020
agaaactaag cacaattaag atgtttgatt gactcattag actcaagttg aactcagtac  40080
aaaatggcca gtgctaagtt atattcagct tagttaaaac ctaaactaca cagctaaata  40140
tatgctcttc attgtttaat ttctatacac agttaaaact agtcctcgaa aacctcgtgg  40200
gagacctaga agtggctctg accgaaattc agctatcctc tcagatccat ctgtgttttc  40260
ccctctaaat aaatcagaga ccaaatctgg agataagatc aagaagaaag attctaaaag  40320
tatagaaaag aagagaggaa gacctcccac cttccctgga gtaaaaaatca aaataacaca  40380
tggaaaggac atttcagagt taccaaaggg aaacaaagaa gatagcctga aaaaaattaa  40440
aaggacacct tctgctacgt ttcagcaagc cacaaagatt aaaaaattaa gagcaggtaa  40500
actctctcct ctcaagtcta agtttaagac agggaagctt caaataggaa ggaagggggt  40560
acaaattgta cgacggagag gaaggcctcc atcaacagaa aggataaaga ccccttcggg  40620
tctcctcatt aattctgaac tggaaaagcc ccagaaagtc cggaaagaca aggaaggaac  40680
acctccactt acaaaagaag ataagacagt tgtcagacaa agccctcgaa ggattaagcc  40740
agttaggatt attccttctt caaaaaggac agatgcaacc attgctaagc aactcttaca  40800
gagggcaaaa aagggggctc aaaagaaaat tgaaaaagaa gcagctcagc tgcagggaag  40860
aaaggtgaag acacaggtca aaaatattcg acagttcatc atgcctgttg tcagtgctat  40920
ctcctcgcgg atcattaaga cccctcggcg gtttatagag gatgaggatt atgaccctcc  40980
aattaaaatt gcccgattag agtctacacc gaatagtaga ttcagtgccc cgtcctgtgg  41040
atcttctgaa aaatcaagtg cagcttctca gcactcctct caaatgtctt cagactcctc  41100
tcgatctagt agccccagtg ttgatacctc cacagactct caggcttctg aggagattca  41160
ggtacttcct gaggagcgga gcgatacccc tgaagttcat cctccactgc ccatttccca  41220
gtccccagaa aatgagagta atgataggag aagcagaagg tattcagtgt cggagagaag  41280
ttttggatct agaacgacga aaaaattatc aactctacaa agtgcccccc agcagcagac  41340
ctcctcgtct ccacctccac ctctgctgac tccaccgcca ccactgcagc cagcctccag  41400
tatctctgac cacacacctt ggcttatgcc tccaacaatc cccttagcat caccattttt  41460
gcctgcttcc actgctccta tgcaagggaa gcgaaaatct attttgcgag aaccgacatt  41520
taggtggact tctttaaagc attctaggtc agagccacaa tacttttcct cagcaaagta  41580
tgccaaagaa ggtcttattc gcaaaccaat atttgataat ttccgacccc ctccactaac  41640
tcccgaggac gttggctttg catctggttt ttctgcatct ggtaccgctg cttcagcccg  41700
```

-continued

```
attgttttcg ccactccatt ctggaacaag gtttgatatg cacaaaagga gccctcttct  41760
gagagctcca agatttactc caagtgaggc tcactctaga atatttgagt ctgtaacctt  41820
gcctagtaat cgaacttctg ctggaacatc ttcttcagga gtatccaata gaaaaaggaa  41880
aagaaaagtg tttagtccta ttcgatctga accaagatct ccttctcact ccatgaggac  41940
aagaagtgga aggcttagta gttctgagct ctcacctctc acccccccgt cttctgtctc  42000
ttcctcgtta agcatttctg ttagtcctct tgccactagt gccttaaacc caacttttac  42060
ttttccttct cattccctga ctcagtctgg ggaatctgca gagaaaaatc agagaccaag  42120
gaagcagact agtgctccgg cagagccatt ttcatcaagt agtcctactc ctctcttccc  42180
ttggtttacc ccaggctctc agactgaaag agggagaaat aaagacaagg cccccgagga  42240
gctgtccaaa gatcgagatg ctgacaagag cgtggagaag gacaagagta gagagagaga  42300
ccgggagaga gaaaaggaga ataagcggga gtcaaggaaa gagaaaagga aaaagggatc  42360
agaaattcag agtagttctg ctttgtatcc tgtgggtagg gtttccaaag agaaggttgt  42420
tggtgaagat gttgccactt catcttctgc caaaaaagca acagggcgga agaagtcttc  42480
atcacatgat tctgggactg atattacttc tgtgactctt ggggatacaa cagctgtcaa  42540
aaccaaaata cttataaaga aagggagagg aaatctggaa aaaaccaact tggacctcgg  42600
cccaactgcc ccatccctgg agaaggagaa aaccctctgc ctttccactc cttcatctag  42660
cactgttaaa cattccactt cctccatagg ctccatgttg gctcaggcag acaagcttcc  42720
aatgactgac aagagggttg ccagcctcct aaaaaaggcc aaagctcagc tctgcaagat  42780
tgagaagagt aagagtctta aacaaaccga ccagcccaaa gcacaggtac tcttttccac  42840
cttgcctatt aaaactaaca gtttattgag ccctttctat gggcaagttt taggctaagt  42900
ggttcaatta catccagtta tgagaaccaa gaaaagtatg gtggaggcag tggtatttgc  42960
agtagtcctt caaggaccag taggattttg ataggtagaa agtggcagga cataacattc  43020
taagtagagg gaacagtgtg ggtagaaatg gaaaagtaag aaatatattt gaggaatact  43080
ggatagctgg attggcatct gtggaaaact ggtgaactaa ggctgaatga actaaggttg  43140
ggactatatc acagaggatg ctgagttgtt tgtaccttat aagtttgatg taattaaacc  43200
agggacttaa ttgtaaaggt acattttaat agtcaaattg ttttactatc cccgatagaa  43260
tagaaaaccg gaggggagca ttctcttcct ctgagtagtg agggattgga gcaatagata  43320
atatgttttt gcagaataca aatgagaagt actggccagg tgcgatggct catgcctgta  43380
atcccatcac tttgggaggc caaggtgggc ggatcacttg aggtcaggag tttgagacca  43440
gcctggcctg gccaacacgg tgaaacctca tctctactaa aaaaaaaaaa aaaattagct  43500
gggcgtggtg atgcatgcct ctagtcccag ctactgggga gattgaggca caagaatctc  43560
ttgaaccccg gaggtagaga tggcagtgag ctgagatccc gccactgcac tccagcctgg  43620
gccaatagag taagtctcta tctcaaaata aataaataaa taaataaaca aacagattag  43680
aagcacttag ccttgagcca tggaacagga aagctataga attcagttag ttaagatgat  43740
gccaaatatt tttacaaaga ccagcatttt tgtttttttt ttattgtttt gtttatttgt  43800
ttaacaaagt aagctagtca ctggcctttt ctgagaaaag ttgctgatct ttagggtttt  43860
aaaaaaatcg tcatgtagta gatgcctatt tatggcagca aatcaggtta ggttaagatg  43920
gccataaact tatatttgta atgttattca cgggctgggt acggtggctt acgcctgtaa  43980
tcccagcact ttgggaggcc gaggcaggtg gatcacgagg tcaggagatc gagaccatcc  44040
tggctaacac ggtgaaaccc tgtctctact aaaaatccaa aaaattagcc agacatggtg  44100
```

gcatgcgcct gtagtcctag ctactcggga ggctgaggca ggagaatcgc ttgaacccgg 44160
gaggcggagg ttgcagtgag ccgagatcac ggcactacac tccagcctgg gtgacagggc 44220
gagactccgt ctctaaaaaa ataaataaat aaaattaatg ttattcaacc tagggccata 44280
gttacattta ctaattctgc cagttgagaa ttgtagcagg aatgtgatgg gacttatttt 44340
taacaccatg ttggatgttt ttgtgatagg agcagcggct ctttaaaatc tgagacattt 44400
cttttggagc cttttatact ttctcttttt tttgagacgg aatttcgctc ttgttgccca 44460
ggctggagtg caatggcgtg atcttggctc actgcaacgt ccgcctccca ggttcaagca 44520
attctcctgc ctcagcctcc caagtagctg ggattacggg catgcaccac cacgcccagc 44580
taattttgta tttttagtag agacagggtt tctccatgtt ggtcaggctg gtctcaaact 44640
cccgacctca ggtgatctac ccgcctcggc ctcccaaagt gctgggagtt gcaggcgtga 44700
gccaccacct atactttcat ttataagtta tttcacccct acttctctga tgatcaagga 44760
aatataagaa atagtttttg gttagataag ccgtatttat accacactga actttttgat 44820
aatatagact ggcagcttga attttgaggg gaatttaaaa tagtagtata attgggaata 44880
gaagcttagt tgtttgtttg tttttaagat agggtctcac tctgtcaccc agggtggctc 44940
aagtgatcct cttgtcccag cctcctgagt agctagaact acaggtgtgt accaccacgc 45000
ccagccaatt tttaaatttt gtgtagagat gggttctcgc tatgttgccc atactggtct 45060
tgaactcctg gcctcaaatg atcttcccac ctcaagctgt tttttatttt ttgattagag 45120
gccttttttt gtgctgccaa ttaggataca gtaatagttg atttctgttt tgatatgatt 45180
tatcagctgg gaataattag agttgtgtgt tttgattcta aatcatactg aaattgatta 45240
agtatacctt ggcttcgttc agttataatt tcaacatgta tggttgttat tgtttttgga 45300
ttgcctcata ttcagggtca agaaagtgac tcatcagaga cctctgtgcg aggaccccgg 45360
attaaacatg tctgcagaag agcagctgtt gcccttggcc gaaaacgagc tgtgtttcct 45420
gatgacatgc ccaccctgag tgccttacca tgggaagaac gagaaaagat tttgtcttcc 45480
atggggaatg atggtaggtc aagaaggtca atcttggagt cggaacagac ttttgatttg 45540
tttgttgatt attctgggga tgcccagtag gctcttcata gttagtaggt cctctgaaaa 45600
acagatggca agaggggatt aaatacatga ggattttatt agaagaaatg cctgagaagg 45660
aaaacgggga ggtagccagg gaaggctggg agagctgtca gactgtgttg cccatctcac 45720
ccccatgaag gagcagggga aggaaggcag aatcttccta gactgctgtg caggtgagaa 45780
agatttggca aagctgtcca ggagtctttg agtaaaagtg gactgtcagg ggagtgggag 45840
gcacattctc atggctgtca tatagttctt aagtgcagag tagccactca gaacaaattt 45900
agaggtttga agaatcctta gaagcatttg gtttctattc tcgattttag attagacttt 45960
tgttttcagt atttggaatt ttgctttcat caagatgcaa gttattggct tttttttttt 46020
tttttttttt ttttttgaga cggagcctca ttgtgttgcc caagctggag tacagtggtg 46080
cgatctcggc tcactacagc ctccacttcc caggttcaag cgattctcct gcctcagcct 46140
cctgagtatc taggattaca ggcatgtgcc accatgcctg gctaattttt gtatttttag 46200
tagagagggg ttttgctatg ttggccaggc tggtctcaaa cccctgacct caggtgatct 46260
gcctggctca gcctcccaaa gtgctaggat tacaggcatg agccaccatt cctggccaag 46320
ttattggcat ttttaaacat ttaaataatt atttaaaata gattctgagt tctgtatata 46380
aatattttat tttaatgtat ttcatttttg gagtaccaat taaaaccagg tttgaattca 46440

-continued

```
gtactccctt ggaactaatg ccacatttct ttaacagaca agtcatcaat tgctggctca  46500
gaagatgctg aacctcttgc tccacccatc aaaccaatta aacctgtcac tagaaacaag  46560
gcaccccagg aacctccagt aaagaaagga cgtcgatcga ggcggtgtgg gcagtgtccc  46620
ggctgccagg tgcctgagga ctgtggtgtt tgtactaatt gcttagataa gcccaagttt  46680
ggtggtcgca atataaagaa gcagtgctgc aagtaagtgg gtgtttcact ctgagatgtt  46740
gacctctcaa ccataaaggt tgcttattta tccctagttt gttgcagaga tacatcagga  46800
aactgaatgt ggttgtaatt gagttgcaag acttgttaca gttagatttt gtggtgtggg  46860
ctgtgcttaa ataagaaata ctctggggcc atgctgtcat taatagaatg ttctgcaaca  46920
atggaaatgt tctattggaa tagtagacaa caataatgga aatgtttagt tcagtatgca  46980
gccattagcc acatgtggct attgagcgct tgacatgtga ttagtgtgac tgaggaacca  47040
cactgtttat ttcgtttaac tttagccatg tgtaactagt ggctaccata tcagactgta  47100
gctctggagg atttctactt aaaacctgac aactttatgt ataattttg ttgggtctac   47160
tgaaattatg ttgacccaac aaaattatga caattcagga aacattggag ataccttgca  47220
taaatatctg tgctttctca ctctctctta gaatatgttc atgcatatgg aattttttt   47280
tttaagagac agggtcttgc tctgttgcca ggctggagtg cagtgacatg atcatagctc  47340
actgccaaca ctgaactcct aggctccagt gatcctcctg ccttggcctc ccaaagtact  47400
gggattacaa acatgagcca cagtgcttgg cctcatatga aatttctttt tttaagaagt  47460
tttgttttaa tttttatggg tacatagtag gtatatatat ttatggtata cataagatgt  47520
tttgatacag gcatgcaatg catcataatc atatcatgca gagtggggta tccattccct  47580
taagcattta tcctttgtat tacaaacaat ccaattatac tctttcagtc atttttaaat  47640
gtacaattaa attattattt actacaatca ccctgttgtg ctatcaaatg ctaagtctta  47700
ttcattcttt ctgattattt ttttgtaccc attagccatc ccctaatatg gaattttta   47760
tgtggaaatt tttattactc tactttttct cctcttttt agtcagtttg tggaggtact   47820
ttctgccatc tggcatactt tatttaaaat agatcgagat agtagcataa acagaaattt  47880
tggtgattaa gcatcttgta aactactggc acaaataata ggtgtcaata gatatttgct  47940
gaatgagtga gtcacatgca agtgattaat ataaagaaca gttgggagaa atgctacatt  48000
atttacttca ggggagataa tttctaggag acaagaagta gttctgtgct ttggtttggt  48060
ctgaccttaa acaagaatct tgtctcagtc ctgttagtgg aaagaagtaa actaattcac  48120
agatcacaaa aaagtacatg atagcaagat aaagttgcat taaatttaag agttaaagtg  48180
gattcagtgc aattgtagac ttcagattac atttgaattt tattaaatct aaatttaggg  48240
gtgaagtata tatcaaagcc accagattta attatagcat tatagtggta gacaaaggag  48300
ttgtttgata attttagtct gttttgtgtt aagattactt gatggatatt aacatcgtaa  48360
gagagtagga ctgatgcgac tacaagaaat actgactgat cattttctgt gtggtgctag  48420
tcagtgttgg attacaagaa atttgagtcc catttcaaaa ataatttgat atttgctcct  48480
tttagatcct aaaggtaggt gaaattgctg atccagggat tcaaaggctc agatttaatc  48540
tgagtaatga gcagtccttt tttcaactat aaaaatgtga acctgaatac agattcactg  48600
attgttgcag acaaaatgaa cacttgtttc agtgcttttc ttctaaattt aatttgtttc  48660
atggtttatt cgttgttttc ctaggatgag aaaatgtcag aatctacaat ggatgccttc  48720
caaagcctac ctgcagaagc aagctaaagg tagtgttgtt aaaaaggtct tcccccaaat  48780
gctccttgct taaatggtgt atagttgtat acacccagta gaagagaata ctttttttt   48840
```

taaagtacaa ctctttctca gggagtagat tgttgaagct aggtaatagg tacatggggg 48900
ttgattggac tatttcctgt attgggggat atttttgaaa ttttccataa taaatttttt 48960
aaatttatat aaaaatcata gttcattata tttcctagag caataaagta tacctatttc 49020
acctgatcaa cttggcatta actttcttta gcctttcaat gctaactttt aactgcagga 49080
aactgagaat gttgtgtcac atttctacgc ttctattttt taaatgtatt tttttaactt 49140
atttttaatt tttgtggata catggcaggt gtatttattt atttgtttat tgagacagag 49200
tctcactctg tctttcaggc tggggtgcag tagcatgatt atgactcact gtagcttcaa 49260
cctcccacgc tcaagccatc ctcccacctc agcctcccta gtagctggga ctacaggtgc 49320
gcaccaccac gcccagctaa tttttgtaaa tttttttgc agagacacga ttttgccatg 49380
ttgcccaggc tggtcttgaa ctcctgggct caagcaatcc tctcgccttg gcctcccaat 49440
gtgctggaat tacaggcatg agccaccact gcacctggcc agcaggtgta tatatttatg 49500
ggggtacatg agatatgttg atacaggcat acaatgggta ataatcacat cagggtacat 49560
gggatgtcca ttacctcaag catttattct ttgtgttaca aacaaactaa ttatactctt 49620
gtaattattt ttaagggtac agtaaattat tgttgactgt aatcaccctg ttgtactatc 49680
aaatactaga tctcattcac ttctatctag ctatattttt gtacccatta accatcccca 49740
ctttccccct caacctcact acccttccca gcctctcata actatcattc tctctgtctc 49800
tatctccata agttcaattg ttttaatttt tagctcccac aaatgagtga gagcatgtga 49860
tgtttgtctc tctgtgtctg gcttatttca cttaacataa tgtcctctag ttccatccat 49920
gttgtttcag atgataggat ctcgttcttt tttatggctg aatagtactc cattgtggat 49980
atgtaccaca ttttctttat ccattcatct gttgatggat gcttagatta ctttcaaatc 50040
ttggctatca taaatagtgc tgcaggaaac atgagagtgc agatatctct ttgatatact 50100
gatttccttt attttggtat atacctagct gtgggattgc tggatcatat ggtggctctg 50160
taattctatt ttaaataaaa ttattctcac tatagacaga tgatgttgtt gtgtttttcc 50220
ctcagctgtg aaaaagaaag agaaaaagtc taagaccagt gaaaagaaag acagcaaaga 50280
gagcagtgtt gtgaagaacg tggtggactc tagtcagaaa cctaccccat cagcaagaga 50340
ggatcctgcc ccaaagaaaa gcagtagtga gcctcctcca cgaaagcccg tcgaggaaaa 50400
gagtgaagaa gggaatgtct cggcccctgg gcctgaatcc aaacaggcca ccactccagc 50460
ttccaggaag tcaagcaagc aggtctccca gccagcactg gtcatcccgc ctcagccacc 50520
tactacagga ccgccaagaa aagaagttcc caaaaccact cctagtgagc ccaagaaaaa 50580
gcagcctcca ccaccagaat caggtgagtg aggagggcaa gaaggaattg ctgaaccaca 50640
agtactaaca aaaaagcact gatgtctcaa acagcatttg aaagcaggaa atgtatgatt 50700
tgaagtcttc agttcaagaa aatcagctct ctttctaact attatgttta ataataaaga 50760
aacagaaaca aaaaaaacag ttaaattgga ggtattgttt taatttcctg ttcgaagcct 50820
agagtttaaa tagttttttt ttttttttc taatggccct ttcttcacag gtcagtcagt 50880
actaaagtag tcgttgccag catctgactg caatttattc tgaatttttt aggtccagag 50940
cagagcaaac agaaaaaagt ggctccccgc ccaagtatcc ctgtaaaaca aaaaccaaaa 51000
gaaaaggtga ggagagattt gtttctctgc catttctcag ggatgtattc tattttgtag 51060
ggaaaagcct tatccttgac ttctatgtag atggcagtgg aatttcttaa aattaagaaa 51120
cttcaagttt aggcttttag ctgggcacgg tggctcacgc tggtaatccc aacacttagt 51180

-continued

```
gaggctgagg tgggaggatt gcttgaggcc agcagttcaa gaccagcctg ggcaacatag  51240
caagaccctg tctttattta aacaaaaaaa aaaaaaagaa gaagaagaag aagttagcca  51300
ggcatggtgg cagttgcgtg tagtcccagg tactcaggag gctgagatag aaggattgtc  51360
ttgagcccag gaattcaagg ctgtagtgag ctatgattgt accactgcag tccagcctgg  51420
gtgacaaagc aaaacactgt ctccaaaaaa aatttaggct tggcaaggcg cagcggctca  51480
cgcctgtgat cccagcactt tgggaagccg aagcaggcag atcacttgag gtcaggagtt  51540
ggagaccagc ctggccaaca tggtgaaacc ctgtctctac tgaaaataca aaaattagcc  51600
ggttgtggta gtgggtgctt gtaatcctag ctacttggga ggctgaggca ggggaattgc  51660
ctgaacctgc gaggcggagg ctgcagtgag ccgagattgc atcattgcac tctagcctgg  51720
acaacagagc tagactccat cccaaaaaaa aaaaaaaaag tagccgggca cggtggctca  51780
cgcctgtaat cccagcactt tgggaggccg aggcgggcgg atcatgaggg caggagatcg  51840
agaccatcct ggctaacacg gtgaaaccct gtctctacta aaaatacaaa aaaattagcc  51900
cggcgaggtg gcgggcgcct gtagtcccag ctactcagga gagtgaggca ggagaatggc  51960
gtgaacccgg ggggcggagc ctgcagtgag ccgagatcgc gccactgcac tccagcttgg  52020
gtgacaccga gactccgtct caaaaaaaaa taaaaagttt aggctttagc ctgtttcttt  52080
tttggtttct tccttgttgc ttttcccttc tttgtggccc cacatgttct agcctaggaa  52140
tctgcttatt ctaaaggcca tttggcgtaa ttattttttg accccaacat cctttagcaa  52200
ttatttgtct gtaaaaatca cccttccctg tattcactat ttttatttat tatggataaa  52260
gagatagtgt ggtggctcac atctataatc ccagcacttt ggggggccaa ggcgggagga  52320
tcacttgagg gcaggagctg gagaccagcc tgggcagcac agtgacacac agttgctata  52380
aaaaatttaa aaatcaacta ggcatggtgg catgcacctg tagtcccagc tactcttgag  52440
aagctgaggc aggaggatca cgagcccaca aggtctaggc tgcagtgagc tgtgactgtg  52500
ccactgtatt gcagcctagg caacaaagca agacccagtc tcttttaaaa aaaaattcaa  52560
agattatttg tttatgttgg aaacatgttt tttagatcta ttaataaaat ttgtcatttg  52620
cattattatc tgttgcaaat gtgaaggcaa atagggtgtg attttgttct atattcatct  52680
tttgtctcct taggaaaaac cacctccggt caataagcag gagaatgcag gcactttgaa  52740
catcctcagc actctctcca atggcaatag ttctaagcaa aaaattccag cagatggagt  52800
ccacaggatc agagtggact ttaaggtaaa ggtgttcagt gatcataaag tatattgagt  52860
gtcaaagact ttaaataaag aaaatgctac taccaaaggt gttgaaagag gaaatcagca  52920
ccaactgggg gaatgaataa gaactcccat tagcaggtgg gtttagcgct gggagagctt  52980
tggtcagtgt tgttaggtca ctgtttgtga actgactgca gaacatacat aatgaaacat  53040
tcctatccat cctgagcagt atcagaggaa gtaattcctt cacatggaaa gtatcaaacc  53100
atgatgattc cttgagtcag caaaactgta agagaaattc aatcccagtg tattttcgca  53160
atatattcaa tatgaattga acaactaggt gagcctttta atagtccgtg tctgagatta  53220
aaacttttta aagcagcagt tatttttgga ctcattgaaa tgaaatactc tgacattgtg  53280
atgtcacact aattttatgc ttttcatcct tattttccat ccaaagttgt gtaattgtaa  53340
aactttccta agtgaccttt ctctctccac aggaggattg tgaagcagaa aatgtgtggg  53400
agatgggagg cttaggaatc ttgacttctg ttcctataac acccagggtg gtttgctttc  53460
tctgtgccag tagtgggcat gtagaggtaa ggcatcctgc ttctttgtac cccaggaagt  53520
acataaatta tttttctgtg gatgaaatta ctatagtctg ttttgttggt atttagcagg  53580
```

tactattccc tgtttaaacc agctaaagaa atgttttgaa gtattttaga gattttagga 53640
aggaatctgc tattagagta gcaaagttat tgagagtgaa aagatcaata atcccatctc 53700
tcttaaattc agtctttatt agagttctga tctttctgtt agatgtctaa ataagagaaa 53760
aaattataca gtggtctatt aaaagggatg ctattgatgg ttattttata ttgtatatca 53820
aagcctcttc atctataagg agctcttacc aattaataag aaaaaggaat gacatccaga 53880
aaaaaaaata ggcaaaagac agaaatagat aattcacaaa attagaaata aatacatgtt 53940
gggtggcagg gggaggtgaa gggagggtgt ctgtttttta gccctctagt gaccaaaaac 54000
tggaaattaa agcatgataa aaaaagaatc ctgaataaat ggggactttc tgttggtgga 54060
aagaaatata gattagttac aatctttctt tctgagggaa ttatttggaa atatatatct 54120
atctttaaaa taggtatatc ctctaacata gcaattgcac ttcaaacact tatggatata 54180
attagataaa ttggcaaatc tgtagatata aagaagtgtt catttcaata ttgctcataa 54240
taataaaaaa ctggaaacaa cccgaaagtc catctatagg gagcatgggt taaaataagc 54300
atagggcata tagctgggca cggtggctca cgcctgtaat cccagcactt tgggaggcca 54360
aggcaggcgg atcacaaggt caggagatcc agaccatcct ggctaacaca gtgaaacccc 54420
gtctctatta aaaatacaaa aaaattagcc gggtgtggtg gcgggcgcct gtagtcccag 54480
ctactcgaga ggctgaggca ggagaacggc atgaacccgg gaggtggagc ttgcagtgag 54540
ccgagatcgc cccactgcac tcccgcctgg gcgacagagc aagactccgt ctcaaaaaaa 54600
aataaaagtg tagggcatat ataatggcaa atatgaagtc ctaaagataa tatatattaa 54660
tattattagg ttggtgcaaa agtaattgca gtaataacat ggaaagatgt ccatgacata 54720
tcactgagtg aaaagagcag gttacaagat aatatataaa gcacaatccc atcttagttt 54780
ggaaaagtgt ttttaaagta tatatctaga aaacaatctg gaaggattca caccaaaata 54840
ttaagagtgt ggttggatta tgggtgacct ttatttgttt ctctggtttt tttttttaa 54900
tctttctgag ttttttgcag tatgtaccac ctttacaatg aggaaggaaa aagtagcaca 54960
attttaaata ggaagcagta gtttgtcatt tataagggac atatcctaca tcctttacag 55020
ttcttaaatt cctggcagat acctctttgg cttattactt accacataag atatgtattc 55080
aaaggtggta aagaaaatcc acgtcgggtg cagtggctca cgcctgtaat cccagtactt 55140
tgggaggctg acgcaggagg accgcttgag ctcaggagtt caagaccagc ctgagcacca 55200
tagtgagacc tcatctctac taaaaaaaaa ataaaatacc aggcatggta gcatgtgcct 55260
gtagtcccag ctactctagt cccagctact tgggaggctg aggtgagagg atcacttgag 55320
cccaggagat cgaggctgca gtgagccatt atcacgccac tgcactccag cctgggcaac 55380
taagcaagac cctgtctcaa aaaaattttt aaaaatttaa aaaataagaa aatccaagct 55440
aggttgaaat ctgaatgttg agcagtcagt gagacacaaa ctagctaaga aagtcaaccc 55500
tgcccacttg ccatttgaag ttattactag caaaattaca aattattgcc tactattcat 55560
ttactaagca aatattctct tagtccctat tacgaacaac ttattgttct aagtgcagaa 55620
gttcagatat cattgagact gagaatattc agtctacaag tgccaggggt ctactgtatc 55680
ctcttttccg tcttaataca gtgctttgca cccatatata tgccacccac aggaataact 55740
ttttttatag caccagtcct tcaacttctg ggattaaaca gattttttt cagggtataa 55800
ttgttctgat ctaaattctt tatagttgta catagcaatc tcacagggtt cctaaaatat 55860
aaattagaga atagcatgct gcctgcactg cactcctaaa gcatgaccag tgcttgataa 55920

-continued actctcctcc atgcgaattt tttaaacttt ttatgttgac atgatttcag acttacaaaa 55980
aaactatgag ttgtacagag aattctaagt acccctcacc caaattccct aagtgttaat 56040
atgtttctct gtgtgtatat attttacaaa ataacaaata aaatacatat acacatttta 56100
cctgtagata cacatgtatc taaaaatttg agaacaagtt gcagacataa accattttac 56160
ctctaaatat tttagtgtat atttttaaaa atcaaggacg ttctcgtatt taaccatggt 56220
ataattacca aatcaggaaa ttaacacact ggtacattac tattatctga tctataggcc 56280
ttatttaggt ttgaccaatt gtcccaataa ttcctttatg gcaaaagaaa attctggatt 56340
atcctagtta gtatttttga aaatcctata tcaatatgaa aataacttat ttctaaaatt 56400
agaaatggag gctgggcgtg gtggctcacg cctataatcc cagcactttg ggaggccgag 56460
gcaggcagat cacaaggtca ggagattgag accatcctcg ctaacacagt gaaaccccat 56520
ctctactaaa aatacaaaaa attagccagg tgtggtggca cgcgcctgtg atcccagcta 56580
ctcaggagac tgaggctgga gaatcgcttg aacccaggag gcggaggttg cagtgagtcg 56640
agatcgcacc actgcacccc agcctgggcg acagcgagac tccgtctcaa aaaaataaat 56700
aaataaaaat taaaacaatt aaaaaaataa aattacaaat ggaaaggaca aaccagacct 56760
tacaactgtt tcgtatatta cagaaaacgt ttaaaccctc cctatttccc ccaccccact 56820
cctttatatt cccatagctc tttgtttata ccactcttag gtcacttagc atgttctgtt 56880
aaatcttgta ttatatttat tttgttactt tctatttcca ctggtattac cactttagta 56940
ctctgaatct cccgcagtgt ccaatactgt actttttttac atagtcattg cttaatgaat 57000
atgtattgaa ttaaatatat gccagtggac tactaaaacc caaagtatat aagaagggta 57060
tggttgatta tgtttttcta catattattt gacatacttc tatcttccca tgttcttact 57120
atagtttgtg tattgccaag tctgttgtga gcccttccac aagttttgtt tagaggagaa 57180
cgagcgccct ctggaggacc agctggaaaa ttggtgttgt cgtcgttgca aattctgtca 57240
cgtttgtgga aggcaacatc aggctacaaa ggtacaaaac ttggtaatag aactacagct 57300
gggcctctgt atcagtgggt tctgtatccc tggactcaac caaccttgga ttgaatgtat 57360
ctgggaaaaa atgagtagtt gcctctgtac tctatgtgaa cagacttttt cttgtcatta 57420
tttcctaaac aatacagtat aacaactatt tacattgtat taggtatgat aagtaatcta 57480
gagataattt aaagtatatg gtgggcggat cacttgaagc caggagttcg agaccagcct 57540
gagccaacat ggtgaaaccc catctctact aaaaatacaa aaaattagcc aggtgtggtg 57600
gtgggcacct gtagtcccag ctacttggga ggctgaggga ggaaaatcgc ttgaactttg 57660
gaggcagagg ttgcagtgag ccactccagc ctgtggtgca gtctgtcact ccagcctggg 57720
tgacacagtg agactccatc tcaaaaaaaa aaaaaaaaaa aaactatatg ggaggatgtg 57780
cattttgtta tatgcaaatg ctgcaccatt ttgtctaggg acttgggcat ccatggactt 57840
tggtatcctc tgggggtcct ggaaccaatc ccccatggaa accaaggatg actgtgctta 57900
gagtattgct ttctttcttg atttgtattt ctgtcttcca gttaagattt tgtatctata 57960
ttatttctct ttttacttag tctgtcttta gcatttaatt gggtgtaatc agttgcctat 58020
tttgtgtttt aattttggga ctatagcaga aaacatgatg ttgaataaaa ttccaaaaat 58080
aagtcaaatc tacctaatat gaatactcat cactgagtgc ctttggcagg aaataaatct 58140
atctcaatgc tttaattggg agtaaataat gtatgaggaa atttaaactc ataattgtgt 58200
gctgtactta cttgccagta aatgtgaaat ggggtactaa gtaataggtg ttgggtgaag 58260
gtaatatgat gcttatcttt ttgccattat attttcttac agcagctgct ggagtgtaat 58320

```
aagtgccgaa acagctatca ccctgagtgc ctgggaccaa actaccccac caaacccaca  58380
aagaagaaga aagtctgggt gagttataca catgatgctc ttttatagag aaccaccatg  58440
tgactattgg acttatgtaa cttgtattac aaatatctat gcttgaggat gtcagtatga  58500
caatcttttt gcctcattac taggaaatca tctcagcaga gaaattaaat ctataaatgg  58560
atgcatttaa gatcttttta gttaagtaaa gatattaaaa acaagaaatt cctattgaat  58620
ttcttttctt cttttctaga tctgtaccaa gtgtgttcgc tgtaagagct gtggatccac  58680
aactccaggc aaagggtggg atgcacagtg gtctcatgat ttctcactgt gtcatgattg  58740
cgccaagctc tttgctaaag gtacccaaaa aagccagttt tgccagcttt cggaggttgt  58800
acttggtgtt ctggaggtga actagactct agtgaaatga aataaaaagt ctcacacatt  58860
atgtcaagga taccatttag acacatttcc taagttcctg tttagaactt agcaactaga  58920
aatgtcttgt tagtttatac gggaagtgtt aaggggactt ttcattataa ctaaccacaa  58980
agaaatcctc taagctagta tttcccaaag tgtgatatat atattatata tttgattatt  59040
tcagacatta ttttagttgc tacccaaaca ttttctttca gtagttatat tagaaaaaaa  59100
tattaatata actaatacat taaacctgtt atattactga cttaggataa tcatataaag  59160
ttcactgttt taagtaagat aagcagatca gtttgaagaa gttcattaag taaaaaataa  59220
tataggagat ctctgtatat aaagaaaatt tatgaaggtt atacagagta ctgaatctta  59280
ggaagtgctc ctctaagctc taatgtaaat gccctagaaa taaggaaaaa gcttacatgt  59340
actgtttctg acttccatat tgccacttct tttaaatatt taaatatttc ttacaaatgt  59400
gtgagaaact tctctcttcc attcttttct attgttttat ctttaaaatc tacctcatga  59460
cctttataaa tgaaaactag taaactaaag aaaactagta gcatatgaag cttttctgtg  59520
agtattcgag ggctcagaa taatcttgag actgcagatg tgtgaacatt ccacagtaga  59580
tccatgctgg tgttcatgat cccagaagaa tatagattta gattgggttg gtaaatgcaa  59640
gtcgagggcc gtaaaaacac gggtatgtga gccaaagcac tgctgtaaac tttgctttgc  59700
tttcaggaaa cttctgccct ctctgtgaca aatgttatga tgatgatgac tatgagagta  59760
agatgatgca atgtggaaag tgtgatcgct gggtccattc caaatgtgag aatctttcag  59820
gtacagaagg ttggagtctt tttatttcag ttttcttctt tctaggtact actacattta  59880
ttagcctcta gagcacttta aacctaaaat tatggttgtg ttgttatttg aaatctctaa  59940
atttattttt tagtctctag aataagcagc attgtattat ttgtgctcac ttatcttgaa  60000
tatatgcctt taaagtattt atttgctgtc ctttgtgtgt tccataacct gattctcaat  60060
aaccaaattc aggattagtg ttaattaata atgccacttt ttgagatcaa tatgtgtcat  60120
atccatgagg acattaaaat cttaatgtgg ttcccaacat atggctttat agtaagttca  60180
gtggaatagt ttcctcttct tcctctctct cattcttcag aggacctcat catggtaggt  60240
ttttgttttc ttagatgaga tgtatgagat tctatctaat ctgccagaaa gtgtggccta  60300
cacttgtgtg aactgtactg agcggcaccc tgcagagtgg cgactggccc ttgaaaaaga  60360
gctgcagatt tctctgaagc aagttctgac agctttgttg aattctcgga ctaccagcca  60420
tttgctacgc taccggcagg taggccaagt ctcatttttt tctgagagct tgttcttagg  60480
tagtctttac ctagtgtttt tcttttgttt tacttcattc tcctcactta atttttagtt  60540
acttgttttg gctataacca ttaggaaaat atttagagcc aagaatagga ccttctttag  60600
cgtaagaaat aggaaggagc tgtatcttca aaggtcttgc tgttacaatg agaaatttgg  60660
```

-continued

```
actttatact ctgaaggtga tagggagcca gtgaagcact tcacccaaga cagtaacctg  60720
atcagagttg cttcttagaa aaaatattgt tctgactgag tggagaggaa ggactggaga  60780
cacctgagcc tagaggcagg attcgtagtt aggggacagt tatagtaatc aactggaaaa  60840
acactttctg tttatgtaag ttgtgaactt tacacattta taaagtagtc attagaagaa  60900
ccacacgggg ccgggcgcgg tggctcacgc ctgtaatccc agcacttcgg gaggccgagg  60960
cgggcggatc acgaggtcag gagatcaaga ccatcctggc taacacggtg aaaccccgtc  61020
tctactaaaa atacaaaaaa ttagccaggc atggtagcgg tcacctgtag tcccagctac  61080
tcggcaggct gaggcaggag aatggcgtga acctgggcgg cggagcttgc agtaagccga  61140
gatcgcgcca ctgcactcaa gcctgggtga cagagcgaga gtccatctca aaacaaaaaa  61200
aagaagaaga accgcatgga tcactttacc tcagagctaa gctgctgttt tatcttttaa  61260
tagagctcca ttttttgaat aggaaaatta gctgctttct atgttaaaag gaactgaaca  61320
caatttcagc ttcttcatac taggtttgga attatcaaga aaagctccta agttacccta  61380
gctaagctat tacataacag tctcattttt aactttcctt ttctatttga gaaatctgat  61440
tattttcatg ttccttgggt tttacaatat taatcattca gtaccatctt tattaatttt  61500
aatagaattt acatggacac cttggtttta gtgttagata aaagcaacat atctttcctg  61560
gcaataggct gccaagcctc cagacttaaa tcccgagaca gaggagagta taccttcccg  61620
cagctccccc gaaggacctg atccaccagt tcttactgag gtcagcaaac aggatgatca  61680
gcagccttta gatctagaag gagtcaagag gaagatggac caagggaatt acacatctgt  61740
ggtatgtttc tacagtgagc catcagaatt tctagtgcca ataaagcttc tttggacctt  61800
tggggcatga aactgagtat aagtaaattt aaaaatgaat tgtattatat ttagaaatgt  61860
cacgtggctt tagataccta aaaatgtatg agttatttta gctttgtgtt tcagaagaag  61920
ggttgtgata gggaagataa tgtcttaaaa tagttctttt atttggcttt catctcagtt  61980
ttctgaaaat tatttttata ttaagaggaa gcactaagaa actgttgatg tgggaaatgc  62040
taatatgaaa ttaattggtt ctccctcccc ttttgagatc agatctgaat aatgtgcctt  62100
tctttataag gtcttcattt gtagatagat gcctgttaat tttatgattt taagtatgta  62160
taggaaatga ttatttatta tctcatgatc tatatttgcg attctgttgt ttatttttat  62220
ttatttattt atttatttga gatggagtct cgctctgtta cccaggctgg catgcagtga  62280
catgatctcg gctcactgca acctctgcct cccgtaatca agtgattctc ctgcctcagc  62340
ctcccaagta gctgggatta cataagcatg tgccaccatg cctggctaat tttgtatttt  62400
tggcggagat tgggtttcac catgttggct aggctggtca tgaactcctg accttaagtg  62460
atccacccac atcagcctcc caaagtgctg ggattacagg cgtgagccac tgtttattta  62520
ttttaatcca aaataaaaac tgtggacctg cttggataat ttatcatgat acagccaatt  62580
tgtttgcatt cttacctcat tagcctggca tctcttaatt gccacaggtt aatcgtgaat  62640
tgaatctcaa aggtctcagc caaagagtat tataccacat taaaataggg tgtgagtttt  62700
ctgttggatc tctgtgctgg atgattaagg agggaagagg aaatggtttt cagagcacac  62760
tgttttaaga ataattaaca ttttgttttt gtatacagtt ggagttcagt gatgatattg  62820
tgaagatcat tcaagcagcc attaattcag atggaggaca gccagaaatt aaaaaaagcca  62880
acagcatggt caagtccttc ttcattcggg tgaatgatat tactaattca tgtttttaat  62940
gcttacctat aagtaattac cctgtgaata caatgaactt gttctcttct actttttgct  63000
ttgtggtgtg tataaaacat ctttggttta atttgatccc ctgattcttt gagaggaact  63060
```

tggtgaggtt gccagagtgg atggatcttt ctcttggtgg cctgaaatta tcctcgtatt 63120
aacagagaag ctggtttgaa gatttttcat gtggtatcta aatgagtgtt tacatattta 63180
cattttgttt gtgttttctt ttagcaaatg gaacgtgttt ttccatggtt cagtgtcaaa 63240
aagtccaggt tttgggagcc aaataaagta tcaagcaagt aagtgaattt agcataactt 63300
ttttttctcc tcatcggcta gaaatctgag agttctcata tttctagatt gcagttttcc 63360
aaaaggtttt aatactagaa atgaattggt tgaaatgcct tttcggtgtg gttttgagga 63420
ctacatttaa tgtttgttat aagcaattgc ctttttgttc tttactttta tatttgtttt 63480
attgtaggga gcttggttta attgtgacaa atgtacaata catgtgtggt acagccatgt 63540
agctggcctt gttataaatg ggttctgttt gactgatagt tcaaatggtg ctttgtactg 63600
ctcttgattt tccatatgta acctttaatt tttattccag taaattcttt tgatttgatt 63660
ttatttattt atttattttt ttttttttga gacggagtct cgttctgtca ccaggctgga 63720
gtgcagtgac atgatctcgg ctcactacaa cctccgcctc cctggttcaa gcgattctcc 63780
tccctcagcc tcccaagtag ctgggaaaac aggcgggcac caccatgccc agctaatttt 63840
tgtattttaa tagagactgg gtttcaccat tttggccagg atggtcttga tctcttgacc 63900
tggtgatccg cctgcctcac cctcccaaaa gtgctgggat tacaggcatg agccaccatg 63960
cccggcctct tttgagtttt tgatagggtt atcatttgtt tcagcaagtt taaccaagag 64020
tcatatgttg agatattttt taaaatattg agttctgtgt acttcagcaa ttttcaaacg 64080
ctgtgacttg ttcttatatt ctgtgaatgg ctcctacatg gggcaacagg tgatatcaag 64140
aatttatttt atacagttct aggtatactg taggagttca ataaatgctt gttgaatcaa 64200
ttattttcag cagtgggatg ttaccaaacg cagtgcttcc accttcactt gaccataatt 64260
atgctcagtg gcaggagcga gaggaaaaca gccacactga gcagcctcct ttaatgaaga 64320
aaatcattcc agctcccaaa cccaaaggtc ctggagaacc agactcacca actcctctgc 64380
atcctcctac accaccaatt ttgagtaagc caccaaaagg agagtcgtca cccatttccc 64440
tctagatgca gatgattgac ttcgtgaatc caattcacta aaattagata tacttggata 64500
tcagaaagga attttcaggt catccttaaa tgtaatacca tcattaattt tgcttcactt 64560
gaggtgttaa tgaggacttg atataaatac tctggagtat tgtaacatag atgatgaggt 64620
agcgtaactc tgaacacttt ttgaaaagtg gttattttat aggctgtggg ctatgtaagc 64680
tgaattattt ctttttttcct tgaaatcaga catagtattg ccaattttaa ctggatctca 64740
aggtattgat gggagtcttt tggatttcaa ggtactgata ggagtcgaga agacagtcca 64800
gagctgaacc cacccccagg catagaagac aatagacagt gtgcgttatg tttgacttat 64860
ggtgatgaca gtgctaatgt aagtactttg caacacaggg ccctagttaa tacatactcc 64920
aaaagaactg tttgtccttg tgtccatact tgatgactgg gtgccattta tttaatgaac 64980
ttacttataa cttactaatt tataactttt atttacctat aacttataac ttattaattt 65040
gtaacttatt ttttgtcact tagttcatgg cacttggagt tttttaatga ctgattttgt 65100
tgattaaaag gtgactgatt tgccttaaat taaacccttg atgtctagta atttctaatg 65160
gaagttcctc aagaatattt tgtgaaagtt aataaaatct aagttgcata ttaaaaagct 65220
tgtgtttcat ataggatagc agaatcgtta agagcccgag ttctgccgcc tgcctgaata 65280
catttctgtg cttaactgcc tacttattga ctttggcaag tagtttaacc tctctgaccc 65340
tcagtttcat ctttaaaatg aagataataa cgcttacctc agagtggctg tgaggattaa 65400
atgaaataat gtatgtaaag cctctatttg gtgcctggca cacacagtaa gctacaattt 65460
ttttaaaagt tttttgtgtt ttttgttttg ttttgttttg tttttttgag cggagtttcg 65520
ctcttgttgc ccaggctgga gtttcgctct tgttgcccag gctggagtgc aatggcgtga 65580
tctcggctca ctacaacctc cgcctcctat gttcaagcaa ttctcctgcc tcagcctccc 65640
gagtagctgg gattacaggc atgtgccacc atgcccggct aattttgtat ttttagtaga 65700
gacggagttt ctccatgttg gtcaggctgg tctcaaactc ccgaccccag gtgatccacc 65760
cacctcatat cccaaagtgg tgggattaca ggcgtgagcc accgtgcccg gccaaaagct 65820
tttaaatacc atctgagaga actggctttg aaatacagtt tatagatgtc actgcacatt 65880
tttataaact taccacctat tgctcttttt gtttgtttcc ttttgagacc aggtcttgct 65940
ctgtcaccca gactagagta cagtggcatg cttttggctc actgcaatct cggcttccgg 66000
ggctcaagtg atcctcctac ctcagcctcc tgagtagctg agaccacaga tgcgcaccac 66060
catgcctggc taatttttgt tttgtttttg ttgagacaaa gtctccctat gttgcccagg 66120
ctggtctcaa actcttgggc tcaagcgatc ctaccacttc agcctccaaa agtgctggga 66180
ttacagacgt gaaccaccat acccagctca tttttttatt ctctagattt gtaaaatagt 66240
ttcagtctat ggaaaaagta atcttgaaaa gaaggaagtg gaaacagagc aacgttgcaa 66300
aaagaattct gatttctgtg tgcctccctc cattaaagaa ttatagttgc tttcttgagg 66360
ttatcttcac tggaaaagct aatgccgagg aaaacctcct ttggcattat attctttagg 66420
aaaaaagaaa tctctttatt ttataggatg ctggtcgttt actatatatt ggccaaaatg 66480
agtggacaca tgtaaattgt gctttgtggt cagcggaagt gtttgaagat gatgacggat 66540
cactaaagaa tgtgcatatg gctgtgatca ggggcaagca gctggtaaga ccttatgggt 66600
aaattttatg aaagagattc cctctcagtt tccagatatt cttcctgtgg gtgaatatgg 66660
cctccctgat atttttcaca gtgccatcag ggtagttagc caacaagtat tgatatacat 66720
aattcaacag ataaaatgat aaattttatc tgttttcaat ttatcaatag ataaaatgaa 66780
ttgtaggaac tgtagaatgg gatgagtcta tagaggagac ggtaaacgtc ttaaaacata 66840
tgaaagtctg aataggactc tgttcttttt ggatttttag agatgtgaat tctgccaaaa 66900
gccaggagcc accgtgggtt gctgtctcac atcctgcacc agcaactatc acttcatgtg 66960
ttcccgagcc aagaactgtg tctttctgga tgataaaaaa gtatattgcc aacgacatcg 67020
ggatttgatc aaaggcgaag tgagagagct ttagttgctt taaaaaaaaa aaaaaagact 67080
tttttagagc agttttaggt tcacagcaaa attgactgga aggtacagag atttcccata 67140
tgccccctgc acccacatat gcacagcctc ccccatgatc agcatccccc accagagtgg 67200
tgcatttgtt acagtggata aacctacact ggacacatgg ttatcaccct gactcctgta 67260
gtttacatca gcattcactc ttggtgttgt acattctgtg ggtttggaca aatgtataat 67320
gatgtatatc caccattata ccatcatatg gagtattttc gctgccttaa acatcctctg 67380
tgctctgcct attcatccct gcctctcccc aaccctgggc aaccactgat gtttttacta 67440
tctccatagt cttgccattt gcagagtttc acatagttgg aatcatatag tacatagcct 67500
tttcagactg gcttcttctg catagcattt aagtttcctt caagtctttt catggcttat 67560
ttagttgctt tttgaattat ttcgaaatgc aaaagaaaaa caaaaataca gcaagatgat 67620
aaactgtttt gcttttctac ttggtgttcc tagaggcacc acctcttttg ggaaatacag 67680
aagtgtcctg ctaagtgaaa cagaaggatg cttttgagat atgctatgtg ccttccactc 67740
tgagacagtc aggatcataa gtataatgtg caaagggaca gcctattaac agctaccatg 67800
ggttttattt aaggtggttc ctgagaatgg atttgaagtt ttcagaagag tgtttgtgga 67860
ctttgaagga atcagcttga gaaggaagtt tctcaatggc ttggaaccag aaaatatcca 67920
catgatgatt ggtatgacct agccttggtt attggggaag gctgtatata tcattgggga 67980
aatttctggt cctcagttat aaaatgaccc tcagccaggt gtggtgtctc acgcctgtaa 68040
tcccagcact ttgggaggct gaggcgggca gatcactgga ggttcaggag ttggagaaca 68100
gcctggccaa tgtggtgaaa ccctgtctct actaaaaaaa attagctggg agtggtggta 68160
catccctata atcccagcta cttgggaggc tgaggcacag gaatcacttg aaccccggag 68220
gcagaggctg cagtgagctg agattgcgcc actgcattcc agcctgggcg acagagtgag 68280
actctctcaa aaaaataaaa tgacgctcat aatcttctct aatcggttct tctttccttg 68340
gtcagggtct atgacaatcg actgcttagg aattctaaat gatctctccg actgtgaaga 68400
taagctcttt cctattggat atcagtaagt agcactataa agagaagaga gcagccccac 68460
aacctgaaca cactgaagcc atgtgcaggt cattaaatgt agaggcatac ctgttagcta 68520
ctttaaactg ctactaaaaa ttaatcactt attttgctag ttctcggatt cgtctgcttg 68580
tagattggga ctatgttagc ggaatccagt tatagaagga aagtattatt gacataattt 68640
cagaattact taaaaataaa accttagtag aaaacacaag gtcagtctct taagattcct 68700
ccaaattcca ttcatctcca tgcagaagtg cagattgttt ttatggataa aacagctcat 68760
gccctgttcc caactttaca gtttataagt ccttctaaaa ctataaatcc acacaataat 68820
gatcaaattt ttcaataaga atttataatc ttacctatat gaagtaagtt gttaaaatgt 68880
ctaacaagct aacaatataa gttcaaaatt cccettctac cactcccgcg ttggagtctc 68940
attttgcaat atatgctcca acttactctg tattcctatt cctatgacac agtctgtgct 69000
ccacatttag ctggcagctt ttcacacaaa ccagattcca ctagcattca gcagatttga 69060
agcagttaca tttctcttgt ctcatggggc tcttctccca aaggaaacac ctcaggtttg 69120
ccctttgttt tattttcagg ccgtactttg tatacattgt aaggcaatag ttcggtcctg 69180
aaggccaaaa ctaatttttg taatggttaa tatttttctt tctcttgctt ttaggatgtt 69240
ttactatatt tggtgcctgc ttatggtaca agaaaaaaag atcttaggct attttctgag 69300
aggctaagaa aaaccaagga cttcaaaaag cttggaacaa cctaactagg ggaatctata 69360
ctaagaaccc ataaaataaa gctaaactct gtaattaaga gggccaggga acctaggata 69420
aagagaggtt ttgaaaaatg ctagtttctg cttctatcct ctcccttatg atgattttcc 69480
caaatctgtt tacccaggtg ttccagggta tactggagca ccacagatgc tcgcaagcgc 69540
tgtgtatata catgcaagat agtggagtgc cgtcctccag tcgtagagcc ggatatcaac 69600
agcactgttg aacatgatga aaacaggacc attgcccata gtccaacatc ttttacaggt 69660
tagtcttgaa tcaagatggg acttgaggct gggcacagtg gctcacgcct gtaatcgcag 69720
cactttggga ggctgaggca ggtgaatcac ttgaggccag gagttcaaga acagcctggc 69780
caacatggtg aaaccccatc tctactaaaa atacaaaaaa attagccagg catggtggca 69840
ggcacctgta atcccagtaa tcccagccac tcaggaggca gaggcacaag aatcacttga 69900
accagggagg cagatgttgc agtcagccaa gatcacgcca ctgccctcca gcctgggtga 69960
cagagtgaga ctgtgtctca aagaaaaaaa aaaaaagatg tgatggaact tgaattcgat 70020
tcagggagta ctatgattga aagctggggg aaaagtcatt tacttgggaa gtctcatttg 70080
cttctagttt tacatttacc tgatagctga ctttttattg gttaatttgt ttgatatttt 70140

-continued

```
aattgggcct ttttagttaa gagtttttat ttcctgccac agaaagttca tcaaaagaga  70200
gtcaaaacac agctgaaatt ataagtcctc catcaccaga ccgacctcct cattcacaaa  70260
cctctggctc ctgttattat catgtcatct caaaggtccc caggattcga acacccagtt  70320
attctccaac acagagatcc cctggctgtc gaccgttgcc ttctgcaggt aaaagacttt  70380
attgacctac ttgacctaag aagatcagcc caaagactaa tttgtaattc tttcaggcaa  70440
ctttatcttg gtgactttta ctgattgaaa atgtagattc cgggtgggtg aggtggctca  70500
tgcctgtaat cctagcactt tgggaggcca gggcaggtgg atcacctgag gtcaggagtt  70560
caagaccagc ctggccaaca tggtgaaacc ctatctctac taaaaattca aaaattagcc  70620
aggtgtggcg gtgcatgcct gtaatcccag ctacccagga ggctaaggca ggagaatcgc  70680
tggaacccag gaggtggagg ttgcagtaag ccgagatcgc accactgcac tccagcttgg  70740
gtgacagagt gagacactgt ctcaaaaaag taataataaa taaatagaaa atgtagattt  70800
ccagttacct ataaatatat atatatatag tcaaatcatt gaaaccagtg acttctacac  70860
atttgttcta tctacaatag catttattac tttttctctc ttgtttagga agtcctaccc  70920
caaccactca tgaaatagtc acagtaggtg atcctttact ctcctctgga cttcgaagca  70980
ttggctccag gcgtcacagt acctcttcct tatcacccca gcggtccaaa ctccggataa  71040
tgtctccaat gagaactggg aatacttact ctaggaataa tgtttcctca gtctccacca  71100
ccgggaccgc tactgatctt gaatcaagtg ccaaagtagt tgatcatgtc ttagggccac  71160
tgaattcaag tactagttta gggcaaaaca cttccacctc ttcaaatttg caaaggacag  71220
tggttactgt aggcaataaa aacagtcact tggatggatc ttcatcttca gaaatgaagc  71280
agtccagtgc ttcagacttg gtgtccaaga gctcctcttt aaagggagag aagaccaaag  71340
tgctgagttc caagagctca gagggatctg cacataatgt ggcttaccct ggaattccta  71400
aactggcccc acaggttcat aacacaacat ctagagaact gaatgttagt aaaatcggct  71460
cctttgctga accctcttca gtgtcgtttt cttctaaaga ggccctctcc ttcccacacc  71520
tccatttgag agggcaaagg aatgatcgag accaacacac agattctacc caatcagcaa  71580
actcctctcc agatgaagat actgaagtca aaaccttgaa gctatctgga atgagcaaca  71640
gatcatccat tatcaacgaa catatgggat ctagttccag agataggaga cagaaaggga  71700
aaaaatcctg taaagaaact ttcaaagaaa agcattccag taaatctttt ttggaacctg  71760
gtcaggtgac aactggtgag gaaggaaact tgaagccaga gtttatggat gaggttttga  71820
ctcctgagta tatgggccaa cgaccatgta acaatgtttc ttctgataag attggtgata  71880
aaggcctttc tatgccagga gtccccaaag ctccacccat gcaagtagaa ggatctgcca  71940
aggaattaca ggcaccacgg aaacgcacag tcaaagtgac actgacacct ctaaaaatgg  72000
aaaatgagag tcaatccaaa aatgccctga aagaaagtag tcctgcttcc cctttgcaaa  72060
tagagtcaac atctcccaca gaaccaattt cagcctctga aaatccagga gatggtccag  72120
tggcccaacc aagccccaat aatacctcat gccaggattc tcaaagtaac aactatcaga  72180
atcttccagt acaggacaga aacctaatgc ttccagatgg ccccaaacct caggaggatg  72240
gctcttttaa aaggaggtat ccccgtcgca gtgcccgtgc acgttctaac atgtttttg  72300
ggcttacccc actctatgga gtaagatcct atggtgaaga agacattcca ttctacagca  72360
gctcaactgg gaagaagcga ggcaagagat cagctgaagg acaggtggat ggggccgatg  72420
acttaagcac ttcagatgaa gacgacttat actattacaa cttcactaga acagtgattt  72480
cttcaggtgg agaggaacga ctggcatccc ataatttatt tcgggaggag gaacagtgtg  72540
```

atcttccaaa aatctcacag ttggatggtg ttgatgatgg gacagagagt gatactagtg 72600
tcacagccac aacaaggaaa agcagccaga ttccaaaaag aaatggtaaa gaaaatggaa 72660
cagagaactt aaagattgat agacctgaag atgctgggga gaaagaacat gtcactaaga 72720
gttctgttgg ccacaaaaat gagccaaaga tggataactg ccattctgta agcagagtta 72780
aaacacaggg acaagattcc ttggaagctc agctcagctc attggagtca agccgcagag 72840
tccacacaag taccccctcc gacaaaaatt tactggacac ctataatact gagctcctga 72900
aatcagattc agacaataac aacagtgatg actgtgggaa tatcctgcct tcagacatta 72960
tggactttgt actaaagaat actccatcca tgcaggcttt gggtgagagc ccagagtcat 73020
cttcatcaga actcctgaat cttggtgaag gattgggtct tgacagtaat cgtgaaaaag 73080
acatgggtct tttgaagta ttttctcagc agctgcctac aacagaacct gtggatagta 73140
gtgtctcttc ctctatctca gcagaggaac agtttgagtt gcctctagag ctaccatctg 73200
atctgtctgt cttgaccacc cggagtccca ctgtccccag ccagaatccc agtagactag 73260
ctgttatctc agactcaggg gagaagagag taaccatcac agaaaaatct gtagcctcct 73320
ctgaaagtga cccagcactg ctgagcccag gagtagatcc aactcctgaa ggccacatga 73380
ctcctgatca ttttatccaa ggacacatgg atgcagacca catctctagc cctccttgtg 73440
gttcagtaga gcaaggtcat ggcaacaatc aggatttaac taggaacagt agcacccctg 73500
gccttcaggt acctgtttcc ccaactgttc ccatccagaa ccagaagtat gtgcccaatt 73560
ctactgatag tcctggcccg tctcagattt ccaatgcagc tgtccagacc actccacccc 73620
acctgaagcc agccactgag aaactcatag ttgttaacca gaacatgcag ccactttatg 73680
ttctccaaac tcttccaaat ggagtgaccc aaaaaatcca attgacctct tctgttagtt 73740
ctacacccag tgtgatggag acaaatactt cagtattggg acccatggga ggtggtctca 73800
cccttaccac aggactaaat ccaagcttgc caacttctca atctttgttc ccttctgcta 73860
gcaaaggatt gctacccatg tctcatcacc agcacttaca ttccttccct gcagctactc 73920
aaagtagttt cccaccaaac atcagcaatc ctccttcagg cctgcttatt ggggttcagc 73980
ctcctccgga tccccaactt ttggtttcag aatccagcca gaggacagac ctcagtacca 74040
cagtagccac tccatcctct ggactcaaga aaagacccat atctcgtcta cagacccgaa 74100
agaataaaaa acttgctccc tctagtaccc cttcaaacat tgccccttct gatgtggttt 74160
ctaatatgac attgattaac ttcacaccct cccagcttcc taatcatcca agtctgttag 74220
atttggggtc acttaatact tcatctcacc gaactgtccc caacatcata aaaagatcta 74280
aatctagcat catgtatttt gaaccggcac ccctgttacc acagagtgtg ggaggaactg 74340
ctgccacagc ggcaggcaca tcaacaataa gccaggatac tagccacctc acatcagggt 74400
ctgtgtctgg cttggcatcc agttcctctg tcttgaatgt tgtatccatg caaactacca 74460
caacccctac aagtagtgcg tcagttccag gacacgtcac cttaaccaac ccaaggttgc 74520
ttggtacccc agatattggc tcaataagca atcttttaat caaagctagc cagcagagcc 74580
tggggattca ggaccagcct gtggctttac cgccaagttc aggaatgttt ccacaactgg 74640
ggacatcaca gacccccctct actgctgcaa taacagcggc atctagcatc tgtgtgctcc 74700
cctccactca gactacgggc ataacagccg cttcaccttc tggggaagca gacgaacact 74760
atcagcttca gcatgtgaac cagctccttg ccagcaaaac tgggattcat tcttcccagc 74820
gtgatcttga ttctgcttca gggccccagg tatccaactt tacccagacg gtagacgctc 74880

-continued

```
ctaatagcat gggactggag cagaacaagg ctttatcctc agctgtgcaa gccagcccca  74940
cctctcctgg gggttctcca tcctctccat cttctggaca gcggtcagca agcccttcag  75000
tgccgggtcc cactaaaccc aaaccaaaaa ccaaacggtt tcagctgcct ctagacaaag  75060
ggaatggcaa gaagcacaaa gtttcccatt tgcggaccag ttcttctgaa gcacacattc  75120
cagaccaaga aacgacatcc ctgacctcag gcacagggtg agagatccaa atactagcta  75180
ggctgggtct gtgggatttc atgttgtaaa ttaggggctg ttgatgtggt agtccgggag  75240
agacactctt ctgttcaagt tgcattacct gggagttttc cgggttttga cttttttttct  75300
ctctgagtgg tgatttatgt aacaaaatgt agttccatcc atgggcagtt tgtctcttga  75360
atagaaccac atctaatcac tttttgctct gatttcaaac agtgttgctg tttgttcctg  75420
tttctttttt actgaggctt atactagaat gattattctt atcttgaggg caaagctccc  75480
tcttgtagat ccacagagtc cttttttttaa aactttatca ttgaaagcca agcacagtgg  75540
ctcatgtctg taatcccagc actttggaag gctgaggcag aaggattgct ggagctcagg  75600
agttcaagat cagtctgtgc aacatagtaa gaccctgtct ctacaaaaaa ttttttaaaa  75660
cagctgggtg tggtgttgca cacctgtagc cccagctatt caggaggctg aggtgggagg  75720
attgcttgag cccaagagtt agaggctaaa tgatccatgg tcatgtcact gcactccagc  75780
ctaggtggag tgcacctatg tagccaccac tcggatcaag atacagaaca tttctagcaa  75840
cccacaaggg tgtcttctct tataaggtca gtgccccctc aaagtaacca ttattctaac  75900
ctttatgacc ttaggtcagt tttgctggct tatagacttt atcagatcct gatagagcca  75960
tttctttcga ctcacctcca cattcagtac atatttactg gtggtttgtc ttgaaaagat  76020
acaaatgcct gtgttccagg actccaggag cagaggctga gcagcaggat acagctagcg  76080
tggagcagtc ctcccagaag gagtgtgggc aacctgcagg gtaagctgaa gaattcgtct  76140
tttaagacta agctctcagt tttgtccacc tcatttaaaa aatagttctt ccaggccggg  76200
cgcagtggct cacgcctgta atcctagtag tctgggaggc cgaggcaggt ggatcacgag  76260
gttagatcga gaccatcctg gctaacatgg tgaaaccccg tctctactaa aaatacaaaa  76320
agaattagcc gggcgtgatg gcgggcgcct gtagtcccag ccactcagga ggctgaggca  76380
ggagaagggc gtgaacccag gaggcggagc ttgcagtgag ctgagatcgc gccactgcac  76440
tccagcctgg gcgatagagc aagactccgt ttccaaaaaa aaggtaaaaa atagttcttc  76500
ctgattcaca ttgattttttg ttttcttgcc aaagtttttt aaatgagaat agtacaggct  76560
tgtaaacaag taaacaaaaa atataacaag aattatttaa ataatggata atagtttcct  76620
atttgtcccc ctcacccccg cccaatctac tccctagagg tggtcattgc taataatttg  76680
tttttatcta tgcagacatc tctctgcata taaagatata acgtggtata tatatgaata  76740
tgtatacact tttttacata aaaggaataa tactgtacat actgttctgt atttggtttt  76800
tcacttatgt acatctttct gtgccaatat atgtaggtgt gcttcacttt ttaaatcgct  76860
gccgccaatt ctattgtgtg gatctacaat attttaatga gtcctctatt gatatacatt  76920
tggattgttt ccagaattta tttagtttaa aaaagtgaaa actggggctg gacacagtgg  76980
ctcatgcctg taatcccaac actttgggag gctgaggcag gaggattgct tgagcccagg  77040
agtttgaaac caaccttggc aacataggga gaccctctct ctacaaaaat taaaagttaa  77100
ccaggcatgg tggtgcacat ccacagtcca agctaaggcg ggaggattgc ttgagcctgg  77160
gagttggagg atgcagcaag ccgtgattgc cactgcactc cagcctggac agcaaagtga  77220
gaacctatct caaaaaaaaa aaaaaaaagg tgaaaattga ttgtggttta taagctcatg  77280
```

cagcttattt tttagtttta gttaagccag cttacttatt taagtaactt tagaattgct 77340
tctgacaagt gtcctttcat ttttttctaa tactgagtat gagaagaatt tcaagggcgc 77400
aatttacaac tttaaaaaca gaaacttaat gtcagtattt ggtaaagaat ctcacaaaag 77460
agttttatgt tatgtaccat acagtggtgt ggtggttgta ttcattcaac aagttctaca 77520
gaaagccccc tgtggctcat tttctagcag ttattttgta taccacagct gtatagaaaa 77580
ttctgggttt tttctttgaa ttgaagaact agctgatatt atatcttaca tttggttttt 77640
atttaggcaa gtcgctgttc ttccggaagt tcaggtgacc caaaatccag caaatgaaca 77700
agaaagtgca ggtatgtggg tgggtaaaag gttagaatca gagaatatca atgctaaaag 77760
gattatgaga atcacccact ttacctactt attttctaca tttaaaaaaa aaaatctaag 77820
ctccaaagaa gttaagtgat ttggcccaca ttggactgaa acttggcgca cctgtctctc 77880
ggtgcagtgt tcttccagta catattgtgt gatcacctgt cagctaagga ctcaagacca 77940
tacccatact cttctgctgt actggtttta ccagcactga ggcttaaata gctagtaata 78000
acctgacttc actttttagt tgttactaaa gaaaactaag aaccattttt attagatagt 78060
cagattttgg ttacaatacc agatacatct ccatggcatt ttccatcagt tctaatgaat 78120
ttgattagga aacaaatggt cacttcaaga ttagagagtt ctgggtataa ctctattgag 78180
gacagttgct tattgaaaaa ctatcagatc gtcatactag aaattctacc acagagagca 78240
taacttcatg taaaaaaaaa tctggtttta gtcaccactt tctagcaatg acctaggcaa 78300
gctctttgag tcttgggttt gttatctata aatgggaata ataaaccaac tgtggaatgt 78360
tgttaggctt agagatcatt tatgtaaagt actctacatg tagtcagtgc tcagtgagca 78420
tttgttactg caaccactat ctattttctc cctattagaa cctaaaacag tggaagaaga 78480
ggaaagtaat ttcagctccc cactgatgct ttggcttcag caagaacaaa agcggaagga 78540
aagcattact gagaaaaaac ccaagaaagg acttgttttt gaaatttcca gtgatgatgg 78600
ctttcagatc tgtgcagaaa gtattgaagg tgagtggatt aaatcaggtt gacccatcag 78660
cagaagccct gtttcagcta gagcttcatt ttctgagtat tagcaccatt taggtggctg 78720
ttttatgcta gatggtaggg ggatacctgg aggcatcata cattttcctt gtccttgaga 78780
agtttgtctt attggagaaa tagccatatt ttacatgaaa agttaatgat acagattatg 78840
ttttcaacat tgcacacacc ttagcggagc ccctgagaac tctgcttccc cctccagcct 78900
tgtttttttgc cattccctca tgcgccttct gtgcccttct ctctcccttg tgtgccttca 78960
cacgtgcttt ctcctctgcc tggagttctc tccctgccct caatcacctg gtgagctcca 79020
gctcaccctt caagatccag ctcagacggt cttccctgac cttctgaggt agctaagccc 79080
tccctctccc tccttttgaa tcttacatgt tcttctctca tagcttacat tttgttttgt 79140
ccgtgtttgt ttacttttat cactcactca acagcgagct ctccataagg gctggaattt 79200
tattttctta ttcatctttg tatcgcaagc atctaagtgt tcatccacct ttgaaggact 79260
agtaaatgtt ctctaggctg taagtactag aagagttcaa agaagagaaa ggtcaccatg 79320
ggtgagttag ggttatcaaa aacccatgaa gataaataga agattctatt aaaggagaaa 79380
atggaatttg ggttaggcaa agaagaatgc agggctctct aggaagaaga agggaggtaa 79440
gcaaagttag aaaggcagga ctgcatttgg tgggtttaga gtagtgtcag gtgagatggc 79500
attgaaatcc atgtgaggta atagtgaaag agaaaattgg gaaggtggat agggcacagg 79560
ttttagaggg ctttcagtgc caaaccttga ggactttgaa aacttgaggg agtgaataga 79620

-continued agcagaattt caggaaacat aatgtgataa gctctctata tgagacagat tgagcatgaa 79680
ctggagatgc tcaaagacga gagtttacta atgagagtat tgctagagta gagatgtctg 79740
gtaataaagc ccacattcgg tgggaaaaga aaggaaagga aagaagaatg agtacacttg 79800
gtggaatatg gagaggggag agtcaaagat gaccctaaag attcaggcct gggtgactaa 79860
aacaaaagat aatgcatgga gaacaaagga gataagtaag gagtatgggg gttccacaga 79920
agacattgat gtggagtgat gtaagaaatc catgtggaaa tgcctagcag acaggaaaag 79980
atcacagaat cttgggttag agctggaagg aactgtaagg attttctagt tctgcctctt 80040
aactttaagg aacagagagg ttatgatctt cccacagtcc tgcttaaatc attattacta 80100
gtgctgtttt gattaggggt acagggaaca taaaaatacc aaacattcag gtgtgagacc 80160
cagacttcca tcaagggatg tgaatgcgtt ggggattcag agttcatttc agaaggtctg 80220
actttcctta gtgcttctgt gtcctccaac agaaagaagc cctgctgggg agtgtacctt 80280
ttcggctcct ttcacatgta atgaactgac ttaaactcta agaaaaataa caaaacactg 80340
ctctaggagg gcaagtgttc acactgtagg gattctaagc agtgcttgtg cacatcattg 80400
gtattaagaa gggtttacgt gcatattttc tggcttacgg gttttcttta tttcctttca 80460
gatgcctgga agtcattgac agataaagtc caggaagctc gatcaaatgc ccgcctaaag 80520
cagctctcat ttgcaggtaa tggctggagg tgttattcca ctcctgtctc agaatattat 80580
ggtaaattgt tcgcctaagg cagagttgat tctgtgaaaa aaaaatcagt taaaaatttt 80640
tttcacagct ttattgagat ttaattcata taccatacag ttcacccatc taaagcatac 80700
aattcagtgg tttttaatat attcagagtt gtataaccac cactactcta taattctaga 80760
acattctcat catccctaaa agaaaccccc tattcattag cagtcattcc tcagcccctg 80820
gccaccacaa atctactttc tgtctctatg tatttgatta ttctggacat ttcatataaa 80880
tgaaatcaga caatatgtag ccttttgtga ccgtcttctt tcactcaaca gaatactttc 80940
caggttcttc ccttctgtta catcttccct tccacatcag tacttcattc ctttttattg 81000
ccaaatattc cattgtgtag atataccata tgttgcttat ccattcatta gtcagtggac 81060
atttgggttt tttctatttt ctgctacgaa taatgttgcc acaaatattc atgttcaagt 81120
tattgtgtag acatgttttt attttttttc agtatatacc tcagagtgga atggctgggt 81180
catatggtaa ctctttaact ttttgaagta ctgccaggtt ttttttccaa agtggctata 81240
ccattttaca tttccacctg caatgcacga gtgttcccat ttctccacct ttgccaacac 81300
ttacctgttt tttgtttttt ttttttttatt ttagacattg tagtgtgaaa tgttatcttt 81360
tcttaaagtt gaaatcattt accattggta ttagacttca tattaaattt aggcagcata 81420
caaacttatt aatacacttg ttttgagcaa acactaaaga ttttaatcag tggatgctgt 81480
ggctcacacc tgtaatccca acactttggg tgaccaaggc agaaggatca tttgaggcca 81540
ggagttcaag accagcctgg gcttcataca gagaatacat ctttacaaaa aataaaaata 81600
tatattagcc ggcaccgtgg catgcacacc tgtactccca gctactctgg aggctgaggc 81660
aggaggatca ctggagccta ggagtatgag actgtattaa gctatgatct tagcactgca 81720
ctccagcctg aacgacagat aaatactttg tcacaaaaaa aagaagaaga agaagaagaa 81780
ggttttaatt aagctaaggt agaaaccttc cattgacttt gttttatcca tatctacctc 81840
tcctacctcc tttcagattg ctcctggaaa ggtgggtgaa tgggtactta caggaatttt 81900 aactttttttt tttttaggaa tttaatttta tcagtgatgt tcttccttta agagggaagg 81960
gaaggaaaat atttggatgc actttagaaa atactaacat ttgttcattt tatgtgacag 82020

-continued gtacatgcat ggctattata acaccctgtg tattttttta tacttaaaat ttttcagaac 82080
ttttttaatt aaaaaaaaga gaaaaagacc caacaggcag tttatctccc acaaaataca 82140
aatggcccat agcatgaaag ggtactcaat ctcagctgga cacagtggct cacacctgaa 82200
ttccaacatc ttgggaggat tgtttgagtc taggagttca agaccatcct gggcaataga 82260
gtgagacctc atctctatat aaaaaaaaat tgtttaaatt aggcaggcat gatggctcat 82320
gcctgtggtc ccagctactt gggaagctga tgtgggagga gcgcattgag cctgggaggt 82380
caagcctaca gtgagccaag attatggcac tgcactccag cctgggtgac agaacaagac 82440
cctgtctcaa aaaaaaaaaa aaaaaaaaag aaaaagaaaa aaaagtcttg ctcataattt 82500
ttaaaattct accccaaaaa tataagtcac atccctttct ttttctctga catatccctt 82560
gttattctct catgcaatgt taaaaagccc tataactgag tctcctatct cacctccttg 82620
taccctcaga gtctccagag gtgcctcaaa atcttactat tgcctactag ttacagagta 82680
taatcttcaa cccttacgta tttgttatta gtaaatattt actgaccact tgtaaaatgc 82740
ctggtaccat gttaaacaca ggatacagtc gctgagtagc gacccagccc tgctctttga 82800
ggtttcctgt ctacggatcc ttacatggcg aggtcctctt cagccggatt catctgttca 82860
gtctcagctt tccccacttc cctcactgct caagattctt tgttctgcag ccacactaca 82920
ctatttactg ttccagatcc atccatgtgt cttttttttt tttttctcca agacagagtc 82980
ttactctgtc acccaggctg gagtgcagtg gcgtgatctc ggctcactgc aacctccatc 83040
tcccaggttc aggtgattct cctgcttcag cctcctgagt agctgggact acaggcgcat 83100
gctaccacac ccggctattt tttgtattat tattattttt ttatttttat ttttattttt 83160
tgagacagag tttctttcct gttgcccagg ctggagtgca atggcgcaat ctcggttcac 83220
cgcaacctcc acctcccgaa ttcaagcgat tctcctgcct cagcctcccg agtagctggg 83280
attacaggca tgtgccacca tgcctggcta attttgtatt tttagtagag tcagggtttc 83340
tccatcttgg taaggctggt cttgaactcc tgacctcagg taatctgccc gcctcagcct 83400
cccaaagtgc tgggattaca ggcgtgagcc accacgcccg gcctaatttt tgtattttta 83460
gtagagacgg ggtttcaccg tgctggtcag gctactctag aactcctgag cttgtgatct 83520
gcccacctcg gcctcccaaa gtgctgggat cacaggcgtg agccactgtg cccggcccat 83580
ccatgtgtct taaagtgtag cctataggtg tgaatcagaa tccctgggct tggagctgag 83640
aaagctgaat ttttaacatg tgcccccaag caattcttat tacttaccct aaatgtgctt 83700
tcatatcagc ataacatggt tgatgcagtt ccctccacca ggacctattt cctccatcta 83760
ctctcttccc tccaaattcc ctggtttaca caacaaactc ctgttaatcc tttaagactt 83820
tgctcaaggt cacctctttt ctttaacctt ttttgatcat tcttcctgtg cctacggaaa 83880
tcccaactct taactgattt aaagagtgag ataatttatc atcttatata acagaaagtc 83940
cagaggtagg gacagacgtg tcaggattga ttggtacagg agcttgcaat gtcatcaaat 84000
acctagattc ttttcttctt tccactttac gatctatagt aaaacttcat cttcaagctg 84060
atagcaaatg gctgcagcag ttcccacaat aacattcagt catcacagtg ttcagaggaa 84120
caggagaggc ttaggaacaa atggacatct cacagaccag aatttggtac catgtccatt 84180
tctttttctg tccttttttt tttttttttt tttttgagac agggtctcac actgttgccc 84240
aggctggagt gtgtagtggt gcaatcttgg ctcactgcaa cctccgcctc ccgggttcaa 84300
gcaatactcc tgcctcagcc tcccgagtag ctgggactac aggtacacgc caccacaccc 84360

-continued agctaatttt tgtattttag tagagacggg atttcaccat gttggccagg atggtctcga 84420
acttctgacc tcaggtaatc tacccacctt ggcctcccaa agcgctgaga gtacaggtac 84480
ccagccccat gtccatttct aagccagtct ctggcaaagg gactgggatt cccaggattg 84540
tcttagatta atcatctggg gtggaaggtt tagcctggag gttaaccaca atgacccttg 84600
tgttccccag tccaaaacct gtccattata ctccatttcc agtgctgcca ccttgtcctt 84660
accctcatgc ccttatattc tagtggtgta tatgtatatg taagtaccat gaagaagata 84720
acatggggaa atgaaataga gagtgacaca gaggtgggta gttggtgaca ggaaatctgg 84780
aatctcttga tgaggcaaca tttgagctta gacctgagtg atgatgagaa gaagccaatc 84840
atgcatatac ataaagcgaa agtcctcgag gcaagctaga aggctgagga aggagagttt 84900
gagcttatag tgtgccaaga tcatacctgt gaatagccac ggcaccagct gagcaacaca 84960
gtgaaactct cttaaaaaaa attaaattaa attaactatg ttttctaaag tcctgacaca 85020
gaggaaacag cagatgaaaa agtcctgaag tgggaatatc tttgatgtgt ttattgtctg 85080
tctcttccat gaagtaaaag ctctatgaat acaggtacct tgcctgtctt gctcacctgt 85140
aagttcctaa ggtcctgtct ggcacagtgg aaagatggaa agagtgcctg ggatatttta 85200
ggtgtgctgt aaatatttat tgaatgaata aatgagtctc ccacaagcag aacagattgt 85260
tccttcttaa gagttcccat agtactttat attatacctt aatttggaca cctgcacatt 85320
gcatggtttg tatacgtctc tgccttcctc tgctgtgagc tccttaagaa cagacggggg 85380
cccacacata atgcatcttt gttttcccat tatcaacaca atattaatct cattgtaatc 85440
tctctggtga gtgagagttg aacattcagt gtacatatta aaaggaactt tctgtgaaaa 85500
tatacttgag tatgtagtat gtttttcaat gtcttttttt tttaacctaa gaattcacag 85560
caatctagaa cttccaggaa aaaattatta aggaaaatta gtggtctgta gaaaagagtt 85620
tgccagctgg gcgcggtggc tcacgcctgt aatcccatca ctttgggagg ctgaggtggg 85680
cagatcacga ggtcaggaga tcgacaccat cctggctaac acagtgaaac cccgtctcta 85740
ctaaaaaata caaaaaatta gccaggcgtg gtggcgggcg cctgtagtcc cagctactcg 85800
ggaggctgag gcagcagaat ggtgtgaacc caggaggcag agcttgcagt gagccaagat 85860
cgcaccactg tactccagcc tgggcgacag ggtgagactc tgtctcaaaa aaaaaaaaaa 85920
aaagaaaaga aaagaaaaaa gagtttgcca ttgccttata tggcttaagt tcttatctta 85980
tacagttgtg ttacatagtg ttacatacct aagccaaatt cttaagggac caacagttgt 86040
gatcataaga atgtcactta tcaggggcca gtgcagtggc tcacacctgt aatcctacct 86100
agcaagttgg gaggccaagg aaggaggatc actcgaggcc aggagttcaa gatcagcctg 86160
ggcaacacag taagaccctg tctccacaag aaatttaaaa attagccaaa cacagtggca 86220
tatatgcctg tagtcccagc tacctgggag gctgaggcgg gagcagcttg agcccagaaa 86280
ttcaaggtta cagtgagcta tgatcatgct actgcactcc agcctgggca acaaagtgaa 86340
acctgtctct tagaaaaaga atattgctta tctagagaca acattctttt tgtttgtttg 86400
tttgtttgtt tttgagatga ggtctcactc tgttgcccaa gctggagtgc agtggcatga 86460
tcgtctgctt tttcatctgc tatttcctct gcaccaggac attacaccaa ggttacatct 86520
ctaaatatgc ttcataatgc aaactgtatg tctgttggaa ttgcatatgt gcaattgcag 86580
tcctaataca attacactta tgaaatggat acctgatcca aaattaacac cattactgtt 86640
tctatatcta ttaataatac caaaccagta ttcgtaaatg aaataatatt gtttacttaa 86700
taaaaatgta aagaacatta gctatttgct agtgtcaaaa agaagtgtgg cagttgtaat 86760

```
tgtgccctgt ccctttaatg gaaaaagcca aataatttta aaatgaaagc ctttcaccat  86820
caatgccagc agacttatat aaatgttgtt ttcataaaat aaaaataaat aaaaaatgct  86880
cattaacagc atgagacggt gagtagaaca aagcagctac tgagtgtatt actccacaca  86940
ttcatcataa caacacaaga gttctgtgtt aggggtgtat taacattgct tttaaacttt  87000
agtgaggctg gctgggtgct gtggctcaca cctgtaatcc cagcactttg ggaagctgag  87060
gcaggtggat cacctgaggt caggagttta agaccagcct ggccaatatg gtgaaacctt  87120
gtctctacta aaaatacaaa aaaattagct gggcatggtg acgtgcccct gtagtcccag  87180
ctacttggga ggctgaggca ggagaattgc ttgaacccag gaggtggagt tgtagcgagc  87240
tgagatcgga ccactgcact ccagcctggg tgacggagtt agagtctgtc tcaaaaaaaa  87300
aaaaaaagcc gggcgcggtg gctcacacct gtaatcccag cattttggaa ggccaaggcg  87360
ggtggatcac gaggtcagga gatcgagacc atcctggcta acatggtgaa actccgtctc  87420
tactaaaaat acgaaaaaaa ttagccaggc gtggtggcgg cgcccgtagt cccagctact  87480
cgggaggctg aggtaggaga atggcgtgaa cccgggaggt ggagcttgca gtgagctgag  87540
atcatgccac tgcactccag cctgggtggc agagtgagac tccatctcaa aaaaaaaaaa  87600
aaaaaaaaaa gaaaattaaa ctttagtgag gtatctgggg gaacataagc ttatagaacc  87660
tagataatcc attcctagat ggattatatt tgtagttatg cagtccagag ttcatatctt  87720
gtcaaatcat gtagccttgg gagtgttaca tcagttctct aagcctgttt gctcacctga  87780
aaatgaagct agtaattcct gccctgtgtg gtcattatga gcacgaaatg aaataacacg  87840
tgtatatagc attagcatat agcatttctg tgtaataaag caaaatagtc catagtttgg  87900
tggcatgctt ttttcactta gccgtctatc acaaacattt tccatattga tagatctgta  87960
tcagcatcat tttaatggct atctgatgct aatttcgagc taatatgtac tataattcac  88020
cctggagcag cctctggcag agtgactata gcataggcat ttctgtagga ccatgctgtt  88080
tcctgttgac tgcgctcctc acttccctgg tgcttctgat tcttctaggt gttaacggtt  88140
tgaggatgct ggggattctc catgatgcag ttgtgttcct cattgagcag ctgtctggtg  88200
ccaagcactg tcgaaattac aaattccgtt tccacaagcc agaggaggcc aatgaacccc  88260
ccttgaaccc tcacggctca gccagggctg aagtccacct caggcaagtt cccttctttt  88320
ctgtcagcag ttttgggtct cgattttctt atctcatgac actgtcatct tcccacatac  88380
cctttgagat ttccagtttt aatgccatca tcctttactg ctttattaaa gcatttctct  88440
aaatatgttt taatcttttg gccccaggaa gtcagcattt gacatgttta acttcctggc  88500
ttctaaacat cgtcagcctc ctgaatacaa ccccaatgat gaagaagagg aggaggtaca  88560
gctgaagtca gctcggtaag tcttgagtgg ggagcagtca ttagaaactg ctttccctct  88620
cctccagctg gtcagggcac tacgtaggaa tttgtttgca tcagaatttc ctggataaga  88680
tttaaaagga ctgaaaacca tttgtgttga agtagcagta ggtgcctggt aaggagtgag  88740
gaatataagg tacagaggag aaattcaaag aactgtaaga tgcctgtttt ctttaatgat  88800
agtatactct gtcagctttg gttgtaccac catagttgtc atggtcagaa agtactatat  88860
atactaaaaa tgggactcat tggccaggca cagtggctca tgcctgtaat tccagcactt  88920
tggaagtccg aggcggacag atcatgaggt caggagttcg agaccagcct gaccaacata  88980
gtgaaaccct atctctacta aaaatacaaa aattagcccg gcgtggtggc gcgcgcctgt  89040
agtcccacct actcagcagg ctgaggcaag agaatcgctt gaacccagga ggcggaggtt  89100
```

acagtgagcc gagatcgcac cactggactc cagcctgggc gacagagcga aactccatct 89160
caaaaaaaaa aggggggcgc tcattttata aggcactcgt tcagtttggc attaaacaaa 89220
gagtgtacta attgtctcta ggaaccttcg attcaagact caaaacatta tttcctgaaa 89280
aaaattcgtt aatagtatgt cttatctctt aggagggcaa ctagcatgga tctgccaatg 89340
cccatgcgct tccggcactt aaaaaagact tctaaggagg cagttggtgt ctacaggtat 89400
gactaaaatt ctagaaagaa ttacagaaaa cgaatgcagt ttttcaaaat caaagcagac 89460
caaatgctgg agtgaccttc ctcactcagt aagtgaggat tttacggaca ctatttattg 89520
accctcatat cctgggatcc tgcacctcct tgtgttgaac aaggacttta acataataag 89580
cattaaaata ttactgcttc cagcgggtca cagaatggaa ataactttca tctttggcca 89640
tgtgttagat ggccaaatca agtgggtcca aatttttatt ttctcaagta tatgtccctc 89700
ctggggaact aacagaccag gagaacttat tcatgtattc acgcacttaa ccttacttgc 89760
aaaatttgtg tctgacctct tttccatctt tgtcctaggt ctcccatcca tggccggggt 89820
cttttctgta agagaaacat tgatgcaggt gagatggtga ttgagtatgc cggcaacgtc 89880
atccgctcca tccagactga caagcgggaa aagtattacg acagcaaggt aagtctccca 89940
cttgcactca cacagttctt ttgttttgct gtagaaaggg accagtatga cccctggatc 90000
acaaaagaaa tagtgtatgt tatcaattca gagacctttc ttaaaaaaat aaactctgaa 90060
atttgtgagg ggcccagtaa aaatacagaa tccactctga ggattagtac agaaagttgc 90120
tcttagaagg tttgtctgag tggctcctag tatcagaagc aaatagctat acaagtttta 90180
ggtttctctc tcctgcagag acattagaaa cctctagact agtggcctgt aatctaggaa 90240
atcctcgtgg aagcatcttg aaagatagta ctgggagaaa tctggaaatt ttactagaag 90300
aaactttctc agccgctata ggtaacatca agagaagatt gggacatgtt cttaaagctg 90360
agtttataag aaatgacaag ttcttctccc ttcttctgca tgtgcagggc attggttgct 90420
atatgttccg aattgatgac tcagaggtag tggatgccac catgcatgga aatgctgcac 90480
gcttcatcaa tcactcgtgt gagcctaact gctattctcg ggtcatcaat attgatgggc 90540
agaagcacat tgtcatcttt gccatgcgta agatctaccg aggagaggaa ctcacttacg 90600
actataagtt ccccattgag gatgccagca acaagctgcc ctgcaactgt ggcgccaaga 90660
aatgccggaa gttcctaaac taaagctgct cttctccccc agtgttggag tgcaaggagg 90720
cggggccatc caaagcaacg ctgaaggcct tttccagcag ctgggagctc ccggattgcg 90780
tggcacagct gaggggcctc tgtgatggct gagctctctt atgtcctata ctcacatcag 90840
acatgtgatc atagtcccag agacagagtt gaggtctcga agaaaagatc catgatcggc 90900
tttctcctgg ggcccctcca attgtttact gttagaaagt gggaatgggg tccctagcag 90960
acttgcctgg aaggagccta ttatagaggg ttggttatgt tgggagattg ggcctgaatt 91020
tctccacaga aataagttgc catcctcagg ttggcccttt cccaagcact gtaagtgagt 91080
gggtcaggca aagccccaaa tggagggttg gttagattcc tgacagtttg ccagccaggc 91140
cccacctaca gcgtctgtcg aacaaacaga ggtctggtgg ttttccctac tatcctccca 91200
ctcgagagtt cacttctggt tgggagacag gattcctagc acctccggtg tcaaaaggct 91260
gtcatggggt tgtgccaatt aattaccaaa cattgagcct gcaggctttg agtgggagtg 91320
ttgcccccag gagccttatc tcagccaatt acctttcttg acagtaggag cggcttccct 91380
ctcccattcc ctcttcactc ccttttcttc ctttcccctg tcttcatgcc actgctttcc 91440
catgcttctt tcgggttgta ggggagactg actgcctgct caaggacact ccctgctggg 91500

-continued

```
cataggatgt gcctgcaaaa agttccctga gcctgtaagc actccaggtg gggaagtgga  91560
caggagccat tggtcataac cagacagaat ttggaaacat tttcataaag ctccatggag  91620
agttttaaag aaacatatgt agcatgattt tgtaggagag gaaaaagatt atttaaatag  91680
gatttaaatc atgcaacaac gagagtatca cagccaggat gacccttggg tcccattcct  91740
aagacatggt tactttattt tccccttgtt aagacatagg aagacttaat ttttaaacgg  91800
tcagtgtcca gttgaaggca gaacactaat cagatttcaa ggcccacaac ttggggacta  91860
gaccacctta tgttgaggga actctgccac ctgcgtgcaa cccacagcta aagtaaattc  91920
aatgacacta ctgccctgat tactccttag gatgtggtca aaacagcatc aaatgtttct  91980
tctcttcctt tccccaagac agagtcctga acctgttaaa ttaagtcatt ggattttact  92040
ctgttctgtt tacagtttac tatttaaggt tttataaatg taaatatatt ttgtatattt  92100
ttctatgaga agcacttcat agggagaagc acttatgaca aggctatttt ttaaaccgcg  92160
gtattatcct aatttaaaag aagatcggtt tttaataatt ttttattttc ataggatgaa  92220
gttagagaaa atattcagct gtacacacaa agtctggttt ttcctgccca acttcccccct  92280
ggaaggtgta ctttttgttg tttaatgtgt agcttgtttg tgccctgttg acataaatgt  92340
ttcctgggtt tgctctttga caataaatgg agaaggaagg tcacccaact ccattgggcc  92400
actcccctcc ttcccctatt gaagctcctc aaaaggctac agtaatatct tgatacaaca  92460
gattctcttc tttcccgcct ctctcctttc cggcgcaact tccagagtgg tgggagacgg  92520
caatctttac atttccctca tctttcttac ttcagagtta gcaaacaaca agttgaatgg  92580
caacttgaca tttttgcatc accatctgcc tcataggcca ctctttcctt tccctctgcc  92640
caccaagtcc tcatatctgc agagaaccca ttgatcacct tgtgccctct tttggggcag  92700
cctgttgaaa ctgaagcaca gtctgaccac tcacgataaa gcagattttt ctctgcctct  92760
gccacaaggt ttcagagtag tgtagtccaa gtagagggtg gggcaccctt ttctcgccgc  92820
aagaagccca ttcctatgga agtctagcaa agcaatacga ctcagcccag cactctctgc  92880
cccaggactc atggctctgc tgtgccttcc atcctgggct cccttctctc ctgtgacctt  92940
aagaactttg tctggtggct ttgctggaac attgtcactg ttttcactgt catgcaggga  93000
gcccagcact gtggccagga tggcagagac ttccttgtca tcatggagaa gtgccagcag  93060
gggactggga aaagcactct acccagacct cacctccctt cctccttttg cccatgaaca  93120
agatgcagtg gccctagggg ttccactagt gtctgctttc ctttattatt gcactgtgtg  93180
aggttttttt gtaaatcctt gtattcctat ttttttaaa gaaaaaaaaa aaaccttaag  93240
ctgcatttgt tactgaaatg attaatgcac tgatgggtcc tgaattcacc ttgagaaaga  93300
cccaaaggcc agtcaggggg tgggggggaac tcagctaaat agacctagtt actgccctgc  93360
taggccatgc tgtactgtga gcccctcctc actctctacc aaccctaaac cctgaggaca  93420
ggggaggaac ccacagcttc cttctcctgc cagctgcaga tggtttgcct tgcctttcca  93480
ccccctaatt gtcaaccaca aaaatgagaa attcctcttc tagctcagcc ttgagtccat  93540
tgccaaattt tcagcacacc tgccagcaac ttgggggaat aagcgaaggt ttccctacaa  93600
gagggaaaga aggcaaaaac ggcacagcta tctccaaaca catctgagtt catttcaaaa  93660
gtgaccaagg gaatctccgc acaaaagtgc agattgagga attgtgatgg gtcattccca  93720
agaatccccc aaggggcatc ccaaatccct gaggagtaac agctgcaaac ctggtcagtt  93780
ctcagtgaga gccagctcac ttatagcttt gctgctagaa cctgttgtgg ctgcatttcc  93840
```

-continued tggtggccag tgacaactgt gtaaccagaa tagctgcatg gcgctgaccc tttggccgga 93900
acttggtctc ttggctccct ccttggccac ccaccacctc tcgcacagcc cctctgtttt 93960
tacaccaata acaagaatta agggggaagc cctggcagct atacgttttc aaccagactc 94020
ctttgccggg acccagcccg ccaccctgct cgcctccgtc aaacccccgg ccaatgcagt 94080
gagcaccatg tagctccctt gatttaaaaa aaataaaaaa taaaaaaaaa aggaaaaaaa 94140
aatacaacac acacacaaaa ataaaaaaaa tattctaatg aatgtatctt tctaaaggac 94200
tgacgttcaa tcaaatatct gaaaatacta aaggtcaaaa ccttgtcaga tgttaacttc 94260
taagttcggt ttgggatttt tttttttaa tagaaatcaa gttgtttttg tttttaagga 94320
aaagcgggtc attgcaaagg gctgggtgta attttatgtt tcatttcctt cattttaaag 94380
caatacaagg ttatggagca gatggttttg tgccgaatca tgaatactag tcaagtcaca 94440
cactctggaa acttgcaact ttttgtttgt tttggttttc aaataaatat aaatatgata 94500
tatataggaa ctaatatagt aatgcaccat gtaacaaagc ctagttcagt ccatggcttt 94560
taattctctt aacactatag ataaggattg tgttacagtt gctagtagcg gcaggaagat 94620
gtcaggctca ctttcctctg attcccgaaa tggggggaac ctctaaccat aaaggaatgg 94680
tagaacagtc cattcctcgg atcagagaaa aatgcagaca tggtgtcacc tggatttttt 94740
tctgcccatg aatgttgcca gtcagtacct gtcctccttg tttctctatt tttggttatg 94800
aatgttgggg ttaccacctg catttagggg aaaattgtgt tctgtgcttt cctggtatct 94860
tgttccgagg tactctagtt ctgtctttca accaagaaaa tagaattgtg gtgtttcttt 94920
tattgaactt ttaacagtct ctttagtaaa tacaggtagt tgaataattg tttcaagagc 94980
tcaacagatg acaagcttct tttctagaaa taagacattt tttgacaact ttatcatgta 95040
taacagatct gtttttttc cttgtgttct tccaagcttc tggttagaga aaaagagaaa 95100
aaaaaaaaag gaaaatgtgt ctaaagtcca tcagtgttaa ctccctgtga cagggatgaa 95160
ggaaaatact ttaatagttc aaaaaataat aatgctgaaa gctctctacg aaagactgaa 95220
tgtaaaagta aaaagtgtac atagttgtaa aaaaaaggag tttttaaaca tgtttatttt 95280
ctatgcactt ttttttattt aagtgatagt ttaattaata aacatgtcaa gtttattgct 95340
gcacatggtt aagcttcctt ttggctttgg ttggagaggg tggagaaaag cgggaggggc 95400
atggcctgtg acctggtcac aaagtacctt ccacagtcct ttactttaag gtggcatcac 95460
taaattattc cctgtagccc accttcaggt ccactccaca ctggctctct tgactatttt 95520
cttcctttat tcatcagtga tgtatgttca ggacctaatt aattgtggat atgaggcagg 95580
gtcaagagga caaaggaaca gggcctttac cttctacata gctcccctgt ttcatccaag 95640
gaggttaagt attgattttt atcggttttc tcaactgtga atataataaa ctgaaagcat 95700
ttcagggaga agctggagaa caccttctct agctgcactc caccttaagg ctgaagctgg 95760
atttgtttac tgtttctcct gggggcaggg gcagttgaga aataaccaag tagtctgcca 95820
agccagggtc aaccctccag gccacaggtt gagcaaatgc tacagccatg gacagggaga 95880
cactcctcac gaaggggtgg tcctcatcct ttcagatcaa cttcctgctg gaggctccac 95940
cctcaccacg tccctccctc ttctctcatc tggagtcacc ttttgggatt ttggagttga 96000
gcaccatggg gactccaaat gatcaggcag tgctgcaggc catcttcaac cctgacaccc 96060
catttggaga cattgttgga ttggacctcg gagaggaagc agaaaaggaa gaacgagaag 96120
aaggtgggca tttgatctgg agtgtagctc tgcacatagg ctggcctgct ggcctcccga 96180
ggtagcagag agggaggtgg ttttataagg ccccttgttc catgattatg attgagattg 96240

-continued

```
gaatcagaga ggttggctgc tccttagcgc actgatgggg gtttggtaag agatgtcctg  96300

ccaagaggag taagctgggg tttgtctctc gatccatcag ctctcatgcc tctgaactta  96360

ccacttaatt gactgtatga tccaagctta actgccaggt gatgttaaac tctcacattt  96420

ttgtcataac agagaatacc accaccagaa cagaagactg aaataaggca gggcatggtt  96480

gctcagttga gtggttccaa tatagcaagc acaaccagta accgttaaac actgtcacaa  96540

gccaagctcc aaactaactc ttccgcagtg agtgcgttca ctggcttttc cattaatccc  96600

taatgaagga gtttttgatc ctttgtttct agaggagtaa agcctacacc ttactaactc  96660

aggccgaaac acagagggat acgtcagaag tgatgttcat gatctgggaa tgtcatggtg  96720

gcctttgcat aagaggcggt gtagtagagt aaaatgcaga caggagccag aatgacctgg  96780

gttcaaatcc aagctctgca acgtatggcc tgttgaggcc atacacaaag aacttgagca  96840

acttctttaa cagattgagg agtctgggct tcattctctt ggcaatgggg aaccaaccaa  96900

ggccccttcc caggtctctt ggaactcagg caatgctagc tcccagcctt agtgacctca  96960

tctcccccta ccccaaacac tgcaactgac ccctgctgtg acccataccc agtcagctct  97020

ggctcagatc tcagaattcc aaagcctgag gtggcttttt cttcttgcta ccaactgcac  97080

acctggcttc tcctggctcc ttccctggcc cagatgaagt tttccctcaa gcacagctgg  97140

aacagtccaa ggccctggag ctgcaggggg tgatggcagc agaggctggg gacctcagca  97200

cagccctgga gaggtttggc caagccatct gcctgctgcc tgagagggct tcagcctaca  97260

acaaccgtgc ccaggcccgg cgactccagg gagacgtggc aggtaagggg agatgccctg  97320

tatcctctgc aaaag                                                   97335
```

<210> SEQ ID NO 47
<211> LENGTH: 568
<212> TYPE: PRT
<213> ORGANISM: Homo sapiens

<400> SEQUENCE: 47

```
Met Ala Ser Ser Cys Ala Val Gln Val Lys Leu Glu Leu Gly His Arg
1               5                   10                  15

Ala Gln Val Arg Lys Lys Pro Thr Val Glu Gly Phe Thr His Asp Trp
            20                  25                  30

Met Val Phe Val Arg Gly Pro Glu His Ser Asn Ile Gln His Phe Val
        35                  40                  45

Glu Lys Val Val Phe His Leu His Glu Ser Phe Pro Arg Pro Lys Arg
    50                  55                  60

Val Cys Lys Asp Pro Pro Tyr Lys Val Glu Glu Ser Gly Tyr Ala Gly
65                  70                  75                  80

Phe Ile Leu Pro Ile Glu Val Tyr Phe Lys Asn Lys Glu Glu Pro Arg
                85                  90                  95

Lys Val Arg Phe Asp Tyr Asp Leu Phe Leu His Leu Glu Gly His Pro
            100                 105                 110

Pro Val Asn His Leu Arg Cys Glu Lys Leu Thr Phe Asn Asn Pro Thr
        115                 120                 125

Glu Asp Phe Arg Arg Lys Leu Leu Lys Ala Gly Gly Asp Pro Asn Arg
    130                 135                 140

Ser Ile His Thr Ser Ser Ser Ser Ser Ser Ser Ser Ser Ser Ser Ser
145                 150                 155                 160

Ser Ser Ser Ser Ser Ser Ser Ser Ser Ser Ser Ser Ser Ser Ser Ser
                165                 170                 175
```

```
Ser Ser Ser Ser Ser Ser Ser Ser Ser Ser Ser Ser Ser Ser Thr Ser
            180                 185                 190

Phe Ser Lys Pro His Lys Leu Met Lys Glu His Lys Glu Lys Pro Ser
        195                 200                 205

Lys Asp Ser Arg Glu His Lys Ser Ala Phe Lys Glu Pro Ser Arg Asp
    210                 215                 220

His Asn Lys Ser Ser Lys Glu Ser Ser Lys Lys Pro Lys Glu Asn Lys
225                 230                 235                 240

Pro Leu Lys Glu Glu Lys Ile Val Pro Lys Met Ala Phe Lys Glu Pro
                245                 250                 255

Lys Pro Met Ser Lys Glu Pro Lys Pro Asp Ser Asn Leu Leu Thr Ile
            260                 265                 270

Thr Ser Gly Gln Asp Lys Lys Ala Pro Ser Lys Arg Pro Pro Ile Ser
        275                 280                 285

Asp Ser Glu Glu Leu Ser Ala Lys Lys Arg Lys Lys Ser Ser Ser Glu
    290                 295                 300

Ala Leu Phe Lys Ser Phe Ser Ser Ala Pro Pro Leu Ile Leu Thr Cys
305                 310                 315                 320

Ser Ala Asp Lys Lys Gln Ile Lys Asp Lys Ser His Val Lys Met Gly
                325                 330                 335

Lys Val Lys Ile Glu Ser Glu Thr Ser Glu Lys Lys Lys Ser Thr Leu
            340                 345                 350

Pro Pro Phe Asp Asp Ile Val Asp Pro Asn Asp Ser Asp Val Glu Glu
        355                 360                 365

Asn Ile Ser Ser Lys Ser Asp Ser Glu Gln Pro Ser Pro Ala Ser Ser
    370                 375                 380

Ser Ser Ser Ser Ser Ser Ser Phe Thr Pro Ser Gln Thr Arg Gln Gln
385                 390                 395                 400

Gly Pro Leu Arg Ser Ile Met Lys Asp Leu His Ser Asp Asp Asn Glu
                405                 410                 415

Glu Glu Ser Asp Glu Val Glu Asp Asn Asp Asn Asp Ser Glu Met Glu
            420                 425                 430

Arg Pro Val Asn Arg Gly Gly Ser Arg Ser Arg Arg Val Ser Leu Ser
        435                 440                 445

Asp Gly Ser Asp Ser Glu Ser Ser Ser Ala Ser Ser Pro Leu His His
    450                 455                 460

Glu Pro Pro Pro Pro Leu Leu Lys Thr Asn Asn Asn Gln Ile Leu Glu
465                 470                 475                 480

Val Lys Ser Pro Ile Lys Gln Ser Lys Ser Asp Lys Gln Ile Lys Asn
                485                 490                 495

Gly Glu Cys Asp Lys Ala Tyr Leu Asp Glu Leu Val Glu Leu His Arg
            500                 505                 510

Arg Leu Met Thr Leu Arg Glu Arg His Ile Leu Gln Gln Ile Val Asn
        515                 520                 525

Leu Ile Glu Glu Thr Gly His Phe His Ile Thr Asn Thr Thr Phe Asp
    530                 535                 540

Phe Asp Leu Cys Ser Leu Asp Lys Thr Thr Val Arg Lys Leu Gln Ser
545                 550                 555                 560

Tyr Leu Glu Thr Ser Gly Thr Ser
                565
```

<210> SEQ ID NO 48
<211> LENGTH: 1157

<212> TYPE: DNA
<213> ORGANISM: Homo sapiens
<220> FEATURE:
<221> NAME/KEY: modified_base
<222> LOCATION: (610)..(709)
<223> OTHER INFORMATION: a, c, t, g, unknown or other

<400> SEQUENCE: 48
gcgttgtttt ctctctctcc ctccctttcc ccctccccac cccctcccca acagccccca 60
actatagcct ccgccgccgc cgccgcctca aaattcaata aaatgagctc ttatttcgtc 120
aactcactgt tctccaaata caaaaccggg gagtccctgc gccccaatta ttatgactgc 180
ggcttcgccc aggacctggg cggccgaccc accgtggtgt acggtcccag cagcggcggc 240
agcttccagc acccgtcgca aatccaggag ttctaccacg ggccgtcgtc gctgtccacg 300
gctccctacc agcagaaccc gtgcgccgtg gcgtgccacg gggaccccgg caatttctac 360
ggctacgacc cgctgcaacg ccagagccta ttcggtgcgc aggatccaga cctggtgcag 420
tacgcagact gcaagcttgc cgccgccagc ggcctgggcg aggaggccga gggctccgag 480
cagagcccgt cgcccacaca gctcttcccc tggatgcgcc cgcaaggtga gctcgcctcg 540
gggccgacaa gggcaggagg gggccggaag ggcccaaggc cgggcagggg gcctggcagg 600
ccggggcgcn nnnnnnnnnn nnnnnnnnnn nnnnnnnnnn nnnnnnnnnn nnnnnnnnnn 660
nnnnnnnnnn nnnnnnnnnn nnnnnnnnnn nnnnnnnnnn nnnnnnnnnt tctccgtccc 720
tgccccctcc cccaccctcc cctcccctct gtctcgccct ttcccccatt cccagcagcc 780
gccggacgca ggcgaggccg acagacctac agccgctacc agaccctgga gctggagaag 840
gagttcctat ttaatcccta tctgactcgt aagcggcgaa tcgaggtatc gcacgccctg 900
ggactgacag agagacaggt caaaatctgg ttccagaacc ggaggatgaa gtggaaaaaa 960
gagaacaaca aagacaagtt ccccagcagc aaatgcgagc aggaggagct ggagaaacag 1020
aagctggagc gggccccaga ggcggcggac gagggcgacg cgcagaaggg cgacaagaag 1080
taggcttcag ctgggactgc cagggccgcg gccgcccgca cgtccgcggg tcccggccgc 1140
gccgccgccg cgcgccc 1157

<210> SEQ ID NO 49
<211> LENGTH: 44725
<212> TYPE: DNA
<213> ORGANISM: Homo sapiens
<220> FEATURE:
<221> NAME/KEY: modified_base
<222> LOCATION: (13983)..(13983)
<223> OTHER INFORMATION: a, c, t, g, unknown or other
<220> FEATURE:
<221> NAME/KEY: modified_base
<222> LOCATION: (26098)..(26098)
<223> OTHER INFORMATION: a, c, t, g, unknown or other
<220> FEATURE:
<221> NAME/KEY: modified_base
<222> LOCATION: (26101)..(26101)
<223> OTHER INFORMATION: a, c, t, g, unknown or other
<220> FEATURE:
<221> NAME/KEY: modified_base
<222> LOCATION: (26111)..(26111)
<223> OTHER INFORMATION: a, c, t, g, unknown or other
<220> FEATURE:
<221> NAME/KEY: modified_base
<222> LOCATION: (26131)..(26131)
<223> OTHER INFORMATION: a, c, t, g, unknown or other
<220> FEATURE:
<221> NAME/KEY: modified_base
<222> LOCATION: (27278)..(27278)
<223> OTHER INFORMATION: a, c, t, g, unknown or other

<400> SEQUENCE: 49
gatctcacag acatctcaac tcaactgttc caaaaccaaa gtcatcatct ctaattaaaa 60
acatctgctt cctcttgttc tctttaactt acttcgtggt accaccatct gccctattga 120
ccccatctag caacctgaga aaagcccttt ttctttattt cctgtatcta aatggacaac 180
aaaagtgatt ctatttgcta aatatctcag caatctgtct tcattcctac atcttcactg 240
tcactgcatt cattaccaat gatctggact actgcatatg gatatatgag tctgaacccc 300
taggaagaga ccagaaatat cctaactaca ttttctgcct ctattatcac taccagcctt 360
atactcagct gccgaaggat gtggtacaaa ttctatcatg tcggttcctg ctcaaaattt 420
ttcaaatgtt tcctaacctt tatagaataa aattcaaact ctttaatatg ctctggccag 480
tcatcttctg acactttccc acatgtatct tttttttttt tttttttttt ccccaaacaa 540
agtctcactc agtctcccag gctggagtgc aatggtgtgg tcacggctca ctgcagcctc 600
aactttccag gctcaaggga tcttcccacc tcagcctccc aagtagctag gactagaggc 660
acataacatc acatccggct aatttttttca tttatttttt gtagaaacaa ggtctcactg 720
tgtttcccag gctgcttttg aactcctagg ctcaagcgat ccgcctgact cagcctccca 780
aagtgctggg attacaggca tgagccacct gcccagccac ccacatatat ctttttttgtt 840
gttgttgagg cagaatctca acctcagcta actgcaacct ccgcctccta ggttcaagca 900
attgtcgtgg agctggaatt acaggcgtgc accaccacac tcagctaatt tttttatttt 960
tagtagagac atggtttcgc cattttggcc aggctggtct cgaactctag cctcaggtga 1020
tctgcccgcc tcggcctcct aaagtgctgg gattaccgtc gtgagccact gcgccccgcc 1080
acatatctta tgtttaaata ataccgaagt actctttgtt tctcaaaaac cccatgcctt 1140
ttcctgcttc tgtgaaagtt ttatgacgta gcacctttgt atctccagct ctaacgtagt 1200
acctggtaca aagtaggtgc tcaacaaatg cttgttgaat aaataaaagg acaaaagaaa 1260
atcagaaagc acaaaggttg aaagtaagga cactgaccag aagactacta tgagagtaca 1320
atttggagta atcaggaaga gaaggaaaga aaatgcttta gtgtaacatt tccttcaagc 1380
ttctacaagg tgaaacaatc ataatcaaat aataattact cctgtaatta gtctctttga 1440
aaaatatgaa cttttgtcat tggtacaatt tcaaatgggg actgcttaag tgatttgaaa 1500
taaaatgttt cttaaaaaca cacacacaca cacaaaaacc caaacagccc aggacatgac 1560
atgtaactgc caaaatcctg acaaaacatg accctttggg tataaatccc aaggtccaag 1620
agtgcatctg ggaagagtca tttgttttgc aaacattaat tgggtggtat agacaccgtt 1680
cagcacaggg gataaaatga taagtaatac acggtttcct gtcctcaaag agctcatggt 1740
ccaagaagca tctagccctt gcctttgcgc agaactctac tgaattcttt tcttttttttt 1800
cgaaatggag tctcactctg tcgccaagtc tagagtgcag tggtgtgatc gcagctcact 1860
gcaacctctg cctcccaggt tcaagcgatt ctcctgcctg ggcctcccga gtagctggga 1920
ctacaggcat tcgccaccat gcctggctaa tttttgtata tttagtagag acagggtttt 1980
gtcatgttgg ccaggctggt ctcgaactcc tgacctcttt acagaaagcc agatgcctat 2040
gctagggttg tatttaaagt ccttttaagc tgggcacggt ggcttatgct tataatccca 2100
gcactttgga agccgaagcc gaactcctga cccgcactta aggtcgggag ttcgagacca 2160
gcctggtcaa ggtggcgaaa ccttatctct actaaaagta caaaaattaa ggctgggtgc 2220
agtggctcac acctgtaatc ccaccatttt gggaggctgg gatggatgga tcacttgagg 2280
tcaggagttc aataccagcc tggccaacat ggtgaaaccc tgtctctact aaaaatacaa 2340

-continued

```
aaattagctg ggcttggtga cacacacctg taatcccagc tactagggag gctgaggtgg   2400
gagaattcct tgagcccgga aggtggaggt tgcagtgaac tgagatcacg ccactgcact   2460
ccagcctggg tgacagagcg agactctgtc tcaaaaaaaa aaaaaaaaaa aaaagtacaa   2520
aaattagccg ggtgtcgtgg tgggcgcctg taatcccagc tactcaggag gctgaggctg   2580
gagaatcgct tgaactctgg ggcggaggtt gcagtgagcc gagtttgcac cactgcaccc   2640
cagcctggac gagagtgaga ttctgtctca aacaaacaaa aaagtccttt tagtcatagg   2700
aatagctata tataatttat ttttttgaga tgaagttttg ctcttgttgc ccaggctgga   2760
gtgcaatgac gcagtctaga ctcaccgcaa cgtgtgcctc ccgggttcaa gcgattctcc   2820
tgcctcagcc tcccaagtag ctgggattac aggcatgcgc caccacgccc agctaatttt   2880
gtatttttag tagagacagg gtttctccca tgttggccgg gctggtttcg aattcccaac   2940
ctcaggtcac ccacccacct tggcctccca aagtgctggg attacaggcg tgagccacca   3000
cgcccggcca atatatataa tttttttttt taaagctcag aaatggaaat tcacggattc   3060
agggtaaaat gcagccattg cttccttaat tagaagagtg tttttgtgga agagtaatgg   3120
actgtaccct tttttcccca gaaaaaaagc agcacctgag gattctgaac agttctctgc   3180
tcagtgatga tcaagccttc ctttggacaa gcttaaataa ctcagccact gttctttgtt   3240
ggaggacttt gggactactg atgcaatgtg tccacttggg ggccctttgg agaaaaaatt   3300
gctaatttca gaggggcagc cgcaccagtg gttaaggaaa tccctgggga gaaaatgttt   3360
ctgtctggat tagagagaag acatcttatt tactcattca atcttcatga taatcttgtg   3420
aagctataat taatatcctt atttttgcag attaggaaac taagacgtac tgaggctggg   3480
tgcctggttc aagatcatat agctaacatt attggacatg caaatcaagc ccagatttgt   3540
gactctgagc tgatgttaat tctgtcacaa tattggttct caagataaat ctttccaggt   3600
gagggggaaa gggaataaat atttagaagt ccccttaaac agaagtaatt aattcgtttg   3660
cagaaattgg caaaatttgg ggttcccttc ttaaaagttt ccttctgtca cttggaaaaa   3720
atttaaaata tgtgcattag gttgacaaag atcaaaaaag ttaaaaaaaa aaccctttttt   3780
ggaatgctgt ggagaaagga gcacttttat ttatctatta tttattttat tttattttat   3840
tttattaatt aattattttt tttctttttc tgagacaagg tctcatctca ctttcttgcc   3900
caggttagag tgcagtggcc tgatttcagc tcagtgcagc ttcagccact tcagctccat   3960
tagcagctgg gactacaggc acatgccaag tttcccaggc tggtctcaaa ctcctgagct   4020
caagatcctc ccatctcagc ctcccgaagt cctggaatta tgaaagaggc actctttttt   4080
tcttcttctt tttttttttt ttttttttga gacactcttc tccgtcttcc aggttagagt   4140
gcagtggggt gattttggct cattgcaacc tccacctccc cggttcaagt gattctggtg   4200
cctcagcctc ctgagtagct aggactacag gtgtgtgcca ccacgccagg ctaatttttc   4260
tatttttagt agagacggag ttttgccatg ttggccaggt tgatcccgaa cccctgacct   4320
caggtgattt gcccacctct gcctcccaga agtgttggaa ttacagtcat gagccactgc   4380
acccagccaa aaggcactct agaacattgc tggtgggagt atgaattagc ataaccttta   4440
ccggggacaa cttggcactg tctattaaaa ctacaaatgt acatacccttt tgactcagca   4500
actgctcttc tagaaatcta tactacagat acatttgaac atttgcaaaa tgacgtatat   4560
taaaggttat gcactgcagc attgtgtgaa atacatgcaa cagattggaa acaactcaag   4620
tgcccaccga tagagaactg attaaagtaa gctctatctc tattccatac agccccaata   4680
```

-continued atgaggaaac tgtctactta tagtaatatt tccaagatat aagtgaaata agcaagattc 4740
aggaaattgg tttgatatgc ttttatttat gcaaaaactt ctatatgtgt atgcttttgt 4800
aggcatagac tatgtatgga agaatataca atagactgat aacagttact cctactaaag 4860
ggtaagtaat attactgagg ttggggagag gatgattcag agcaaaaata aagtgaggac 4920
tttaaggact ttaattccct taattttttt tttttttttt tttttttttt ttgagatgga 4980
gtcttgctct gtcgcccagg ctggagtgca atggtgggat ctaagctccc tgcaacctct 5040
gcctcccagg ttcaagcgat tctcctgctt caacctccca agtagctggg attacaggca 5100
cttgccacca cacccggcta atttttgtat ttttcataga gatggggttt caccatgtta 5160
gccaggctgg tttcaaactc ctgacctcat gattcgcccg ctttggcctc ccaaattacg 5220
gagtgagcca caacgcccgg cctcctttta aatttttttt tttaattttt tttttttttt 5280
aaagatggag tctcactctg tcgcccaggc tggagtgcag tggtgcgatt tcggctcact 5340
gcaacctccg ccccccgggt tcaagtgatt cccctgcctc agcctcccga gtagctgatt 5400
acaggcaccc gccaccacac ccgctaattt ttgtattttt agtcgagacg gggtttcac 5460
catgttggct aggctgttct tgaactcctg acctcaggtg atctgcccag ctcagcctcc 5520
caaagtactg ggattacagg cgtgagccac cgtgcccggc cttaaatttt taaccatatg 5580
aatgtattag gtattcaaga aaaatatgtt gaatgaaaat ttaaaataaa aaataagtaa 5640
agcacatcga atttaaggta cctaatgtgt aaggcacaga atgtcttttt tttttttttt 5700
ttttttgag acggagtctt gctgtcgccc aggctggagt gcagtggcgc gatctcggct 5760
cactgcaggc tccacccccc ggggttcacg ccattctcct gcctcagcct cccgagaagc 5820
tgggaataca ggcgcccgcc acctcgccca gctaattttt tgtattttta gtagagacgg 5880
ggtttcagtg ttagccagaa tggtctcgat ctcctgacct catgatccgc ctgcctcggc 5940
ctcccaaagt gctgggatta caggagtcgt aatgtctttt tatgatcagc aggatggtta 6000
acggatattt gctgtcagac cccagtgagt tttagcactt ctacttacta gctgtgtgac 6060
tttagacatt attctaagcc tcagtttccc catatgtaaa atcaaactta tagaattgga 6120
gagaattgag tgcacataaa gcacttaggc tcacagaaag cactgaaaaa tgttattatt 6180
aatattttcg ccctaaaatc tccaacaata aaccaaattc tgacttgctc tggctccttt 6240
tggactagtc tagaggcaaa gagacaaact atatgatttc tcaaggagtt tttctgctca 6300
gaggcttgag tctggggact ccacacaata ttcgaagaca ttcttccttc tttctgctgc 6360
cttgcaacct gcagacctcc cacctgtgtt aaatgaagaa tgcttgaagt gaggttactc 6420
agaacccacc cggttcatgt tttctcaagg gtagaaggcg ggaagaaatc tgttgacaca 6480
gttatataaa gcctgtcatt cagtcccctg cctattacct ctgcagaccg ttatgcatat 6540
taaagaaggg ggggtcggca aatacaaaag aaaaataaga gagacgagag agagagagaa 6600
agagagagag agagagagag aacgaacaaa tcaggatgct tgagggaatc cacgtggtcg 6660
ccaatctgta actgatcaga gcagctacac tgaagcaaaa accccagcgc ccaacgctaa 6720
atatattgca atggagaaac cgtccacaat ggggtgtctc tgtccttagc agagccttgg 6780
ggctgccgtt taagaccctc ctgctactcc caccctttta gcatctagta aaccacgcgc 6840
tgtaacaacg gaatcttgtt ctgtgtattg cgttgtgcga gtgtgcgctt tgcaaaccat 6900
ctgggcccca tcctgcgcgg ttggaacgaa gatcgattcg ggacgagttg ggggagttga 6960
ggcttgcctg tgtctcctcc ctttcattgc tcctctccag cccccatccc atcgtccgct 7020
ctgcacaaat gtttcgccag tggagggacg taggttttca gcaccaggag gctgtggacc 7080

-continued

```
ttctctggag gcgtgaagtg caccctccgg agggccagag ctgagtgcaa cctgctcaca   7140
acgaccctct ccctccttcc caaattcgcc gccccaggct gtaatattac atgcagtgcg   7200
ctgtaccggt gcgggagtcc aggaaggctg catgaccttc cagcgaactc cccctcggct   7260
tgggggatgg aggctgcccc ggggcctgca ggctgtgtat cgatccccca gcctcagcca   7320
acgcaagttc tcccgacaca aacccctccc taccctctcg gctttcccag ccttgcaggc   7380
gtctaacgct atgctcgaag cgccctcccc tctttcccgc aataaagtaa acccggtgga   7440
tattcattcc cctccctaac tcgcctcctt ctttcccccct cccccctcag cttactaacc   7500
ccgcgcacag agctcgccgc cggcgggccc cttccaccca gtgtatcata atgcccaacg   7560
ctctcctcct ccccctctct taatcagaaa cgtgctcgcg agccccccctc cctctgcgtg   7620
catacattag ggtctgcttt gcatgcagcg gcaggcagag accggaggaa gaaggggcgg   7680
gggcgctttt gcccgcctct tccctccagg ccccgttagc cacccagctt cagcttcgtt   7740
gtaacaccgc gtcgttagcg gagcacgccg tggcctcagt gcccgggctg gagaaacaca   7800
acccaactcc ctgcagaagg gcacgaaagc cagacgagtg cacagtagag cgaggaggtg   7860
gcaggagacc tgccactcgg tgtgtgcttt ttggaaagag ctccagcatg aaaatgggag   7920
gggctccttt tttatttttt aaagtgcgtt cattgagggc ctttctgttt tgcatatagt   7980
aaactgggca gcgcttctgt tttgcatgta gtacaataag ggctctttta ttctagaagc   8040
gttcaattcg ggctaaccca tcttgtatcc gtgccctggg gcggaggaga aggctcactg   8100
ctccccgacc cagccgccgc gttatactgg aagctgctct cccgggctgt tcgattccca   8160
gcgcgtcccg ggaacgtgtg taatcggcct ctcggcgctc aaggctgcag gcggcccggc   8220
tccctacgcc tccatcctcc gcgtagtcct cgccccctcc ccctctctcc ggaacccgcg   8280
ctctgctccg ggctcccggg cttccttccc ccctcctttt cccgagcaat gcctctcccg   8340
gagggcgggg catgcagtta tccaggttgc ggggccggcg ggcgggcagg aggcggcggc   8400
ccgggcctcg ggatggagtt gcagcgccca ggcgtcagag gcggaggccc gaggccgcta   8460
tacagattgc ggggctggcg ggcgcggccc ggcgctctgc atagcggccg gcagggtgca   8520
ggcggccggg cggcgcagag ctggttaggc aggttccggg gccccgtgcc ccccccctccg   8580
cctccccgcc cccctgtgtt gtcgcctctc cctctcgctg cttcacttca cggggcgaac   8640
atggcgcaca gctgtcggtg gcgcttcccc gcccgacccg ggaccaccgg gggcggcggc   8700
ggcgggggggc gccggggcct agggggcgcc ccgcggcaac gcgtcccggc cctgctgctt   8760
cccccgggc ccccggtcgg cggtggcggc cccggggcgc ccccctcccc cccggctgtg   8820
gcggccgcgg cggcggcggc gggaagcagc ggggctgggg ttccaggggg agcggccgcc   8880
gcctcagcag cctcctcgtc gtccgcctcg tcttcgtctt cgtcatcgtc ctcagcctct   8940
tcagggccgg ccctgctccg ggtgggcccg ggcttcgacg cggcgctgca ggtctcggcc   9000
gccatcggca ccaacctgcg ccggttccgg gccgtgtttg gggagagcgg cgggggaggc   9060
ggcagcggag aggtaagggg gcgaggaacc cccaagtccg gggtctcgac cctctgcgga   9120
gacccctccc ctcccccatc cgggattgag gagcatccca attctgggac catctcgggg   9180
tccctgaccc ggggcgaatg gctctcccat cttgggaccc ccatgcaggg ctgcagaccc   9240
ccaggcgccc ccaccccggg gtttgggccc atctggctga aggcgtttgc cccccgctct   9300
cctccccctg acccttcccc aaatcccttg gcacagaccc cctcgccggg gtttcccatc   9360
ccgggactga acccctcctc cctttcacag attacctcat ccgagcaaga ttcctccctc   9420
```

```
cctccctcct agagacctga tcccgccaca tccccgcctc cctctctggg cagatgtgtt   9480
actcctaggg cagttttcct ctcgggcgtc tctcgggtga tggcctcatc cagggccacg   9540
ttctcctggc ccttggggat cgtgtccctt ccagcacctt gctttcgaaa acccgatgaa   9600
ccctcgcgcc atccccgggc caggtcccta tactgccagc cactccccct tccttcacct   9660
ccaccctcta cccccacccc aagcagaccg atcctccccc atcccgccct accccaccgg   9720
ggaaaatctc tcctctgcac cttgcctggt ctcacctcct ttccctctga agataacggt   9780
gattcctcat acagcagtct cttccccccc ccgccccgtc ttacagggct acagtttcta   9840
gcctattggt agccgggaat tactctacct tcactccacc ctttccctcc tttagaatga   9900
aggattagtg gcatcttgga ggggaaaata gtccactgtc ccctaggctt agagaagagc   9960
agctttccac cactcccctt ggagaggagg caggctttcc ctccagctct ggggaagggg  10020
gcccctgtga ggggaggtgt ttgttggggg actgaggcag catcctccca ggggaagcag  10080
ctgctctcct accccaccca ctgcgcctga gagcacgcag tctccaaccc gagctccctc  10140
ccgcccttct cttctcgtca tttcattatt gatccacctt ttcctaggcc aatcctgggg  10200
cttggaaggg gtgggggaag ccaggttggg gtgaggagag tagataaggg acagttatac  10260
tttagtgtgg tggcggtggt tgctttggga tgggagaaaa aggattatca agcaaagtta  10320
ttccttagaa aggacttggg gttgtctctg attcttgtaa ggggacccaa ggtggatgaa  10380
gggtcagagc gttgcccctt ccccattagt actggggcaa gaacggagtt gcttctataa  10440
acattattcg gccccccttca gcaaaaagga aagttgccca aggaagggaa gttgagttca  10500
ggttcagcca gtggcgttgc gcatttgttt tccattggat gcagaagggg ggagttcgaa  10560
ttgtagaggg gggaggatgg catgggggat gctaggagga ggaagagcag ctgctagggg  10620
ctgaagcgaa ggggggtagg gggttgctgc tctggagtgc tcttgattga aacagaaagg  10680
gaaagataac aaccagccgt ttcctgcgtg ctctgccgtt ggtgcacaca aaatatcctg  10740
ggcaaacccc ttgtccccta ttgtgccccg caccccttta gatttacgga aagatcctgg  10800
gaagaagggg agggaggaga tcccaaggac cctggcccct cctttcaagg agctggcatt  10860
ttttagttgt tagtcttcct gcctcctttt ttttaatcgt ttctaaggca gcctgatcag  10920
gagactgaca acaacccgcc ttctgacaga gcaaggagga catgatgggg gcgtgttcct  10980
tgctatgtag ctagctgcag cgtccccttt ccctgcctct ttctgctcta tctccacctc  11040
cttttcccag ccttcagaag gcagctgcag tcagcagggt tgtttgagac tatttattgg  11100
ttgctgtaga ttattatttt tttttgaaag gccaattttg tattttttaa gctaacaaca  11160
cagatcccat gtagttggag aaccaaaggc cacatacatg acaaaaagac tgaaccgttc  11220
aggttacttg catggagttg gtgcttaaat gtgagttgat tttgcttttt taaaagatac  11280
agcagcaaaa aaaaaaaaaa aagaaaaaaa agaaaaaact gacatttcat ttacctgctt  11340
attttcaaaa ttgagacttg cctggttata tgtagcattt tagccccatg tatatttgag  11400
tttaataaga aagtctctat taggagaagt tagtccattt taaggggatc ctaagaagca  11460
ttttcttctt gttcagtatg cttatttatt ttgtatagaa ggactaagca ttcacattcc  11520
aaatattatc acatattcaa aagcaaagtt ttatgctgac agcttccaat catagttttt  11580
caagagactg gttagaaaga gagccacctg gattcaggga cctaatgtct gggcaccaga  11640
atattttatc tgttggtctt tgacaaatca cttttaaagt tttaatcagg ggctaaacgt  11700
tttcttatct actggcatta tgagataatt gtaaactact gttttatttt tcttaacact  11760
agtatataat gtaaagcctg tcaaggaatt gcagttattt caaataggat catatttata  11820
```

agggggtttt gtctttaaaa ctttttcctg aacagtagtt gctgcttcat tatgagaaga 11880
gtggttgact ccttacatta aacttgagta ttttttctga attggacttg aatgagctct 11940
gttccatggg taagcttttt atgtggtgtt tgaggcaatc cagtatgagt tgatggtatg 12000
cattgagtag tggtaaacct ctgagctggt agttttcagt gtagaagcaa gcactttttt 12060
ttttttttta acatagcctt actaatcaat gataaagttc caaaagggaa gtttagggtt 12120
caccctgggc tgacatagaa ttctaaagac tgcttctcag aactcactca tagctctgta 12180
tcaagtctta tctggattca tgaagaaatg gttatatgat ccaaaatgat tctaacctct 12240
ttaaactctg gttcgccttc agtgaataat gactataact tgcctatgta acaacaccta 12300
tgttaatact tctaaaacta ggtaacagaa cttccagatg actttgctgt ttgaactccc 12360
ttagccatag gagacttgtc cttcactgct gttggttcct aacttccttt gtatgacaat 12420
taggaagtag aattgaggtt ttgttttatt gagcactgta agaaatcaga ggtccatttt 12480
ttgcctttcc ccttccctct gtagtgtcag tatcccattt ttctaaggat tctctcaggt 12540
aatgttcata ctactgtact ttgccatcta aataaacata gtacagcagc accctttctg 12600
ttgactagaa gttaggctgt tgtaataata aacccctgaa acagtgtgtt tatcagtaac 12660
tagtcttcgt ttattaatgt cataatccag ttaccttccc tactacttca caaaatatta 12720
aaagcaaaat ttccatcctg atcataacat agcaaacttt aattagatac aaattgaaac 12780
tgagttacag cattggtgtg tatttatttt cacttgaaat tgcagtttag ttcatgtgga 12840
ctgagacagg cttttggatt ggacttgaaa agatagtact cctgcagctg aaaggtagta 12900
ggagagcgtg attttttttt ttttttttta atgtttactg gtcatgtatg taccaagagt 12960
gggagttgct ccttcgttgc cttcacagct agtcctaaga ttggcagaag gtaaatgaag 13020
gagggaacac aagcagagtg gagtgcacga agcctccgag tagaagtcag tggatgtggg 13080
ctctcatctc cgttactgaa cagttatgag accctgggca aattcacttt taaccttaaa 13140
tttctgatct gtaaaatgaa aagtttggac taaatagctc atgaatctgt tctgtgtcag 13200
tattatgatt cctttctgtt gtattaaact tttggtcaaa tcagaatttc ttattctgag 13260
tttatttcaa aagtcagagt caagtgagac gatttgataa tttttgtttt ttttttgagt 13320
cagggtctca ctatgttgcc caggtgcatc ttgaactcct gatcctcctg ccttagcctc 13380
ctgagtagct gggattctgt ttggtaattt ttaatatcag attatacatt tgcctatata 13440
actggcatta ttattaggag gagaaatttc aacttggaaa gttttcgttg tgtggaaaaa 13500
acataaggac tttggggaag ttgaccagtt tcatttataa gaaaaatgag gataaagttt 13560
ttacacatag ttctgaaaac ctacagaatc ccaggcatta tctggtgttt agaggccctc 13620
ttgtttggct aaatgtgttg tcattgttgt gaattccaga ctatccaaaa gagaagttat 13680
tttcagtcta cgtggtatat tcctgtaggt gtatgaattt tgaatgaaaa gaaaaatcca 13740
atacatcaat gtatttataa atctgaagtg atagtaccta cttcatagga tgtagttatt 13800
aatatgttct gaaatggttt atactgagca ttaaaaattc agtctttaga acttttcttc 13860
ctctgtgact gaaaaccaga tgacatgtcc ccatctttca cttccattta attatcttaa 13920
ggcacatact cctggaggaa atcatcattc acacaatagt gatccatctt cttattggaa 13980
gtngagagaa actattccca tcttgactta attctcacct ctctgctcac ataacaactg 14040
tccttccgtg gggcaactgt gcaaactcta taccaaaggc ctcccttacc ctgtggctaa 14100
agggggtggc aacagtgctt tgcttgctca gaggcataac agactgcagt gcctctctct 14160

-continued

```
tttggaaact cgctgtgttt taattgtagg tctcctaatt aagatctctt tgtgcctgcc  14220
cacattccac tagtgttggc acagagcttc agcttccttc tagcacttaa ctgaaggcct  14280
tcaatcgggc cttttgtgaa tatcttgtct ctttccattc ttcctctgcc aaggtggaga  14340
gcccagtggc atagaccttt gagaaggggg aagctttgtg actatcacta ctttgggagg  14400
aatttattcg aggattgctg ggatgggacc ttcctttgtt tgcatatgtt attttcaggg  14460
attaagaaag gttaaattac taatgagtct ggcatgatgt acctacattt taatcagatt  14520
cttaaccctg taggcactag taggaaagag gatgccacag agttcactgt tacaaagtat  14580
ttccttggat cttatctaga ctggtttatg aaacttgatg agtaaaatat tgtcgtggag  14640
taaatctcag actcgtgatt tttgtggact ctgaggttgt tgaagacaag acaatcagat  14700
gaaattattg attgctccta agttgtatcg gctttgagac acagactgaa ttaaagttag  14760
ctttcagatc tgagttaact tttgattaga aagactttag gaggttctgg aaattgttga  14820
gttaattaag aatacccttg taggctccac tatttcttga gattttcagg aattgtctag  14880
gcttctagag tattttcaga ataagataaa atagcttttc tggaaaaagt agttgaactt  14940
tagtttccag gaccttcgta ttcaaaatac agtatgttct ttactagatc tacatgtggc  15000
atgctagaga aaatgctatc ttttattaag aaaaaggaat cttaagtcct ttacctggac  15060
ccagatggct tcattgatca catcagtatg aggttacgca gacaaagggc tatttttgtt  15120
gttgttattg tcatttcatt ggttgttgaa gaaggcctgg gagaaggaag tacaggatct  15180
tttatggcat gcattaaata aagctggagg cctgcactct tatacctgag tgggtggttt  15240
tatggcctaa ttctctaatt gctggcattt atgacagtgt ggatgctact ggccctgtgg  15300
ctgaggtaga ttatgctggg aatagggagg aaaaaggggt ccttttgtta gccttttcat  15360
tttgcccctc aataaagtct ctgcaaaaac cctgaggaaa tacagagaca cttggactga  15420
gggaatgact tcccataaaa tggttcttta tgtttttaaa atgatgagcc gcttttcttg  15480
acctatccaa agaaatccat accaccactg ttaaatattt caatgagttt tttaccttgt  15540
caggttacac accaggggaa gccaaccatg agactgtagc tgctgccaaa cattcgcttc  15600
taaagactta agacatttga aagaagaatt ttgttacgtg atttgtaatt gttgtggatg  15660
atataaatcc ccttgaagga ttagtccaaa acttctaaga ggccaagctt ggtttaactt  15720
ttagatgttg aattgaatgt attgccctaa tgagttttag ttttaaggaa acaacaaaga  15780
tataagagtt agttggcagt tttgtgtgca gtgtatgaaa attccccttc ccttgaaatg  15840
agtagttgtt tttctatttg acaaatagac tgaagggatt tccccagata tcttaccttc  15900
aattattgct gcagcagtac cctgtgaagt accagtgggc agcatcggtc cagtagcatt  15960
tatttcagga gctggagttt cttccgtata tagtgtttta tccattttct tgcatttctg  16020
gttttgtgtt ttgttgggat gtttgggtat agatgttttg atgtctttca gcaacaaaag  16080
atatgaatct ttctaacatt catactgttt tagagagatc cacttgtatt atctatgctt  16140
tgctgaagca tcattgtttc attcttattt tacagcatca aggtaatggt agctttctgt  16200
cttgaattag gagagtgata ttacttgtga gaagggtttt ggagaatagt tttttcttta  16260
ggctgtcctt tatactatct cagttctaaa cactagggaa aagttaattc ttatctctaa  16320
taaatatcct acacctagag aaagaaatat ttacacatgc ccatattcaa cttctgtcca  16380
tccatgagga ttgaccactt tttagatcaa acacaaacat tgtccctaga ttattgcctt  16440
taattataag cagtaaaacc ttgtggataa catctcttta agcttagcta atgaggaaat  16500
ccttttgtaa tctctttggc taggattttt tatttgtgca tatataaata cctttacaga  16560
```

agaaagggag aatctcataa tctaatctgt agtggtgtga gatcgtttag catagtaatt 16620
aagagttgtt aagaccatgg gctctggatt taaactgcct gagttcaaat ctaagctcag 16680
ccatcttgaa aaagtttttt ttgtgttttg tttggtttgt ttgagacagg atcttgcttt 16740
gttgcctagg ctagagtgta atggcacaaa catttcattt cagcctcaac ctccagggct 16800
caagcaatcc tcttgtctca gcctcctaag tagctgggac tacaggcatg caccaccaca 16860
ctcagctaat tgttttattt gttgtagaga tgggagtctc accatgttgc ccaggttggt 16920
cttgaactcc tggcctcaag tggtccccct acctcagcct cccaaagtgt tgggattaca 16980
aatgtgaggc actgcaccca accagaaaag tttttgaacc tctccatacc tctgtttctt 17040
catttgtaac tgagaggtac tcatgcttca tagtctcatt gtgaggctta agtgagatca 17100
tgcatgtaag cacttagcat tttgcctggc acataggaag ccctaattgt tagaaccaag 17160
agattgaaag gagagcaggg ttataatctt ttttttcat caaaataact ggtttgtatt 17220
acattaagtt atacctgtat atgtatgcat acatacacct atttgagtgc tataatctta 17280
gaatgttctt gatattagtc tgagtgtcaa gttcttctat aaactaggtg gaaccaaatt 17340
gaaggccagc cacccgtctt ggtaacaaca ttagtgtcca actaaagcat attaaagata 17400
aggcaaaaaa gaagaaagag aacaagatgg taaataggca agtaagatac cgaggaacac 17460
agtgcctcca tgagttgcta attatcaggc caaggcagct ataatggggt tgctacctgt 17520
tgtctctata actagtgttc ctgatatttt tatgaggagg cacttggtcg ttccttataa 17580
cagctctgag gctcttcagg gttcttgggc tccaggttca gacccattag tctatacttg 17640
atgacatttg ttcttaagtg tcagcttgag gagaatgagt gctggtctac agagatcaat 17700
gcaagtaacc atttaattat agaagaaatg ctgaattgta ggttgcaatt tctgggggtt 17760
ggaacttgag cagaatggtc aaaagcagat tagagtttaa gaataactag taaagagtag 17820
tgtgtttaag gaggaaaagt acagttttgg gttgggcgca gtggctcacg cctataatcc 17880
cagcactttg ggaggccaag gcgggaagat tgcctgaggt caggagttcg agaccagcct 17940
ggctaacatg gtgaaacccct gtctctacta aaaatacaaa aattagctgg gtgtggtggt 18000
tgcgcacctg tatccccagt actcgggagg ctgaggcagg agaatcgcct gaacccagga 18060
ggtggaggtt gcagtaagct gagattccgc cactacactc cagcctgggc gaaagagcaa 18120
gactctgtct ccaaaaaaaa gaaagaaaaa aagaaaagta cagttttgct gtactctctt 18180
taaaaagatt tgcaggccgg gtggggtggc tcaatcctgt aatcccaaca ctttggaagg 18240
ccgaggcagg cagatcactt gaggtcagga gtttgagacc agcctggcca acatggtgga 18300
accctgtctc tacttaaaat acaataatta gctacatgtc gtggtgcaca cctgcaatcc 18360
cagctacttg ggaggctgag gcatgagaat cgcttgaacc cgggaggcag aggttgcagt 18420
gagctgagat cacaccactg cattccatcc tggaggatag agtgagactg tgtctcaaaa 18480
gaaagaaaag aaaagaaaag aaaagatttg ctaacatact cagtacacca tcagaaacca 18540
tcaatacacc tcagaaactg aggcacagac aagttaaaca gttttcctta agttatatgg 18600
ctagtaagtg gcagggctag aatttaaatc tgaacctaca tctgtttgaa agttgattct 18660
tgctctctac actgtgctgt ctttaagtcc tttctcttcc cactcacatc caatcaattt 18720
ctgagtcttg tccattatat tattgtagtg tttctttcat ttgtccctgc tgttctgttc 18780
ctgctgtcct agtttaaatt tccattactt ttggatagtt tattgtggta atcttctcat 18840
tggtcttccc acctatcttt tcaccctaca cagtgcttca caatatgata gtttcttaa 18900

-continued atacagatca gagtatgtca ctttattcct aaaattcttt ggcttctcac tgaatatgaa 18960
ataaaatttc agatcccaac cgctccatga gctcgccagc caagacgcaa aaattttgaa 19020
ccgtgtctcc tgaatgtaca tcgttactgc ttcaaccaca ttggactact gaactattag 19080
gtgttctcca cagtctttgt ttatctgcct ttgtaccttt gctaaagcct ctcctttgcc 19140
ttaaagtctt tcccattttg acctgtcttg ggcttattat tcgtctccca tggttcaact 19200
cagatcccca gatcctaact cttccatgaa gttttcacag attgtactgc tagttgaaac 19260
tgaacttctt tcctgttttc tttttgtgtt ttgtatgtta tccttaaaaa atttaaccct 19320
gtatacctta tgtcgtggta cttttgaaat gtgtctgtct ttgtcccatt agatagtgac 19380
tcccttaaga cacgggccat ttctaagtca tcatttatgt tttatgtttt ttataatggt 19440
gactttttat atagtatttg ttgaattgaa aattgatgtc catacacttt taggaatact 19500
tgctgggaca cattacataa actaggagaa cttaagacta cgaacagaat atttggacta 19560
atcattaaga aatactaatt taagtatggc aaaggaaagc acaggtgcca tgatgcgaca 19620
tttttgtaaa ggtattgatt ggggtttgaa agcgatgtta gggtatcctg atgggatggc 19680
attatctttt atgtagataa tacttagcac tgatcatccc cttacttgag tgttgtttcc 19740
atttctaggt tcctcaactt aaaagggatg aggagacctt ggagacggtt ctgaggagac 19800
tcaaaagatg attatatgat tggaagtcag tcctatgagg aaaggttgag agaatgaaag 19860
gttaagaggc aacttaataa ctcttcaaaa aacatgaatg gatccattat taggaatggt 19920
aaccagcggt ttcccagctc cactgacagc agaataagag aaaataggtt taaaccgaaa 19980
tcaggagtag ttgtgtaaag aacttattgg taatgatggt tgtcattaca gtcatggtaa 20040
aaaggttacc aaaataattt tattatcttc tctggaagta tattttaaaa gtacagtcct 20100
gcctacataa gaataaaatg acctcttaag ctaccttttc cttctgtgaa tcagtaaata 20160
aattcttatt cagctcctcg aagcaataat tactttccag taggaagctt ccagagatat 20220
ttctttagga agtaatggtt tttgtagtgg ctttatagga gaatacaaat ttttaagtgg 20280
agctaagaga gaaatcttaa acatcaagag aaaccaagga aaacagtagg tgtggtatca 20340
atataggaaa caaataagta tttgtagctt ttatgtccat tttcagttgt catttaaaga 20400
ggtatagttc agaatagctc ttgttaaggc tgtcactgct tgtggataca ttgtaacaaa 20460
tgcttataaa tcatttccaa actaatagaa gtttgcttca tgttagttag tattataaaa 20520
gcctctgacc cttggctttt gaggctgtgt agagggcttg catcactcag aatgaaacct 20580
ttttagatat gttgggttgc agaaagcatt tcctgtacag tcagaatgaa aacttgaatt 20640
gggattattc atatagatta ccaaaagtct gggcagagct gatattacca ccagccagtt 20700
ttcctactaa ctcttaactc caaaaccttc attgggttat tgaagcttta ggacttttga 20760
atttcctact ggaattgtgt atgaattcct tctttcaagt gaactgatac tagatttatt 20820
taagattagt tatacatctt aagtattttt taagtggcat ataatgaatg gtctctactt 20880
ttaaccagtc tcataaaatg cctggggttc ataggtgaag ctggattgtt gcaggaattc 20940
tgcaattgtt ggcaaagcga agggcagttt gactccttaa ttataaagtt ggatgtcatt 21000
tgagaaactc tgggaattgg aagtagaaca aattcatact ttccctataa cttttaattt 21060
cttgtcatac attcagaaaa caagagatgt aaaattcata aaactgcttg tataaattca 21120
gaaaacggga ttataaaagc aaagacaaat tgtcttacga ttctttgttc tacttgagag 21180
attcaagtgt tggagtaata aaaaatacca gggactttct tttttttaat aggttaatgc 21240
cacctaatgt gggcttctca caatgtgatg gcaaacttcc aaatatgatg tgggagccaa 21300
aagagaccaa ctggttttac aaaatattaa gaacacaaaa tttcccaact catatatttg 21360
aatattccta aaaaataata agtcaaaatt gtgttggtgg gctgggcaca gtggctcaca 21420
actgtaatac caccactgtg ggaggctgag gtgggaggat tgcttaaggc caggagttca 21480
agactagcct gggcaacttg gtaagacctg atctctacaa aataaaaatt ttaaatttaa 21540
aaaattaaaa aaaaaaaatt agccaagcat ggtggcctgg cgccttgtag tcccagctac 21600
tcaggaagct gtgatgggag gattgcttga gcccaatggg tcgaggctgc agtgagccat 21660
gatcatgaca ctgcactcca gcctgggcaa cagagtgaga ctccatctca aaaaaaaaaa 21720
aaaaaaaaga gaaaaaaaat tgcattggcc aacttggagg cttcagtgtt attttgccaa 21780
gaagaatgtt cacttttgtc atctaatttt acactgctcc ttcagcaaac tgactttatg 21840
gagagataac cctgtttacc tttagaaaga aggaagttgt ggattcctca gtcttactcc 21900
cattactatt ggtcattcaa cagcccatct tcccagaagg aaagatgtaa cctgactttt 21960
gcaccagaat aagaacaaca aacggaagaa aaaaactgag ttttatagta gaagtttgta 22020
gttgaatgag catgtagctc aaaatgaagt taaccactta aacttgtcat atgggggacc 22080
aaaatttctt ataataaaaa gaactatatc tgaaaataaa gttggtgttt gtttaatttt 22140
tctagcctat tcaaatcaat ctggtcattt atggtacttt cctattagag aaaaataaac 22200
cctgtgattg tgatgcttaa cttaattttc tacagtgaat cagttaagtg ggcttatttt 22260
ttctgcttta gcaagtagat aaaccagttc agacttggaa cctgaggatt ctggaaatac 22320
acctttcttg agtttttggt ttttttttt aaagattctg cagaataatt tgggacattg 22380
ccaggaatca gaatagttta ctatctgaag tagtgcattc atttgctgt tttttgtttt 22440
tttgttttta agacagataa gctactttat gactacctct ttttctgaag cagggtgggt 22500
ggaggtcacc tgtctcattt gctttgctgt tttcagcatc tttgctgctt attcttgttg 22560
acatggagtg gggatgaggg gtactaccta tttctctagt tacaaagtga gtagcatttg 22620
tgtttcttag gtgacagttg ctaggtagaa ttgaattaaa tatttgaaaa ctggacttca 22680
ttcttgtgtg ggtgaaattt ttaccttctg ttgttattga agaacagaga attattgtct 22740
tagcgctctt taatcccaag tgaccttttt gtgttaacat ttctcaatat caggcagaga 22800
tcatatttaa acagtttcaa tctcttccta tctgttatgc attcaaataa tcattgttct 22860
cttgatgcac caataaccag agagaatctg cccttgttcc tgcccctgac aatctgttca 22920
caagagaata tgatgtcagt tcaataacag catacatttc ttgactggtt gaatttcatt 22980
aactatttgg cttaagaagt ttgccccttg atgtctgtgt atttgactgt gcttgggtat 23040
attatacttt tcttactgat tgagcagcat tatttttata ttctgctttt ggaaatgatt 23100
tacaggtgtc actacatttt ttttctacta caaataatga aaaagtacct gcaaagaggc 23160
tcatcttcct aaaaaatggct atcataaata ttgcattaca aagtaagaaa tagaaattga 23220
aaaatcgaat tcatttatca aagaacatct tttatactct aggtggatga ccagctactg 23280
gggctctacc attggagacg tcccttccct catgaaactt gctatctaat tcttttttt 23340
ttttttttt ttttagagac aggtttttgc tcttccaccc aggctgggat gcagtggcac 23400
aaacacagct cactgcagcc tcaaactcct gggctcaagg gatcctcctt cctcagcctc 23460
ctgagtagct gggaccatag gctcacaaca ccatgcctac taatttttaa ttttcttttc 23520
tgtcctcttt agagacagga atcttgccct gtcacccagg ctggagtgca gatggcgcaa 23580
tttcggctca ttgcaacctc cacctcctgg gctcaagtga ttctcgtgcc tcagcccccc 23640

-continued

```
gaagaactga gactacaggc acatgccacc acatctggct aatttttat gtttttagta  23700
aagacggggt ttcaccatgt tagccaggct ggtctcgaac tcctgacctc aggtgatcca  23760
cccacctcgg cctcccaaag tgaatttttt tttttttttt gtagagatgg ggtctcacca  23820
tcttatgtag ctggtctcga actcccaggc tcaagcagtc gtcctgcctt gacctctcaa  23880
agtgctggga ttataggtgc gacccaccat gcccagcctc tcattctttt taatgagctc  23940
agcttaaaat gtagcaggaa tataagtatt cacattttta atactttgca agatactttg  24000
gaaattgata atctgaaggt tgaagctctc agaactaatg ttaacagaat tgtccttggg  24060
agcaattcag ctattcttca tttacggatt tagtgattct tgagtcagtt gtcttacacc  24120
aaatgtaata catgaatcag gagggttttt ctttgtttgc tttttgtttt tttaagagac  24180
gaggtctcac tatgttacct gcgctggagg gcagtggctg ttcacaggca taatcatcat  24240
gtattacaga cttgaaatcc tgagcttaag cgattctact ccctcagcct ccaaaatagc  24300
tgagaccata gtgcacacaa ctacgtctgg ctctgaatca ggagatttta aatgttctca  24360
aagtatgtaa tagctttttc agtcaggcat ggtggctcac acctgtaatg ccagcacttt  24420
gggaggccaa agaggaagga ccgcatgagc tcaggagttc aagacagtct gaacaacata  24480
gtgagacccc ttctctacaa cagaataaga ataaccaggc atggtggtga gcactgtagt  24540
cccagctcct caggagactg agatgggagc atcacttaag cccaggaata ggaggctgcc  24600
gtgaggtatg atcataccac tgcactccag cctgggcgac agaataagac cctgtctcaa  24660
aaaacaaaac tttttccctc ctgttaaaat ggaacttaga tgtgactaca tgctctgctg  24720
ccttctacca tcaaagaagt gccccccttct ttttttttc ctttcttgtt ttttttttga  24780
aatggagtct cactctgctg cccaggctgg attgcattgg cgccatctcg gctcacagca  24840
acctccgcct cctgggttca agcgattgtt ctgcctcagc ctcccaatta gctgggatta  24900
caggcgccca ccaccacgcc ctgctaattt ttgtattttt agtagagatg gggtttcacc  24960
atattggcca ggctggtctc gaactcctga cctcgtgatc tgcccacctc ggcctcccaa  25020
agtgctggga ttgcaggcgt gagccactgt gcctggcgga agtgcccct tctatctaag  25080
gccaacctct ccatttgagc tctggatccc atctcctctc atctagtcag ggttgtacct  25140
gcagttatct catctctcct gctgcatagg taatttctct ctcacaacta gattggtccc  25200
atcaccatat aaaactatct gccttaatat aatcctttaa aaaaacgctt gaccccacgt  25260
ccacctttag ctgctacctg attcttttct cccttttcac agcaaaactc cttgaaagtg  25320
ctgtgtgtaa ttgctatttc tactttctca cctttcattc tttcctcaac tactccagtt  25380
gggcttttat ccccatgatg cctctgaaat agctcttatc aaggttctca aggagctcta  25440
ttttaccaga ttgaatagat aattctcagt tctcatcttg ttaaaccctt tggcagcctt  25500
tgaaccagct gaccactccc ttcttggatt tttttttttt aacattgtac tcacctgttt  25560
ttcttcttaa ctcattggct gttaattttc agtattctgt atggcttccc tcctctgctt  25620
aactctcctg aataaggttc ccaggagtct actttcact gctttctctg tctacacact  25680
cttcctaggt catctcatcc aggcctcatc tatacgctga caactaagaa atctttttct  25740
ctaacactga ctacttctca gagttccagg cttgtatagc ctgctgccaa tttgatattt  25800
ccatttggct aatatttact gagtgtttat tgtgggccag gctatattct gagcacttca  25860
catgaattat ctcacctaac cttcatgacc attgtctgaa gtatcactaa tattcccatt  25920
tcataggcaa ggaaacacat atacattgaa gcacttggat acctaatagg tatctcttac  25980
ttaccatatc taaaaagtct tgactttctt cctcaaacct tttccattcc cagtctcttt  26040
```

gtttcttaat tattccacca aaaatccagt tgctcaggcc taacatgtaa gatttatngt 26100
ngatttatct nttttattca catctcacat ntatcccatc agcaaattct gtctgtatta 26160
catccaaaat aagccttaaa ttcaactacc tctcaacaac tttgctacca aaacctcaga 26220
ctctcccatt atagtctctt ggttggagtt gcttatgtta ttacctcact aaagtttgtt 26280
tctcacatag caacagtaaa ctctggtatc aaatcctatt ccttcacttt aaacctatct 26340
gtgtctcccc acactgctag gataaatcca gattccttac tatggccaac aaagccacac 26400
gtaagctggc ctctggtcaa gcctacttct cgagcattgt ctcttctcat ctcatccatt 26460
ctgctatata gccacactag cctttttctg tctgtcatgc atgctgtgcc tgttgctgtc 26520
ttggggcctt tgcacttgct ctcaggctag aacactactc caccaaggtc tttatatgtc 26580
tgactttttc tcatttaggc ctaaccaggt ttggcaagtt tttttctgca aagggccaga 26640
tggcctctgt tgaaactact ccactctgtt gttgtaagtg caaaagcaac cataggcaat 26700
acagatgctc cccaacttac gaaggggcta catcctgaaa aacccataca tcaaaaatgt 26760
cataagtcaa agatacgttt aatacactta caagctcgtc gtaaagtcaa aaattgtaag 26820
tcagaccatt gtaagtcagg gactgtctgt ccattaacaa ctgaacgtgg ccatgttcca 26880
atacaatttt atttatgaac actgaaattt gaatttcata tagttttcat gtacacaaaa 26940
tattcttttg actttaaaaa aatggttaat tttttttttt tttaatttta acttgcagaa 27000
caattgatgg tgggccaaat tcggcctgtg gcccatagtt ttccagtctt cggtaaacta 27060
ttgccttaga gaagcctttc ctgtgtaccc tagcgaatat aaccccacag ctaacacctc 27120
tccacccccc actcctgtca attcttattg tcctagtgtc ttttttcttc ttagagacag 27180
ggtttcactc tgtcacccag gttggagcgc agtggctcag tcagttcact gcagcctcaa 27240
attgttgggc taacatgaac ctcctgcctc agccttcntg gtagctagga ttacaggcga 27300
gagccaccat gcccagcccc tagtgtcttt tatttatttg ttatatgttt attttctgtc 27360
tctccattag attgtagctt catggggcag gaattttgtt agttctttac atgtatcttg 27420
agagtcaaac agtacctggc aatactcaat aaatacttat tgaatgattg agtgacagtc 27480
atatttgaat tatgcctgta gcctgctatc tggtcccccct tttttaagtc tttcttactc 27540
tagttcatta tatataccat ttccagaata aacttcacag ttaatgcctt ctctacattt 27600
gagaaccaat ggtagcagtc tgtattcatt gcatttgctt tgaccatacc atacaagaat 27660
taacaaggtt ctgattattt catttgtctt ctatcttggc cctactctgg ctaccccttt 27720
tcagcctaat cagtttttac caatcctcca atccttgcat ctgattttct tccccctctc 27780
tgccccttat tattattatt ttttttattt tttattttta tttttattta tttatttttt 27840
tttgaggcag ggtctcactc tgttatccag gctggagttc agtggcgcaa tcatggctca 27900
ctgcaacctt gacctcctgg gctctggtga tcctcccatc tcagacttct gagtagttga 27960
gactacacca cacccagcta atttttgtgt ttttctttgt acagatgggg tttcacattg 28020
ttgcccaggc tggtcttgaa ctgctgtctc aagcaagctg cctgcttcag cctcccaaaa 28080
gtgctaggat tacaggcatg agccactgtg cccagccttg gctacatttt taatacattt 28140
ttaatttttt tttagacaag tcatctccct ttgttgccca ggctgatctc aaactcctgg 28200
aatatcccac tgcctcaggc ccccaaagtg ctaggattat agatgtgagc cactgcacct 28260
ggcctctccc tgttactgtt aatcagccat tgctcattac cttcatgatc tattttcttc 28320
agagctgcat tctttaaaac ttttagggcc atgcatggtg gctaacacct gtaatcccag 28380

-continued

```
cactttggga ggattgcttg agctcaggag tttcagacca gcctgggcaa tatagtgaga  28440
cctcatctct actaaaaatt taaaaaatga accttttttt tttttgagac agagtctcac  28500
attgtcaccc gggctggagt gcaatggcgt gaccttggtt tactgcaacc tccgcctcct  28560
gggctcaagc aattctcttg cttcagcctc ccaagtagct gggattacag gcacctgcca  28620
ccacgcccag ctaatttttt gtgtttttag tagagatggg gtttcactat gttggccagg  28680
ctggtctcaa actcctgacc tcatgattcg cccaccttgg cctcccaaag tgctgggatt  28740
acaggcatga gccgccgcgc ctggcatgcc tatatatttc taagtatgta ggtattcctc  28800
agaactctgc catctaccct ccttttcttt cagtactata ttctttccct gggtgactga  28860
attcatacac agtttcagca ttcatatatt cattgagtca gatgtgtttt cttcagatca  28920
ttatacccctt tagacaacgt ggataaacat ttcaaattca gatgtctaaa atgatctctc  28980
ttcccactcc tttaaacctg tctcctttct gtgttcccag tcttggtaaa taccaccata  29040
aacctaatca acctaagcca gacatccaca agtgttttat tgattctttg cactccctta  29100
aacctttata tcaaagtctt gtccattttg cctcctaatg tctataggat ctgtcctttt  29160
ccccttaatc cgtatggcca ctacagtcat tttacaactg ttcttcctgc ctctacttct  29220
ctactgctgt catagctttt ggcagcaaaa atccaaatct aatcatactt ctctcctacc  29280
agagtcacta atctgctata gccttcagga tgaggtctac acgtcctcaa agataaactt  29340
caaactcatg aaggcatata agacctttca tgatacacct cctgcctttt tttttttttt  29400
tttttttttt tttgaaacaa aatcttgctc tgtcacccag gctggagtgc agtggcatga  29460
tcttagctca ctgcaacctc tgccttctgg gttcaagcga ttctccgcct cagcctcctg  29520
agtagctggg actacaggtg cccaccacca cgcctggcta attttttttt tgtatttttt  29580
agtaaagaca gggtttcacc atgttggcca agctggtctc aaactcctga cctcatgatc  29640
cacctgcgtt ggcctcccaa agtgctggga ttacaggtgt gagccaccat gcctgaccgc  29700
cttttttttcc cttcaatatc ttttgcccct ttcccacatc agctaaggcc tcagtcatcc  29760
agaactattt ttaatttcac tccatgccac attcttttgt gtctctgtgc ctttgtatgt  29820
gttattctct ctgcttgcac tacactcctc ccccaccccc caccagcttt atcatccttc  29880
gaaagattaa gttttcatcc tctctgcaat ggccttcccg atcctttctc cttgagtggg  29940
ttaattgtct ttctgctgtg ctcctccagc agtgtcttcc tctagcatag caggcaacat  30000
acgatacttc attaatttac tcatctgttt ttaagattag caggtcctta aagacagaag  30060
ctgtccttta tctctgtttt cataccgtag cctaggaatg gccgatatat attttaatga  30120
gtgagtgaat gaatgaattg gtacagtctg tcctcccaac ctgagggcat tctccctatg  30180
catttttttt tgagatgctt tcaaatttat tttattttgg tttattttttg agacaggatc  30240
tcactctgtc acccagcctg gagtgcagtg tctcgatcac agttcactgc agcctgtatc  30300
ttctggactt aagtgattct cccacctcaa cctcccaagt agctgggact acaggcaccc  30360
accacaccca gttaattttt tctatttttt atagaaagaa ggtttcacta tgttggtcta  30420
gaactaggct ggtctacaac tcctgggctc aagccatcct ccctcctcgg cctcccattg  30480
ttaggatttc aggtgtgagc cacctcgtcc tgcccctata cattcttaaa agtaagaatc  30540
atattgtgta attctttgaa gtccctcagt attttctact atagtactat taccacagta  30600
ggtatttaat gttcttaaaa caagtttatt gcatttcttt tattttcatt ttacaaacat  30660
ttattgggtg ccaaatttgt gctagatatt agaaatacaa aaatgaatag gaaaactgtt  30720
tctatcctca gagtacacac tctaaagaag acaaatgtgt gaacacattt tttaaaattc  30780
```

cttctgctaa tactagtaat tatgtgagca tgtctttaag gtgcaacatt aagaccttgg 30840
tattttgaag cttgtagcag tagccacaag gggaaatgtg ccagctgaag tgatagctac 30900
ctggaataaa ttcccaaagg ggaagtggta ttctttttaa acttatcgct gccaagatgc 30960
acagtttgcc tcctggatat ttcttcaact ttagttgttc tcaataattt tgttagttct 31020
cctgtggcct cctcatttga tggaatgata tataatggta ctagaagcct tcaaaacaaa 31080
gtatttcaaa aaacaagtgc atcaggagtg attttgatac tgtctatggt attgatgtta 31140
ttttcaattg attcattgaa atttgttttg taattgaagg gatttgattt ttcaaactct 31200
tttttttccc ccctttgaga cagagtcttg ctctgtcacc caggctggag tgcagtgcac 31260
aatctcagct cactgcaacc tctgcctcct gggttcaagt gattcttgtg catcagccac 31320
ccaagaagct gggattaaag gcatgtacca ctatgcccac caaattttta tttttggtag 31380
agacagggtt tcaccatgtt ggccaggctg atcttgaact ctggcctcaa gtgatccatc 31440
catctcagcc tcccaaagtg ctgggattac aggtgtgagc caccatgcca ggccctgatt 31500
tttcataaga ctaaaaattt tggaaacaga agaatgctaa gatatagctg ctaaagggca 31560
tgtttgagat gcctaccact taattaagtg ctgtgaagta cctaggagtc tcttgctaga 31620
aaaggaaggt gagggtgtga gcaaagtcat cctaggctgt attcatctga ggccaggagt 31680
attggagctt attcaataga ggaattctca aagtagctct ggagcctcca tcttagcctg 31740
gtaggtaaag aactctaggc gggtgatttt tgctctgact atggtatatt gaaaataatt 31800
tttttttttt tgaaatggag tcttgctccg ttgcccaggc tggagtacag tggcatgagc 31860
tcttggctca ctgcaacctc tacccggccc tcccaacccc ccgccccggg ttcaagcaat 31920
tctccttcct cagcctcccg agtagctagg attacaggcg ggcactacca cgcccggcta 31980
atttttgtat ttttggtaga gacagggttt caccatgtct ctggtcatgt caggatggtc 32040
tcaaactcct gacctcaagt gatctgcctg ccttggcctc ccaaagtgct gggattacag 32100
gcttgagcca ctgcctcagg cccaattggg aagaatttaa gggaggaact aaaagctatg 32160
cattttagtt ggggataggg aagaaaacat tacagtttat cagttgaaat tttatcagat 32220
cagtggtatt actagaaact gtgtcacatc tagttactat agataattta ggtcttgatt 32280
gcctaaactc tgatttctag ctctggagtg cctagttaca atactgagga atggagatat 32340
acattgccat cctttggaag aattttgaaa tttgaatatt tctccatgaa ccacatacta 32400
atatagaagg aagaatagac tttttctttt ttctgagata gggacttgct ctgtcaccca 32460
ggctggagtg cagtggcacg atctcagccc actgcaacct ccgtccccca ggctcaggga 32520
tcctcctacc tcagcctccc gagtagctgg accacaggca tgcaccaaca cacccagcta 32580
ttttttgta ttttagtgg agatgggggt ctcaccatgt tgcccagcct ggtctcaaac 32640
tccctgagct caagcaatcc acctgccttg gcctcacaaa atgctgggtt tacagtcagg 32700
agacaccaca cccagccttc aagagttaag caaaattttt tattccagaa tatgaatatg 32760
aattacacat agtattttat ccttcagtaa cattgttttt ttagagacag gatctggcta 32820
tgttgctcag gctggagtgc agtggattca caggtgcaat aataggggac cacagccttg 32880
aactcctggt ctccagtgat ccttctgttt cagcctccca aatagttggg actacaggcg 32940
cacaccacca tacccagcta ttctttagtg acattttaat gcaactgatt tttaaaagga 33000
aggctgaaat tgcacactgc ctgtctgcct tagatacttc ttgggagcag gaatcatgtc 33060
ttactcaatg tcgtatctgg aacatatagc cctagggcaa gtgtataaat gtttttttgag 33120

-continued tgaacaaatg aattaaatat tgctttgttt gaaaagttgt cttagtagta cataattcct 33180
tgaaacacag aatttcatgt atttttctaa tataccttat attttataca caaacattat 33240
gtttaatact tatttagggt tcacttaggt tcttttgtgg gagaaatatt cctattgctt 33300
cgtcactcac agaaataact ggccactaaa gaattaaagt tttgccacta aaataaaatt 33360
tctgaatatt aagatattta tgaataacgt gaatttagtg gtaaaggtat gcttggaagc 33420
tctcaaataa ctggttaccc cagagtggag atgcaggggt cagaaagaaa ttctacatgt 33480
ttattatttt tacaactaga tttcacttag gaagtgacat tacatagctt aatttgctgt 33540
cttaatcact ggaagctaaa tatgagttaa cagtattttg cagtgctcta cttggcaagg 33600
gtgtttttct atctttgctg gtaagaaaat gaaatattgg tgatctagtc tccaaggaca 33660
tcagtgtcag caaggtttag gttttgtggc tatactgtct tggaatgctg tgctcatcag 33720
agtaggccaa gttgaaagga aaagtgtgtg atgaatggtt gcctgagccc agttcccagg 33780
agtccctagt catgtatagc atgatgtctc ctgtaccctc tctcttcagg gctgtccagg 33840
cttatgatgc cacgatgcca aatgtggatt taattgtagc ttctttttgtc tttttttatac 33900
acatattact gtagtctttt gatttctaga taagtttaaa tccttgggaa gccaacactc 33960
ttaccttgtt tccaacctcc agggatccca tgtgcttaag gagaatgatg gagcaagacc 34020
agaagcctgt tgctcatgat agtgcagtga aaggaagact tttttgcagc accctcttta 34080
tttatttatt tatttttgag acggagtttt gctttatcac ccaggctgga gtgcagtggc 34140
gtgagctttt ggctcaatgc aacctctgcc tcccaggttc aagtaattct cgtgcctcag 34200
cctcccgagt acctgggact acaggcgcgt gccaccataa ctggataatt tttgtatatt 34260
ttgtaaagac ggggtttcac caggctggcc aggctgatct cgaactcctg gcctcaggtg 34320
acccaaccat ctctaacttc caaagtgctg ggattacagg tgtgaaccac catgcccggc 34380
tgcagcaccc tcttgtagcc ttctttccca gtgcttactc aacttggctt tacttaatta 34440
tcccgttttg ttttgtcttg ttttgttttg ttttttaggg ctcttacata ggcttggaaa 34500
ttccaagtta gaagactgga gctctttaac ataacaatga cagcttttgt ttttggctaa 34560
gctgtccgga ttatttaaac aatgggtact tattttttaa agcatgcttc aagaaatcaa 34620
tcaatatttc aagtgcaaag aaaattcttg ggtaaaagta tagttcattt tgactactta 34680
tttttattta tttatttatt ttttgagaca gagtctcgct ctgtcgccca ggctggagtg 34740
cagtggtgcg atctcggctc actgcaggct ccgcctcccg ggttcacgcc attctcctgc 34800
ctcagcctcc tgagtagctg ggactacagg cgcccgccat cacgcccggc taattttttt 34860
gtattttttt tagtagagac agggtttcac cgtgttagcc aggatggtct cgatctcctg 34920
actttgtgat cctcccacgt cggcctccta aagtcctggg attacaggcg tgagccactg 34980
cacccggcct gactacttat tttttatttc cttattccaa gtacaagacc agaaggaaaa 35040
cgaattaatg cttcctgtca ttttggaaag tacttagaaa ctttaaatat tggcagttaa 35100
actgcctgac agctcagtgg aactcttgtt ttggaataca ttgcagttag gattatatag 35160
ttacattttg taaaagtttg aaatatataa aaatgactca ttaggttgtt aataatgaac 35220
ctaacagtgt gtatctctca catttatctt tatttttttt ttttaaataa agatggggtc 35280
ttgctatgtt gcccaggctg gtcttgcact cctggggtca agcaatcctc ctaccttgtc 35340
ctcccaaagt gctgggatta caggcatgag ccactgcacc cagcccattt cttttaaaga 35400
ttaataactt tttattacct gttgaatact ttacctattg attattatat gtatagttgc 35460
ttgagctgtc aatcattgta gcatttggaa cataaaatgc gtgtatttag caatgtagtc 35520

-continued

```
ccttagtaag tgttgggaaa tccccagaag gctttgtgaa atgcatagat tagcaggttg  35580
ttccacgagt ataattcagg aaaagaatga attaatcaga aatttgaagg atctgaaaat  35640
ggccatcatg tgacttttac agtagctaaa agaatagcaa tttttgtact ttagacaact  35700
tattcaattc ctttaaatat ttattgtttt atattgtatc tattatggta ggaaaactat  35760
tctacagcca gtttagacac ttaggttctt tgtagctaac tgtgtgatct tgggcaagtc  35820
atttggcctt ttagagcttc attttcttca aacacaacaa taagaactac tatgtgaggg  35880
gacttcaaag aaaactcatg gaaaaataca tattatgaaa aaactgcaga atttcaaaat  35940
tttgtatgca ccaaaataaa cttgcactaa cttgtcataa catatctgaa caggatgtag  36000
tttgaggcac taagaaggat aagacatcag tttgaaaaga gcccctatca gagcaacata  36060
agttctgcta aaattgaagc aaaaacaaac ataaaattta tggtgaagct gggtgaaaga  36120
atggtgaaat cattgatgct ttacataaag tttatgggga caatgcccca aataaataat  36180
tggatggctc attttaagaa gggacaagat gatgttgaag atgaagcctg tagtagcaga  36240
ctgtccagtt tgcaaggaaa aaattcatct tgttcatgcc gtaattgaag aggaatgatg  36300
attaacagca caaataatag ccaacaccat agacatctca attggttcag cttacacaat  36360
tctgactgaa aaactaaagt tggctgggcg tggtggctca cgcctgttat cccagcactt  36420
tcagaggcca aggtgggtgg atcacctgag gtgaggagtt cgagaccagc ctggccaaca  36480
tgacgaaacc ccatctccac taaaaataca aaaataacca ggtgtagtag tgcatgcctg  36540
tagtcccagc tacttgggag gttgagacag gagaatcact tgaacccaag aggcagaggt  36600
tgcagtgagt gagccaagat tgtgccattg cactccagca tgggtggcaa gagggaaact  36660
ctgtctcaaa aaaaaaaaaa aaaaacctaa agttgagcaa ctttctacca aatgggtgcc  36720
aaaaccattg cacccaaatc agctgcagac aagtgtagag cattcaatgg aaattttaaa  36780
caagtggcag caagatcctg aagcatgtct ttgaagaatt gtaacaggag atgaaacatg  36840
gctttaccaa tacgatcctg aaaacaaagc acaatcaaag taatggctac caggaggtag  36900
aagtggtcca gtcaaagcaa aagcagactg tttaagagca aaggtcatgg caacagtttt  36960
ttggggatgc tcaaggcatt ttgcttgttg actttctgga ggaccaaaga atgatagcat  37020
cagcttattt gaaagtgttt tgagaaagtt aaccaaagct ttactacaaa aatgccaagg  37080
aaagcttcac cagaatcctg ctccatcatg gcaatgtccc tgctcattcc tctcatcaaa  37140
caagggcaac tttgtgagaa ttttcatgag aagtcattca gtatcattaa gtatgctgat  37200
ttgtctcctt tgccttttttt gtttcccaat cttaaaaatc tatgaaggag gcggagcatc  37260
taggctgagg caggagaatc gcttgaaccc aggagacgga ggttgcagtg agccaagatt  37320
gtgccactgc actatagcta ggtgacagag tgaaactctt atcttaaaaa gaaaaaaaag  37380
aaatctatga agggcaccca tttttcttca gttaataatg taaaaaagac tgcattaaaa  37440
tgtttcagtt cccacgaccc ccagttcttt agggatgggc taaatagctg gtatcatggc  37500
ttacaaaagt gtcttgacct tggagattat gttgagaaat aaaatttata tttttaattt  37560
ttatctttta attccatttt ccatgaacct tttgaagtcc catcatatgt atgttgccta  37620
tagctttcca agtgatttca cataaattat ttattcctta cagtgctcaa ataaaaaatg  37680
aaattgaggg atagatacag taagtgagtt gtctaagatt acatagtctg agagaatcag  37740
actgagaccc taaaccaacc cttctctccc cacatccagc actctcctca ctggcatcac  37800
gtatgagaag actggattgg ccccctctac aattataata ttctatgatt tttttgtttc  37860
```

-continued

```
tgaagtgatt tgccattacc tattttattt gctttttcct caaaatatat tttagggtta  37920
ctatttttaa tgtctttttt ttctgcctga aagtacattt taaaagttaa cagtatggaa  37980
tttcattatt gtgataagat tttatattaa ttgtgctgtt aggagttttg gctgtttttg  38040
ttttgttttg tttttttggt aacattgtag cctacaagtg taaaccctga aaatgattcc  38100
agaaatttat ttggggttca gattcacatg ttgtaggtta gttatatact aacttgtttt  38160
aagatgaaga gagataattt ttttatttta aaattacttt tagatttttt ttagattggg  38220
aggccagtat gggaggatca cttgagccca gaagtttgag accagcctgg gcaacatagt  38280
gagaccccgt ctctgtaaat aattttaaaa ttagctgagt gctggtacat gcctgtagtc  38340
ccagctgccc aggaggctaa ggcaggagca ttgctagagc ccaggagttt gaggctgcag  38400
tgagccgtga tcacaccact gcagtacagc ctgagtgaca gagtgagcac tggcaaattt  38460
taaaattttc tgtaaagact cactatgttg cccaggctag ccttgaactc ctggcctcaa  38520
gcagtcctcc catattggcc tctcaaggcg ctgggattac aggtatgagc tactgtgctg  38580
gccaagagag aatttttctt attcacaaat aatgttcaca gtaagaattt acttaaaatt  38640
tttttaaagt aaaaagaact ggctgggcac agtggctcac gcctgtaaat cccagcactt  38700
tgggaagcca aggtgggtgg atcacttgag gccaggagtt caagaccagc ctggccaaca  38760
ttgcaaaagc ccatctctac taaaaataca aaattagcca ggtgtggtgg cacacgcctg  38820
taattccagc tacttgggag ggtgaggtat gagaatctct tgaacctggg aggctgaggt  38880
ggcgccattg tactccagcc tgggcgacag agcaagactc tgcctcaaaa aaaacaaaac  38940
aaaacaaaac aaaaacaaca aaaaaccaac aaaaaaagaa cttacgtgta agaatttaaa  39000
ttagtgatga aagaagaaac tgtaaaaagt actccagtaa gccaggcata gtggtgcatg  39060
tatgtagtcc gagctatgca ggaggctgag gcaggagtat cacttgagac caggaattaa  39120
agaccagcct gagcaaaata tgtaattaaa aaaaaaatta ctgtagtctg tgttccttaa  39180
atttaggttt catacattct tagaattata atactttttc atggctgggc acagtggtgc  39240
atgcctgtaa tcccagcact ttgggaggcc gaggtgggca gatcacttga ggtcaggagt  39300
ttgagaccaa cctgcccaac atggtaaaac cctgtctcta ctaaaaatac aaaaatgagc  39360
tgagcatggt gacaagggcc tctagtctta gctattcagg aggctgaggc aagagaatcg  39420
cttgaaccca ggaggcggag gttgcagtga gctgagatcg cgccactgca ctccagcctg  39480
ggtgacagag caagactccg tctcaaaaaa aaaaaaaaaa ttataatact ttttcagatg  39540
tctttgaaga ggagaatttc agccttttct taaatagtcc aatactttaa tcttagcaat  39600
ctcagagcaa aagccttttt agatgccagt aagacttttc tctcagttgc ctagtatgca  39660
aaggctgggc cttaaatgtt ttgctcctct aaagcattta aatttaagag ataaacctgc  39720
taatttgtcc taaaagttat atatgtcttt taatatagtc atggctgaaa aatggctaag  39780
acagttagca cctgactcta gttttaaatt aactgagaaa ataatccttc agaaaatcat  39840
tgatgttgtc cacatacatg tgttcttacc tctcgagagg aaaatgttaa tgcttttgtc  39900
attggaactc agtttgggac ttaccactat aaattggagg ttccagaatg tctgttcttc  39960
attccttatt ttgttcttgt tttatgtgga ttttgtttct ggaatctgaa attctatcat  40020
tctgtgtctg tctctggaaa gaactcaatc tctgaatcat tgaatttcta ttaatcagtt  40080
tgtttaaata gaccatcttt cttgagaact tgtgcaaaat aggttaaaca aatccttttt  40140
ttttttatag agcaggttaa aattagaggt aagcacaagc ttttgctttt tgtcctttcc  40200
aactataact gaaaatagga tgcttcccta agttttagta aaggatttca tcctatatgc  40260
```

agtcaattca tgatcccttt cacaaacgct gctgcccacc attaagtctc ttatcacagg 40320
catttttaaa attataccat aaaatgcatg ttgagactct ctggatctca aatgtacaga 40380
aatcacatct aaatgtcaat tcctgagtta aggaactgac aattatggca ctttcagtct 40440
ctattaatat ttagaaggca agagattatt atattgttta tattactcct tatgtgtctg 40500
tagacttaaa tactttttga aaagcatttg tttgttgtat tggggctgta tgtttctgcc 40560
attatactta tttgcttacc tgatttaaag ttgtccttta attgttttgg gctgtatcta 40620
tagtttgaaa ttaggactat cctctgtgta ctatgcacca aagatgacat tctcaatgca 40680
ttgttcagtt actacacagc tcctatttgt ctgtaataaa gctgtatggc tgggtccatt 40740
tatttcaata ttagttattt tatagtatcc attggaatga tgataattaa tatataaagg 40800
caacttttcc aaattcattt gtgtctcctc tgggcatttc tttgggatgt gtttgtatgc 40860
acgtttttgc ttctgatttt aaaataattt tcctttgttg taggatgagc aattcttagg 40920
ttttggctca gatgaagaag tcagagtgcg aagtcccaca aggtctcctt caggtacggc 40980
caattaagtg catggtgcct tttaagtttt gtttgttagg agattgtggc ttcctcttgc 41040
cttctttaca tgtaaaggat gctctaccat acttgggtta ggaaatggct gatgagctag 41100
acttcttttt atttatttat ttattgatta ttgttatact ttaagtttta ggtacatgtg 41160
cacaatgtgc aagttagtaa catatgtata catgtgccat gatggtgcgc tgcacccact 41220
aactggtcat ctagcattag gtatatctcc caatgctatc cctccccct cccccagct 41280
agacttcttt atgggactct tatctatcag gccacattgg gtttattctt tctctctggg 41340
aactacttgg ggcatgggaa gtaggtttcc acagaattac tgggaaatct ggtaggcaaa 41400
gtgaaggtaa cctagtaaga gtatcctcag atttacacat tttgtgttat gtggtagtgt 41460
atatgtcttt gggaataatt tggccattat ttttttgga tgaaatttgg tccactattg 41520
tcaaagaacc aaaaacaaaa tattggcatt atgtgaaaca tttttacctg attcttgaaa 41580
ggctgtatta aaataaaaaa atggaaaatt agcaatattt gtcattattc tcaccaacaa 41640
aatatctaga atatcttgaa attctagact tacaagcagt ttcctaagag aagaccctca 41700
atggaaataa catttaatgg cttgcctaat tcagttctgt ataggagaaa gctatgtatc 41760
ttttgatgaa aatgcattcc ccatctgtgc tgccattctg acttcatata tggttttctt 41820
tgattttatg tggatagaca ctccagctaa atatgatatt gttagctgtt tctgctttta 41880
gacattgact tagcttgtga tgtgtgctag cattagggtc tcacttaaga gtcatcatat 41940
attatcatct aattcaaaca tccaagttga cagtttttct tttcttaaag aggagtggta 42000
ttgtcattct agttgggggc agttggccag tagtgtccca gtatctgtgc tattcagaca 42060
gtagcagtgt tctctttaac atgtgatgaa gtcttaaaac ttcatatagg aaaggaatta 42120
gagagatcat ctgggatttt tgtttgtttg tttatagatg aaaaaatgag gtccatgaaa 42180
tacatgagta atgatttata accagtttga gagttctttg gatatgttgt ggatcaggga 42240
agttagcagc agtgctggga ctcttctctg ttctgctgct tctacttatc taccaaaaga 42300
gtttttttaaa aagtaggata gaagaggttt tcagaattga taaagccctc tgattggcca 42360
ggttcaagtc taccacaatg gtaaggaatc ttttgatgta tttccgggca ggagttgttt 42420
tgtttgtttg ttgtttttgt ttttgttttt gagacggagt ctcactctgt cacccaggct 42480
ctgggcagga gttttatttt gttaattcac aactttttca tggtagtttc ctcttaagtt 42540
ttttttcatg actaccagtc taccttgaat gttgtcttgt tttctaagaa accatctcga 42600
tatgcttcat tatttgagaa atgagacatg gtttctctgc tgtctcctag tttattacct 42660
ttgttgtaat taggatatgt tgagaaagga gctgtgaatc cttaatctat taaaggaagt 42720
ctcataaatt aattgatgag gaatgcattt atatttagaa agctcaacaa taaaaccttt 42780
gttgacttct gttctgttag caagcagttc cattgtaaaa atgttcatct cttttggtgc 42840
ctattaaggg aagttttagt ctcagaagaa tgttatcaaa agggaaaaga agatttgagt 42900
gaagatagcc tagtcttact actttttaaa atacaggttt atacaaggtg ttttagaaac 42960
agtcttgttt tcttgaatgg cttgaaaagc agcaaactga gcttatttat aaattggcaa 43020
attcctttta tttagaatag aactttgatt taataagttg tcattttgct gttgacatca 43080
gttaaggtta aatctttttg caacttgaga ctagctcaag aacctctaag caggggagta 43140
gatttagtgg acacattatg tcacttcact gattagttca catgccactg agttcagtgg 43200
tcttattctg atgtgtcata aatgaacatt tttctattca gtaaaacttt cttagtctac 43260
tttggcaaaa cagattgaaa tatgggactc tgagctgccc aaggagttgg tatgttgatg 43320
attgaagagc agcgtattca aatttgttca aagccagaat tctgaattga aaagatggga 43380
tgactaacta gaagcatatt cttaaatgtt aatcttggtg gctaggatat ggcgaggaag 43440
ttcagatgtt ttttctttac aattcctttg aattcagaaa aaaccttctt gctcatctaa 43500
aattgtaaga aaatcagttt tgtggattaa ttgttcaact gaaaactttt tattatcttt 43560
ttgtatcaaa aaagtaatta aatgttcttt caggtggaat gttatttgct gacttctttg 43620
aggcaaattt tgggtgaaaa gaaactaagc acaattaaga tgtttgattg actcattaga 43680
ctcaagttga actcagtaca aaatggccag tgctaagtta tattcagctt agttaaaacc 43740
taaactacac agctaaatat atgctcttca tggtttaatt tctatacaca gttaaaacta 43800
gtcctcgaaa acctcgtggg agacctagaa gtggctctga ccgaaattca gctatcctct 43860
cagatccatc tgtgttttcc cctctaaata aatcagagac caaatctgga gataagatca 43920
agaagaaaga ttctaaaagt atagaaaaga agagaggaag acctcccacc ttccctggag 43980
taaaaatcaa aataacacat ggaaaggaca tttcagagtt accaaaggga aacaaagaag 44040
atagcctgaa aaaaattaaa aggacacctt ctgctacgtt tcagcaagcc acaaagatta 44100
aaaaattaag agcaggtaaa ctctctcctc tcaagtctaa gtttaagaca gggaagcttc 44160
aaataggaag gaaggggggta caaattgtac gacggagagg aaggcctcca tcaacagaaa 44220
ggataaagac cccttcgggt ctcctcatta attctgaact ggaaaagccc cagaaagtcc 44280
ggaaagacaa ggaaggaaca cctccactta caaaagaaga taagacagtt gtcagacaaa 44340
gccctcgaag gattaagcca gttaggatta ttccttcttc aaaaaggaca gatgcaacca 44400
ttgctaagca actcttacag agggcaaaaa agggggctca aaagaaaatt gaaaaagaag 44460
cagctcagct gcagggaaga aaggtgaaga cacaggtcaa aaatattcga cagttcatca 44520
tgcctgttgt cagtgctatc tcctcgcgga tcattaagac ccctcggcgg tttatagagg 44580
atgaggatta tgaccctcca attaaaattg cccgattaga gtctacaccg aatagtagat 44640
tcagtgcccc gtcctgtgga tcttctgaaa aatcaagtgc agcttctcag cactcctctc 44700
aaatgtcttc agactcctct cgatc 44725

<210> SEQ ID NO 50
<211> LENGTH: 987
<212> TYPE: DNA
<213> ORGANISM: Homo sapiens

<400> SEQUENCE: 50

-continued aatataagtg gaggcgtcgc gctggcgggc attcctgaag ctgacagcat tcgggccgag 60
atgtctcgct ccgtggcctt agctgtgctc gcgctactct ctctttctgg cctggaggct 120
atccagcgta ctccaaagat tcaggtttac tcacgtcatc cagcagagaa tggaaagtca 180
aatttcctga attgctatgt gtctgggttt catccatccg acattgaagt tgacttactg 240
aagaatggag agagaattga aaaagtggag cattcagact tgtctttcag caaggactgg 300
tctttctatc tcttgtacta cactgaattc acccccactg aaaaagatga gtatgcctgc 360
cgtgtgaacc atgtgacttt gtcacagccc aagatagtta agtgggatcg agacatgtaa 420
gcagcatcat ggaggtttga agatgccgca tttggattgg atgaattcca aattctgctt 480
gcttgctttt taatattgat atgcttatac acttacactt tatgcacaaa atgtagggtt 540
ataataatgt taacatggac atgatcttct ttataattct actttgagtg ctgtctccat 600
gtttgatgta tctgagcagg ttgctccaca ggtagctcta ggagggctgg caacttagag 660
gtggggagca gagaattctc ttatccaaca tcaacatctt ggtcagattt gaactcttca 720
atctcttgca ctcaaagctt gttaagatag ttaagcgtgc ataagttaac ttccaattta 780
catactctgc ttagaatttg ggggaaaatt tagaaatata attgacagga ttattggaaa 840
tttgttataa tgaatgaaac attttgtcat ataagattca tatttacttc ttatacattt 900
gataaagtaa ggcatggttg tggttaatct ggtttatttt tgttccacaa gttaaataaa 960
tcataaaact tgatgtgtta tctctta 987

<210> SEQ ID NO 51
<211> LENGTH: 10420
<212> TYPE: DNA
<213> ORGANISM: Homo sapiens

<400> SEQUENCE: 51
tttgtaaatg aaaagcaatc agattaggca atttttttct gcacagcaaa agaaactatc 60
atcaatcaga gtgaacagac atgctacaga atgggagaaa aattttgcca tctgttcatc 120
tgacaaaagt ctagtattca gaatccacaa agaacttaag caaatttaca tgaaaaaaaa 180
cttcattaaa tagtggacaa agaacatgaa cagacacttc taaagaagac atacatgtgg 240
ccaacaaaaa tatgaaaaag aaagctccca tcactgatca ttagagaaat gcaaatcaaa 300
acgacaaatg agataccatt ttatgccagt cagaatggca attattaaat agtcaagaaa 360
caacagatgc tggcaaggtt gcagagaaat aggaatgctt ttacactgtt ggtggaaaag 420
taaatggtta atccattgtg gaagacagtg acagtgtggc gattcctcaa agatttagaa 480
ccagaaatac catttgaccc agcaatccca ttgcagggta tatacccaaa ggaatataaa 540
tcattctatt ataaagacat atgcatgttt acattcatgg cagcactatt cacaatagca 600
aagacatgga atcaacccaa atgcccatca atgatggtct ggataaagaa aatatggtac 660
atatacacca tggaatatta tgcagccata aaaaggaagg agatcaagtc ctttgcaggg 720
atatggatga aggtggaagc cattatcctc agcaaactca cacaggaaca gaaaaccaaa 780
caccacatgt tctcatatat aactgggaac tgagcaatga gaacacatgg acacagggag 840
aggaacaaca cacactgggg cctgttgggg gagggtggtg atgggaggat cattagcaaa 900
aatagctaat gcatgccagg gttaatacct aggtgatgag ttgacaggtg cagcaaacca 960
acatggcaca catttaccta tgtaacaaac ctgcacatcc tacacatgta ccctggaact 1020
taaaaaaaaa ttaaattaaa agacaagctt aaagagttaa tgaaaaataa ttagatacaa 1080

-continued

```
gaagactttg attttcagaa acctgaaaca atagttataa ttttgctttt aacatatatt   1140
caaatccttt gatactgttc ctttctagag gtgcagctta attccctctc ttgagtgtgg   1200
cttggactta atgaggcact tctgaaatgg cctggttctg tgttcccacc caaatctcat   1260
cttgagttgt tatgcaaatt gtaatcccta cctattgggg gagggacctc atgggagttg   1320
attggatcat ggggacggtg cccccatgct gttctcctga tgctgaggga attctcatga   1380
gatctgatgg ttttataagg ggcttttccc tgcttcattg tgcatttctc tctcctgtca   1440
ccacatgaag aaggacgggt ttgcttccac ttctgccatg actgtaagtt tcctggggca   1500
gcctcctcag tcatgcagaa ctgtgggtca attaaacctc tttcctttat aaattaccca   1560
gtctcaggca tttctttata gcagtgtgag aatggactaa tacaacttct aacttataga   1620
atagtgccaa cataacagtt tgtgactctg ggtgtagaac ataaaactaa ctgcggcttc   1680
caccttctct ctctctgaat ctgggatcat gagctctggg ggaagccagc cgctgtgcca   1740
taagcagccc tgcaggaagg tccacatgac tgagaactga ggccttctgg gaacagacaa   1800
caaggaacca ggccttttcc aacagccatg tgactgatcc atgtttcttg tgaattccca   1860
gccccagcga agccctcaga tgctgcggcc cctggctgac aactggagtg caaccttgtg   1920
agaggccctg agcaggaagc actcagggaa acctctcctg gattcctgac gattggaaac   1980
tgtgggagat gagaaacatt tgttgtttcg agctaagttt tacgtaattt gttatgcaac   2040
agtaaataat atattttcac aagagaggat gtattattac acattaaatt gcatttgctc   2100
taaatgtgtc atcatcatca ttattatttt tgagacaggg tcttgctctg tcacccaggc   2160
tggaatgcag tggcatgatc accatgcact gcagtgtcga actcctgggg tcaagggact   2220
ctctgacctc agcctcctga gtagctgcga ctaccatcat gaactaccat gcctggctaa   2280
ttttctaatt ttttgtatag atggaggttt tgcccaggct gatcttgaac ttctggagtc   2340
aacaaatctc cattcctctg ccttccacag tgctaggatg acagacgtga gccaccacac   2400
ctggcctaaa ttaattataa gatattaaac atgtaactta gttttaaaaa gtaaggacaa   2460
tttccatggc tgaagaggat gtattttatg accattcaca atgatcacgt tacttgaact   2520
tcactttcca actgtgtccc aattaaacac aaaaggaaga tccaaccctt gctaggctga   2580
ttctatgatg gcctcaacaa gcagctcctg gtcattcacc ttcctccagt tattcaacca   2640
actctaatgt aggtgctgct gtgaagggat ttagcagata taattaaggg tctcaattag   2700
ttgactttat gctgcgttta tcctgcttgg actgtcctaa tcaggtgagc ccttgaaagg   2760
actgggttct tcatgagcat agagacttac agtgtgaaag ggactcagca tgaggggttt   2820
cctccaccat gggctttgaa aaggaagggg ctatgggccg ggcgcggtgg ctcacgcctg   2880
taatcccgac actttgggag gccgaggcgg gcggatcatg aggtcaggag gtcgagacaa   2940
tcttggctaa caaggtgaaa ccctgtctct actaagaaaa aaaaaaatta gagcatagtg   3000
gtgggcgcct gtagtcccag ctacttggga ctgagacagg agaatggtgt gaacccagga   3060
ggcggagctt gtagtgagca gagatcattg ggccactgta ccccagcctg ggctacagag   3120
ccagactccg tctcaaaaaa aaaaaaaaaa gaaaaaagaa aaattaaggg gctgtgtagg   3180
aaagaacgct ggtgagcacc gggaattgag cccctcccag ttctctacat tgacagctag   3240
ccaggaacag ggacctcagt cttacaactg caagaaactg cattctgcca cctctgtata   3300
aacccgaagg aggattcaaa atgaaaacac agcttttgga agcccagaat ggagattcta   3360
tccacatctt gcccagattt ctgaccaagg aactataagc agataaatgt gtgttgtttt   3420
gccaggcgtg gtagtgagcg aatgaattga tgaattgata tacacactag ttgcataaaa   3480
```

```
taaaatcttt ctgaactttt tcagtgtttt acagtttata attatctgtg atgcaattta   3540
atacactcat atttcattca ttaagtcaac aaaaattaac ttagtcccta caatgaacga   3600
ggtatcccct catatgctca agtgcctgac actccagaag cttcacaaga ccgaggtgga   3660
gacactggag tgttttaagt ggagaaatga cacactccga ctcacaggag cagggccact   3720
gtgaaaagaa cagttacgta gcaggtcatg ggacagtgct agtgtcacaa ttcatgagtg   3780
agagtgtggt gggaactaag gggagaggag ggcctgaagg atgagaagga tagagggaag   3840
ggctggagaa gcaggaggtg aggaaaagga gcagaggaaa gaatttgaaa gcagcagaat   3900
tcttaggttt aaagacattg ttttatggat tttaatacat ccatctacag agcctagcag   3960
ggtgttcttg gcagttggcc tttaatacct catgtgggtc tgcctaaaaa ctattttta   4020
tgttaatcag gtttaaaaat tactaagtgt tcctataaaa tatacacaac acttagaagt   4080
ggatacttcc taaaaacagg cagtgcatga gcactagtga ggggcattgt gactgccttg   4140
aacagttgca actttgaggt gaataaagcc tgtaatggct tctggttgca acatatagga   4200
acacagtggc tactttgtat tgaggagatg tcgtggactc acacagaaac tcagagctaa   4260
ggaatgatgg caaatttaaa gtaagacaag caggagtcac agatacattg tctgggaaag   4320
tgcaacttag tagctttgtg agtcctgttg taatgctttt ggacacattt atacattaag   4380
gggccaaagt cacatttttt acctattaga ttcctgatca ttcaggggtt accaagattc   4440
tgctacccac tgtagttaat aaacaaagag caaattggtc tctattctgt ctcatgcact   4500
caggcacaac ttttccggat taaaaacaaa aacaacaaca aaaatctaca cctctattcc   4560
cagagcaagc ttactctctg gcaccaaact ccatggggtg atttttcttc tagaagagtc   4620
caggtggaca ggtaaggagt gggagtcagg gagtccagtt cagggacaga gataatggga   4680
tgaaaagtga aaggagaggg acggggccca tgccgagggt ttctcccttg tttctcagac   4740
agctcctggg ccaagactca gggagacatt gagacagagc gcttcgcaca ggagcagagg   4800
ggtcagggcg aagtcccagg gccccaggcg tggctctcag ggtctcaggc cccgaaggcg   4860
gtgtatggat tggggagtcc cagccttggg gattccccaa ctccgcagtt tcttttctcc   4920
ctctcccaac ctacgtaggg tccttcatcc tggatactca cgacgcggac ccagttctca   4980
ctcccattgg gtgtcgggtt tccagagaag ccaatcagtg tcgtcgcggt cgctgttcta   5040
aagtccgcac gcacccaccg ggactcagat tctccccaga cgccgaggat ggccgtcatg   5100
gcgccccgaa ccctcctcct gctactctcg ggggccctgg ccctgaccca gacctgggcg   5160
ggtgagtgcg gggtcgggag ggaaaccgcc tctgcgggga gaagcaaggg gccctcctgg   5220
cgggggcgca ggaccggggg agccgcgccg ggaggagggt cgggcaggtc tcagccactg   5280
ctcgccccca ggctcccact ccatgaggta tttcttcaca tccgtgtccc ggcccggccg   5340
cggggagccc cgcttcatcg ccgtgggcta cgtggacgac acgcagttcg tgcggttcga   5400
cagcgacgcc gcgagccaga agatggagcc gcgggcgccg tggatagagc aggaggggcc   5460
ggagtattgg gaccaggaga cacggaatat gaaggcccac tcacagactg accgagcgaa   5520
cctggggacc ctgcgcggct actacaacca gagcgaggac ggtgagtgac cccggcccgg   5580
ggcgcaggtc acgacccctc atcccccacg gacgggccag gtcgcccaca gtctccgggt   5640
ccgagatcca ccccgaagcc gcgggactcc gagacccttg tcccgggaga ggcccaggcg   5700
cctttacccg gtttcatttt cagtttaggc caaaaatccc cccgggttgg tcggggcggg   5760
gcggggctcg gggactgggc ctgaccgcgg ggtcggggcc aggttctcac accatccaga   5820
```

-continued taatgtatgg ctgcgacgtg gggccggacg ggcgcttcct ccgcgggtac cggcaggacg 5880
cctacgacgg caaggattac atcgccctga acgaggacct gcgctcttgg accgcggcgg 5940
acatggcagc tcagatcacc aagcgcaagt gggaggcggt ccatgcggcg gagcagcgga 6000
gagtctacct ggagggccgg tgcgtggacg ggctccgcag atacctggag aacgggaagg 6060
agacgctgca gcgcacgggt accaggggcc acggggcgcc tccctgatcg cctatagatc 6120
tcccgggctg gcctcccaca aggaggggag acaattggga ccaacactag aatatcaccc 6180
tccctctggt cctgagggag aggaatcctc ctgggtttcc agatcctgta ccagagagtg 6240
actctgaggt tccgccctgc tctctgacac aattaaggga taaaatctct gaaggagtga 6300
cgggaagacg atccctcgaa tactgatgag tggttccctt tgacaccggc agcagccttg 6360
ggcccgtgac ttttcctctc aggccttgtt ctctgcttca cactcaatgt gtgtgggggt 6420
ctgagtccag cacttctgag tctctcagcc tccactcagg tcaggaccag aagtcgctgt 6480
tcccttctca gggaatagaa gattatccca ggtgcctgtg tccaggctgg tgtctgggtt 6540
ctgtgctctc ttccccatcc cgggtgtcct gtccattctc aagatggcca catgcgtgct 6600
ggtggagtgt cccatgacag atgcaaaatg cctgaatttt ctgactcttc ccgtcagacc 6660
cccccaagac acatatgacc caccacccca tctctgacca tgaggccacc ctgaggtgct 6720
gggccctggg cttctaccct gcggagatca cactgacctg gcagcgggat ggggaggacc 6780
agacccagga cacggagctc gtggagacca ggcctgcagg ggatggaacc ttccagaagt 6840
gggcggctgt ggtggtgcct tctggagagg agcagagata cacctgccat gtgcagcatg 6900
agggtctgcc caagcccctc accctgagat ggggtaagga gggagatggg ggtgtcatgt 6960
ctcttaggga aagcaggagc ctctctggag acctttagca gggtcagggc ccctcacctt 7020
cccctctttt cccagagctg tcttcccagc ccaccatccc catcgtgggc atcattgctg 7080
gcctggttct ccttggagct gtgatcactg gagctgtggt cgctgccgtg atgtggagga 7140
ggaagagctc aggtggagaa ggggtgaagg gtggggtctg agatttcttg tctcactgag 7200
ggttccaagc cccagctaga aatgtgccct gtctcattac tgggaagcac cttccacaat 7260
catgggccga cccagcctgg gccctgtgtg ccagcactta ctcttttgta aagcacctgt 7320
taaaatgaag gacagattta tcaccttgat tacggcggtg atgggacctg atcccagcag 7380
tcacaagtca caggggaagg tccctgagga cagacctcag gagggctatt ggtccaggac 7440
ccacacctgc tttcttcatg tttcctgatc ccgccctggg tctgcagtca cacatttctg 7500
gaaacttctc tggggtccaa gactaggagg ttcctctagg accttaaggc cctggctcct 7560
ttctggtatc tcacaggaca ttttcttccc acagatagaa aaggagggag ttacactcag 7620
gctgcaagta agtatgaagg aggctgatgc ctgaggtcct tgggatattg tgtttgggag 7680
cccatggggg agctcaccca ccccacaatt cctcctctag ccacatcttc tgtgggatct 7740
gaccaggttc tgtttttgtt ctaccccagg cagtgacagt gcccagggct ctgatgtgtc 7800
tctcacagct tgtaaaggtg agagcttgga gggcctgatg tgtgttgggt gttgggtgga 7860
acagtggaca cagctgtgct atggggtttc tttgcgttgg atgtattgag catgcgatgg 7920
gctgtttaag gtgtgacccc tcactgtgat ggatatgaat ttgttcatga atattttttt 7980
ctatagtgtg agacagctgc cttgtgtggg actgagaggc aagagttgtt cctgcccttc 8040
cctttgtgac ttgaagaacc ctgactttgt ttctgcaaag gcacctgcat gtgtctgtgt 8100
tcgtgtaggc ataatgtgag gaggtgggga gagcacccca cccccatgtc caccatgacc 8160
ctcttcccac gctgacctgt gctccctctc caatcatctt tcctgttcca gagaggtggg 8220
gctgaggtgt ctccatctct gtctcaactt catggtgcac tgagctgtaa cttcttcctt 8280
ccctattaaa attagaacct gagtataaat ttactttctc aaattcttgc catgagaggt 8340
tgatgagtta attaaaggag aagattccta aaatttgaga gacaaaatta atggaacgca 8400
tgagaacctt ccagagtcca cgtgttgctt atgctgattt gttgcagggg aggagagtag 8460
atggggctgt gcccagtttc tgttccggcc accatgggct ttatgtggtc acagctcacc 8520
tgggtcatct ttgctgctcc attgtccttg gcccttcagt agaaccttgt cccaccaaga 8580
cctgtgatca cagggagttg gatgtcacct agggtggtcc ctgcatacaa atctccttgt 8640
ggtatcaaga gacaaatttt cagacctgtc caggtcttgc cttcctccca gggctttttc 8700
cttaacggta ttttcgattt ttctccaatc tttttaaagg aaccagattg tgacatttgc 8760
agagaggagg ggtcccatag tttctcatca tggttaactt tctgttggaa ctcctcttct 8820
gccctcctac tcttcttcct gctctgagtt gtagtaatcc tagtgctggc tccaatccaa 8880
actcatagat ttataaagca gagtctaatt tagattcata tgtggttgga aaattgtacc 8940
cataaggcta gggttattgt tcctgaagag aaatatatgg ttttgtgctg aagtgtgcag 9000
gagggttggt gtgggaggag ggaggacaca caagcagccc tggtgagaaa agcactggcg 9060
gcatggatgt ccacgtgaac ttatgttctt tagctgccac aaaacagcat ttgccctgtg 9120
gctacattaa taaagatatg ggctttagaa tagggaggtg ctctacagtg atcattcatt 9180
caactgacat ttgttgtctg ctagggatat gactgctttt gcatttagaa agcatcctta 9240
aagtaaaaac agaaaaatgt ctggggttat ggtgcatacg ttctagatgc aagcttgtcc 9300
aacccgcggc tcgtgggctg catgtggccc aggacaattt tgaatgtgag gactttttttg 9360 cttatctgtg gtgaacctga gtcctggagt gagtgcaccc acctccctca gggtcaggag 9420
tgaatgcttt aggaaccctc cttttcagtg acctacaaaa gatagagggc acatttactg 9480
tgataaccca gagtatcagc caagggggct tgaccttcaa ggagtcgtgg ggaaggttaa 9540
taaagggtgg tgtcccaggg tcagaaaaga tgggcagaca gcaagggcac tgcttgatat 9600
ctatgataag catgtggaat tgaggagcaa gcttcagatt cagaatccag tgactaagga 9660
catatctata tccctaagag aaagaacctt gggacacgat gatggttata tgctgggaca 9720
attccatcag cccttctgca aaggagccta tagccattta atcaggagat gggataagta 9780
ttaacattgg gtgtgagctg acattgctgc ccagattcct acagcaccat tatgtccccc 9840
atcacactgg ggcttacaga agccagggaa taaacctaga cacattatgc cccatggtgg 9900
aatcaccagt tccataaatc ctgtcctggt tatctcccca ttctctgagt gcataattgg 9960
ccttgatgca ctggcaactg gagtcacccc acactgtgtc cctagtctgg agagtaaggg 10020
atctcactgt gctgaagccc aaagggaaac atccctcatc caagccaaac cagaagcaat 10080
attgtgcctc agggtgggtc ttgtggaggg tactgcaggt attatagggg tggcactgcc 10140
attacagacc tgaacgatgc ggggtggtgt tgggattgcc tgttatctcc atataactca 10200
gcaatctgta cctgcagaag cctgatatgg ctaaagaatg aatggaatta ctccagactt 10260
gaccaagtag gagtcctgat tgcagctgcc atgctggctg gatatcactg cctggggaga 10320
ttaataaggc ctcaggcaca tggcaagcag ctgtggattt ggtgagtgca ttccctccca 10380
tttcatttag aagatggata tggaatgatt cacattcaca 10420

<210> SEQ ID NO 52
<211> LENGTH: 10341
<212> TYPE: DNA

<213> ORGANISM: Homo sapiens

<400> SEQUENCE: 52 atttcttta ccaattgtaa ttgtacagat ctgctggtga caaattcttt taattttctt 60
ttacctgaaa tatctcattt gcctatcctt gaaggacatc tatgctggat atagaattct 120
tagttgatct ttttgtcttc cagcacttta aagatgttat tctactttct tttgtttcta 180
tggtttctaa taaaaagtca ttgatcagga caagaggaac agagaaacaa aaaccgggaa 240
aataacatgg tagacgtgaa acttatcata tcaataatga caaaaaccta tatgaatcaa 300
cactccaatg aagggcagag attgtgtgac ttggtttaaa aaaacacgga acccaaccat 360
acgctctttc cagacatgca ctttctttgt tttttttttt aatttaactt ttatttttag 420
ttaaggggta catgtgcagg tttgttatat aggtaaactt gtgtcatggg gttttgtttc 480
acaaattatt tctatgccca ttagtaccca cccaagtatt aagtcttagt tcccattagc 540
tatttttcct gatcctctcc ctcctcccac cctccaccct caagtggacc ccagtgtgtg 600
ttgttcccct ctgcatgtcc atgtgttctc atcatttagc tcccacttat aagtgagaac 660
atgtggtata tagttttctg ttcctgcatt agtttgctaa gaataatggc ctccagctcc 720
atccatgttc ctgcaaagga cgtaatctca ttctttttta tggctgtata gtattctatg 780
gtgtatatgt gccacatttt ctttatccag tctaccattg atgggcattt aggttgattc 840
caagtctttg ctatggtgaa tagtgcttca atgaacatat gtgtacatgt aagtcactca 900
ctttctcttt ttatttaatt tattttattt tgctttaagt tccagataca tgtgcagaac 960
gtgcaggttt gttacatacg tatagtctgc catagtggtt tgctgcacct attcacccat 1020
cctctaagtt ccctcctctt acccccgact ccccaaaagg ccctggtgtg tgttgttccc 1080
ctccctgtgt ccatgtgttc tcattgttca cctcccactt aagagtgagg acacgtggtg 1140
ttaggttttc tgttcccatg ttagtttgct gacgatgact tccagcttca tccatgtccc 1200
tgcaaaggac atgaactcat tcctttttat ggccgtgtag tattccatgg tgtatatcta 1260
ccacatttc tttacccaga ctatcattga tgggcatgtg ggttggttcc atgtctttgc 1320
tattgaaaat agtgctgcaa taaacatacc tgtgcatgtg tctttatagt agaatgattg 1380
atattccttt gggtatatac ccagtaaagg gattgctggg tcaaatagta tttctggttc 1440
tacatctctg aggaatggtc acaccatcct ccataatggt tgaactattt tacattccca 1500
ccaacagtga aaaagcattc ctatttctcc acagcctcac cagcatctat tgtttcctca 1560
ctttttaata atcgccattc tggctcgcag gagatagtac atcattgtgg ttttgatttg 1620
cttttctcta atgatcattg atattgagct ttttttttcat atgtttttttc ttctgagaag 1680
tgtctgttca taccctttgc caatttttga tagggctgtt ttttttcttg taaatttgtt 1740
taagttcctt gtaaacatac atgtgagctc tcatcattct tgtttaaaca cctaagaggc 1800
atccaaatca gtgcaacatg gcaagaaaat gaaataagaa accaatagaa ggaccaggca 1860
tggtggctca tgcctgtaat ccctgcattt tgggaggttg aggtggaagg atcacttgag 1920
ttcaggagtt tgagaccagc ctgatagtga gacctcatct ctaccaaata aaaataattt 1980
taaaagaaaa aagatcaata gataggaaag gaagaaacaa aagtctttgt caccaacttc 2040
attgcatatg tagaaaacac tagggaattc tgaaaaagtc tctggaatta atcactgaat 2100
ttgcaaaata gttcataaaa tatatgtagt aagtcactta gatgaacatg aaaagacagc 2160
aaacaatact agtcatcaaa gaagtgcaag ttaaaaccac aatgagaaac catcacacat 2220
cacctagaat agataaagtt aaaaagacat tggataagtc taaatactgt caagaatatg 2280

```
gaaaaaatag gaatgtctga tattgctggt aggaatgcaa aaaatgtggc agccaatttg   2340
taaagtggta tggcagtttc ttatacagtt acccatctat taccacatgg cccagcaatt   2400
ccacaaatat gtatttatcc aaaagaaata aaaatgtaag gccacacttg taagcagtta   2460
tttatagtgg cttcattaat aacaaaccct aactggagga atccacatgt ctatcaactg   2520
gaggcagaga aaccaatgaa taagctggga ttccagcaat actcagcagc tgctcagcaa   2580
caaaaatgaa tgaatggcat catctcacac atcgttatgc taaaggagag accaaacgaa   2640
ggactacata acatacgact gcacgtccat tacattctag aaatttcagt attgcagtga   2700
cagaaaacag agtggtggtt gagtgaaggg aaggggtgag ggtgggaggc aaggattaaa   2760
tagaaagggg cagaaagaaa gtttttaggg aaaagaaacg gttctctaca gcgccacaac   2820
tcagaggtaa ctgggtggtg ggaactaagg ggagaggagg gtgtgaggga agaggacaga   2880
gagaagggct ggggaagcag gaggtgagga caaggagcag gagaaaggac tctaaagcag   2940
tggaggagcc tagcagggga ttctttgcat tctgggtttc tctactgggc agtgtggtag   3000
ttacatgact ataaataatt accaatattc gccaaaaaag cgcagctaaa actggtgaat   3060
tttattacac ataaatgccc taataagcaa aaaaaaaaaa aaagggggggg gggaggggag   3120
gcaaaaataa agacattttt agataatcaa agccataaaa ttaatttcct aggggtcctg   3180
tactacattt aattttaaag gaagtgcttc agggtgaagg aaaatgatac tagatggtga   3240
cccagatata cagaaaggaa caattaacaa cagaaatgat gcacatacac atgtcacatt   3300
cacactcatt ttcttaattt cctgaagaca tatggctact tgtttaaaac aaaaagtatt   3360
gcactgtatc actgagtcta taatataggt tgatgtaata tatacaacaa taatagcaca   3420
atggtaggtt acaagaaact acactgttag aagtgtcctt tattttgctg gatgcagctt   3480
aatataacct gaacttcact gtgaaaagtc aaggaatcgg gtttccattc tttgctattg   3540
tgtaaagaaa tatagccaaa agccactagg agaattaaaa ccataaacta aaaaatgttt   3600
atttgacaca taagaaagta gtaaaggagg aacagaaaca aaaagatatg agacaaattg   3660
aaaacgtata gcaaaatggt agaccaaaac ccaaccattg caagtgaaga aatgacatga   3720
cctgagtcac attagcagga ctgctgagca ctgtggggag aacagatatg ggcaggaggt   3780
gagggacagt gttagtgcca caattcagga gtgacagggt ggcggggact aaggggagcg   3840
ggggtgtgag ggatgagagg ggcagacaga agggctggag aggcaggagg tgaggaaaag   3900
gagcaggaga aagaattcta aagcagtgga agagcctggc agagggttct ttgcattcgg   3960
tatttaatac attttgttgg acttcctaaa aactaattgg ctccttatga ttaaaaaaaa   4020
aaagagttac aaaaatacca agtgttcaga taaaatacgc acactgcttg gatgtgcaga   4080
gttcaggaaa acaggcagtg cttcagcgtc ggtgaagagc attgggactg catggagcac   4140
tcgcaacttt gaggtgatga ctacaggctc ccggttgcaa tagacagtaa caaaccctgc   4200
ttctttatat tcaggagatg ttctggactc acacagggaa actcagggtg gggaatgaag   4260
ataattttaa atgcaacaac ccagagttac agatccacag tctgggaaag taaaacttag   4320
gagctttgag agtttaattg taatgctgtt ttgacacagg tcttttacaa attggaattc   4380
taatcattca gggattacca atattgtgct acctactgta ttaacaaaca aaaaggaaac   4440
tggtctctat gagaatccct atgcggtgcc ttcagagaaa acttcaccag gtttaaagag   4500
aaaacccctg tctctacacc tccattccca gggcgagctc actctctggc atcaagttcc   4560
ccgtgctcag tttccctaca caagagtcca agaggagagg taaggagtgg gaggcaggga   4620
```

-continued

```
gtccagttca gggacaggga ttccaggacg agaagtgaag gggaaggggc tgggcgcagc   4680
ctgggggtct ctccctggtt tccacagaca gatccttgtc caggactcag gcagacagtg   4740
tgacaaagag gcttggtgta ggagaagagg gatcaggacg aagtcccagg tcccggacgg   4800
ggctctcagg gtctcaggct ccgagggccg cgtctgcaat ggggaggcgc agcgttgggg   4860
attccccact cccctgagtt tcacttcttc tcccaacttg tgtcgggtcc ttcttccagg   4920
atactcgtga cgcgtcccca cttcccactc ccattgggta ttggatatct agagaagcca   4980
atcagcgtcg ccgcggtccc agttctaaag tccccacgca cccacccgga ctcagagtct   5040
cctcagacgc cgagatgctg gtcatggcgc cccgaaccgt cctcctgctg ctctcggcgg   5100
ccctggccct gaccgagacc tgggccggtg agtgcgggtc gggagggaaa tggcctctgc   5160
cgggaggagc gaggggaccg caggcggggg cgcaggacct gaggagccgc gccgggagga   5220
gggtcgggcg ggtctcagcc cctcctcacc cccaggctcc cactccatga ggtatttcta   5280
cacctccgtg tcccggcccg gccgcgggga gccccgcttc atctcagtgg gctacgtgga   5340
cgacacccag ttcgtgaggt tcgacagcga cgccgcgagt ccgagagagg agccgcgggc   5400
gccgtggata gagcaggagg ggccggagta ttgggaccgg aacacacaga tctacaaggc   5460
ccaggcacag actgaccgag agagcctgcg gaacctgcgc ggctactaca accagagcga   5520
ggccggtgag tgaccccggc ccggggcgca ggtcacgact ccccatcccc cacgtacggc   5580
ccgggtcgcc ccgagtctcc gggtccgaga tccgcctccc tgaggccgcg ggacccgccc   5640
agaccctcga ccggcgagag ccccaggcgc gtttacccgg tttcattttc agttgaggcc   5700
aaaatccccg cgggttggtc ggggcggggc ggggctcggg ggactgggct gaccgcgggg   5760
ccggggccag ggtctcacac cctccagagc atgtacggct gcgacgtggg gccggacggg   5820
cgcctcctcc gcgggcatga ccagtacgcc tacgacggca aggattacat cgccctgaac   5880
gaggacctgc gctcctggac cgccgcggac acggcggctc agatcaccca gcgcaagtgg   5940
gaggcggccc gtgaggcgga gcagcggaga gcctacctgg agggcgagtg cgtggagtgg   6000
ctccgcagat acctggagaa cgggaaggac aagctggagc gcgctggtac caggggcagt   6060
ggggagcctt ccccatctcc tataggtcgc cggggatggc ctcccacgag aagaggagga   6120
aaatgggatc agcgctagaa tgtcgccctc cgttgaatgg agaatggcat gagttttcct   6180
gagtttcctc tgagggcccc ctcttctctc tagacaatta aggaatgacg tctctgagga   6240
aatggagggg aagacagtcc ctagaatact gatcaggggt ccccctttgac ccctgcagca   6300
gccttgggaa ccgtgacttt tcctctcagg ccttgttctc tgcctcacac tcagtgtgtt   6360
tggggctctg attccagcac ttctgagtca ctttacctcc actcagatca ggagcagaag   6420
tccctgttcc ccgctcagag actcgaactt tccaatgaat aggagattat cccaggtgcc   6480
tgcgtccagg ctggtgtctg ggttctgtgc cccttcccca ccccaggtgt cctgtccatt   6540
ctcaggctgg tcacatgggt ggtcctaggg tgtcccatga aagatgcaaa gcgcctgaat   6600
tttctgactc ttcccatcag accccccaaa gacacacgtg acccaccacc ccatctctga   6660
ccatgaggcc accctgaggt gctgggccct gggtttctac cctgcggaga tcacactgac   6720
ctggcagcgg gatggcgagg accaaactca ggacactgag cttgtggaga ccagaccagc   6780
aggagataga accttccaga agtgggcagc tgtggtggtg ccttctggag aagagcagag   6840
atacacatgc catgtacagc atgaggggct gccgaagccc ctcaccctga gatggggtaa   6900
ggagggggat gaggggtcat atctcttctc agggaaagca ggagcccttc agcagggtca   6960
gggcccctca tcttcccctc ctttcccaga gccgtcttcc cagtccaccg tccccatcgt   7020
```

gggcattgtt gctggcctgg ctgtcctagc agttgtggtc atcggagctg tggtcgctgc 7080
tgtgatgtgt aggaggaaga gttcaggtag ggaaggggtg aggggtgggg tctgggtttt 7140
cttgtcccac tgggggtttc aagccccagg tagaagtgtt ccctgcctca ttactgggaa 7200
gcagcatgca cacaggggct aacgcagcct gggaccctgt gtgccagcac ttactctttt 7260
gtgcagcaca tgtgacaatg aaggatggat gtatcacctt gatggttgtg gtgttggggt 7320
cctgattcca gcattcatga gtcaggggaa ggtccctgct aaggacagac cttaggaggg 7380
cagttggtcc aggacccaca cttgctttcc tcgtgtttcc tgatcctgcc ctgggtctgt 7440
agtcatactt ctggaaattc cttttgggtc caagactagg aggttcctct aagatctcat 7500
ggccctgctt cctcccagtg ccctcacagg acattttctt cccacaggtg gaaaaggagg 7560
gagctactct caggctgcgt gtaagtggtg ggggtgggag tgtggaggag ctcacccacc 7620
ccataattcc tcctgtccca cgtctcctgc gggctctgac caggtcctgt ttttgttcta 7680
ctccaggcag cgacagtgcc cagggctctg atgtgtctct cacagcttga aaaggtgaga 7740
ttcttggggt ctagagtggg tggggtggcg ggtctggggg tgggtggggc agaggggaaa 7800
ggcctgggta atggggattc tttgattggg atgtttcgcg tgtgtggtgg gctgtttaga 7860
gtgtcatcgc ttaccatgac taaccagaat ttgttcatga ctgttgtttt ctgtagcctg 7920
agacagctgt cttgtgaggg actgagatgc aggatttctt cacgcctccc ctttgtgact 7980
tcaagagcct ctggcatctc tttctgcaaa ggcacctgaa tgtgtctgcg tccctgttag 8040
cataatgtga ggaggtggag agacagccca cccttgtgtc cactgtgacc cctgttccca 8100
tgctgacctg tgtttcctcc ccagtcatct ttcttgttcc agagaggtgg ggctggatgt 8160
ctccatctct gtctcaactt tacgtgcact gagctgcaac ttcttacttc cctactgaaa 8220
ataagaatct gaatataaat ttgttttctc aaatatttgc tatgagaggt tgatggatta 8280
attaaataag tcaattcctg gaatttgaga gagcaaataa agacctgaga accttccaga 8340
atctgcatgt tcgctgtgct gagtctgttg caggtggggt gtggagaagg ctgtgggggg 8400
ccgagtgtgg atggggcctg tgcccatttg gtgttgagtc catcatgggc tttatgtggt 8460
tagtcctcag ctgggtcacc ttcactgctc cattgtcctt gtcccttcag tggaaacttg 8520
tccagtggga gctgtgacca cagaggctca cacatcgccc agggcggccc ctgcacacgg 8580
gggtctctgt gcattctgag acaaattttc agagccattc acctcctgct ctgcttctag 8640
agctcctttt ctgctctgct cttctgccct ctctccctgc cctggttcta gtgatcttgg 8700
tgctgaatcc aatcccaact catgaatctg taaagcagag tctaatttag acttacattt 8760
gtctgtgaaa ttggacccgt catcaaggac tgttctttcc tgaagagaga acctgattgt 8820
gtgctgcagt gtgctggggc agggggtgcg gggagggggt tgctgtcgaa agagggatgg 8880
ggagggaggg cacacaagca gcactgctga gaaaaacata ggcggcctct atctcagtgt 8940
gaggggtcct tgtgctgtag ctgccacaaa acagcacttg gcctgaggct atgttaataa 9000
agatactgcc ttcaaaatag ggaggtgctc tacagtgatc attcattcaa ctgacctttg 9060
tcattggcca gacataggac agaatggttc tgcatctggg gaacaccact gaagtaaaag 9120
aaaaatctct ggccttttgt agcatatgtt ccagtgggaa gaggcagacg atagatacat 9180
tataaccaga gtaaggaagg aaagtgctag aaggtggtaa gtgctgtgag gcaggtgatc 9240
caggatgtgg gcagtgggga cagggaaggt ggctgttgtg ctgggtagtc agtgtgtgcc 9300
ttgttgcaaa ggtgactttt gaggaaagat ttgagagaca tgaggatgtc tggggaagtt 9360

```
ctttccaggc agaggaagct ccagtccaaa tgcactatgg caggaaggtg tttgtgttcc   9420

cagaagaaca aggaggccag gagggctgga cggagagaaa ctgaggtgag gtcagaggtg   9480

cggccagaac aggtgggctt gaggggagtg gggttggatc tggcctttgc tctgagtggg   9540

atggggagtt agaggacagt tttgagcaga agagagccat gatatgactt ctgttttaaa   9600

aggatctctc tgacggctgt gctgagaaca gaattgagag gcgagggacg agggaggcag   9660

aagggaaaac agtaggaatc gagtgcagta ttccaggctg gagatgtcgg tttccttgac   9720

tggggcgtga gcaggggaaa tagtggggcg tgaggggatt ctggatgcat ttgaagatgg   9780

actcacagca tttgccaatg gattgtatct gtggtgtgag aaagacgaat caaggacacc   9840

catagttgta aaatgagtga gtagaaggat ggagctgctg tcagtggaga tggggagact   9900

ctggcaggag cgtcctgagg agggggcatc acaggcactc agtggaggag atgtctacta   9960

ggaaggcagg tgggggagct ggggtggaat ttggacagac aactccagag tttaggggaa  10020

aggactgggc tggagaaata gatttaggag gtcacaccat atatatgaga cttaaaacct  10080

caggcatgga tgaagcacca agggagtgac tgactatgga aaagaatgag cacaaggact  10140

gaaccctgga ccagttctaa ggggtgtgat cagaccacac ccagagcaga ctgcacagtt  10200

ctggtcccac gtctagagga cactcagaca aggaaccccc atgtgcacca ggatcacctg  10260

gatgtggtgc tgagatccag gaagtctgga gttgagcaag agattctgga tttatgacaa  10320

ggctggagct catgttgctg g                                            10341
```

<210> SEQ ID NO 53
<211> LENGTH: 10385
<212> TYPE: DNA
<213> ORGANISM: Homo sapiens

<400> SEQUENCE: 53

```
ggttgaacat cttctccccc tgtcctctac agacttctcg gcaccagagg tttcatgatc     60

acttttactt tgtcttttta ctcttgttat ttctttgccc ttctttgctg agatttcttt    120

atccactttc ttggcctgtt cacgttcttt cttctccatt tcttcttttg ctttttgttg    180

cttctgtgta atttcatttt cttcagcttc ttgtttcttt ttggcttttt gctcgtgttc    240

ttccctcctc agtttctttc tgtttccctt gctgtctttc ctgaagttct ttttcttgtt    300

tgtttttctc cattagaaga gcagtttctg catgaatatg agccttttct tcatctgtta    360

acatgagagt tggagaggaa actactggct tggcggaaca atcaggaata actttttcat    420

tctgaggaga ctgttgctca tgatttgtac tttcagattt gattatatgc tcttcaggca    480

atttgactgc cagtttttta gtatgatcaa tctgtggaac attctttatg ctaggcactg    540

gctgaatgat gggtgaaaca tcagatttag aagcagcaac tgattcaact ggaattgata    600

tattcagtgg tcctgtcctc tcattttgat cattatcact tatttgatca cttatcaatt    660

ctatgtcttc atccacttct ataggtggag gtggcatctc ggcagcaggt ttagaaggaa    720

ttgattcttc caatgaggga taagtaaaat ccaatgagat agacaactct tcattctggt    780

gttgtggggg tggagtgacc ttagcatttg ttgtatactg ggaatagcaa aggaaccagt    840

ttttatagcc tccctctaaa accaaagccc aaggcccatt gcacaggaca gtcttacttt    900

cccacttgaa aagtgcatct ttcagatgcc agagagttgt tctaatctgt aaatcttttg    960

cagaactaaa ccagtcaaga agtaccatat actccacatt ccccctcttc ttccatgtgt   1020

ctatagaatt atctgggagg tgtgcttcaa tccaactagc agtgactact ggactgatgg   1080

cttcttcagg aacactgaga gaatgtaaaa tacaggaatc ctgataatcc tgcattcttt   1140
```

-continued gagcatccat tataatcaag ctgatgtttt tatccatcat cattgtgtat agttcctttg 1200
ctgtgattgc tcctttctct ttggtctcac atttttcatt cttttcacca ttgctctttt 1260
gggttttgtc tttggaatcc aatacaatct ccaaagaacc tttagccaac gtgctgccat 1320
cctctcttcc tgtttcctgc ctttttgtt gtagccactg tgcttccccc tgcttgtcct 1380
tttcctcaag ttttttccag atttcaactt cttcatatct tagtttaagg ctttcagaga 1440
gtcgttcagt ttctccagtg gcttttttga tgtttgcagg tccaagtatt gaatggaagt 1500
aatactgctg ttgcttgaaa tcagttcttt tttggatagg attataaaca gtcacgtttc 1560
atatacgtgt gtgagctttt tttcatatgt ttcttggcca cgtaaatgtc ttcctctgag 1620
aagtgtctgt ttatatcctt tgcccacttt ttgatgggga tgggtttttt tcttgtaaat 1680
ttgtttaagt tccttgtaaa caaacatgtg agctctcatc attcttgttt aaacacctaa 1740
cagtcatcct aaccagtgca acaaggacca ggcatggtgg ctcatgcctg taatccctgc 1800
attttgggag gctgaggtgg gaggatcact tgagatcagg agtttgagac cagcctgata 1860
agtgagacct catctctacc aaataataat aattttaaaa gaaaaaagat caatggataa 1920
gaaaggaaga aatgaaagtc tttctttgtc accagcttca ttgtatatgt agaaaacact 1980
agggaattct gaaaaagtct ctggaattaa tcattgaatt tgcaaaatag ttcataaaat 2040
atatgtaata agtcgcttag atgaacatga aaagatagca aacaatacta gtcatcaaag 2100
aagtgcaagt taaaaccaca atgagaaacc atcacacatc acctagagca gataaagtta 2160
aaaagacata tgataagtct taacactggc aagaatatgg aaaaaatagg aatgtctgat 2220
attgctggta ggaatgcaaa aaatgtggca gccaatttgt aaagcggtat ggcaatttct 2280
tatacagtta cccatctatt accacatggc ccagcaattc cacaaatacg tatttatcca 2340
aaagaaataa aaatgtaagt ccacacttgt aagcagttat ttatagtggc ttcattaata 2400
acaagcccta actggaggaa tccacatgtc tatcaactgg agacacagaa accaatgaat 2460
aaactgggat tccagcaata ctcggcagct gctcagcaac aaaaatgaat gaatggcatc 2520
atctcaaaca tcgttatgct aagggagaga ccaaacaaaa gactacataa catatgattg 2580
catgtccatg aaattctaga aatgtcacta ttgcagtgac agaaagcaca gcagtggttg 2640
aatgaaggga aggggtgagg gtgggaggca aggattaaat agaaaggggg ataaagaaag 2700
tttttaggga aaagaaactg ttctctacag cgccacaact caggagtgac tgggaggggg 2760
aggtaagggg agaagaaggt ctgagggata aggggcagag agaagggctg gggaagcagg 2820
aggtgaggac aaggagcagg ggaaaggact ctaaagcagt ggaggggcct agtaggagga 2880
tctttgcatt tggtgtttct ctactgggca gtgtggtagt tacactataa ataattacca 2940
atatccacca aaaagtgcag ctaaaactgg tgaatttttt tacacgtaaa cgccctaata 3000
agcaaaaaaa aaaaaaaaaa aaaaaaaaaa aagggggggg ggagggggga ggaaagaagg 3060
caaaaataaa gacattgtta gatcatcaaa cccataaaat tcatttccta ggggtcctgt 3120
actacatgta attttaaagg acgttctaca ggctgaaggg aaatgatact agatggtgac 3180
ccagatatac agaaaggaac aattaacaac agaaatgatg cacatacaca tatcacatac 3240
acactcattt tcttaatttc ctgaagatac gtgactgctt gtctaaaaca aaaagtatta 3300
cactgtatcg ttgagtttat aacgtatatt gatgtaacat atacaataat aatagcataa 3360
tgatagttta aatgaaacta caccatttga agtgtccttt attttgctgg atgcagctta 3420
atattacctg aatttcactg tgaaaagtca aggaattggg tttcaattct tacaacaata 3480

-continued

```
aaaaattaat gtaaagaaat atagctaaaa gccactagga gaattaaaac cataagctaa   3540
aaaatgttta cttgacacat aagaaagtag caaaggagga acagaaacaa aaagatacga   3600
gacaaattga aaacgtatag caaaatggta gaccaaaatc caaccattat aagtgaagaa   3660
atgacacgac ctgagtcaca ttagcaggac tgctgagcac tgtggggaga acagacatgg   3720
gcaggaggtg agggacagtg ttagtgccac aattcaggag tgacagggtg gcggggacta   3780
aaggggaaag agggtgtgag ggatgagagg ggcagagaga agggctggag aagcaggagg   3840
tgaggaaaag gagcagagga aagaattcta aagcagtaga agagcctggc agggggttct   3900
ttgcattcgg tatttaatac attttgtgtg actgccttaa aactaatggg ctccttatga   3960
ttttttttta aaaaggggtt acaaaaatat caagtgtcca aataaaaatat gcacactgct   4020
tagatgtgca tagttcacga aaacgggcag tgctggagcg ctggtgaaga gcattgggac   4080
tgcatggagc cctcgcaact ttgaggtgat gactacaggc tcccggttgc aatagacagt   4140
aacaaaccct gcttctttgt attcaggaga tgttctggac tcacacaggg aaactctggc   4200
tagagaatga ggataacttt aaatgcaaca acccagagtc acagatccat agtctgcgaa   4260
agtaaaacag gagctttgag aatttaattg taatgcagtt ttgacacagg tctttcacag   4320
attggaattc taatcattca gggattacca atattgtgct acctactgta tcaataaaca   4380
aaaaggaaac tggtctctat gagaatctct acctggtgct ttcagacaaa acttcaccag   4440
gtttaaagag aaaactcctg actctacacg tccattccca gggcgagctc actgtctggc   4500
atcaagttcc ccatggtgag tttccctgta caagagtcca aggggagagg taagtgtcct   4560
ttattttgct ggatgtagtt taatattacc tgaggtgagg taaggtaagg caaagggtgg   4620
gaggcaggga gtccagttca gggacgggga ttccaggagg agaagtgaag gggaaggggc   4680
tgggcgcagc cttggggtct ctccctggtt tccacagaca gatccttgtc caggactcag   4740
gcacacagtg tgacaaagat gcttggtgta ggagaagagg gatcaggacg aagtcccagg   4800
tcccgggcgg ggctctcagg gtctcaggct ccaagggccg tgtctgcatt ggggaggcgc   4860
cgcgttgggg attctccact cccctgagtt tcacttctcc caacctgcgt cgggtccttc   4920
ttcctgaata ctcatgacgc gtccccaatt cccactccca ttgggtgtcg ggttctagag   4980
aagccaatca gcgtctccgc agtcccggtt ctaaagtccc cagtcaccca cccggactca   5040
cattctcccc agaggccgag atgcgggtca tggcgccccg agccctcctc ctgctgctct   5100
cgggaggcct ggccctgacc gagacctggg cctgtgagtg cggggttggg agggaagcgg   5160
cctctgcgga gaggagcgag gggcccgccc ggcgagggcg caggacccgg ggagccgcgc   5220
agggaggtgg gtcgggcggg tctcagcccc tcctcgcccc caggctccca ctccatgagg   5280
tatttcgaca ccgccgtgtc ccggcccggc cgcggagagc cccgcttcat ctcagtgggc   5340
tacgtggacg acacgcagtt cgtgcggttc gacagcgacg ccgcgagtcc gagaggggag   5400
ccgcgggcgc cgtgggtgga gcaggagggg ccggagtatt gggaccggga gacacagaac   5460
tacaagcgcc aggcacaggc tgaccgagtg agcctgcgga acctgcgcgg ctactacaac   5520
cagagcgagg acggtgagtg accccggccc ggggcgcagg tcacgacccc tccccatccc   5580
ccacggacgg cccgggtcgc cccgagtctc cccgtctgag atccacccca aggtggatct   5640
gcggaacccg cccagaccct cgaccggaga gagccccagt cgcctttacc cggtttcatt   5700
ttcggtttag gccaaaatcc ccgcgggttg gtcggggcgg ggcggggctc gggggactgg   5760
gctgaccgcg ggggcggggc cagggtctca caccctccag aggatgtatg gctgcgacct   5820
ggggcccgac gggcgcctcc tccgcgggta tgaccagtcc gcctacgacg gcaaggatta   5880
```

-continued

```
catcgccctg aacgaggacc tgcgctcctg gaccgccgcg gacaccgcgg ctcagatcac   5940
ccagcgcaag ttggaggcgg cccgtgcggc ggagcagctg agagcctacc tggagggcac   6000
gtgcgtggag tggctccgca gatacctgga gaacgggaag gagacgctgc agcgcgcagg   6060
taccaggggc agtggggagc cttccccatc tcctatagat ctcccgggat ggcctcccac   6120
gaggagggga ggaaaatggg atcagcactg gaatatcgcc ctcccttgaa tggagaatgg   6180
catgagtttt cctgagtttc ctctgagggc cccctctgct ctctaggaca attaagggat   6240
gaagtctctg aggaaatgga ggggaagaca gtccctggaa tactgatcag ggtctcctt   6300
tgaccacttt gaccactgca gcagctgtgg tcaggctgct gacctttctc tcaggccttg   6360
ttctctgcct cacactcaat gtgtctgaag gtttgattcc agcttttctg agtcctgcag   6420
cctccactca ggtcaggacc agaagtcgct gttcctccct cagagactag aactttccaa   6480
tgaataggag attatcccag gtgcctgtgt ccaggctggc gtctgggttc tgtgccgcct   6540
tccccacccc aggtgtcctg tccattctca ggatggtcac atgggcgctg ctggagtgtc   6600
ccaagagaga tgcaaagtgt ctgaattttc tgactcttcc cgtcagaacc cccaaagaca   6660
cacgtgaccc accacccct ctctgaccat gaggccaccc tgaggtgctg ggccctgggc   6720
ttctaccctg cggagatcac actgacctgg cagcgggatg gggaggacca gacccaggac   6780
accgagcttg tggagaccag gccagcagga gatggaacct tccagaagtg ggcagctgtg   6840
gtggtgcctt ctggacaaga gcagagatac acgtgccata tgcagcacga ggggctgcaa   6900
gagcccctca ccctgagctg ggtaaggag gggaatgggg ggtcacatct cttatcagag   6960
aaagcagaag tccttctgga gcccttcagc cgggtcaggg ctgaggcttg gggtcaggg   7020
cccctcacct tctcctcctt tcccagagcc atcttcccag cccaccatcc ccatcatggg   7080
catcgttgct ggcctggctg tcctggttgt cctagctgtc cttggagctg tggtcaccgc   7140
tatgatgtgt aggaggaaga gctcaggtag ggaaggggtg aagagcgggg tctgggtttt   7200
cttgtcccac tgggagtttc aagccccagg tagaagtgtg ccccgccttg ttactggaag   7260
caccatccac acatgggcca tcccagcctg ggaccctgtg tgccagcact tactcttttg   7320
tgaagcacat gtgacaatga aggacggatg tatcaccttg atgattatgg tgttggggtc   7380
ctgattccag cattcatgag tcaggggaag gtccctgcta aggacagacc ttaggagggc   7440
agttggtcca gaacccacaa ctgctttccc catgtttcct gatcctgccc tgggtctgca   7500
gtcgtagttc tggaaacttc tcttgggtcc aagactagga ggttccccta agatcacatg   7560
gccctgcctc ctcccagtcc cctcataggg cattttcttc ccacaggtgg aaaaggaggg   7620
agctgctctc aggctgcgtg taagtgatgg cggcgggcgt gtggaggagc tcacctactc   7680
cataattcct cttgtcccac atctcctgcg ggctctgacc aggtcttttt ttttgttcta   7740
ccccaggcag caacagtgcc cagggctctg atgagtctct catcacttgt aaaggtgaga   7800
ttctggggag ctgaagtggt cgggggtggg gcagagggaa aaggcctggg taatggggat   7860
tctttgattg ggacgtttcg agtgtgtggt gggccgttca gagtgtcatc acttaccatg   7920
actgacctga atttgttcat gactattgtg ttctgtagcc tgagacagct gcctgtgtgg   7980
gactgagatg caggatttct tcacacctct cctttgtgac ttcaagagcc tctggcatct   8040
ctttctgcaa aggcgtctga atgtgtctgc gttcctgtta gcataatgtg aggaggtgga   8100
gagacagccc acccccgtgt ccaccgtgac ccctgtcccc acactgacct gtgttccctc   8160
cccgatcatc tttcctgttc cagagaggtg gggctggatg tctccatctc tgtctcaaat   8220
```

-continued

```
tcatggtgca ctgagctgca acttcttact tccctaatga agttaagaac ctgaatataa   8280

atttgtgttc tcaaatattt gctatgaagc gttgatggat taattaaata agtcaattcc   8340

tagaagttga gagagcaaat aaagacctga gaaccttcca gaatttgcat gttcgctgtg   8400

ctgagtctgt tgcaggtggg ggtggggaag gctgtgagga gccgagtgtg gacggggcct   8460

gtgcctagtt gctgttcagt tcttcatggg ctttatgtgg tcagtcctca gctgggtcac   8520

cttcactgct ccattgtcct tgtcccttca gtggaaactt gtccagcgga agctgtgacc   8580

acagaggctc acccatcgcc cagggcagcc cctgcacacg ggagtccctg tgctttctga   8640

gacaaatttt cagacccatt cagctcctgc cctccttcta gggctcctct tctgctttgg   8700

tctcctgccc tctctccctt ccctgattcc agtgatcttc gtgctgactc caatcccaac   8760

tcatgaatct aaagcagagc ctaatttaga tttgtatttg tttgtaaaat tgggtccata   8820

gtctagaatt gttccttcct gaagagagaa acctgatcgt gtgctgcagt gtgcggggcg   8880

gttggtgtgg gaggagggat aggggaggga ggacacacaa gcagccctgc tgagaaaagt   8940

acaggcggcc tcggtgtcag tgtgagggga ccttgtgctg cagctgccac aaaacagcac   9000

ttggcctgag gctatgttaa taaagatact ggctttagag taggaggtgc tctacactga   9060

tcattcaact gacctttgtt gtcagccaga cacaggacag aaaagttctg catctgggga   9120

acaccattga agtaaaatca gaaaaatatc tgagcatatg cttcagtggt aagaggcaga   9180

cgatacatac actataacca cagtaagaaa agaaagtgat ggaaggtggt aagtgccatg   9240

aggcaggtga tccgggtatg ggcagtgggg acagggaagg tggctgttgg acaggagttg   9300

tcaatgtgtg ccttgttgca aagatgacct ttgaggaaag atttgaggga catgaggatg   9360

tctggggaag ttctttctag gcaaggaaac tccagtccaa atgtactagg gcaggaaggt   9420

gtctgtgttc ccagaagagc aaggaggcca ggagggctgg acagagaaac tagatgaggt   9480

cagaggtatg gccagagcag gtgggcttga ggggagtggg gttgcgtctg acctcgctct   9540

gagtgggatg gggagttaga ggacagtttt gagcagaaga gagccatgat atgacttctt   9600

tcttaaaagg atctctgatg gctgtgctga gaacagaatt gagaggcgag ggatgaggga   9660

ggcagaaggg aaaacagtag gaatcgagtg cagtattcca ggctggagat gtcggttacc   9720

ttgactgggg tgtgagcaca ggaaatagtg ggacgtgagg ggattctgga tgcatttgaa   9780

gatggactca cagcatttgc caatggattg tatctgtggt gtgagaaaga cgaatcaagg   9840

acacccatag ttgtaaaatg agtgagtaga aggaagggtg gagctgctgt cagtggagat   9900

ggggagactc tggcaggagc atcctgagga gggggcatca caggcactca gtggaggaga   9960

tgtctactag gaatgcaggt gggggagctg gggtggcagc tgggcagaca actccacagt  10020

tcaggggaaa ggactgggct ggagaaatag atttaggagc tcacaccaca taaacgatac  10080

ttaaaacctc aagcatggat gaagcaccaa gggagtgatt gactgtggaa aagaatcagc  10140

gcaaggactg aaccctggac ctccagttct aagggatctg atcagaccac agagcagact  10200

gcacagttct ggccccatgt ctagaggacg cttagacaag gaactcccgt gtgcaccagg  10260

atcacctgga tgtggtgctg agatccagga agtctggagt cgagcaagag attctggatt  10320

tatgacaagg ctggagctca cgttgctggt ctccagatca cacttggagt agccagaaca  10380

ccagg                                                               10385
```

<210> SEQ ID NO 54
<211> LENGTH: 365
<212> TYPE: PRT
<213> ORGANISM: Homo sapiens

<400> SEQUENCE: 54

Met Ala Val Met Ala Pro Arg Thr Leu Leu Leu Leu Leu Ser Gly Ala
1 5 10 15

Leu Ala Leu Thr Gln Thr Trp Ala Gly Ser His Ser Met Arg Tyr Phe
20 25 30

Phe Thr Ser Val Ser Arg Pro Gly Arg Gly Glu Pro Arg Phe Ile Ala
35 40 45

Val Gly Tyr Val Asp Asp Thr Gln Phe Val Arg Phe Asp Ser Asp Ala
50 55 60

Ala Ser Gln Lys Met Glu Pro Arg Ala Pro Trp Ile Glu Gln Glu Gly
65 70 75 80

Pro Glu Tyr Trp Asp Gln Glu Thr Arg Asn Met Lys Ala His Ser Gln
85 90 95

Thr Asp Arg Ala Asn Leu Gly Thr Leu Arg Gly Tyr Tyr Asn Gln Ser
100 105 110

Glu Asp Gly Ser His Thr Ile Gln Ile Met Tyr Gly Cys Asp Val Gly
115 120 125

Pro Asp Gly Arg Phe Leu Arg Gly Tyr Arg Gln Asp Ala Tyr Asp Gly
130 135 140

Lys Asp Tyr Ile Ala Leu Asn Glu Asp Leu Arg Ser Trp Thr Ala Ala
145 150 155 160

Asp Met Ala Ala Gln Ile Thr Lys Arg Lys Trp Glu Ala Val His Ala
165 170 175

Ala Glu Gln Arg Arg Val Tyr Leu Glu Gly Arg Cys Val Asp Gly Leu
180 185 190

Arg Arg Tyr Leu Glu Asn Gly Lys Glu Thr Leu Gln Arg Thr Asp Pro
195 200 205

Pro Lys Thr His Met Thr His His Pro Ile Ser Asp His Glu Ala Thr
210 215 220

Leu Arg Cys Trp Ala Leu Gly Phe Tyr Pro Ala Glu Ile Thr Leu Thr
225 230 235 240

Trp Gln Arg Asp Gly Glu Asp Gln Thr Gln Asp Thr Glu Leu Val Glu
245 250 255

Thr Arg Pro Ala Gly Asp Gly Thr Phe Gln Lys Trp Ala Ala Val Val
260 265 270

Val Pro Ser Gly Glu Glu Gln Arg Tyr Thr Cys His Val Gln His Glu
275 280 285

Gly Leu Pro Lys Pro Leu Thr Leu Arg Trp Glu Leu Ser Ser Gln Pro
290 295 300

Thr Ile Pro Ile Val Gly Ile Ile Ala Gly Leu Val Leu Leu Gly Ala
305 310 315 320

Val Ile Thr Gly Ala Val Val Ala Ala Val Met Trp Arg Arg Lys Ser
325 330 335

Ser Asp Arg Lys Gly Gly Ser Tyr Thr Gln Ala Ala Ser Ser Asp Ser
340 345 350

Ala Gln Gly Ser Asp Val Ser Leu Thr Ala Cys Lys Val
355 360 365

<210> SEQ ID NO 55
<211> LENGTH: 362
<212> TYPE: PRT
<213> ORGANISM: Homo sapiens

<400> SEQUENCE: 55

```
Met Leu Val Met Ala Pro Arg Thr Val Leu Leu Leu Leu Ser Ala Ala
1               5                   10                  15

Leu Ala Leu Thr Glu Thr Trp Ala Gly Ser His Ser Met Arg Tyr Phe
            20                  25                  30

Tyr Thr Ser Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Tyr Lys Ala Gln Ala Gln
                85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
        115                 120                 125

Pro Asp Gly Arg Leu Leu Arg Gly His Asp Gln Tyr Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Arg Arg Ala Tyr Leu Glu Gly Glu Cys Val Glu Trp Leu
            180                 185                 190

Arg Arg Tyr Leu Glu Asn Gly Lys Asp Lys Leu Glu Arg Ala Asp Pro
        195                 200                 205

Pro Lys Thr His Val Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Ser
    290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
        355                 360
```

```
<210> SEQ ID NO 56
<211> LENGTH: 366
<212> TYPE: PRT
<213> ORGANISM: Homo sapiens

<400> SEQUENCE: 56

Met Arg Val Met Ala Pro Arg Ala Leu Leu Leu Leu Leu Ser Gly Gly
```

-continued

```
1               5                   10                  15

Leu Ala Leu Thr Glu Thr Trp Ala Cys Ser His Ser Met Arg Tyr Phe
            20                  25                  30

Asp Thr Ala Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Asn Tyr Lys Arg Gln Ala Gln
                85                  90                  95

Ala Asp Arg Val Ser Leu Arg Asn Leu Arg Gly Tyr Tyr Asn Gln Ser
            100                 105                 110

Glu Asp Gly Ser His Thr Leu Gln Arg Met Tyr Gly Cys Asp Leu Gly
        115                 120                 125

Pro Asp Gly Arg Leu Leu Arg Gly Tyr Asp Gln Ser Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Leu Glu Ala Ala Arg Ala
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Ala Glu Pro
        195                 200                 205

Pro Lys Thr His Val Thr His His Pro Leu Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Met Gln His Glu
        275                 280                 285

Gly Leu Gln Glu Pro Leu Thr Leu Ser Trp Glu Pro Ser Ser Gln Pro
    290                 295                 300

Thr Ile Pro Ile Met Gly Ile Val Ala Gly Leu Ala Val Leu Val Val
305                 310                 315                 320

Leu Ala Val Leu Gly Ala Val Val Thr Ala Met Met Cys Arg Arg Lys
                325                 330                 335

Ser Ser Gly Gly Lys Gly Gly Ser Cys Ser Gln Ala Ala Cys Ser Asn
            340                 345                 350

Ser Ala Gln Gly Ser Asp Glu Ser Leu Ile Thr Cys Lys Ala
        355                 360                 365
```